(12) United States Patent
TenHoor et al.

(10) Patent No.: US 8,273,351 B2
(45) Date of Patent: Sep. 25, 2012

(54) FC RECEPTOR BINDING PROTEINS

(75) Inventors: Christopher TenHoor, Hopkinton, MA (US); Arumugam Muruganandam, Bangalore (IN); Robert Charles Ladner, Ijamsville, MD (US); Clive Wood, Boston, MA (US); Alan J. Bitonti, Acton, MA (US); James Stattel, Hagerstown, MD (US); Kevin McDonnell, Waltham, MA (US); Liming Liu, Upper Dublin, PA (US); Jennifer Dumont, Groton, MA (US); Aaron Sato, Richmond, CA (US)

(73) Assignees: Dyax Corp., Burlington, MA (US); Syntonix Pharmaceuticals, Inc., Waltham, MA (US)

( * ) Notice: Subject to any disclaimer, the term of this patent is extended or adjusted under 35 U.S.C. 154(b) by 220 days.

(21) Appl. No.: 12/429,529

(22) Filed: Apr. 24, 2009

(65) Prior Publication Data

US 2009/0324614 A1    Dec. 31, 2009

Related U.S. Application Data

(60) Provisional application No. 61/048,152, filed on Apr. 25, 2008, provisional application No. 61/048,500, filed on Apr. 28, 2008.

(51) Int. Cl.
  *A61K 39/395* (2006.01)
  *C07K 16/00* (2006.01)
  *C07H 21/00* (2006.01)
  *G01N 33/53* (2006.01)

(52) U.S. Cl. .................... 424/133.1; 530/389.1

(58) Field of Classification Search ............ 424/133.1; 530/389.1
See application file for complete search history.

(56) References Cited

U.S. PATENT DOCUMENTS

| | | | |
|---|---|---|---|
| 5,658,727 A | 8/1997 | Barbas et al. | |
| 6,030,613 A | 2/2000 | Blumberg et al. | |
| 6,086,875 A | 7/2000 | Blumberg et al. | |
| 7,662,928 B2 | 2/2010 | Balthasar et al. | |
| 2007/0092507 A1* | 4/2007 | Balthasar et al. | 424/133.1 |
| 2010/0266530 A1* | 10/2010 | Roopenian et al. | 424/85.2 |

FOREIGN PATENT DOCUMENTS

| | | |
|---|---|---|
| WO | WO 00/71694 | 11/2000 |
| WO | WO 02/43658 | 6/2002 |
| WO | WO 2006/118772 A2 | 11/2006 |
| WO | WO 2006/118772 A3 | 11/2006 |
| WO | WO 2007/087289 A2 | 8/2007 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Akilesh et al., The MHC class I-like Fc receptor promotes humorally mediated autoimmune disease. J Clin Invest. May 2004;113(9):1328-33.
Getman et al., Pharmacokinetic effects of 4C9, an anti-FcRn antibody, in rats: implications for the use of FcRn inhibitors for the treatment of humoral autoimmune and alloimmune conditions. J Pharm Sci. Apr. 2005;94(4):718-29.
Liu et al., Amelioration of experimental autoimmune myasthenia gravis in rats by neonatal FcR blockade. J Immunol. Apr. 15, 2007;178(8):5390-8.
Roopenian et al., FcRn: the neonatal Fc receptor comes of age. Nat Rev Immunol. Sep. 2007;7(9):715-25. Epub Aug. 17, 2007.
Yu, Zhiya and Lennon, Vanda; "Mechanism of Intravenous Immune Globulin Therapy in Antibody-Mediated Autoimmune Diseases"; The New England Journal of Medicine, Clinical Implications of Basic Research; (1999); 34(3): 227-228.
Burmeister et al., *Crystal structure of the complex of rat neonatal Fc receptor with Fc*, Nature 372:366 (1994).
Israel et al., *Expression of the neonatal Fc receptor, FcRn, on human intestinal epithelial cells*, Immunology 92:69 (1997).
Junghans, *Finally! The Brambell Receptor (FcRB)*, Immunologic Research 16(1):29-57 (1997).
Junghans et al., *The protection receptor for IgG catabolism is the β-microglobulin-containing neonatal intestinal transport receptor*, Proc. Natl. Acad. Sci. USA 93:5512-5516 (1996).
Kobayashi et al., *FcRn-mediated transcytosis of immunoglobulin G in human renal proximal tubular epithelial cells*, Am J Physiol Renal Physiol 282:F358 (2002).
Leach et al., *Isolation from Human Placenta of the IgG Transporter, FcRn, and Localization to the Syncytiotrophoblast*, J Immunol 157:3317 (1996).
Li et al., *Complete FcRn dependence for intravenous Ig therapy in autoimmune skin blistering diseases*, J Clin Invest 115:3440-3450 (2005).
Roopenian et al., *The MHC Class I-Like IgG Receptor Controls Perinatal IgG Transport, IgG Homeostatis, and Fate of IgG-Fc-Coupled Drugs*, J. Immunology 170:3528 (2003).

* cited by examiner

*Primary Examiner* — Lynn Bristol
(74) *Attorney, Agent, or Firm* — Wolf, Greenfield & Sacks, P.C.

(57) ABSTRACT

This disclosure provides, inter alia, proteins that bind to FcRn, e.g., immunoglobulins that inhibit FcRn with high affinity and selectivity. The FcRn-binding proteins can be used to treat a variety of disorders including autoimmune disorders.

6 Claims, 46 Drawing Sheets

0: TMFI of the tube containing Alexa fluor 488 labeled hIgG1 alone.

1: TMFI of positive control 15B6.1 (anti-hFcRn blocking mAB from #182 fusion 2-4, 6-7, 9, 12-13, 15-17, 19-20, 22-28, 31-32: anti-hFcRn mAB sups.

5, 8, 10, 11, 14, 18, 21, 29 and 30: anti-human β-2M mAB sups.

X is fluorescent intensity

Y is cell number

X is fluorescent intensity

Y is cell number

X is fluorescent intensity

Y is cell number

X is fluorescent intensity

Y is cell number

X is fluorescent intensity

Y is cell number

FIGURE 29

```
532A-M0090-F11 (532A-R0004-E04)
LIGHT: V:VL3_2b2; J:JL1

FR1-L                    CDR1-L              FR2-L           CDR2-L
532A-M0090-F11:  QSVLTQPASVSGSPGQSITISC  TGTSSDVGSYNLVS  WYQKYPGKAPKLIIY  GDSQRPS
GERMLINE:        QSALTQPASVSGSPGQSITISC  TGTSSDVGSYNLVS  WYQQHPGKAPKLMIY  EVSKRPS

FR3-L                              CDR3-L         FR4-L
532A-M0090-F11:  GLSSRFSGSKSGNSASLTISGLQAEDEADYYC  SYAGSGIYYV  FGSGTKVTVL
GERMLINE:        GVSNRFSGSKSGNTASLTISGLQAEDEADYYC  SYAGSSTFYV  FGTGTKVTVL

532A-M0090-F11 (SEQ ID NO: 177);
GERMLINE (SEQ ID NO: 178)
------------------------------------------------------------------------------
LC-lambda1

532A-M0090-F11-C
SPKANPTVTLFPPSSEELQANKATLVCLISDFYPGAVTVAWKADGSPVKAGVETTKPSKQSNNKYAASSYL

GERMLINE-C:
GPKANPTVTLFPPSSEELQANKATLVCLISDFYPGAVTVAWKADGSPVKAGVETTKPSKQSNNKYAASSYL

532A-M0090-F11-C   SLTPEQWKSHRSYSCQVTHEGSTVEKTVAPAECS (SEQ ID NO: 179)
GERMLINE-C:        SLTPEQWKSHRSYSCQVTHEGSTVEKTVAPTECS (SEQ ID NO: 180)
------------------------------------------------------------------------------
HEAVY: V:VH3-23; J:JH4

FR1-H                    CDR1-H           FR2-H              CDR2-H
532A-M0090-F11:  EVQLLESGGGLVQPGGSLRLSCAASGFTFS  SYAMS  WVRQAPGKGLEWVS  SISGSGGYTKY
GERMLINE:        EVQLLESGGGLVQPGGSLRLSCAASGFTFS  SYAMS  WVRQAPGKGLEWVS  AISGSGGSTYY

FR3-H                              CDR3-H   FR4-H
532A-M0090-F11:  ADSVKG RFTISRDNSKNTLYLQMNSLRAEDTAVYYCAR  LSTGEIY  WGQGTLVTVSS
GERMLINE:        ADSVKG RFTISRDNSKNTLYLQMNSLRAEDTAVYYCAK     Y   WGQGTLVTVSS

532A-M0090-F11 (SEQ ID NO: 111);
GERMLINE (SEQ ID NO: 113)
```

FIGURE 30

```
* (a,z)  ASTKGPSVFPLAPSSKSTSGGTAALGCLVKDYFPEPVTVSWNSGALTS
* (f)    ------------------------------------------------
* (a,z)  GVHTFPAVLQSSGLYSLSSVVTVPSSSLGTQTYICNVNHKPSNTKVDKK
* (f)    -----------------------------------------------K
* (a,z)  VEPKSCDKTHTCPPCAPELLGGPSVFLFPPKPKDTLMISRTPEVTCVVV
* (f)    ------------------------------------------------
* (a,z)  DVSHEDPEVKFNWYVDGVEVHNAKTKPREEQYNSTYRVVSVLTVLHQDW
* (f)    ------------------------------------------------
* (a,z)  LNGKEYKCKVSNKALPAPIEKTISKAKGQPREPQVYTLPPSREEQVYT
* (f)    ------------------------------------------------
* (a,z)  LPPSRDELTKNQVSLTCLVKGFYPSDIAVEWESNGQPENNYKTTPPVLD
* (f)    -----DE-----------------------------------------
* (a,z)  SDGSFFLYSKLTVDKSRWQQGNVFSCSVMHEALHNHYTQKSLSLSPGK*
* (f)    ------------------------------------------------
```

(a, z) (SEQ ID NO: 115)

(f) (SEQ ID NO: 116)

FIGURE 31
A
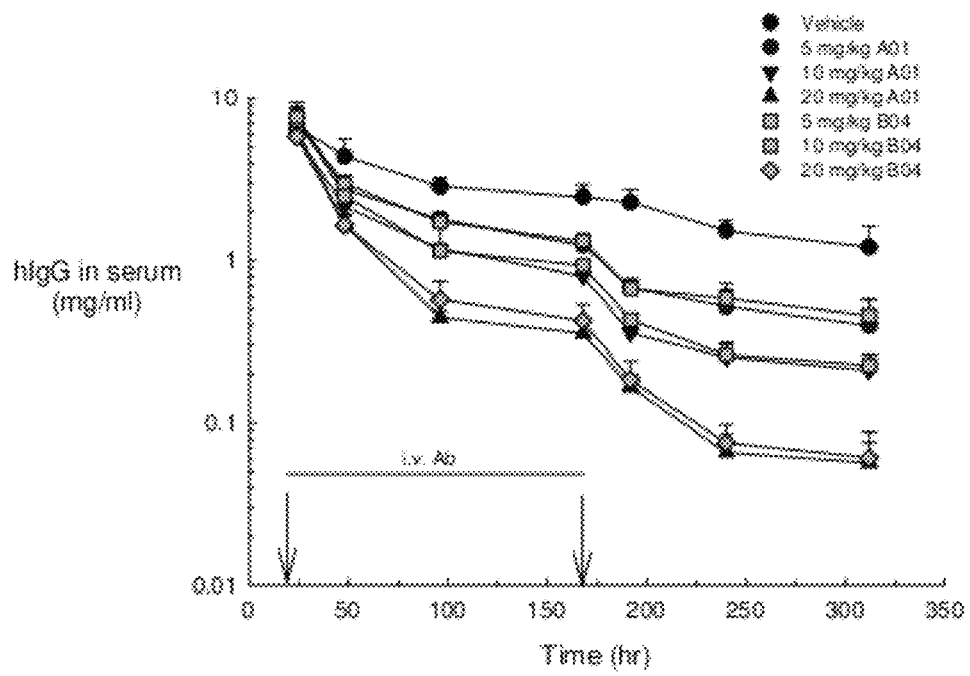
B
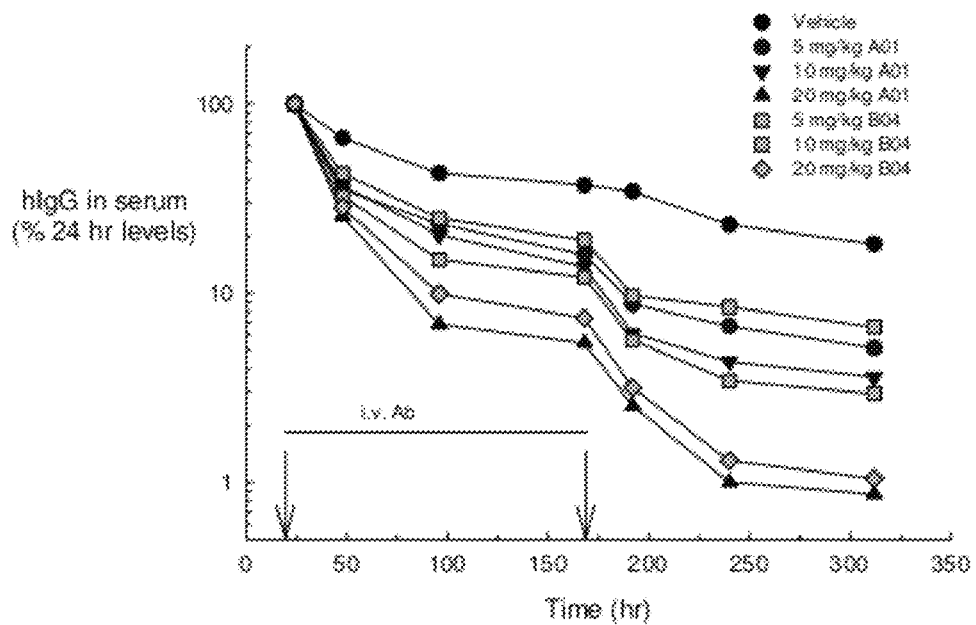

FIGURE 33
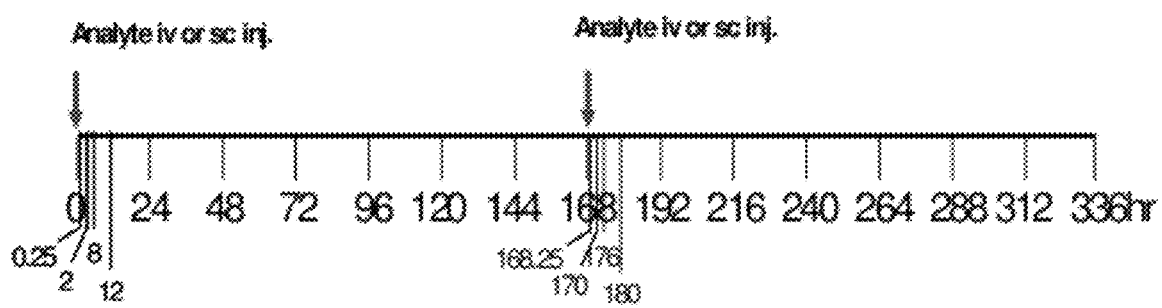
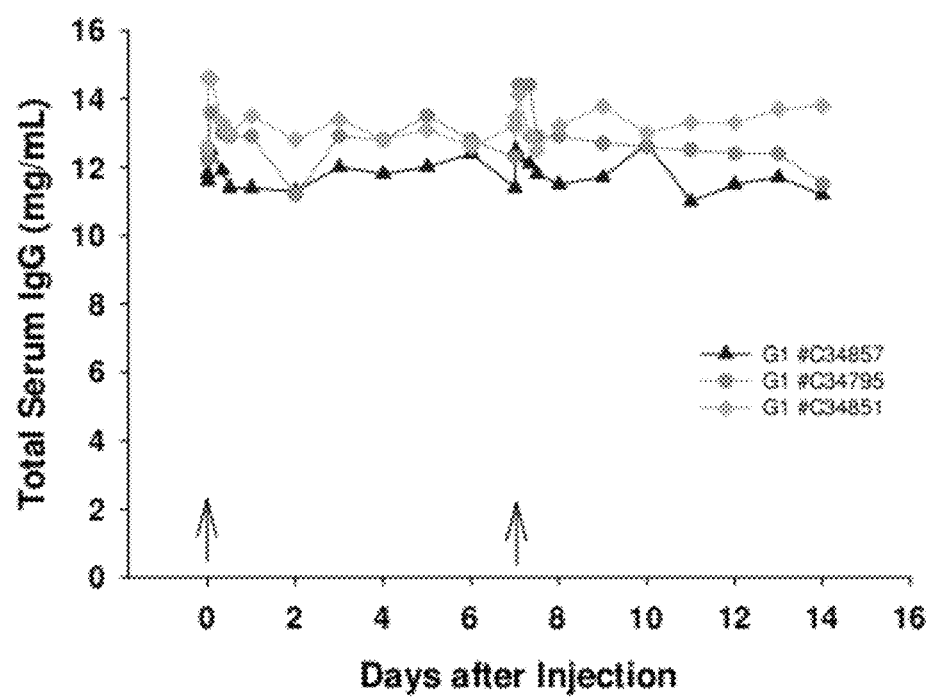

FIGURE 34
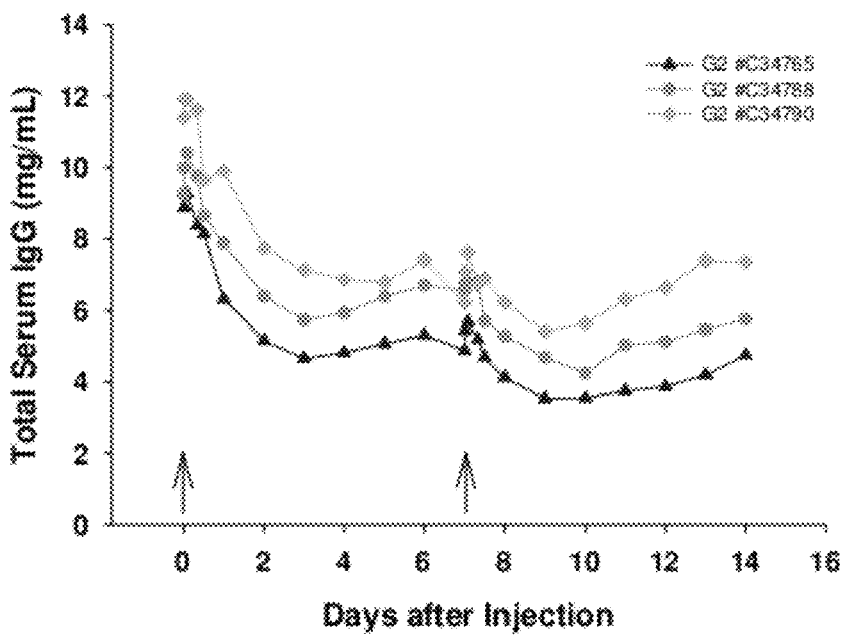
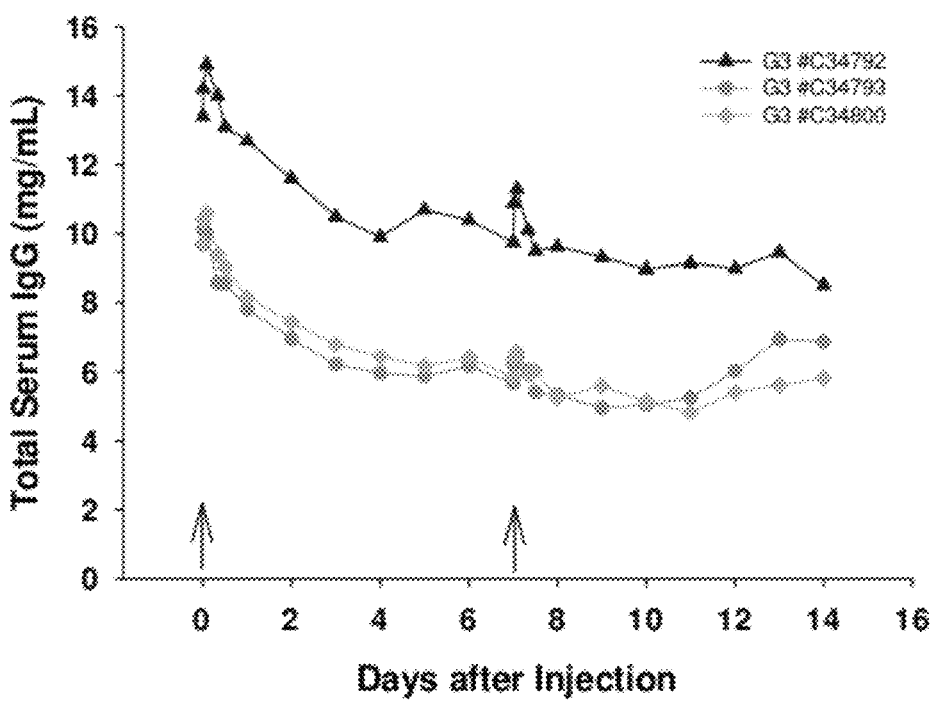

FIGURE 35
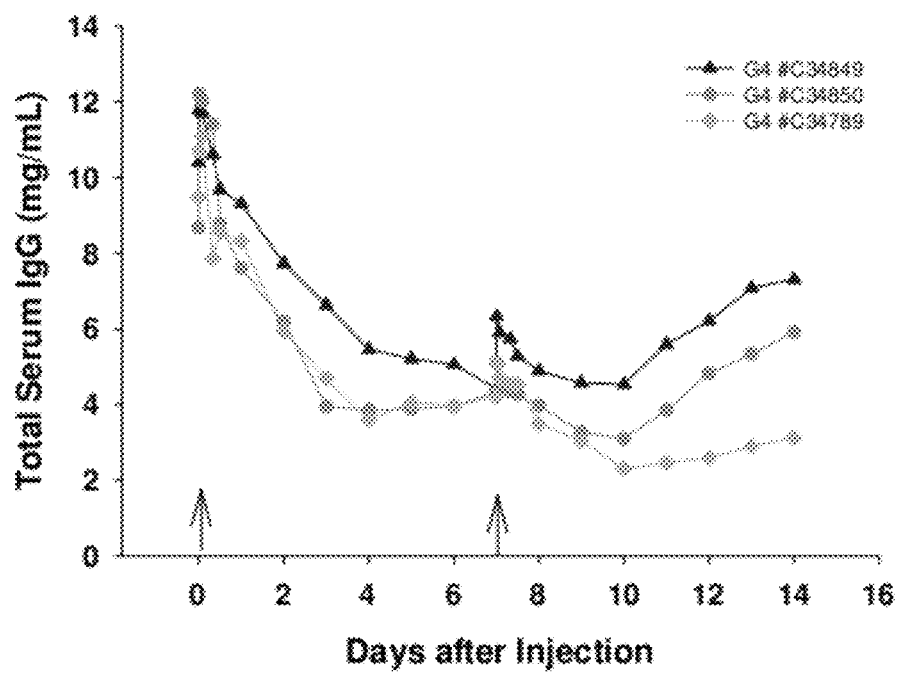
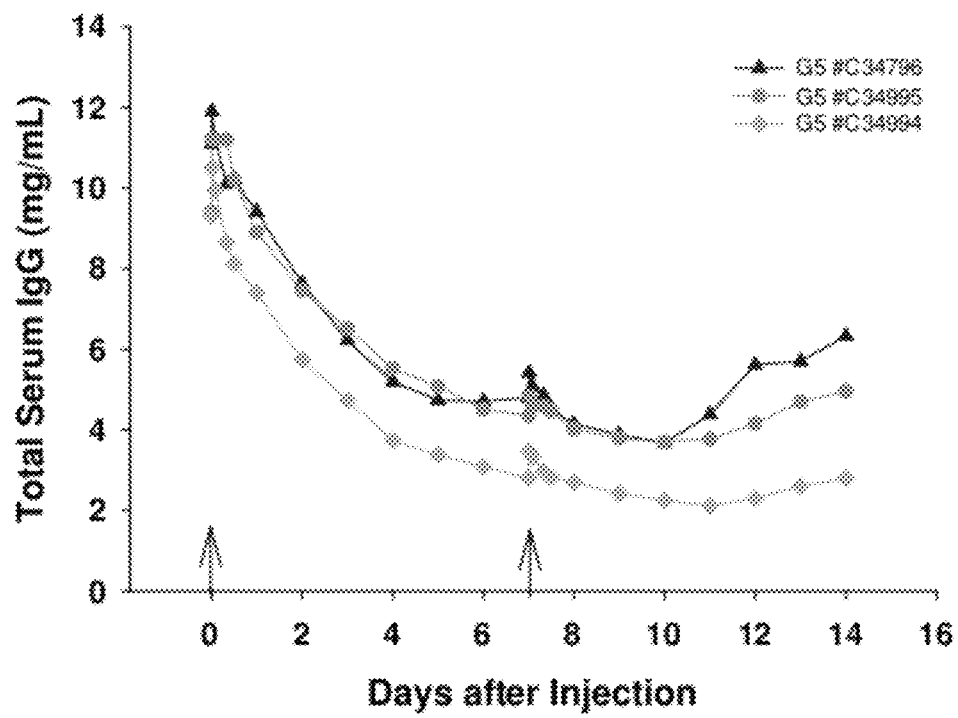

Light V gene = VL2_2b2; J gene = JL1

```
                 FR1-L                    CDR1-L              FR2-L           CDR2-L
GERMLINE:  QSALTQPASVSGSPGQSITISC  [_____]  WYQQHPGKAPKLMIY  [____]
DX-2504:   QSALTQPASVSGSPGQSITISC  [_____]  WYQQHPGKAPKLMIY  [____]

FR3-L                              CDR3-L        FR4-L
GERMLINE:  GVSNRFSGSKSGNTASLTISGLQAEDEADYYC  [_____]  FGTGTKVTVL
DX-2504:   GVSNRFSGSKSGNTASLTISGLQAEDEADYYC  [_____]  FGTGTKVTVL
```

GERMLINE (SEQ ID NO: 181); DX-2504 (SEQ ID NO: 182)

Heavy V gene = VH3-23; J gene = JH3

```
                 FR1-H                          CDR1-H       FR2-H
CDR2-H
GERMLINE:  EVQLLESGGGLVQPGGSLRLSCAASGFTFS  [____]  WVRQAPGKGLEWVS
[_____]
DX-2504:   EVQLLESGGGLVQPGGSLRLSCAASGFTFS  [____]  WVRQAPGKGLEWVS
[_____]

FR3-H                              CDR3-H     FR4-H
GERMLINE:  RFTISRDNSKNTLYLQMNSLRAEDTAVYYCAK  [___]  WGQGTMVTVSS
DX-2504:   RFTISRDNSKNTLYLQMNSLRAEDTAVYYCAR  [___]  WGQGTMVTVSS
```

GERMLINE (SEQ ID NO: 183); DX-2504 (SEQ ID NO: 184)

Top Alignments against Germline sequences

```
DX-2504:  QSALTQPASVSGSPGQSITISC  [_____]  WYQQHPGKAPKLMIY  [____]
VL2_2b2:  QSALTQPASVSGSPGQSITISC  [_____]  WYQQHPGKAPKLMIY  [____]
VL3_3e3:  QSALTQPSVBGSPGQSVTISC   [_____]  WYQQHPGKAPKLMIY  [____]
VL2_2a2:  QSALTQPASVSGSPGQSITISC  [_____]  WYQQHPGKAPKLMIY  [____]
VL2_c:    QSALTQPPSASGSPGQSVTISC  [_____]  WYQQHPGKAPKLMIY  [____]
VL3_d:    QSALTQPPSVSGSPGQSVTISC  [_____]  WYQQPPGTAPKLMIY  [____]

DX-2504:  GVSNRFSGSKSGNTASLTISGLQAEDEADYYC  [_____]  FGTGTKVTVL
VL2_2b2:  GVSNRFSGSKSGNTASLTISGLQAEDEADYYC  [_____]
VL3_3e3:  GVPDRFSGSKSGNTASLTISGLQAEDEADYYC  [_____]
VL2_2a2:  GVSNRFSGSKSGNTASLTISGLQAEDEADYYC  [_____]
VL3_c:    GVPDRFSGSKSGNTASLTVSGLQAEDEADYYC  [_____]
VL3_d:    GVPDRFSGSKSGNTASLTISGLQAEDEADYYC  [_____]
```

DX-2504: SEQ ID NO: 185; VL2_2b2: SEQ ID NO: 186; VL2_2a2: SEQ ID NO: 187;
VL2_2a2: SEQ ID NO: 188; VL2_c: SEQ ID NO: 189; VL2_d: SEQ ID NO: 190;

SEQUENCE LISTING

<160> NUMBER OF SEQ ID NOS: 190

<210> SEQ ID NO 1
<211> LENGTH: 365
<212> TYPE: PRT
<213> ORGANISM: Homo sapiens

<400> SEQUENCE: 1

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
    290                 295                 300

Ile Gly Val Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 2
<211> LENGTH: 366
<212> TYPE: PRT
<213> ORGANISM: Rattus norvegicus

<400> SEQUENCE: 2

```
Met Gly Met Ser Gln Pro Gly Val Leu Leu Ser Leu Leu Val Leu
1               5                   10                  15

Leu Pro Gln Thr Trp Gly Ala Glu Pro Arg Leu Pro Leu Met Tyr His
            20                  25                  30

Leu Ala Ala Val Ser Asp Leu Ser Thr Gly Leu Pro Ser Phe Trp Ala
                35                  40                  45

Thr Gly Trp Leu Gly Ala Gln Gln Tyr Leu Thr Tyr Asn Asn Leu Arg
        50                  55                  60

Gln Glu Ala Asp Pro Cys Gly Ala Trp Ile Trp Glu Asn Gln Val Ser
65                  70                  75                  80

Trp Tyr Trp Glu Lys Glu Thr Thr Asp Leu Lys Ser Lys Glu Gln Leu
                85                  90                  95

Phe Leu Glu Ala Ile Arg Thr Leu Glu Asn Gln Ile Asn Gly Thr Phe
            100                 105                 110

Thr Leu Gln Gly Leu Leu Gly Cys Glu Leu Ala Pro Asp Asn Ser Ser
        115                 120                 125

Leu Pro Thr Ala Val Phe Ala Leu Asn Gly Glu Glu Phe Met Arg Phe
    130                 135                 140

Asn Pro Arg Thr Gly Asn Trp Ser Gly Glu Trp Pro Glu Thr Asp Ile
145                 150                 155                 160

Val Gly Asn Leu Trp Met Lys Gln Pro Glu Ala Ala Arg Lys Glu Ser
                165                 170                 175

Glu Phe Leu Leu Thr Ser Cys Pro Glu Arg Leu Leu Gly His Leu Glu
            180                 185                 190

Arg Gly Arg Gln Asn Leu Glu Trp Lys Glu Pro Pro Ser Met Arg Leu
        195                 200                 205

Lys Ala Arg Pro Gly Asn Ser Gly Ser Ser Val Leu Thr Cys Ala Ala
    210                 215                 220

Phe Ser Phe Tyr Pro Pro Glu Leu Lys Phe Arg Phe Leu Arg Asn Gly
225                 230                 235                 240

Leu Ala Ser Gly Ser Gly Asn Cys Ser Thr Gly Pro Asn Gly Asp Gly
                245                 250                 255

Ser Phe His Ala Trp Ser Leu Leu Glu Val Lys Arg Gly Asp Glu His
            260                 265                 270

His Tyr Gln Cys Gln Val Glu His Glu Gly Leu Ala Gln Pro Leu Thr
        275                 280                 285

Val Asp Leu Asp Ser Pro Ala Arg Ser Ser Val Pro Val Val Gly Ile
    290                 295                 300

Ile Leu Gly Leu Leu Leu Val Val Val Ala Ile Ala Gly Gly Val Leu
305                 310                 315                 320

Leu Trp Asn Arg Met Arg Ser Gly Leu Pro Ala Pro Trp Leu Ser Leu
                325                 330                 335

Ser Gly Asp Asp Ser Gly Asp Leu Leu Pro Gly Gly Asn Leu Pro Pro
            340                 345                 350

Glu Ala Glu Pro Gln Gly Val Asn Ala Phe Pro Ala Thr Ser
        355                 360                 365
```

<210> SEQ ID NO 3

<211> LENGTH: 119
<212> TYPE: PRT
<213> ORGANISM: Homo sapiens

<400> SEQUENCE: 3

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 4
<211> LENGTH: 119
<212> TYPE: PRT
<213> ORGANISM: Rattus norvegicus

<400> SEQUENCE: 4

Met Ala Arg Ser Val Thr Val Ile Phe Leu Val Leu Val Ser Leu Ala
1               5                   10                  15

Val Val Leu Ala Ile Gln Lys Thr Pro Gln Ile Gln Val Tyr Ser Arg
            20                  25                  30

His Pro Pro Glu Asn Gly Lys Pro Asn Phe Leu Asn Cys Tyr Val Ser
        35                  40                  45

Gln Phe His Pro Pro Gln Ile Glu Ile Glu Leu Leu Lys Asn Gly Lys
    50                  55                  60

Lys Ile Pro Asn Ile Glu Met Ser Asp Leu Ser Phe Ser Lys Asp Trp
65                  70                  75                  80

Ser Phe Tyr Ile Leu Ala His Thr Glu Phe Thr Pro Thr Glu Thr Asp
                85                  90                  95

Val Tyr Ala Cys Arg Val Lys His Val Thr Leu Lys Glu Pro Lys Thr
            100                 105                 110

Val Thr Trp Asp Arg Asp Met
        115

<210> SEQ ID NO 5
<211> LENGTH: 1510
<212> TYPE: DNA
<213> ORGANISM: Homo sapiens

<400> SEQUENCE: 5
gttcttcagg tacgaggagg gcattgttgt cagtctggac cgagcccgca gagcccctcc      60
tcggcgtcct ggtcccggcc gtgcccgcgg tgtcccggga ggaaggggcg ggccgggggt     120
cgggaggagt cacgtgcccc ctcccgcccc aggtcgtcct ctcagcatgg gggtcccgcg     180
gcctcagccc tgggcgctgg ggctcctgct ctttctcctt cctggagcc tgggcgcaga     240 aagccacctc tccctcctgt accaccttac cgcggtgtcc tcgcctgccc cggggactcc     300

```
tgccttctgg gtgtccggct ggctgggccc gcagcagtac ctgagctaca atagcctgcg      360
gggcgaggcg gagccctgtg gagcttgggt ctgggaaaac caggtgtcct ggtattggga      420
gaaagagacc acagatctga ggatcaagga gaagctcttt ctggaagctt caaagctttt      480 gggggggaaaa ggtccctaca ctctgcaggg cctgctgggc tgtgaactgg ccctgacaa      540 cacctcggtg cccaccgcca agttcgccct gaacggcgag gagttcatga atttcgacct      600
caagcagggc acctggggtg gggactggcc cgaggccctg ctatcagtc agcggtggca      660 gcagcaggac aaggcggcca acaaggagct caccttcctg ctattctcct gcccgcaccg      720
cctgcgggag cacctggaga ggggccgcgg aaacctggag tggaaggagc cccctccat      780 gcgcctgaag gcccgaccca gcagccctgg cttttccgtg cttacctgca gcgccttctc      840
cttctaccct ccggagctgc aacttcggtt cctgcggaat gggctggccg ctggcaccgg      900
ccagggtgac ttcggcccca acagtgacgg atccttccac gcctcgtcgt cactaacagt      960
caaaagtggc gatgagcacc actactgctg cattgtgcag cacgcggggc tggcgcagcc     1020
cctcagggtg gagctggaat tccagccaa gtcctccgtg ctcgtggtgg aatcgtcat     1080 cggtgtcttg ctactcacgg cagcggctgt aggaggagct ctgttgtgga aaggatgag     1140 gagtgggctg ccagcccctt ggatctccct tcgtggagac gacaccgggg tcctcctgcc     1200
cacccagggg gaggcccagg atgctgattt gaaggatgta aatgtgattc cagccaccgc     1260
ctgaccatcc gccattccga ctgctaaaag cgaatgtagt caggccccctt tcatgctgtg     1320 agacctcctg gaacactggc atctctgagc ctccagaagg ggttctgggc ctagttgtcc     1380
tccctctgga gccccgtcct gtggtctgcc tcagtttccc ctcctaatac atatggctgt     1440
tttccacctc gataatataa cacgagtttg ggcccgaaaa aaaaaaaaa aaaaaaaaa     1500 aaaaaaaaaa                                                                                                    1510

<210> SEQ ID NO 6
<211> LENGTH: 984
<212> TYPE: DNA
<213> ORGANISM: Homo sapiens

<400> SEQUENCE: 6 atggggtcc cgcggcctca gccctgggcg ctggggctcc tgctcttttct ccttcctggg       60 agcctgggcg cagaaagcca cctctccctc ctgtaccacc ttaccgcggt gtcctcgcct      120
gccccgggga ctcctgcctt ctgggtgtcc ggctggctgg gcccgcagca gtacctgagc      180
tacaatagcc tgcggggcga ggcggagccc tgtgagcttg ggtctgggga aaaccaggtg      240
tcctggtatt gggagaaaga gaccacagat ctgaggatca aggagaagct ctttctggaa      300
gctttcaaag ctttgggggg aaaaggtccc tacactctgc agggcctgct gggctgtgaa      360
ctgggccctg acaacacctc ggtgcccacc gccaagttcg ccctgaacgg cgaggagttc      420
atgaatttcg acctcaagca gggcacctgg ggtggggact ggcccgaggc cctggctatc      480
agtcagcggt ggcagcagca ggacaaggcg ccaacaagg agctcacctt cctgctattc      540
tcctgcccgc accgctgcgg ggagcacctg gagggggcc gcgaaacct ggagtggaag      600 gagccccct ccatgcgcct gaaggcccga ccagcagcc ctggctttc cgtgcttacc      660 tgcagcgcct tctccttcta ccctccggag ctgcaacttc ggttcctgcg gaatgggctg      720
gccgctggca ccggccaggg tgacttcggc cccaacagtg acggatcctt ccacgcctcg      780
tcgtcactaa cagtcaaaag tggcgatgag caccactact gctgcattgt gcagcacgcg      840
gggctggcgc agcccctcag ggtggagctg gaatctccag ccaagtcctc ccggccgctc      900
```

```
gacgggctac gagcatcagt aacactacta ggcgcaggcc tactactatc actactacca    960
gcactactac gatttgggcc ataa                                            984

<210> SEQ ID NO 7
<211> LENGTH: 987
<212> TYPE: DNA
<213> ORGANISM: Artificial Sequence
<220> FEATURE:
<223> OTHER INFORMATION: recombinant polynucleotide

<400> SEQUENCE: 7
aatataagtg gaggcgtcgc gctggcgggc attcctgaag ctgacagcat tcgggccgag     60
atgtctcgct ccgtggcctt agctgtgctc gcgctactct ctctttctgg cctggaggct    120
atccagcgta ctccaaagat tcaggtttac tcacgtcatc cagcagagaa tggaaagtca    180
aatttcctga attgctatgt gtctgggttt catccatccg acattgaagt tgacttactg    240
aagaatggag agagaattga aaaagtggag cattcagact tgtctttcag caaggactgg    300
tctttctatc tcttgtacta cactgaattc accccactg aaaaagatga gtatgcctgc    360
cgtgtgaacc atgtgacttt gtcacagccc aagatagtta agtgggatcg agacatgtaa    420
gcagcatcat ggaggtttga agatgccgca tttggattgg atgaattcca aattctgctt    480
gcttgctttt taatattgat atgcttatac acttacactt tatgcacaaa atgtagggtt    540
ataataatgt taacatggac atgatcttct ttataattct actttgagtg ctgtctccat    600
gtttgatgta tctgagcagg ttgctccaca ggtagctcta ggagggctgg caacttagag    660
gtggggagca gagaattctc ttatccaaca tcaacatctt ggtcagattt gaactcttca    720
atctcttgca ctcaaagctt gttaagatag ttaagcgtgc ataagttaac ttccaattta    780
catactctgc ttagaatttg ggggaaaatt tagaaatata attgacagga ttattggaaa    840
tttgttataa tgaatgaaac attttgtcat ataagattca tatttacttc ttatacattt    900
gataaagtaa ggcatggttg tggttaatct ggtttatttt tgttccacaa gttaaataaa    960
tcataaaact tgatgtgtta tctctta                                        987

<210> SEQ ID NO 8
<211> LENGTH: 12
<212> TYPE: PRT
<213> ORGANISM: Artificial Sequence
<220> FEATURE:
<223> OTHER INFORMATION: recombinant peptide

<400> SEQUENCE: 8

Ser Ala Ser Ser Ser Ile Ser Ser Asn Tyr Leu His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: recombinant peptide

<400> SEQUENCE: 9

Arg Thr Ser Asn Leu Ala Ser
1               5

<210> SEQ ID NO 10
<211> LENGTH: 9
<212> TYPE: PRT
<213> ORGANISM: Artificial Sequence
<220> FEATURE:
```

<223> OTHER INFORMATION: recombinant peptide

<400> SEQUENCE: 10

Gln Gln Gly Ser Asn Ile Pro Leu Thr
1               5

<210> SEQ ID NO 11
<211> LENGTH: 5
<212> TYPE: PRT
<213> ORGANISM: Artificial Sequence
<220> FEATURE:
<223> OTHER INFORMATION: recombinant peptide

<400> SEQUENCE: 11

Arg Ser Trp Met Asn
1               5

<210> SEQ ID NO 12
<211> LENGTH: 17
<212> TYPE: PRT
<213> ORGANISM: Artificial Sequence
<220> FEATURE:
<223> OTHER INFORMATION: recombinant peptide

<400> SEQUENCE: 12

Arg Ile His Pro Gly Asp Gly Asp Thr Asn Tyr Asn Gly Lys Phe Lys
1               5                   10                  15

Gly

<210> SEQ ID NO 13
<211> LENGTH: 8
<212> TYPE: PRT
<213> ORGANISM: Artificial Sequence
<220> FEATURE:
<223> OTHER INFORMATION: recombinant peptide

<400> SEQUENCE: 13

Glu Gly Ser Pro Tyr Phe Asp Tyr
1               5

<210> SEQ ID NO 14
<211> LENGTH: 11
<212> TYPE: PRT
<213> ORGANISM: Artificial Sequence
<220> FEATURE:
<223> OTHER INFORMATION: recombinant peptide

<400> SEQUENCE: 14

Lys Ala Ser Gln Asp Ile Asn Asn Tyr Ile Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: recombinant peptide

<400> SEQUENCE: 15

Tyr Thr Ser Thr Leu Gln Pro
1               5

<210> SEQ ID NO 16
<211> LENGTH: 9
<212> TYPE: PRT
<213> ORGANISM: Artificial Sequence
<220> FEATURE:

-continued

```
<223> OTHER INFORMATION: recombinant peptide

<400> SEQUENCE: 16

Leu Gln Tyr Asp Asn Leu Leu Arg Thr
1               5

<210> SEQ ID NO 17
<211> LENGTH: 5
<212> TYPE: PRT
<213> ORGANISM: Artificial Sequence
<220> FEATURE:
<223> OTHER INFORMATION: recombinant peptide

<400> SEQUENCE: 17

Asp Tyr Ala Met His
1               5

<210> SEQ ID NO 18
<211> LENGTH: 17
<212> TYPE: PRT
<213> ORGANISM: Artificial Sequence
<220> FEATURE:
<223> OTHER INFORMATION: recombinant peptide

<400> SEQUENCE: 18

Val Ile Thr Asn Tyr Tyr Gly Asp Ala Ser Tyr Asn Gln Lys Phe Lys
1               5                   10                  15

Gly

<210> SEQ ID NO 19
<211> LENGTH: 12
<212> TYPE: PRT
<213> ORGANISM: Artificial Sequence
<220> FEATURE:
<223> OTHER INFORMATION: recombinant peptide

<400> SEQUENCE: 19

Gly Gly Tyr Asp Gly Tyr Tyr Val Asp Phe Asp Tyr
1               5                   10

<210> SEQ ID NO 20
<211> LENGTH: 214
<212> TYPE: PRT
<213> ORGANISM: Artificial Sequence
<220> FEATURE:
<223> OTHER INFORMATION: recombinant peptide

<400> SEQUENCE: 20

Asp Ile Gln Leu Thr Gln Ser Pro Thr Thr Val Ala Ala Ser Pro Gly
1               5                   10                  15

Glu Lys Ile Thr Ile Thr Cys Ser Ala Ser Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Asn Ile Pro
                85                  90                  95

Leu Thr Phe Gly Ala Gly Thr Lys Leu Glu Leu Lys Arg Ala Asp Ala
            100                 105                 110

Ala Pro Thr Val Ser Ile Phe Pro Pro Ser Ser Glu Gln Leu Thr Ser
```

```
                115                 120                 125
Gly Gly Ala Ser Val Val Cys Phe Leu Asn Asn Phe Tyr Pro Lys Asp
            130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
                195                 200                 205

Ser Phe Asn Lys Asn Glu
            210

<210> SEQ ID NO 21
<211> LENGTH: 214
<212> TYPE: PRT
<213> ORGANISM: Artificial Sequence
<220> FEATURE:
<223> OTHER INFORMATION: recombinant peptide

<400> SEQUENCE: 21

Val Lys Leu Gln Glu Ser Gly Pro Glu Leu Val Lys Pro Gly Ala Ser
1               5                   10                  15

Val Lys Ile Ser Cys Lys Ala Ser Gly Tyr Ala Phe Ser Arg Ser Trp
            20                  25                  30

Met Asn Trp Val Lys Gln Arg Pro Gly Gln Gly Leu Glu Trp Ile Gly
        35                  40                  45

Arg Ile His Pro Gly Asp Gly Asp Thr Asn Tyr Asn Gly Lys Phe Lys
50                  55                  60

Gly Lys Ala Thr Leu Thr Val Ala Lys Ser Ser Ser Thr Ala Tyr Met
65                  70                  75                  80

Gln Leu Ser Ser Leu Thr Ser Val Asp Ser Ala Val Tyr Phe Cys Ala
                85                  90                  95

Asn Glu Gly Ser Pro Tyr Phe Asp Tyr Trp Gly Gln Gly Thr Thr Leu
            100                 105                 110

Thr Val Ser Ser Ala Lys Thr Thr Pro Pro Ser Val Tyr Pro Leu Ala
            115                 120                 125

Pro Gly Ser Ala Ala Gln Thr Asn Ser Met Val Thr Leu Gly Cys Leu
        130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Leu Glu
        210

<210> SEQ ID NO 22
<211> LENGTH: 213
<212> TYPE: PRT
<213> ORGANISM: Artificial Sequence
<220> FEATURE:
<223> OTHER INFORMATION: recombinant peptide
```

<400> SEQUENCE: 22

Asp Ile Gln Leu Thr Gln Ser Pro Ser Ser Leu Ser Ala Ser Leu Gly
1               5                   10                  15

Asp Lys Val Thr Ile Thr Cys Lys Ala Ser Gln Asp Ile Asn Asn Tyr
            20                  25                  30

Ile Ala Trp Tyr Gln His Lys Pro Gly Lys Arg Ser Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Arg
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Lys Asn Glu
    210

<210> SEQ ID NO 23
<211> LENGTH: 218
<212> TYPE: PRT
<213> ORGANISM: Artificial Sequence
<220> FEATURE:
<223> OTHER INFORMATION: recombinant peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 23

Val Xaa Leu Gln Gln Ser Gly Ala Glu Leu Val Arg Pro Gly Val Ser
1               5                   10                  15

Val Lys Ile Ser Cys Lys Gly Ser Gly Tyr Thr Phe Thr Asp Tyr Ala
            20                  25                  30

Met His Trp Val Lys Gln Ser His Ala Lys Ser Leu Glu Trp Ile Gly
        35                  40                  45

Val Ile Thr Asn Tyr Tyr Gly Asp Ala Ser Tyr Asn Gln Lys Phe Lys
    50                  55                  60

Gly Lys Ala Thr Met Thr Val Asp Lys Ser Ser Ser Thr Ala Tyr Met
65                  70                  75                  80

Glu Leu Ala Arg Leu Thr Ser Glu Asp Ser Ala Ile Tyr Tyr Cys Ala
                85                  90                  95

Arg Gly Gly Tyr Asp Gly Tyr Tyr Val Asp Phe Asp Tyr Trp Gly Gln
            100                 105                 110

Gly Thr Thr Leu Thr Val Ser Ser Ala Lys Thr Thr Pro Pro Ser Val

```
                115                 120                 125
Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Leu Glu
    210                 215

<210> SEQ ID NO 24
<211> LENGTH: 20
<212> TYPE: PRT
<213> ORGANISM: Artificial Sequence
<220> FEATURE:
<223> OTHER INFORMATION: recombinant peptide

<400> SEQUENCE: 24

Ser Cys Pro His Arg Leu Arg Glu His Leu Glu Arg Gly Arg Gly Asn
1               5                   10                  15

Leu Glu Trp Lys
            20

<210> SEQ ID NO 25
<211> LENGTH: 20
<212> TYPE: PRT
<213> ORGANISM: Artificial Sequence
<220> FEATURE:
<223> OTHER INFORMATION: recombinant peptide

<400> SEQUENCE: 25

Glu Arg Gly Arg Gly Asn Leu Glu Trp Lys Glu Pro Pro Ser Met Arg
1               5                   10                  15

Leu Lys Ala Arg
            20

<210> SEQ ID NO 26
<211> LENGTH: 20
<212> TYPE: PRT
<213> ORGANISM: Artificial Sequence
<220> FEATURE:
<223> OTHER INFORMATION: recombinant peptide

<400> SEQUENCE: 26

Cys Ser Ala Phe Ser Phe Tyr Pro Pro Glu Leu Gln Leu Arg Phe Leu
1               5                   10                  15

Arg Asn Gly Leu
            20

<210> SEQ ID NO 27
<211> LENGTH: 20
<212> TYPE: PRT
<213> ORGANISM: Artificial Sequence
<220> FEATURE:
<223> OTHER INFORMATION: recombinant peptide

<400> SEQUENCE: 27

Ala Pro Gly Thr Pro Ala Phe Trp Val Ser Gly Trp Leu Gly Pro Gln
1               5                   10                  15
```

Gln Tyr Leu Ser
        20

<210> SEQ ID NO 28
<211> LENGTH: 13
<212> TYPE: PRT
<213> ORGANISM: Artificial Sequence
<220> FEATURE:
<223> OTHER INFORMATION: recombinant peptide

<400> SEQUENCE: 28

Ser Gly Ser Ser Ser Asn Ile Gly Ser Asn Thr Val Ser
1               5                   10

<210> SEQ ID NO 29
<211> LENGTH: 7
<212> TYPE: PRT
<213> ORGANISM: Artificial Sequence
<220> FEATURE:
<223> OTHER INFORMATION: recombinant peptide

<400> SEQUENCE: 29

Ser Asp Asn Gln Arg Pro Ser
1               5

<210> SEQ ID NO 30
<211> LENGTH: 11
<212> TYPE: PRT
<213> ORGANISM: Artificial Sequence
<220> FEATURE:
<223> OTHER INFORMATION: recombinant peptide

<400> SEQUENCE: 30

Ala Ala Trp Asp Asp Ser Leu Lys Gly Trp Val
1               5                   10

<210> SEQ ID NO 31
<211> LENGTH: 5
<212> TYPE: PRT
<213> ORGANISM: Artificial Sequence
<220> FEATURE:
<223> OTHER INFORMATION: recombinant peptide

<400> SEQUENCE: 31

Asp Tyr Thr Met Ser
1               5

<210> SEQ ID NO 32
<211> LENGTH: 17
<212> TYPE: PRT
<213> ORGANISM: Artificial Sequence
<220> FEATURE:
<223> OTHER INFORMATION: recombinant peptide

<400> SEQUENCE: 32

Ser Ile Trp Ser Ser Gly Gly Ala Thr Val Tyr Ala Asp Ser Val Lys
1               5                   10                  15

Gly

<210> SEQ ID NO 33
<211> LENGTH: 11
<212> TYPE: PRT
<213> ORGANISM: Artificial Sequence
<220> FEATURE:
<223> OTHER INFORMATION: recombinant peptide

<400> SEQUENCE: 33

```
Asp Ile Arg Gly Ser Arg Asn Trp Phe Asp Pro
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: recombinant peptide

<400> SEQUENCE: 34

```
Thr Gly Thr Gly Ser Asp Val Gly Ser Tyr Asn Leu Val Ser
1               5                   10
```

<210> SEQ ID NO 35
<211> LENGTH: 7
<212> TYPE: PRT
<213> ORGANISM: Artificial Sequence
<220> FEATURE:
<223> OTHER INFORMATION: recombinant peptide

<400> SEQUENCE: 35

```
Gly Asp Ser Gln Arg Pro Ser
1               5
```

<210> SEQ ID NO 36
<211> LENGTH: 10
<212> TYPE: PRT
<213> ORGANISM: Artificial Sequence
<220> FEATURE:
<223> OTHER INFORMATION: recombinant peptide

<400> SEQUENCE: 36

```
Cys Ser Tyr Ala Gly Ser Gly Ile Tyr Val
1               5                   10
```

<210> SEQ ID NO 37
<211> LENGTH: 5
<212> TYPE: PRT
<213> ORGANISM: Artificial Sequence
<220> FEATURE:
<223> OTHER INFORMATION: recombinant peptide

<400> SEQUENCE: 37

```
Glu Tyr Ala Met Gly
1               5
```

<210> SEQ ID NO 38
<211> LENGTH: 17
<212> TYPE: PRT
<213> ORGANISM: Artificial Sequence
<220> FEATURE:
<223> OTHER INFORMATION: recombinant peptide

<400> SEQUENCE: 38

```
Ser Ile Gly Ser Ser Gly Gly Gln Thr Lys Tyr Ala Asp Ser Val Lys
1               5                   10                  15

Gly
```

<210> SEQ ID NO 39
<211> LENGTH: 7
<212> TYPE: PRT
<213> ORGANISM: Artificial Sequence
<220> FEATURE:
<223> OTHER INFORMATION: recombinant peptide

<400> SEQUENCE: 39

Leu Ser Thr Gly Glu Leu Tyr
1               5

<210> SEQ ID NO 40
<211> LENGTH: 16
<212> TYPE: PRT
<213> ORGANISM: Artificial Sequence
<220> FEATURE:
<223> OTHER INFORMATION: recombinant peptide

<400> SEQUENCE: 40

Arg Ser Ser Gln Ser Leu Leu His Ser Asn Gly Tyr Asn Tyr Leu Asp
1               5                   10                  15

<210> SEQ ID NO 41
<211> LENGTH: 7
<212> TYPE: PRT
<213> ORGANISM: Artificial Sequence
<220> FEATURE:
<223> OTHER INFORMATION: recombinant peptide

<400> SEQUENCE: 41

Leu Val Ser Asn Arg Ala Ser
1               5

<210> SEQ ID NO 42
<211> LENGTH: 9
<212> TYPE: PRT
<213> ORGANISM: Artificial Sequence
<220> FEATURE:
<223> OTHER INFORMATION: recombinant peptide

<400> SEQUENCE: 42

Met Gln Ala Gln Gln Thr Pro Ile Thr
1               5

<210> SEQ ID NO 43
<211> LENGTH: 5
<212> TYPE: PRT
<213> ORGANISM: Artificial Sequence
<220> FEATURE:
<223> OTHER INFORMATION: recombinant peptide

<400> SEQUENCE: 43

Ile Tyr Ser Met Thr
1               5

<210> SEQ ID NO 44
<211> LENGTH: 17
<212> TYPE: PRT
<213> ORGANISM: Artificial Sequence
<220> FEATURE:
<223> OTHER INFORMATION: recombinant peptide

<400> SEQUENCE: 44

Ser Ile Val Pro Ser Gly Gly Glu Thr Ser Tyr Ala Asp Ser Val Lys
1               5                   10                  15

Gly

<210> SEQ ID NO 45
<211> LENGTH: 9
<212> TYPE: PRT
<213> ORGANISM: Artificial Sequence
<220> FEATURE:
<223> OTHER INFORMATION: recombinant peptide

<400> SEQUENCE: 45

Gly His Ser Gly Val Gly Met Asp Val
1               5

<210> SEQ ID NO 46
<211> LENGTH: 16
<212> TYPE: PRT
<213> ORGANISM: Artificial Sequence
<220> FEATURE:
<223> OTHER INFORMATION: recombinant peptide

<400> SEQUENCE: 46

Arg Ser Ser Gln Ser Leu Leu His Gly Asn Gly His Thr Tyr Leu Asp
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: recombinant peptide

<400> SEQUENCE: 47

Leu Val Ser Asn Arg Ala Ser
1               5

<210> SEQ ID NO 48
<211> LENGTH: 9
<212> TYPE: PRT
<213> ORGANISM: Artificial Sequence
<220> FEATURE:
<223> OTHER INFORMATION: recombinant peptide

<400> SEQUENCE: 48

Met Gln Gly Leu Gln Thr Pro Arg Thr
1               5

<210> SEQ ID NO 49
<211> LENGTH: 5
<212> TYPE: PRT
<213> ORGANISM: Artificial Sequence
<220> FEATURE:
<223> OTHER INFORMATION: recombinant peptide

<400> SEQUENCE: 49

Phe Tyr Ser Met Thr
1               5

<210> SEQ ID NO 50
<211> LENGTH: 17
<212> TYPE: PRT
<213> ORGANISM: Artificial Sequence
<220> FEATURE:
<223> OTHER INFORMATION: recombinant peptide

<400> SEQUENCE: 50

Gly Ile Arg Ser Ser Gly Gly Ser Thr Arg Tyr Ala Asp Ser Val Lys
1               5                   10                  15
Gly

<210> SEQ ID NO 51
<211> LENGTH: 9
<212> TYPE: PRT
<213> ORGANISM: Artificial Sequence
<220> FEATURE:
<223> OTHER INFORMATION: recombinant peptide

<400> SEQUENCE: 51

```
Gly Trp Gly Leu Asp Ala Phe Asp Val
1               5
```

<210> SEQ ID NO 52
<211> LENGTH: 16
<212> TYPE: PRT
<213> ORGANISM: Artificial Sequence
<220> FEATURE:
<223> OTHER INFORMATION: recombinant peptide

<400> SEQUENCE: 52

```
Arg Ser Ser Leu Ser Leu Leu His Ser Asn Gly Tyr Ile Tyr Leu Asp
1               5                   10                  15
```

<210> SEQ ID NO 53
<211> LENGTH: 7
<212> TYPE: PRT
<213> ORGANISM: Artificial Sequence
<220> FEATURE:
<223> OTHER INFORMATION: recombinant peptide

<400> SEQUENCE: 53

```
Leu Gly Ser His Arg Ala Ser
1               5
```

<210> SEQ ID NO 54
<211> LENGTH: 9
<212> TYPE: PRT
<213> ORGANISM: Artificial Sequence
<220> FEATURE:
<223> OTHER INFORMATION: recombinant peptide

<400> SEQUENCE: 54

```
Met Gln Pro Leu Gln Thr Pro Tyr Thr
1               5
```

<210> SEQ ID NO 55
<211> LENGTH: 5
<212> TYPE: PRT
<213> ORGANISM: Artificial Sequence
<220> FEATURE:
<223> OTHER INFORMATION: recombinant peptide

<400> SEQUENCE: 55

```
Tyr Tyr His Met Asn
1               5
```

<210> SEQ ID NO 56
<211> LENGTH: 17
<212> TYPE: PRT
<213> ORGANISM: Artificial Sequence
<220> FEATURE:
<223> OTHER INFORMATION: recombinant peptide

<400> SEQUENCE: 56

```
Val Ile Ser Pro Ser Gly Gly Val Thr Met Tyr Ala Asp Ser Val Lys
1               5                   10                  15
Gly
```

<210> SEQ ID NO 57
<211> LENGTH: 6
<212> TYPE: PRT
<213> ORGANISM: Artificial Sequence
<220> FEATURE:
<223> OTHER INFORMATION: recombinant peptide

<400> SEQUENCE: 57

```
Gly Lys Ala Phe Asp Ile
1               5
```

<210> SEQ ID NO 58
<211> LENGTH: 11
<212> TYPE: PRT
<213> ORGANISM: Artificial Sequence
<220> FEATURE:
<223> OTHER INFORMATION: recombinant peptide

<400> SEQUENCE: 58

```
Ser Gly Asp Lys Leu Gly Asp Lys Tyr Val Ser
1               5                   10
```

<210> SEQ ID NO 59
<211> LENGTH: 7
<212> TYPE: PRT
<213> ORGANISM: Artificial Sequence
<220> FEATURE:
<223> OTHER INFORMATION: recombinant peptide

<400> SEQUENCE: 59

```
Gln Asp Asn Arg Arg Pro Ser
1               5
```

<210> SEQ ID NO 60
<211> LENGTH: 11
<212> TYPE: PRT
<213> ORGANISM: Artificial Sequence
<220> FEATURE:
<223> OTHER INFORMATION: recombinant peptide

<400> SEQUENCE: 60

```
Gln Ala Trp Leu Ser Asn Thr Ala Ser Val Ala
1               5                   10
```

<210> SEQ ID NO 61
<211> LENGTH: 5
<212> TYPE: PRT
<213> ORGANISM: Artificial Sequence
<220> FEATURE:
<223> OTHER INFORMATION: recombinant peptide

<400> SEQUENCE: 61

```
Phe Tyr Gly Met His
1               5
```

<210> SEQ ID NO 62
<211> LENGTH: 17
<212> TYPE: PRT
<213> ORGANISM: Artificial Sequence
<220> FEATURE:
<223> OTHER INFORMATION: recombinant peptide

<400> SEQUENCE: 62

```
Gly Ile Tyr Ser Ser Gly Gly Ile Thr Gly Tyr Ala Asp Ser Val Lys
1               5                   10                  15

Gly
```

<210> SEQ ID NO 63
<211> LENGTH: 7
<212> TYPE: PRT
<213> ORGANISM: Artificial Sequence
<220> FEATURE:
<223> OTHER INFORMATION: recombinant peptide

<400> SEQUENCE: 63

```
Gly Leu Arg Thr Phe Asp Tyr
1               5
```

<210> SEQ ID NO 64
<211> LENGTH: 11
<212> TYPE: PRT
<213> ORGANISM: Artificial Sequence
<220> FEATURE:
<223> OTHER INFORMATION: recombinant peptide

<400> SEQUENCE: 64

```
Arg Ala Ser Gln Pro Val Gly Ser Tyr Leu Ala
1               5                   10
```

<210> SEQ ID NO 65
<211> LENGTH: 7
<212> TYPE: PRT
<213> ORGANISM: Artificial Sequence
<220> FEATURE:
<223> OTHER INFORMATION: recombinant peptide

<400> SEQUENCE: 65

```
Gly Ala Ser Asn Arg Ala Thr
1               5
```

<210> SEQ ID NO 66
<211> LENGTH: 10
<212> TYPE: PRT
<213> ORGANISM: Artificial Sequence
<220> FEATURE:
<223> OTHER INFORMATION: recombinant peptide

<400> SEQUENCE: 66

```
Gln His Tyr Gly His Ser Pro Pro Tyr Thr
1               5                   10
```

<210> SEQ ID NO 67
<211> LENGTH: 5
<212> TYPE: PRT
<213> ORGANISM: Artificial Sequence
<220> FEATURE:
<223> OTHER INFORMATION: recombinant peptide

<400> SEQUENCE: 67

```
Ser Tyr Ala Met Tyr
1               5
```

<210> SEQ ID NO 68
<211> LENGTH: 17
<212> TYPE: PRT
<213> ORGANISM: Artificial Sequence
<220> FEATURE:
<223> OTHER INFORMATION: recombinant peptide

<400> SEQUENCE: 68

```
Arg Ile Val Pro Ser Gly Gly Thr Met Tyr Ala Asp Ser Val Gln
1               5                   10                  15

Gly
```

<210> SEQ ID NO 69
<211> LENGTH: 4
<212> TYPE: PRT
<213> ORGANISM: Artificial Sequence
<220> FEATURE:
<223> OTHER INFORMATION: recombinant peptide

<400> SEQUENCE: 69

```
Gly Met Asp Val
1

<210> SEQ ID NO 70
<211> LENGTH: 11
<212> TYPE: PRT
<213> ORGANISM: Artificial Sequence
<220> FEATURE:
<223> OTHER INFORMATION: recombinant peptide

<400> SEQUENCE: 70

Arg Ala Ser Gln Ser Val Ser Ser Tyr Leu Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: recombinant peptide

<400> SEQUENCE: 71

Asp Ala Ser Asn Arg Ala Thr
1               5

<210> SEQ ID NO 72
<211> LENGTH: 9
<212> TYPE: PRT
<213> ORGANISM: Artificial Sequence
<220> FEATURE:
<223> OTHER INFORMATION: recombinant peptide

<400> SEQUENCE: 72

Gln Gln Arg Ser Asn Trp Pro Leu Thr
1               5

<210> SEQ ID NO 73
<211> LENGTH: 5
<212> TYPE: PRT
<213> ORGANISM: Artificial Sequence
<220> FEATURE:
<223> OTHER INFORMATION: recombinant peptide

<400> SEQUENCE: 73

Asn Tyr Asn Met Ser
1               5

<210> SEQ ID NO 74
<211> LENGTH: 17
<212> TYPE: PRT
<213> ORGANISM: Artificial Sequence
<220> FEATURE:
<223> OTHER INFORMATION: recombinant peptide

<400> SEQUENCE: 74

Tyr Ile Ser Pro Ser Gly Gly Ser Thr Trp Tyr Ala Asp Ser Val Lys
1               5                   10                  15

Gly

<210> SEQ ID NO 75
<211> LENGTH: 7
<212> TYPE: PRT
<213> ORGANISM: Artificial Sequence
<220> FEATURE:
<223> OTHER INFORMATION: recombinant peptide

<400> SEQUENCE: 75
```

Tyr His Tyr Gly Met Asp Val
1               5

<210> SEQ ID NO 76
<211> LENGTH: 11
<212> TYPE: PRT
<213> ORGANISM: Artificial Sequence
<220> FEATURE:
<223> OTHER INFORMATION: recombinant peptide

<400> SEQUENCE: 76

Arg Ala Ser Gln Ser Ile Ser Asn His Leu Val
1               5                   10

<210> SEQ ID NO 77
<211> LENGTH: 7
<212> TYPE: PRT
<213> ORGANISM: Artificial Sequence
<220> FEATURE:
<223> OTHER INFORMATION: recombinant peptide

<400> SEQUENCE: 77

Asp Ala Ser Asn Arg Ala Thr
1               5

<210> SEQ ID NO 78
<211> LENGTH: 9
<212> TYPE: PRT
<213> ORGANISM: Artificial Sequence
<220> FEATURE:
<223> OTHER INFORMATION: recombinant peptide

<400> SEQUENCE: 78

Gln Gln Arg Ser Asn Trp Pro Pro Thr
1               5

<210> SEQ ID NO 79
<211> LENGTH: 5
<212> TYPE: PRT
<213> ORGANISM: Artificial Sequence
<220> FEATURE:
<223> OTHER INFORMATION: recombinant peptide

<400> SEQUENCE: 79

Tyr Tyr Gly Met Thr
1               5

<210> SEQ ID NO 80
<211> LENGTH: 17
<212> TYPE: PRT
<213> ORGANISM: Artificial Sequence
<220> FEATURE:
<223> OTHER INFORMATION: recombinant peptide

<400> SEQUENCE: 80

Ser Ile Ser Pro Ser Gly Gly His Thr Ser Tyr Ala Asp Ser Val Lys
1               5                   10                  15

Gly

<210> SEQ ID NO 81
<211> LENGTH: 9
<212> TYPE: PRT
<213> ORGANISM: Artificial Sequence
<220> FEATURE:
<223> OTHER INFORMATION: recombinant peptide

<400> SEQUENCE: 81

Gly Pro Glu Tyr Phe Phe Gly Val Tyr
1               5

<210> SEQ ID NO 82
<211> LENGTH: 11
<212> TYPE: PRT
<213> ORGANISM: Artificial Sequence
<220> FEATURE:
<223> OTHER INFORMATION: recombinant peptide

<400> SEQUENCE: 82

Arg Ala Ser Gln Ser Val Gly Ser Tyr Leu Asn
1               5                   10

<210> SEQ ID NO 83
<211> LENGTH: 7
<212> TYPE: PRT
<213> ORGANISM: Artificial Sequence
<220> FEATURE:
<223> OTHER INFORMATION: recombinant peptide

<400> SEQUENCE: 83

Ala Ala Tyr Ile Leu Gln Ser
1               5

<210> SEQ ID NO 84
<211> LENGTH: 9
<212> TYPE: PRT
<213> ORGANISM: Artificial Sequence
<220> FEATURE:
<223> OTHER INFORMATION: recombinant peptide

<400> SEQUENCE: 84

Gln Gln Ser Tyr Ser Asn Arg Ile Thr
1               5

<210> SEQ ID NO 85
<211> LENGTH: 5
<212> TYPE: PRT
<213> ORGANISM: Artificial Sequence
<220> FEATURE:
<223> OTHER INFORMATION: recombinant peptide

<400> SEQUENCE: 85

Ala Tyr Asn Met Ile
1               5

<210> SEQ ID NO 86
<211> LENGTH: 17
<212> TYPE: PRT
<213> ORGANISM: Artificial Sequence
<220> FEATURE:
<223> OTHER INFORMATION: recombinant peptide

<400> SEQUENCE: 86

Ser Ile Gly Pro Ser Gly Gly Lys Thr Val Tyr Ala Asp Ser Val Lys
1               5                   10                  15

Gly

<210> SEQ ID NO 87
<211> LENGTH: 11
<212> TYPE: PRT
<213> ORGANISM: Artificial Sequence
<220> FEATURE:
<223> OTHER INFORMATION: recombinant peptide

<400> SEQUENCE: 87

```
Val Arg Ser Gly Phe Trp Ser Gly His Asp Tyr
1               5                   10

<210> SEQ ID NO 88
<211> LENGTH: 12
<212> TYPE: PRT
<213> ORGANISM: Artificial Sequence
<220> FEATURE:
<223> OTHER INFORMATION: recombinant peptide

<400> SEQUENCE: 88

Arg Ala Ser Gln Ser Val Ser Ser Ser Tyr Leu Ala
1               5                   10

<210> SEQ ID NO 89
<211> LENGTH: 7
<212> TYPE: PRT
<213> ORGANISM: Artificial Sequence
<220> FEATURE:
<223> OTHER INFORMATION: recombinant peptide

<400> SEQUENCE: 89

Gly Ala Ser Ser Arg Ala Thr
1               5

<210> SEQ ID NO 90
<211> LENGTH: 9
<212> TYPE: PRT
<213> ORGANISM: Artificial Sequence
<220> FEATURE:
<223> OTHER INFORMATION: recombinant peptide

<400> SEQUENCE: 90

Gln Gln Tyr Gly Ser Ser Pro Arg Thr
1               5

<210> SEQ ID NO 91
<211> LENGTH: 5
<212> TYPE: PRT
<213> ORGANISM: Artificial Sequence
<220> FEATURE:
<223> OTHER INFORMATION: recombinant peptide

<400> SEQUENCE: 91

His Tyr Gly Met Ser
1               5

<210> SEQ ID NO 92
<211> LENGTH: 17
<212> TYPE: PRT
<213> ORGANISM: Artificial Sequence
<220> FEATURE:
<223> OTHER INFORMATION: recombinant peptide

<400> SEQUENCE: 92

Tyr Ile Arg Pro Ser Gly Gly Lys Thr Ile Tyr Ala Asp Ser Val Lys
1               5                   10                  15
Gly

<210> SEQ ID NO 93
<211> LENGTH: 13
<212> TYPE: PRT
<213> ORGANISM: Artificial Sequence
<220> FEATURE:
<223> OTHER INFORMATION: recombinant peptide

<400> SEQUENCE: 93
```

```
Asp Ser Trp Gly Ser Phe Pro Asn Asp Ala Phe Asp Ile
1               5                   10
```

<210> SEQ ID NO 94
<211> LENGTH: 339
<212> TYPE: DNA
<213> ORGANISM: Artificial Sequence
<220> FEATURE:
<223> OTHER INFORMATION: recombinant polynucleotide

<400> SEQUENCE: 94

```
caagacatcc agatgaccca gtctccagac tccctgcccg tcaccctgg agagccggcc      60 tccatctcct gcaggtctag tcagagcctc ctgcatagta atggatacaa ctatttggat    120
tggtacctgc agaggccagg gcagtctccg cagctcctga tctatttggt ttctaatcgg    180
gcctccgggg tccctgacag gttcagtggc agtgggtcag gcacagattt tacactgaaa    240
atcagcagag tggaggctga agatgctgga ttttattact gcatgcaagc tcaacaaact    300
ccgatcacct tcggccaagg gacacgactg gagattaaa                            339
```

<210> SEQ ID NO 95
<211> LENGTH: 339
<212> TYPE: DNA
<213> ORGANISM: Artificial Sequence
<220> FEATURE:
<223> OTHER INFORMATION: recombinant polynucleotide

<400> SEQUENCE: 95

```
caagacatcc agatgaccta gtctccactc tccctgcccg tcaccctgg agccggcc        60 tccatgtcct gcaggtctag tctgagcctc ctgcatagta atggatacat ctatttggat    120
tggtacctgc agaggccagg acagtctcca cagctcctga tgtatttggg ttctcatcgg    180
gcctccgggg tccctgacag gttcagtggc agtgggtcag gcacagattt tacactgaac    240
atcagcagag tggaggcgga ggatgttggg gtttattact gcatgcaacc tctacaaact    300
ccgtacactt ttggccaggg gaccaagctg gagatcaaa                            339
```

<210> SEQ ID NO 96
<211> LENGTH: 324
<212> TYPE: DNA
<213> ORGANISM: Artificial Sequence
<220> FEATURE:
<223> OTHER INFORMATION: recombinant polynucleotide

<400> SEQUENCE: 96

```
caagacatcc agatgaccca gtctccatcc tccctgtctg catctgtagg agacagagtc     60
accatcactt gccgggcaag tcagagcgtt ggcagttatt taaattggta tcagcagaaa    120
ccaggcgaag cccctaaggc cctgatctat gctgcataca ttttgcaaag tggggtccca    180
tcgaggttca gtggcagcgg ctctgggaca gatttcactc tcaccatcaa cagtctacaa    240
cctgaagatt ttgcaactta ttactgtcaa cagagttaca gtaatagaat cactttcggc    300
cctgggacca gagtggatgt caaa                                             324
```

<210> SEQ ID NO 97
<211> LENGTH: 339
<212> TYPE: DNA
<213> ORGANISM: Artificial Sequence
<220> FEATURE:
<223> OTHER INFORMATION: recombinant polynucleotide

<400> SEQUENCE: 97

```
caagacatcc agatgaccca gtctccactc tccctgcccg tcacccctgg agagccggcc      60
tccatctcct gcaggtctag tcagagcctc ctgcacggaa atggacacac ctatttggat     120
tggtatctgc agaagccagg gcagtctcca cagctcctga tctatttggt ttctaatcgg     180
gcctccgggg tccctgacag gttcagtggc agtggatcag gcacagattt tacactgaaa     240
atcagcagag tggaggctga agatgttggg gtttattact gcatgcaagg tctacaaact     300
ccgaggacgt tcggccaggg gaccaaggtg gaaatcaaa                            339

<210> SEQ ID NO 98
<211> LENGTH: 324
<212> TYPE: DNA
<213> ORGANISM: Artificial Sequence
<220> FEATURE:
<223> OTHER INFORMATION: recombinant polynucleotide

<400> SEQUENCE: 98
caagacatcc agatgaccca gtctccagcc accctgtctt tgtctccagg ggaaagagcc      60
accctctcct gcagggccag tcagagtatt agcaaccact tagtctggtt ccaacagaaa     120
cctggccagg ctcccaggct cctcatctat gatgcatcca cagggccac tggcatccca      180 gccaggttca gtggcagtgg gtctgggaca gacttcactc tcaccatcag cagcctagag     240
cctgaagatt ttgcagttta ttactgtcag cagcgtagca actggcctcc caccttcggc     300
caagggacac gactggagat taaa                                            324

<210> SEQ ID NO 99
<211> LENGTH: 327
<212> TYPE: DNA
<213> ORGANISM: Artificial Sequence
<220> FEATURE:
<223> OTHER INFORMATION: recombinant polynucleotide

<400> SEQUENCE: 99
caagacatcc agatgaccca gtctccagcc accctgtctt tgtctccagg ggaaacagcc      60
accctctcct gccgggccag tcagcctgtt ggcagctact tagcctggta ccaacagaaa     120
cctggccagg ctcccaggct cctcatctat ggtgcatcca tagggccac tggcatccca      180 gccaggttca gtggcagtgg gtctgggaca gacttcactc tcgccatcag cagcctggag     240
cctgaagatt ttggagtgta ttactgtcag cactatggtc actcacctcc gtacactttt     300
ggccagggga ccaagctgga gatcaaa                                         327

<210> SEQ ID NO 100
<211> LENGTH: 327
<212> TYPE: DNA
<213> ORGANISM: Artificial Sequence
<220> FEATURE:
<223> OTHER INFORMATION: recombinant polynucleotide

<400> SEQUENCE: 100
caagacatcc agatgaccca gtctccaggc accctgtctt tgtctccagg ggaaagagcc      60
accctctcct gcagggccag tcagagtgtt agcagcagct acttagcctg gtaccagcag     120
aaacctggcc aggctcccag gctcctcatc tatggtgcat ccagcagggc cactggcatc     180
ccagacaggt tcagtggcag tgggtctggg acagacttca ctctcaccat cagcagactg     240
gagcctgaag attttgcagt gtattactgt cagcagtatg gtagctcacc tcggacgttc     300
ggccaaggga ccaaggtgga aatcaaa                                         327

<210> SEQ ID NO 101
```

```
<211> LENGTH: 330
<212> TYPE: DNA
<213> ORGANISM: Artificial Sequence
<220> FEATURE:
<223> OTHER INFORMATION: recombinant polynucleotide

<400> SEQUENCE: 101
cagagcgctt tgactcagcc accctcagcg tctgagaccc ccgggcagag agtcaccatc    60
tcttgttctg gaagcagctc caacatcgga agtaatactg taagctggta ccagcagctc   120
ccaggaacgg cccccaaact cctcatctat agtgataatc agcggccctc aggggtccct   180
gaccgattcg ctggctccaa gtctggcacc tctgcctccc tggccatcag tgggctccag   240
tctgaggatg aggctgaata tcactgtgca gcatgggatg acagcctgaa gggttgggtg   300
ttcggcggag ggacaaagct gaccgtccta                                    330

<210> SEQ ID NO 102
<211> LENGTH: 324
<212> TYPE: DNA
<213> ORGANISM: Artificial Sequence
<220> FEATURE:
<223> OTHER INFORMATION: recombinant polynucleotide

<400> SEQUENCE: 102
cagagcgctt tgactcagac accctcagtg tccgtgtccc ccggacagac agccaccatc    60
acctgctctg gagataaatt gggggataag tatgtttctt ggtttcaaca gaagccaggc   120
cagtccccta tcctactcct ttatcaagac aacaggcggc cctctgggat ccctgaacga   180
ttctctggct ccaattctgg gaacacagcc tctctgacca tcagcgggac ccaggctatg   240
gatgaggctg actaccactg tcaggcgtgg ctcagcaata ctgcttccgt ggcattcggc   300
ggagggacca ggctgaccgt cctc                                          324

<210> SEQ ID NO 103
<211> LENGTH: 324
<212> TYPE: DNA
<213> ORGANISM: Artificial Sequence
<220> FEATURE:
<223> OTHER INFORMATION: recombinant polynucleotide

<400> SEQUENCE: 103
caagacatcc agatgaccca gtctccagcc accctgtctt tgtctccagg ggaaagagcc    60
accctctcct gcagggccag tcagagtgtt agcagctact tagcctggta ccaacagaaa   120
cctggccagg ctcccaggct cctcatctat gatgcatcca cagggccac tggcatccca   180 gccaggttca gtggcagtgg gtctgggaca gacttcactc tcaccatcag cagcctagag   240
cctgaagatt ttgcagttta ttactgtcag cagcgtagca actggcccct cactttcggc   300
ggagggacca aggtggagat caaa                                          324

<210> SEQ ID NO 104
<211> LENGTH: 330
<212> TYPE: DNA
<213> ORGANISM: Artificial Sequence
<220> FEATURE:
<223> OTHER INFORMATION: recombinant polynucleotide

<400> SEQUENCE: 104
cagagcgtct tgactcagcc tgcctccgtg tcggggtctc ctggacagtc gatcaccatc    60
tcctgcactg ggaccgggag tgatgttgga agttataacc ttgtctcctg gtaccaaaag   120
taccccggca aagcccccaa actcatcatt tatggggaca gtcagcggcc ctcgggactt   180
```

```
tctagtcgct tctctggctc caagtctggc aactcggcct ccctgacaat ctctgggctc        240
caggctgagg acgaggctga ttattactgt tgctcatatg caggtagtgg catttacgtc        300
tttggcagtg ggaccaaggt caccgtccta                                         330
```

<210> SEQ ID NO 105
<211> LENGTH: 10
<212> TYPE: PRT
<213> ORGANISM: Artificial Sequence
<220> FEATURE:
<223> OTHER INFORMATION: recombinant peptide

<400> SEQUENCE: 105

```
Glu Pro Pro Ser Met Arg Leu Lys Ala Arg
1               5                   10
```

<210> SEQ ID NO 106
<211> LENGTH: 19
<212> TYPE: PRT
<213> ORGANISM: Artificial Sequence
<220> FEATURE:
<223> OTHER INFORMATION: recombinant peptide

<400> SEQUENCE: 106

```
Cys Ser Ala Phe Tyr Pro Pro Glu Leu Gln Leu Arg Phe Phe Leu Arg
1               5                   10                  15

Asn Gly Leu
```

<210> SEQ ID NO 107
<211> LENGTH: 106
<212> TYPE: PRT
<213> ORGANISM: Artificial Sequence
<220> FEATURE:
<223> OTHER INFORMATION: recombinant peptide

<400> SEQUENCE: 107

```
Ser Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105
```

<210> SEQ ID NO 108
<211> LENGTH: 318
<212> TYPE: DNA
<213> ORGANISM: Artificial Sequence
<220> FEATURE:
<223> OTHER INFORMATION: recombinant polynucleotide

<400> SEQUENCE: 108

```
agtcagccca aggccaaccc cactgtcact ctgttcccgc cctcctctga ggagctccaa        60
gccaacaagg ccacactagt gtgtctgatc agtgacttct acccgggagc tgtgacagtg        120
gcctggaagg cagatggcag ccccgtcaag gcggagtggg acaccaccaa acctccaaa         180
```

```
cagagcaaca acaagtacgc ggccagcagc tacctgagcc tgacgcccga gcagtggaag    240
tcccacagaa gctacagctg ccaggtcacg catgaaggga gcaccgtcca aagacagtg    300 gccccctgcag aatgctct                                                 318
```

<210> SEQ ID NO 109
<211> LENGTH: 106
<212> TYPE: PRT
<213> ORGANISM: Artificial Sequence
<220> FEATURE:
<223> OTHER INFORMATION: recombinant peptide

<400> SEQUENCE: 109

```
Gly Gln Pro Lys Ala Asn Pro Thr Val Thr Leu Phe Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 110
<211> LENGTH: 317
<212> TYPE: DNA
<213> ORGANISM: Artificial Sequence
<220> FEATURE:
<223> OTHER INFORMATION: recombinant polynucleotide

<400> SEQUENCE: 110

```
ggtcagccca aggccacccc acggtcactc tgttcccgcc ctcctctgag gagctccaag    60
ccaacaaggc cacactagtg tgtctgatca gtgacttcta cccgggagct gtgacagtgg   120
cttggaaggc agatggcagc cccgtcaagg cgggagtgga gaccaccaaa ccctccaaac   180
agagcaacaa caagtacgcg gccagcagct acctgagcct gacgcccgag cagtggaagt   240
cccacagaag ctacagctgc caggtcacgc atgaagggag caccgtggag aagacagtgg   300
cccctacaga atgttca                                                   317
```

<210> SEQ ID NO 111
<211> LENGTH: 116
<212> TYPE: PRT
<213> ORGANISM: Artificial Sequence
<220> FEATURE:
<223> OTHER INFORMATION: recombinant peptide

<400> SEQUENCE: 111

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ala Met Gly Trp Val Arg Gln Ala Pro Gly Lys Gly Leu Glu Gln Val
        35                  40                  45

Ser Ser Ile Gly Ser Ser Gly Gly Gln Thr Lys Tyr Ala Asp Ser Val
```

```
                  50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Leu Ser Thr Gly Glu Leu Tyr Trp Gly Gln Gly Thr Leu Val
                100                 105                 110

Thr Val Ser Ser
            115

<210> SEQ ID NO 112
<211> LENGTH: 349
<212> TYPE: DNA
<213> ORGANISM: Artificial Sequence
<220> FEATURE:
<223> OTHER INFORMATION: recombinant polynucleotide

<400> SEQUENCE: 112
gaagttcaat tgttagagtc tggtggcggt cttgttcagc ctggtggttc tttacgtctt      60
tcttgcgctg cttccggatt cactttctct gagtacgcta tgggttgggt tcgccaagct     120
cctggtaaag gtttggagtg ggtttcttct atcggttctt ctggtggcca gactaagtat     180
gctgactccg ttaaaggtcg cttcactatc tctagagaca acttctaaga atactctcta     240
cttgcagatg aacagcttaa gggctgagga cacggccgtg tattactgtg cgagactctc     300
aacaggggag ctctactggg gccagggcac cctggtcacc gtctcaagc                 349

<210> SEQ ID NO 113
<211> LENGTH: 110
<212> TYPE: PRT
<213> ORGANISM: Artificial Sequence
<220> FEATURE:
<223> OTHER INFORMATION: recombinant peptide

<400> SEQUENCE: 113

Glu Val Gly Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Ala
                 20                  25                  30

Tyr Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Tyr Trp Gly Gln Gly Thr Leu Val Thr Val Ser Ser
                100                 105                 110

<210> SEQ ID NO 114
<211> LENGTH: 331
<212> TYPE: DNA
<213> ORGANISM: Artificial Sequence
<220> FEATURE:
<223> OTHER INFORMATION: recombinant polynucleotide

<400> SEQUENCE: 114
gaggtgcagc tgttggagtc tgggggaggct tggtacagcc tgggggggtcc ctgagactct     60 cctgtgcagc ctctggattc acctttagca gctatgccat gagctgggtc cgccaggctc    120
```

-continued

```
cagggaaggg gctggagtgg gtctcagcta ttagtggtag tggtggtagc acatactacg    180
cagactccgt gaagggccgg ttcaccatct ccagagacaa ttccaagaac acgctgtatc    240
tgcaaatgaa cagcctgaga gccgaggaca cggccgtata ttactgtgcg aaagatactg    300
gggccagggc accctggtca ccgtctcatc a                                    331
```

```
<210> SEQ ID NO 115
<211> LENGTH: 338
<212> TYPE: PRT
<213> ORGANISM: Artificial Sequence
<220> FEATURE:
<223> OTHER INFORMATION: recombinant peptide

<400> SEQUENCE: 115
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Pro Lys Ser Cys Asp Lys Thr His Thr Cys Pro Pro Cys Ala Pro Glu
            100                 105                 110

Leu Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Pro Gln Val Tyr
225                 230                 235                 240

Thr Leu Pro Pro Ser Arg Asp Glu Leu Thr Lys Asn Gln Val Ser Leu
                245                 250                 255

Thr Cys Leu Asx Lys Gly Phe Tyr Pro Ser Asp Ile Ala Val Glu Trp
            260                 265                 270

Glu Ser Asn Gly Gln Pro Glu Asn Asn Tyr Lys Thr Pro Pro Val
        275                 280                 285

Leu Asp Ser Asp Gly Ser Phe Phe Leu Tyr Ser Lys Leu Tyr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro

```
                     325                 330                 335

Gly Lys

<210> SEQ ID NO 116
<211> LENGTH: 338
<212> TYPE: PRT
<213> ORGANISM: Artificial Sequence
<220> FEATURE:
<223> OTHER INFORMATION: recombinant peptide

<400> SEQUENCE: 116

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Pro Lys Ser Cys Asp Lys Thr His Thr Cys Pro Pro Cys Ala Pro Glu
            100                 105                 110

Leu Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Asx Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Tyr Ser Lys Leu Tyr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys
```

```
<210> SEQ ID NO 117
<211> LENGTH: 29
<212> TYPE: PRT
<213> ORGANISM: Artificial Sequence
<220> FEATURE:
<223> OTHER INFORMATION: recombinant peptide

<400> SEQUENCE: 117

Val Tyr Ala Met Gly Ser Ile Gly Ser Ser Gly Gly Pro Thr Lys Tyr
1               5                   10                  15

Ala Asp Ser Val Lys Gly Leu Ser Ile Arg Glu Leu Val
            20                  25

<210> SEQ ID NO 118
<211> LENGTH: 29
<212> TYPE: PRT
<213> ORGANISM: Artificial Sequence
<220> FEATURE:
<223> OTHER INFORMATION: recombinant peptide

<400> SEQUENCE: 118

Val Tyr Ala Met Gly Ser Ile Gly Ser Ser Gly Gly Pro Thr Lys Tyr
1               5                   10                  15

Ala Asp Ser Val Lys Gly Leu Ser Ile Val Asp Ser Tyr
            20                  25

<210> SEQ ID NO 119
<211> LENGTH: 29
<212> TYPE: PRT
<213> ORGANISM: Artificial Sequence
<220> FEATURE:
<223> OTHER INFORMATION: recombinant peptide

<400> SEQUENCE: 119

Glu Tyr Ala Met Gly Ser Ile Gly Ser Ser Gly Gly Gln Thr Lys Tyr
1               5                   10                  15

Ala Asp Ser Val Lys Gly Leu Ala Ile Gly Asp Ser Tyr
            20                  25

<210> SEQ ID NO 120
<211> LENGTH: 29
<212> TYPE: PRT
<213> ORGANISM: Artificial Sequence
<220> FEATURE:
<223> OTHER INFORMATION: recombinant peptide

<400> SEQUENCE: 120

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu Ile
            20                  25

<210> SEQ ID NO 121
<211> LENGTH: 29
<212> TYPE: PRT
<213> ORGANISM: Artificial Sequence
<220> FEATURE:
<223> OTHER INFORMATION: recombinant peptide

<400> SEQUENCE: 121

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu Ser
            20                  25
```

```
<210> SEQ ID NO 122
<211> LENGTH: 29
<212> TYPE: PRT
<213> ORGANISM: Artificial Sequence
<220> FEATURE:
<223> OTHER INFORMATION: recombinant peptide

<400> SEQUENCE: 122

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu Val
            20                  25

<210> SEQ ID NO 123
<211> LENGTH: 29
<212> TYPE: PRT
<213> ORGANISM: Artificial Sequence
<220> FEATURE:
<223> OTHER INFORMATION: recombinant peptide

<400> SEQUENCE: 123

Glu Tyr Ala Met Gly Ser Ile Gly Ser Ser Gly Gly Gln Thr Lys Tyr
1               5                   10                  15

Ala Asp Ser Val Lys Gly Leu Ser Leu Gly Asp Ser Tyr
            20                  25

<210> SEQ ID NO 124
<211> LENGTH: 29
<212> TYPE: PRT
<213> ORGANISM: Artificial Sequence
<220> FEATURE:
<223> OTHER INFORMATION: recombinant peptide

<400> SEQUENCE: 124

Glu Tyr Ala Met Gly Ser Ile Gly Ser Ser Gly Gly Gln Thr Lys Tyr
1               5                   10                  15

Ala Asp Ser Val Lys Gly Leu Ser Ile Val Asp Ser Phe
            20                  25

<210> SEQ ID NO 125
<211> LENGTH: 29
<212> TYPE: PRT
<213> ORGANISM: Artificial Sequence
<220> FEATURE:
<223> OTHER INFORMATION: recombinant peptide

<400> SEQUENCE: 125

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu Asp
            20                  25

<210> SEQ ID NO 126
<211> LENGTH: 29
<212> TYPE: PRT
<213> ORGANISM: Artificial Sequence
<220> FEATURE:
<223> OTHER INFORMATION: recombinant peptide

<400> SEQUENCE: 126

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu His
            20                  25
```

<210> SEQ ID NO 127
<211> LENGTH: 29
<212> TYPE: PRT
<213> ORGANISM: Artificial Sequence
<220> FEATURE:
<223> OTHER INFORMATION: recombinant peptide

<400> SEQUENCE: 127

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu Ser
            20                  25

<210> SEQ ID NO 128
<211> LENGTH: 29
<212> TYPE: PRT
<213> ORGANISM: Artificial Sequence
<220> FEATURE:
<223> OTHER INFORMATION: recombinant peptide

<400> SEQUENCE: 128

Glu Tyr Ala Met Gly Ser Ile Gly Ser Ser Gly Gly Gln Thr Lys Tyr
1               5                   10                  15

Ala Asp Ser Val Lys Gly Leu Ser Ile Asp Asp Ser Tyr
            20                  25

<210> SEQ ID NO 129
<211> LENGTH: 29
<212> TYPE: PRT
<213> ORGANISM: Artificial Sequence
<220> FEATURE:
<223> OTHER INFORMATION: recombinant peptide

<400> SEQUENCE: 129

Glu Tyr Ala Met Gly Ser Ile Gly Ser Ser Gly Gly Gln Thr Lys Tyr
1               5                   10                  15

Ala Asp Ser Val Lys Gly Leu Ser Ile Val Glu Leu Asp
            20                  25

<210> SEQ ID NO 130
<211> LENGTH: 29
<212> TYPE: PRT
<213> ORGANISM: Artificial Sequence
<220> FEATURE:
<223> OTHER INFORMATION: recombinant peptide

<400> SEQUENCE: 130

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu Phe
            20                  25

<210> SEQ ID NO 131
<211> LENGTH: 29
<212> TYPE: PRT
<213> ORGANISM: Artificial Sequence
<220> FEATURE:
<223> OTHER INFORMATION: recombinant peptide

<400> SEQUENCE: 131

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Asp Ser Tyr
            20                  25

```
<210> SEQ ID NO 132
<211> LENGTH: 29
<212> TYPE: PRT
<213> ORGANISM: Artificial Sequence
<220> FEATURE:
<223> OTHER INFORMATION: recombinant peptide

<400> SEQUENCE: 132

Glu Tyr Ala Met Gly Ser Ile Gly Ser Ser Gly Gly Gln Thr Lys Tyr
1               5                   10                  15

Ala Asp Ser Val Lys Gly Leu Ser Ile Asp Asp Phe Tyr
            20                  25

<210> SEQ ID NO 133
<211> LENGTH: 29
<212> TYPE: PRT
<213> ORGANISM: Artificial Sequence
<220> FEATURE:
<223> OTHER INFORMATION: recombinant peptide

<400> SEQUENCE: 133

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu Phe
            20                  25

<210> SEQ ID NO 134
<211> LENGTH: 29
<212> TYPE: PRT
<213> ORGANISM: Artificial Sequence
<220> FEATURE:
<223> OTHER INFORMATION: recombinant peptide

<400> SEQUENCE: 134

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu Tyr
            20                  25

<210> SEQ ID NO 135
<211> LENGTH: 29
<212> TYPE: PRT
<213> ORGANISM: Artificial Sequence
<220> FEATURE:
<223> OTHER INFORMATION: recombinant peptide

<400> SEQUENCE: 135

Glu Tyr Ala Met Gly Ser Ile Gly Ser Ser Gly Gly Gln Thr Lys Tyr
1               5                   10                  15

Ala Asp Ser Val Lys Gly Leu Ser Ile Val Asp Ser Tyr
            20                  25

<210> SEQ ID NO 136
<211> LENGTH: 29
<212> TYPE: PRT
<213> ORGANISM: Artificial Sequence
<220> FEATURE:
<223> OTHER INFORMATION: recombinant peptide

<400> SEQUENCE: 136

Val Tyr Ala Met Gly Ser Ile Gly Ser Ser Gly Gly Pro Thr Lys Tyr
1               5                   10                  15

Ala Asp Ser Val Lys Gly Leu Ser Thr Gly Glu Leu Tyr
            20                  25
```

```
<210> SEQ ID NO 137
<211> LENGTH: 29
<212> TYPE: PRT
<213> ORGANISM: Artificial Sequence
<220> FEATURE:
<223> OTHER INFORMATION: recombinant peptide

<400> SEQUENCE: 137

Glu Tyr Ala Met Gly Ser Ile Gly Ser Ser Gly Gly Gln Thr Lys Tyr
1               5                   10                  15

Ala Asp Ser Val Lys Gly Leu Ser Ile Arg Glu Leu His
            20                  25

<210> SEQ ID NO 138
<211> LENGTH: 29
<212> TYPE: PRT
<213> ORGANISM: Artificial Sequence
<220> FEATURE:
<223> OTHER INFORMATION: recombinant peptide

<400> SEQUENCE: 138

Glu Tyr Ala Met Gly Ser Ile Gly Ser Ser Gly Gly Gln Thr Lys Tyr
1               5                   10                  15

Ala Asp Ser Val Lys Gly Leu Ser Thr Gly Glu Leu Tyr
            20                  25

<210> SEQ ID NO 139
<211> LENGTH: 29
<212> TYPE: PRT
<213> ORGANISM: Artificial Sequence
<220> FEATURE:
<223> OTHER INFORMATION: recombinant peptide

<400> SEQUENCE: 139

Glu Tyr Ala Met Gly Ser Ile Gly Ser Ser Gly Gly Gln Thr Lys Tyr
1               5                   10                  15

Ala Asp Ser Val Lys Gly Leu Ser Thr Gly Ala Leu Ser
            20                  25

<210> SEQ ID NO 140
<211> LENGTH: 29
<212> TYPE: PRT
<213> ORGANISM: Artificial Sequence
<220> FEATURE:
<223> OTHER INFORMATION: recombinant peptide

<400> SEQUENCE: 140

Glu Tyr Ala Met Gly Ser Ile Gly Ser Ser Gly Gly Gln Thr Lys Tyr
1               5                   10                  15

Ala Asp Ser Val Lys Gly Leu Ser Thr Gly Glu Leu Tyr
            20                  25

<210> SEQ ID NO 141
<211> LENGTH: 14
<212> TYPE: PRT
<213> ORGANISM: Artificial Sequence
<220> FEATURE:
<223> OTHER INFORMATION: recombinant peptide

<400> SEQUENCE: 141

Thr Gly Thr Gly Ser Asp Val Gly Ser Tyr Asn Leu Val Ser
1               5                   10

<210> SEQ ID NO 142
<211> LENGTH: 7
<212> TYPE: PRT
```

```
<213> ORGANISM: Artificial Sequence
<220> FEATURE:
<223> OTHER INFORMATION: recombinant peptide

<400> SEQUENCE: 142

Gly Asp Ser Gln Arg Pro Ser
1               5

<210> SEQ ID NO 143
<211> LENGTH: 10
<212> TYPE: PRT
<213> ORGANISM: Artificial Sequence
<220> FEATURE:
<223> OTHER INFORMATION: recombinant peptide

<400> SEQUENCE: 143

Cys Ser Tyr Ala Gly Ser Gly Ile Tyr Val
1               5                   10

<210> SEQ ID NO 144
<211> LENGTH: 5
<212> TYPE: PRT
<213> ORGANISM: Artificial Sequence
<220> FEATURE:
<223> OTHER INFORMATION: recombinant peptide

<400> SEQUENCE: 144

Glu Tyr Ala Met Gly
1               5

<210> SEQ ID NO 145
<211> LENGTH: 17
<212> TYPE: PRT
<213> ORGANISM: Artificial Sequence
<220> FEATURE:
<223> OTHER INFORMATION: recombinant peptide

<400> SEQUENCE: 145

Ser Ile Gly Ser Ser Gly Gly Gln Thr Lys Tyr Ala Asp Ser Val Lys
1               5                   10                  15

Gly

<210> SEQ ID NO 146
<211> LENGTH: 7
<212> TYPE: PRT
<213> ORGANISM: Artificial Sequence
<220> FEATURE:
<223> OTHER INFORMATION: recombinant peptide

<400> SEQUENCE: 146

Leu Ser Thr Gly Glu Leu Tyr
1               5

<210> SEQ ID NO 147
<211> LENGTH: 14
<212> TYPE: PRT
<213> ORGANISM: Artificial Sequence
<220> FEATURE:
<223> OTHER INFORMATION: recombinant peptide

<400> SEQUENCE: 147

Thr Gly Thr Gly Ser Asp Val Gly Ser Tyr Asn Leu Val Ser
1               5                   10

<210> SEQ ID NO 148
<211> LENGTH: 7
<212> TYPE: PRT
```

```
<213> ORGANISM: Artificial Sequence
<220> FEATURE:
<223> OTHER INFORMATION: recombinant peptide

<400> SEQUENCE: 148

Gly Asp Ser Gln Arg Pro Ser
1               5

<210> SEQ ID NO 149
<211> LENGTH: 10
<212> TYPE: PRT
<213> ORGANISM: Artificial Sequence
<220> FEATURE:
<223> OTHER INFORMATION: recombinant peptide

<400> SEQUENCE: 149

Cys Ser Tyr Ala Gly Ser Gly Ile Tyr Val
1               5                   10

<210> SEQ ID NO 150
<211> LENGTH: 5
<212> TYPE: PRT
<213> ORGANISM: Artificial Sequence
<220> FEATURE:
<223> OTHER INFORMATION: recombinant peptide

<400> SEQUENCE: 150

Glu Tyr Ala Met Gly
1               5

<210> SEQ ID NO 151
<211> LENGTH: 17
<212> TYPE: PRT
<213> ORGANISM: Artificial Sequence
<220> FEATURE:
<223> OTHER INFORMATION: recombinant peptide

<400> SEQUENCE: 151

Ser Ile Gly Ser Ser Gly Gly Gln Thr Lys Tyr Ala Asp Ser Val Lys
1               5                   10                  15

Gly

<210> SEQ ID NO 152
<211> LENGTH: 7
<212> TYPE: PRT
<213> ORGANISM: Artificial Sequence
<220> FEATURE:
<223> OTHER INFORMATION: recombinant peptide

<400> SEQUENCE: 152

Leu Ser Thr Gly Glu Leu Tyr
1               5

<210> SEQ ID NO 153
<211> LENGTH: 14
<212> TYPE: PRT
<213> ORGANISM: Artificial Sequence
<220> FEATURE:
<223> OTHER INFORMATION: recombinant peptide

<400> SEQUENCE: 153

Thr Gly Thr Gly Ser Asp Val Gly Ser Tyr Asn Leu Val Ser
1               5                   10

<210> SEQ ID NO 154
<211> LENGTH: 7
<212> TYPE: PRT
```

-continued

```
<213> ORGANISM: Artificial Sequence
<220> FEATURE:
<223> OTHER INFORMATION: recombinant peptide

<400> SEQUENCE: 154

Gly Asp Ser Gln Arg Pro Ser
1               5

<210> SEQ ID NO 155
<211> LENGTH: 10
<212> TYPE: PRT
<213> ORGANISM: Artificial Sequence
<220> FEATURE:
<223> OTHER INFORMATION: recombinant peptide

<400> SEQUENCE: 155

Cys Ser Tyr Ala Gly Ser Gly Ile Tyr Val
1               5                   10

<210> SEQ ID NO 156
<211> LENGTH: 5
<212> TYPE: PRT
<213> ORGANISM: Artificial Sequence
<220> FEATURE:
<223> OTHER INFORMATION: recombinant peptide

<400> SEQUENCE: 156

Val Tyr Ala Met Gly
1               5

<210> SEQ ID NO 157
<211> LENGTH: 17
<212> TYPE: PRT
<213> ORGANISM: Artificial Sequence
<220> FEATURE:
<223> OTHER INFORMATION: recombinant peptide

<400> SEQUENCE: 157

Ser Ile Gly Ser Ser Gly Gly Pro Thr Lys Tyr Ala Asp Ser Val Lys
1               5                   10                  15

Gly

<210> SEQ ID NO 158
<211> LENGTH: 7
<212> TYPE: PRT
<213> ORGANISM: Artificial Sequence
<220> FEATURE:
<223> OTHER INFORMATION: recombinant peptide

<400> SEQUENCE: 158

Leu Ser Ile Arg Glu Leu Val
1               5

<210> SEQ ID NO 159
<211> LENGTH: 14
<212> TYPE: PRT
<213> ORGANISM: Artificial Sequence
<220> FEATURE:
<223> OTHER INFORMATION: recombinant peptide

<400> SEQUENCE: 159

Thr Gly Thr Gly Ser Asp Val Gly Ser Tyr Asn Leu Val Ser
1               5                   10

<210> SEQ ID NO 160
<211> LENGTH: 7
<212> TYPE: PRT
```

```
<213> ORGANISM: Artificial Sequence
<220> FEATURE:
<223> OTHER INFORMATION: recombinant peptide

<400> SEQUENCE: 160

Gly Asp Ser Gln Arg Pro Ser
1               5

<210> SEQ ID NO 161
<211> LENGTH: 10
<212> TYPE: PRT
<213> ORGANISM: Artificial Sequence
<220> FEATURE:
<223> OTHER INFORMATION: recombinant peptide

<400> SEQUENCE: 161

Cys Ser Tyr Ala Gly Ser Gly Ile Tyr Val
1               5                   10

<210> SEQ ID NO 162
<211> LENGTH: 5
<212> TYPE: PRT
<213> ORGANISM: Artificial Sequence
<220> FEATURE:
<223> OTHER INFORMATION: recombinant peptide

<400> SEQUENCE: 162

Val Tyr Ala Met Gly
1               5

<210> SEQ ID NO 163
<211> LENGTH: 17
<212> TYPE: PRT
<213> ORGANISM: Artificial Sequence
<220> FEATURE:
<223> OTHER INFORMATION: recombinant peptide

<400> SEQUENCE: 163

Ser Ile Gly Ser Ser Gly Gly Pro Thr Lys Tyr Ala Asp Ser Val Lys
1               5                   10                  15

Gly

<210> SEQ ID NO 164
<211> LENGTH: 7
<212> TYPE: PRT
<213> ORGANISM: Artificial Sequence
<220> FEATURE:
<223> OTHER INFORMATION: recombinant peptide

<400> SEQUENCE: 164

Leu Ser Ile Val Asp Ser Tyr
1               5

<210> SEQ ID NO 165
<211> LENGTH: 14
<212> TYPE: PRT
<213> ORGANISM: Artificial Sequence
<220> FEATURE:
<223> OTHER INFORMATION: recombinant peptide

<400> SEQUENCE: 165

Thr Gly Thr Gly Ser Asp Val Gly Ser Tyr Asn Leu Val Ser
1               5                   10

<210> SEQ ID NO 166
<211> LENGTH: 7
<212> TYPE: PRT
```

```
<213> ORGANISM: Artificial Sequence
<220> FEATURE:
<223> OTHER INFORMATION: recombinant peptide

<400> SEQUENCE: 166

Gly Asp Ser Gln Arg Pro Ser
1               5

<210> SEQ ID NO 167
<211> LENGTH: 10
<212> TYPE: PRT
<213> ORGANISM: Artificial Sequence
<220> FEATURE:
<223> OTHER INFORMATION: recombinant peptide

<400> SEQUENCE: 167

Cys Ser Tyr Ala Gly Ser Gly Ile Tyr Val
1               5                   10

<210> SEQ ID NO 168
<211> LENGTH: 5
<212> TYPE: PRT
<213> ORGANISM: Artificial Sequence
<220> FEATURE:
<223> OTHER INFORMATION: recombinant peptide

<400> SEQUENCE: 168

Glu Tyr Ala Met Gly
1               5

<210> SEQ ID NO 169
<211> LENGTH: 17
<212> TYPE: PRT
<213> ORGANISM: Artificial Sequence
<220> FEATURE:
<223> OTHER INFORMATION: recombinant peptide

<400> SEQUENCE: 169

Ser Ile Gly Ser Ser Gly Gly Gln Thr Lys Tyr Ala Asp Ser Val Lys
1               5                   10                  15

Gly

<210> SEQ ID NO 170
<211> LENGTH: 7
<212> TYPE: PRT
<213> ORGANISM: Artificial Sequence
<220> FEATURE:
<223> OTHER INFORMATION: recombinant peptide

<400> SEQUENCE: 170

Leu Ser Leu Gly Asp Ser Tyr
1               5

<210> SEQ ID NO 171
<211> LENGTH: 14
<212> TYPE: PRT
<213> ORGANISM: Artificial Sequence
<220> FEATURE:
<223> OTHER INFORMATION: recombinant peptide

<400> SEQUENCE: 171

Thr Gly Thr Gly Ser Asp Val Gly Ser Tyr Asn Leu Val Ser
1               5                   10

<210> SEQ ID NO 172
<211> LENGTH: 7
<212> TYPE: PRT
```

```
<213> ORGANISM: Artificial Sequence
<220> FEATURE:
<223> OTHER INFORMATION: recombinant peptide

<400> SEQUENCE: 172

Gly Asp Ser Gln Arg Pro Ser
1               5

<210> SEQ ID NO 173
<211> LENGTH: 10
<212> TYPE: PRT
<213> ORGANISM: Artificial Sequence
<220> FEATURE:
<223> OTHER INFORMATION: recombinant peptide

<400> SEQUENCE: 173

Cys Ser Tyr Ala Gly Ser Gly Ile Tyr Val
1               5                   10

<210> SEQ ID NO 174
<211> LENGTH: 5
<212> TYPE: PRT
<213> ORGANISM: Artificial Sequence
<220> FEATURE:
<223> OTHER INFORMATION: recombinant peptide

<400> SEQUENCE: 174

Glu Tyr Ala Met Gly
1               5

<210> SEQ ID NO 175
<211> LENGTH: 17
<212> TYPE: PRT
<213> ORGANISM: Artificial Sequence
<220> FEATURE:
<223> OTHER INFORMATION: recombinant peptide

<400> SEQUENCE: 175

Ser Ile Gly Ser Ser Gly Gly Gln Thr Lys Tyr Ala Asp Ser Val Lys
1               5                   10                  15

Gly

<210> SEQ ID NO 176
<211> LENGTH: 7
<212> TYPE: PRT
<213> ORGANISM: Artificial Sequence
<220> FEATURE:
<223> OTHER INFORMATION: recombinant peptide

<400> SEQUENCE: 176

Leu Ala Ile Gly Asp Ser Tyr
1               5

<210> SEQ ID NO 177
<211> LENGTH: 111
<212> TYPE: PRT
<213> ORGANISM: Artificial Sequence
<220> FEATURE:
<223> OTHER INFORMATION: recombinant peptide

<400> SEQUENCE: 177

Gln Ser Val Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Lys Tyr Pro Gly Lys Ala Pro Lys Leu
```

```
                    35                  40                  45
Ile Ile Tyr Gly Asp Ser Gln Arg Pro Ser Gly Leu Ser Ser Arg Phe
 50                  55                  60

Ser Gly Ser Lys Ser Gly Asn Ser Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Gly Ile Tyr Tyr Val Phe Gly Ser Gly Thr Lys Val Thr Val Leu
            100                 105                 110

<210> SEQ ID NO 178
<211> LENGTH: 111
<212> TYPE: PRT
<213> ORGANISM: Artificial Sequence
<220> FEATURE:
<223> OTHER INFORMATION: recombinant peptide

<400> SEQUENCE: 178

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Thr Phe Tyr Val Phe Gly Thr Gly Thr Lys Val Thr Val Leu
            100                 105                 110

<210> SEQ ID NO 179
<211> LENGTH: 105
<212> TYPE: PRT
<213> ORGANISM: Artificial Sequence
<220> FEATURE:
<223> OTHER INFORMATION: recombinant peptide

<400> SEQUENCE: 179

Ser Pro Lys Ala Asn Pro Thr Val Thr Leu Phe Pro Pro Ser Ser Glu
 1               5                  10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Gly Ser Pro Val
            35                  40                  45

Lys Ala Gly Val Glu Thr Thr Lys Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Ala Glu Cys Ser
            100                 105

<210> SEQ ID NO 180
<211> LENGTH: 105
<212> TYPE: PRT
```

```
<213> ORGANISM: Artificial Sequence
<220> FEATURE:
<223> OTHER INFORMATION: recombinant peptide

<400> SEQUENCE: 180

Gly Pro Lys Ala Asn Pro Thr Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Gly Ser Pro Val
        35                  40                  45

Lys Ala Gly Val Glu Thr Thr Lys Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 181
<211> LENGTH: 110
<212> TYPE: PRT
<213> ORGANISM: Artificial Sequence
<220> FEATURE:
<223> OTHER INFORMATION: Recombinant peptide

<400> SEQUENCE: 181

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Tyr Val Phe Gly Thr Gly Thr Lys Val Thr Val Leu
            100                 105                 110

<210> SEQ ID NO 182
<211> LENGTH: 110
<212> TYPE: PRT
<213> ORGANISM: Artificial Sequence
<220> FEATURE:
<223> OTHER INFORMATION: Recombinant peptide

<400> SEQUENCE: 182

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Gln Arg Pro Ser Gly Val Ser Asn Arg Phe
    50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Gly Ile Tyr Val Phe Gly Thr Gly Thr Lys Val Thr Val Leu
            100                 105                 110

<210> SEQ ID NO 183
<211> LENGTH: 113
<212> TYPE: PRT
<213> ORGANISM: Artificial Sequence
<220> FEATURE:
<223> OTHER INFORMATION: Recombinant peptide

<400> SEQUENCE: 183

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Phe Asp Ile Trp Gly Gln Gly Thr Met Val Thr Val Ser
            100                 105                 110

Ser

<210> SEQ ID NO 184
<211> LENGTH: 116
<212> TYPE: PRT
<213> ORGANISM: Artificial Sequence
<220> FEATURE:
<223> OTHER INFORMATION: Recombinant peptide

<400> SEQUENCE: 184

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Glu Tyr
            20                  25                  30

Ala Met Gly Trp Val Arg Gln Ala Pro Gly Lys Gly Leu Glu Trp Val
        35                  40                  45

Ser Ser Ile Gly Ser Ser Gly Gln Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser
        115

<210> SEQ ID NO 185
<211> LENGTH: 111
<212> TYPE: PRT

```
<213> ORGANISM: Artificial Sequence
<220> FEATURE:
<223> OTHER INFORMATION: Recombinant peptide

<400> SEQUENCE: 185

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Gly Ile Tyr Tyr Val Phe Gly Thr Gly Thr Lys Val Thr Val Leu
            100                 105                 110

<210> SEQ ID NO 186
<211> LENGTH: 99
<212> TYPE: PRT
<213> ORGANISM: Artificial Sequence
<220> FEATURE:
<223> OTHER INFORMATION: Recombinant peptide

<400> SEQUENCE: 186

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe

<210> SEQ ID NO 187
<211> LENGTH: 99
<212> TYPE: PRT
<213> ORGANISM: Artificial Sequence
<220> FEATURE:
<223> OTHER INFORMATION: Recombinant peptide

<400> SEQUENCE: 187

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
```

```
65                  70                  75                  80
Gln Ala Glu Asp Glu Ala Asp Tyr Tyr Cys Cys Ser Tyr Ala Gly Ser
                85                  90                  95

Tyr Thr Phe

<210> SEQ ID NO 188
<211> LENGTH: 99
<212> TYPE: PRT
<213> ORGANISM: Artificial Sequence
<220> FEATURE:
<223> OTHER INFORMATION: Recombinant peptide

<400> SEQUENCE: 188

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 189
<211> LENGTH: 99
<212> TYPE: PRT
<213> ORGANISM: Artificial Sequence
<220> FEATURE:
<223> OTHER INFORMATION: Recombinant peptide

<400> SEQUENCE: 189

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe

<210> SEQ ID NO 190
<211> LENGTH: 99
<212> TYPE: PRT
<213> ORGANISM: Artificial Sequence
<220> FEATURE:
<223> OTHER INFORMATION: Recombinant peptide

<400> SEQUENCE: 190

Gln Ser Ala Leu Thr Gln Pro Pro Ser Val Ser Gly Ser Pro Gly Gln
1               5                   10                  15
```

```
Ser Val Thr Ile Ser Cys Thr Gly Thr Ser Ser Asp Val Gly Ser Tyr
            20              25              30

Asn Arg Val Ser Trp Tyr Gln Gln Pro Pro Gly Thr Ala Pro Lys Leu
        35              40              45

Met Ile Tyr Glu Val Ser Asn Arg Pro Ser Gly Val Pro Asp Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Tyr Cys Ser Leu Tyr Thr Ser Ser
                85              90              95

Ser Thr Phe
```

FC RECEPTOR BINDING PROTEINS

RELATED APPLICATIONS

This application claims the benefit under 35 U.S.C. §119 (e) of U.S. provisional application 61/048,152, filed Apr. 25, 2008, and U.S. provisional application 61/048,500, filed Apr. 28, 2008, the entire disclosures of which are incorporated herein by reference in their entirety.

BACKGROUND

The most abundant antibody isotype in the serum is IgG and it has a critical role in mediating protection against pathogens as well as in mediating allergic and inflammatory responses that hasten recruitment of immune system components to the tissues, mucosae, and dermal surfaces (Junghans, Immunologic Research 16 (1):29 (1997)). Moreover, it is also a key component of a variety of autoimmune diseases. Under normal conditions, the halflife of IgG in the serum is in the range of 5-7 days in mice and 22-23 days in humans, which is a prolonged period, relative to the serum half life of other plasma proteins. In part, this occurs because the neonatal FcRn receptor (FcRn) rescues pinocytosed IgG from degradative lysosomes and recycles it back to the extracellular compartment (Junghans and Anderson, Proc. Natl. Acad. Sci. USA 93:5512 (1996), Roopenian et al. J. Immunology 170: 3528 (2003)).

FcRn binds to the Fc portion of IgG. The interaction between the IgG Fc region and FcRn is pH-dependent. Upon entry into cells by fluid phase endocytosis, IgG is sequestered into endosomes and binds to FcRn with high affinity at acidic pH (6~6.5); when the IgG-FcRn complex cycles to the plasma membrane, IgG dissociates rapidly from FcRn in the bloodstream at slightly basic pH (~7.4). By this receptor-mediated recycling mechanism, FcRn effectively rescues the IgG from degradation in lysosomes, thereby prolonging the half-life of circulating IgG.

FcRn is a non-covalent heterodimer that typically resides in the endosomes of endothelial and epithelial cells. It is a membrane bound receptor with a single-pass transmembrane having three heavy chain alpha domains ($\alpha 1$, $\alpha 2$, and $\alpha 3$) and a single soluble light chain β2-microglobulin (β2M) domain. Structurally, it belongs to a family of major histocompatibility complex class 1 molecules that have β2M as a common light chain. The FcRn α chain is a 46 kD protein composed of an extracellular domain containing the $\alpha 1$, $\alpha 2$, and $\alpha 3$ heavy chain domains, a transmembrane region, and a relatively short cytoplasmic tail (Burmeister et al. Nature 372:366 (1994)).

FcRn was first identified in the neonatal rat gut, where it functions to mediate the absorption of IgG antibody from the mother's milk and facilitates its transport to the circulatory system (Leach et al. J Immunol 157:3317 (1996)). FcRn has also been isolated from human placenta, where it also mediates absorption and transport of maternal IgG to the fetal circulation. In adults, FcRn is expressed in a number of tissues, including epithelial tissues of the lung, intestine, kidney, as well as nasal, vaginal, and biliary tress surfaces (U.S. Pat. Nos. 6,030,613 and 6,086,875; Israel et al. Immunology 92:69 (1997); Kobayashi et al. Am J Physiol (2002); Renal Physiol 282:F358 (2002)).

In order to study the contributions of FcRn to IgG homeostasis, mice have been engineered so that at least part of the genes encoding β2M and FcRn heavy chains have been "knocked out" so that these proteins are not expressed (WO 02/43658; Junghans and Anderson, Proc Natl Acad Sci US 93:5512 (1996)). In these mice, the serum half-life and concentrations of IgG were dramatically reduced, suggesting a FcRn dependent mechanism for IgG homeostasis.

It has also been suggested that anti-human FcRn antibodies may be generated in these FcRn knockout mice and that these antibodies may prevent the binding of IgG to FcRn. However, such antibodies have not been generated or tested (WO 02/43658).

The inhibition of IgG binding to FcRn negatively alters IgG serum half-life by preventing IgG recycling. This principle has been shown to be therapeutically effective in a mouse model of autoimmune cutaneous bullous diseases (Li et al. J Clin Invest 115:3440-3450 (2005)). Accordingly, agents that block or antagonize the binding of IgG to FcRn may be used in a method to treat or prevent autoimmune and inflammatory diseases or disorders characterized by the presence of inappropriately regulated IgG antibodies.

SUMMARY

This invention relates, inter alia, to antibodies that bind FcRn, and methods of identifying and using such antibodies.

In one aspect the invention provides an isolated antibody comprising a heavy chain (HC) immunoglobulin variable domain sequence and a light chain (LC) immunoglobulin variable domain sequence, wherein the heavy chain and light chain immunoglobulin variable domain sequences form an antigen binding site that binds to human FcRn; and wherein the antibody includes one or more of the following characteristics:

(a) a human CDR or human framework region;
(b) the LC immunoglobulin variable domain sequence comprises one or more CDRs that are at least 85% identical to a CDR of a LC variable domain of M0171-A03, M0171-A01, M0159-A07, M0161-B04, M0090-F11 or DX2500;
(c) the HC immunoglobulin variable domain sequence comprises one or more CDRs that are at least 85% identical to a CDR of a HC variable domain of M0171-A03, M0171-A01, M0159-A07, M0161-B04, M0090-F11 or DX2500;
(d) the LC immunoglobulin variable domain sequence is at least 85% identical to a LC variable domain of M0171-A03, M0171-A01, M0159-A07, M0161-B04, M0090-F11 or DX2500;
(e) the HC immunoglobulin variable domain sequence is at least 85% identical to a HC variable domain of M0171-A03, M0171-A01, M0159-A07, M0161-B04 M0090-F11 or DX2500; and
(f) the antibody binds an epitope that overlaps with an epitope bound by M0171-A03, M0171-A01, M0159-A07, M0161-B04, M0090-F11 or DX2500.

In one aspect the invention provides an isolated antibody that is at least 85% identical to an antibody selected from the group consisting of M0171-A03, M0171-A01, M0159-A07, M0161-B04, M0090-F11 and DX2500.

In one aspect the invention provides an isolated antibody selected from the group consisting of M0171-A03, M0171-A01, M0159-A07, M0161-B04, M0090-F11 and DX2504.

In one aspect the invention provides an isolated antibody comprising the CDRs of M0161-B04. In one aspect the invention provides an isolated antibody that is at least 85% identical to M0161-B04. The CDRs of M0161-B04 are represented in Table 17A.

In one aspect the invention provides an isolated antibody comprising the CDRs of M0171-A03. In one aspect the invention provides an isolated antibody that is at least 85% identical to M0171-A03. The CDRs of M0171-A03 are represented in Table 17A.

In one aspect the invention provides an isolated antibody comprising the CDRs of M0171-A01. In one aspect the invention provides an isolated antibody that is at least 85% identical to M0171-A01. The CDRs of M0171-A01 are represented in Table 17A.

In one aspect the invention provides an isolated antibody comprising the CDRs of M0159-A07. In one aspect the invention provides an isolated antibody that is at least 85% identical to M0159-A07. The CDRs of M0159-A07 are represented in Table 17A.

In one aspect the invention provides an isolated antibody comprising the CDRs of M0090-F11. In one aspect the invention provides an n isolated antibody that is at least 85% identical to M0090-F11. The CDRs of M0090-F11 are represented in Table 17A.

In one aspect the invention provides an isolated antibody comprising the CDRs of DX-2500. In one aspect the invention provides an isolated antibody that is at least 85% identical to DX-2500. The CDRs of DX-2500 are represented in Table 17A.

In some embodiments of the antibodies provided herein the HC variable domain sequence comprises a variable domain sequence of M0161-B04 and the LC variable domain sequence comprises a variable domain sequence of M0161-B04.

In some embodiments of the antibodies provided herein the HC variable domain sequence comprises a variable domain sequence of M0171-A03 and the LC variable domain sequence comprises a variable domain sequence of M0171-A03.

In some embodiments of the antibodies provided herein the HC variable domain sequence comprises a variable domain sequence of M0171-A01 and the LC variable domain sequence comprises a variable domain sequence of M0171-A01.

In some embodiments of the antibodies provided herein the HC variable domain sequence comprises a variable domain sequence of M0159-A07 and the LC variable domain sequence comprises a variable domain sequence of M0159-A07.

In some embodiments of the antibodies provided herein the HC variable domain sequence comprises a variable domain sequence of M0090-F11 and the LC variable domain sequence comprises a variable domain sequence of M0090-F11.

In some embodiments of the antibodies provided herein the HC variable domain sequence comprises a variable domain sequence of DX2500 and the LC variable domain sequence comprises a variable domain sequence of DX2500.

In some embodiments of the antibodies provided herein the antibody binds to an FcRn epitope bound by M0171-A03, M0171-A01, M0159-A07, M0161-B04, M0090-F11 or DX2500.

In some embodiments of the antibodies provided herein the antibody competes with M0171-A03, M0171 A01, M0159-A07, M0161-B04, M0090-F11 or DX2500 for binding to FcRn.

As used herein M0171-A03 is also referred to as M171-A03 and M00171-A03. As used herein M0171-A01 is also referred to as M171-A01 and M00171-A01. As used herein M0159-A07 is also referred to as M159-A07 and M00159-A07. As used herein M0161-B04 is also referred to as M161-B04, M00161-B04 and DX-2504. As used herein M0090-F11 is also referred to as M090-F11 and M90-F11.

In one aspect the invention provides an isolated antibody, or a fragment thereof, which binds to human FcRn, wherein the antibody is generated against the heavy chain of human FcRn or a fragment thereof, wherein the antibody functions as a non-competitive inhibitor of IgG binding to human FcRn, and wherein the antibody does not bind β2-microglobulin.

In one aspect the invention provides an isolated antibody, or fragment thereof, that binds to human FcRn, wherein the antibody is generated against the heavy chain of human FcRn or a fragment thereof, wherein the antibody does not bind β2-microglobulin when it is not complexed with FcRn, and wherein the antibody is not produced from a FcRn−/− knockout mouse.

In some of the embodiments of the antibodies provided herein the antibody is selected from the group consisting of 3B3.11, 31.1, 4B4.12, and 17D3.

In some of the embodiments of the antibodies provided herein the antibody binds human FcRn at about pH range 5-7.4 with a dissociation constant ($K_D$) of less than 100 nM.

In some of the embodiments of the antibodies provided herein the antigen binding site specifically binds to human FcRn.

In some of the embodiments of the antibodies provided herein the antibody binds a stable FcRn expressing cell line.

In some of the embodiments of the antibodies provided herein the antibody modulates (e.g., inhibits) FcRn binding to an antibody/immunoglobulin constant region.

In some of the embodiments of the antibodies provided herein the antibody binds to the alpha subunit of FcRn.

In some of the embodiments of the antibodies provided herein the antibody binds the $\alpha1$, $\alpha2$, or $\alpha3$ domain of the FcRn alpha chain.

In some of the embodiments of the antibodies provided herein the antibody does not bind a beta subunit of FcRn, i.e., the protein only binds an alpha subunit.

In some of the embodiments of the antibodies provided herein the antibody binds to a beta subunit of FcRn, wherein the beta subunit is associated with an alpha subunit.

In some of the embodiments of the antibodies provided herein the alpha and beta subunit are correctly assembled into FcRn.

In some of the embodiments of the antibodies provided herein the antibody binds an FcRn that contains both an alpha subunit and a beta subunit and is correctly assembled.

In some of the embodiments of the antibodies provided herein the antibody inhibits the binding of IgG-Fc with an $IC_{50}$ of less than about 800 nM, less than about 600 nM, less than about 300 nM, less than about 100 nM, less than about 50, nM, less than about 25 nM, less than about 10 nM, or less than about 5 nM at about pH 6.

In some of the embodiments of the antibodies provided herein the antibody is soluble Fab.

In some of the embodiments of the antibodies provided herein the antibody binds to FcRn through its antigen binding domain and also through its Fc region.

In some of the embodiments of the antibodies provided herein the binding of the antibody to FcRn is substantially pH independent in the range of 2-10.

In some of the embodiments of the antibodies provided herein the binding of the antibody to FcRn is substantially pH independent in the range of 6-8.

In some of the embodiments of the antibodies provided herein the antibody has a $k_{off}$ of less than 0.01, 0.001, 0.0001, 0.00001 $s^{-1}$ at pH 7.5.

In some of the embodiments of the antibodies provided herein the binding of the antibody to FcRn is substantially pH dependent.

In some of the embodiments of the antibodies provided herein the antibody preferentially binds human FcRn as compared to rat FcRn in a pH-dependent or pH-independent manner.

In some of the embodiments of the antibodies provided herein the antibody binds FcRn in endosomes or under endosomal conditions.

In some of the embodiments of the antibodies provided herein the antibody does not release FcRn at pH 7.5.

In some of the embodiments of the antibodies provided herein the antibody causes an amelioration of symptoms associated with an autoimmune disorder when administered to a subject.

In some of the embodiments of the antibodies provided herein the HC and LC variable domain sequences are components of the same polypeptide chain.

In some of the embodiments of the antibodies provided herein the HC and LC variable domain sequences are components of different polypeptide chains.

In some of the embodiments of the antibodies provided herein the antibody is a full-length antibody.

In some of the embodiments of the antibodies provided herein the antibody is a human or humanized antibody or is non-immunogenic in a human.

In some of the embodiments of the antibodies provided herein the antibody comprises a human antibody framework region.

In some of the embodiments of the antibodies provided herein the antibody comprises an Fc domain.

In some of the embodiments of the antibodies provided herein the antibody is a murine antibody.

In some of the embodiments of the antibodies provided herein the antibody is a monoclonal antibody.

In some of the embodiments of the antibodies provided herein the antibody is chimeric or humanized.

In some of the embodiments of the antibodies provided herein the antibody is selected from the group consisting of Fab, F(ab)'2, Fv and ScFv.

In some of the embodiments of the antibodies provided herein the antibody binding to FcRn is independent of the pH over a pH range of 6.0 to 8.0.

In one aspect the invention provides a pharmaceutical composition comprising the any one of the antibodies provided herein and a pharmaceutically acceptable carrier.

In one aspect the invention provides an isolated nucleic acid comprising a sequence that encodes a polypeptide that includes a sequence at least 80% identical to the sequence of a variable domain of M0171-A03, M0171-A01, M0159-A07 or M0161-B04.

In one aspect the invention provides an isolated nucleic acid comprising a sequence that encodes a polypeptide comprising the first and/or the second immunoglobulin variable domain of the any one of the antibodies provided herein.

In one aspect the invention provides a vector or host cell comprising the nucleic acid sequence provided herein In one aspect the invention provides a method of detecting an FcRn in a sample, the method comprising: contacting the sample with any one of the antibodies provided herein and detecting an interaction between the antibody and the FcRn if present. In some embodiments the antibody further comprises a detectable label.

In one aspect the invention provides a method of detecting FcRn in a subject, the method comprising: administering any one of the antibodies provided herein that further comprises a detectable label, to a subject; and detecting the label in the subject. In some embodiments detecting comprises imaging the subject.

In one aspect the invention provides a method of modulating an FcRn activity, the method comprising: contacting an FcRn with any one of the antibodies provided herein, thereby modulating the activity of the FcRn. In some embodiments the FcRn is in a human subject. In some embodiments the antibody prevents binding of the FcRn to an endogenous Ig. In some embodiments the antibody prevents binding of the FcRn to a therapeutic antibody. In some embodiments the FcRn is in an epithelial cell endosome. In some embodiments the FcRn is in an endothelial cell endosome. In some embodiments the FcRn is on the cell surface.

In one aspect the invention provides a method of treating an autoimmune disorder and/or modulating symptoms of an autoimmune disorder, the method comprising: administering any one of the antibodies provided herein in an amount sufficient to modulate the symptoms. In some embodiments the autoimmune disorder is a disorder selected from the group consisting of: rheumatoid arthritis (RA), systemic lupus erythematosus (SLE), Myasthenia Gravis (MG), Graves Disease, Idiopathic Thrombocytopenia Purpura (ITP), Guillain-Barre Syndrome, autoimmune myocarditis, Membrane Glomerulonephritis, diabetes mellitus, Type I or Type II diabetes, multiple sclerosis, Reynaud's syndrome, autoimmune thyroiditis, gastritis, Celiac Disease, Vitiligo, Hepatitis, primary biliary cirrhosis, inflammatory bowel disease, spondyloarthropathies, experimental autoimmune encephalomyelitis, immune neutropenia, juvenile onset diabetes, and immune responses associated with delayed hypersensitivity mediated by cytokines, T-lymphocytes typically found in tuberculosis, sarcoidosis, and polymyositis, polyarteritis, cutaneous vasculitis, pemphigus, pemphigold, Goodpasture's syndrome, Kawasaki's disease, systemic sclerosis, anti-phospholipid syndrome, and Sjogren's syndrome. In some embodiments the pemphigus is pemphigus vulgaris, pemphigus foliaceus or paraneoplastic pemphigus.

In some embodiments the antibody decreases the half-life of endogenous IgG.

In one aspect the invention provides a method of modulating the half life/levels of circulating IgG, the method comprising: identifying a subject in need of modulated circulating IgG half life/levels; and administering the antibody of any one of the antibodies provided herein to the subject in amount effective to modulate the half life/levels of circulating IgG in the subject. In some embodiments the method reduces circulating IgG half life/levels. In some embodiments the subject is a human. In some embodiments the antibody is administered to decrease the half life/levels of circulating IgG and in combination with an anti-autoimmune disorder agent or therapy that is not any one of the antibodies provided herein. In some embodiments the anti-autoimmune disorder agent or therapy that is not any one of the antibodies provided herein comprises intravenous Ig therapy; nonsteroidal anti-inflammatory drugs (NSAID); corticosteroids; cyclosporins, rapamycins, ascomycins, or their immunosuppressive analogs, e.g., cyclosporin A, cyclosporin G, FK-506, rapamycin, 40-O-(2-hydroxy)ethyl-rapamycin; cyclophosphamide; azathioprene; methotrexate; brequinar; FTY 720; leflunomide; mnizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; other immunomodulatory compounds, e.g. CTLA4Ig; or other adhesion molecule inhibitors, e.g., mAbs or low molecular weight inhibitors including selectin antagonists and VLA-4 antagonists.

In one aspect the invention provides a method of treating or preventing an autoimmune disorder, the method comprising:

administering any one of the antibodies provided herein to a subject having the disorder or at risk of developing the disorder. In some embodiments the autoimmune disorder is characterized by unwanted circulating IgG. In some embodiments the antibody decreases the half-life of endogenous IgG. In some embodiments the autoimmune disorder is a disorder selected from rheumatoid arthritis (RA), systemic lupus erythematosus (SLE), Myasthenia Gravis (MG), Graves Disease, Idiopathic Thrombocytopenia Purpura (ITP), Guillain-Barre Syndrome, autoimmune myocarditis, Membrane Glomerulonephritis, diabetes mellitus, Type I or Type II diabetes, multiple sclerosis, Reynaud's syndrome, autoimmune thyroiditis, gastritis, Celiac Disease, Vitiligo, Hepatitis, primary biliary cirrhosis, inflammatory bowel disease, spondyloarthropathies, experimental autoimmune encephalomyelitis, immune neutropenia, juvenile onset diabetes, and immune responses associated with delayed hypersensitivity mediated by cytokines, T-lymphocytes typically found in tuberculosis, sarcoidosis, and polymyositis, polyarteritis, cutaneous vasculitis, pemphigus, pemphigold, Goodpasture's syndrome, Kawasaki's disease, systemic sclerosis, anti-phospholipid syndrome, and Sjogren's syndrome. In some embodiments the pemphigus is pemphigus vulgaris, pemphigus foliaceus or paraneoplastic pemphigus.

In one aspect the invention provides a method of treating or preventing an autoimmune disorder, the method comprising: administering any one of the antibodies provided herein, in combination with a second therapy for treating or preventing the disorder to a subject having the disorder or at risk of developing the disorder. In some embodiments the second therapy comprises intravenous Ig therapy; nonsteroidal anti-inflammatory drugs (NSAID); corticosteroids; cyclosporins, rapamycins, ascomycins, or their immunosuppressive analogs, e.g., cyclosporin A, cyclosporin G, FK-506, rapamycin, 40-O-(2-hydroxy)ethyl-rapamycin; cyclophosphamide; azathioprene; methotrexate; brequinar; FTY 720; leflunomide; mnizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; other immunomodulatory compounds, e.g. CTLA4Ig; or other adhesion molecule inhibitors, e.g., mAbs or low molecular weight inhibitors including selectin antagonists and VLA-4 antagonists.

In one aspect the invention provides a method of reducing the concentration of undesired antibodies in an individual comprising the steps of administrating to the individual a therapeutically effective dose of any one of the antibodies or antibody fragments provided herein. In some embodiments the antibody or a fragment thereof is administered in a pharmaceutically acceptable carrier. In some embodiments the individual is a human. In some embodiments the antibody or fragment thereof is administered with an adjuvant. In some embodiments the undesired antibody is natalizumab. In some embodiments the undesired antibody is non-self Human Leukocyte Antigen. In some embodiments the administered antibody or fragment thereof is administered in connection with organ transplant.

In one aspect the invention provides a method of reducing the binding of IgG to FcRn in an individual comprising the steps of providing an antibody or a fragment thereof which binds to human FcRn, is generated against the heavy chain of human FcRn or a fragment thereof, is a non-competitive inhibitor of IgG binding to human FcRn and does not bind β2-microglobulin; and administering the antibody or the fragment thereof to an individual in an amount sufficient to reduce the binding of IgG to FcRn in the individual. In some embodiments the individual has an autoimmune or alloimmune disease. In some embodiments the individual is an organ transplant recipient. In some embodiments the individual has been administered a therapeutic antibody. In some embodiments the autoimmune disease is immune thrombocytopenia. In some embodiments the autoimmune disease is immune pemphigus. In some embodiments the individual is a human. In some embodiments the antibody is administered at a dosage of 1 mg/kg to 2 g/kg. In some embodiments the antibody is administered at a dosage of 1 mg/kg to 200 mg/kg.

In one aspect the invention provides a method for suppressing the level of an IgG antibody in an individual comprising the steps of providing an antibody or a fragment thereof which binds to human FcRn, is generated against the heavy chain of human FcRn or a fragment thereof, is a non-competitive inhibitor of IgG binding to human FcRn and does not bind β2-microglobulin; and administering the antibody or the fragment thereof to an individual in an amount sufficient to suppress the level of an IgG antibody in an individual. In some embodiments the IgG antibody is a therapeutic IgG antibody. In some embodiments the therapeutic IgG antibody is natalizumab. In some embodiments n the IgG antibody is non-self Human Leukocyte Antigen. In some embodiments the method further comprises a plasma exchange step.

In one aspect, the invention relates to antibodies which inhibit the constant region of an IgG molecule from binding to FcRn. The invention thus relates to an antibody comprising at least one variable region that specifically binds a FcRn molecule epitope. In some embodiments, the antibodies of the invention bind to human FcRn. In other embodiments, the antibodies bind to rodent or monkey FcRn. Some exemplary antibodies of the invention include, e.g., 4B4.12, 3B3.11, 31.1, and 17D3.

In one aspect, the disclosure features an antibody (e.g., an isolated antibody) that includes a heavy chain (HC) immunoglobulin variable domain sequence and a light chain (LC) immunoglobulin variable domain sequence. The first and second immunoglobulin variable domain sequences form an antigen binding site that binds to FcRn (e.g., human FcRn). In one embodiment, the antibody has one or more of the following characteristics:

(a) the LC immunoglobulin variable domain sequence is at least 85% identical to a LC variable domain of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11, or one or more CDRs thereof;

(b) the HC immunoglobulin variable domain sequence is at least 85% identical to a HC variable domain of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11, or one or more CDRs thereof; and (c) the antibody binds an epitope that overlaps with an epitope bound by 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11.

In one embodiment, the antibody binds FcRn (e.g., human FcRn), e.g., in about pH range 5-8, e.g., with a dissociation constant ($K_D$) of less than 100, 50, 10, 5, 1, or 0.1 nM. In one embodiment, the antigen binding site specifically binds to human FcRn. As used herein, "specific binding" or "specifically binds" refers to the ability of a FcRn binding antibody to preferentially bind to human FcRn, with an affinity that is at least two-fold, 10-fold, 50-fold, 100-fold, or better (smaller $K_D$) than its affinity for binding to a non-specific antigen (e.g., actin, casein) other than FcRn. In one embodiment, the antibody binds human FcRn with a $k_{off}$ of less than 0.01, 0.001, 0.0001, 0.00001 s$^{-1}$.

In one embodiment, the antibody binds the extracellular domain of FcRn; for example, one of the alpha subunits of FcRn, i.e., the α1, α2, or α3 domain of the FcRn alpha chain. In one embodiment, the antibody does not bind the beta (β2M) subunit of FcRn, e.g., the antibody binds only the alpha subunit. In one embodiment, the antibody does bind to the beta subunit of FcRn, but, only when β2M is in association with the alpha subunit. For example, the antibody does not bind to either alpha or beta subunit unless both are present and correctly assembled into FcRn. In one embodiment, the antibody binds to the FcRn that contains both the alpha and beta subunits and is correctly assembled.

In one embodiment, the antibody modulates (e.g., inhibits) FcRn binding to an antibody/immunoglobulin constant region. For example, the antibody can have a $K_i$ of better than (e.g., numerically less than) 5 nM, 500 pM, 200 pM, 150 pM, 100 pM, or 75 pM, e.g., between 50 nM and 1 pM, or 200 pM and 5 pM.

In one embodiment, the antibody binds to FcRn and decreases or prevents FcRn binding to an antibody/immunoglobulin constant region. For example, the antibody can bind to FcRn (e.g., human FcRn) with an affinity ($K_D$) of better than (i.e., numerically smaller than) 1×10$^{-8}$ M. In one embodiment, the antibody is a Fab that binds to FcRn in a substantially pH independent or substantially pH dependent manner and with a $K_D$ in the range of about 3.0-82 nM at pH 6. In one embodiment, the antibody is a Fab that binds to FcRn in a substantially pH independent or substantially pH dependent manner and with a $K_D$ in the range of about 9.7-about 39.7 nM at pH 7.5. In one embodiment, the antibody is an IgG that binds to FcRn in a substantially pH independent or substantially pH dependent manner and with a $K_D$ in the range of about 0.409-about 29.5 nM, about 2.44-about 29.5 nM, about 0.13-about 1.03 nM, about 6.43-about 30.2 nM, about 0.2-about 2.87 nM, about 0.34-about 2.87 nM, or about 0.2-about 30.2 nM at pH 6. In one embodiment, the antibody is an IgG that binds to FcRn in a substantially pH independent or substantially pH dependent manner and with a $K_D$ in the range of about 0.675-24.2 nM, 2.1-24.2 nM, 0.158-10 nM, or about 2.04-about 80 nM at pH 7.5.

In one embodiment, the antibody inhibits the binding of FcRn to IgG-Fc with an IC$_{50}$ of less than 800 nM, 600 nM, or 300 nM, 200 nM, 100 nM, 1 nM, 50 pM at about pH 6. In one embodiment, the antibody is a Fab that inhibits the binding of FcRn to IgG-Fc in a substantially pH independent or substantially pH dependent manner and with an IC$_{50}$ in the range of about 13-754 nM or about 13-80 nM at pH 6. In one embodiment, the antibody is an IgG that inhibits the binding of FcRn in a substantially pH independent or substantially pH dependent manner and with an IC$_{50}$ in the range of about 1.2-36 nM, 36-120 nM, 120-562 nM, 1.5-5.4 nM, 5.4-50 nM, 51-161 nM at pH 6.

In one embodiment, the antibody is, e.g., a single chain antibody, a Fab, an sFab fragment, an F(ab')2, an Fd fragment, an Fv fragment, an scFv, or a dAb fragment.

In some embodiments, the antibody monospecific, e.g., a monoclonal antibody or recombinant antibody. The term "monospecific antibody" refers to an antibody that displays a single binding specificity and affinity for a particular target, e.g., epitope. This term includes a "monoclonal antibody" or "monoclonal antibody composition," which as used herein refer to a preparation of an antibody of a single molecular composition.

In one embodiment, the antibody is a recombinant or modified anti-FcRn antibody, e.g., a chimeric, a humanized, a deimmunized, or an in vitro generated antibody. The term "recombinant" or "modified" human antibody, as used herein, is intended to include all antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, deimmunized, in vitro generated antibodies, and may optionally include constant regions derived from human germline immunoglobulin sequences. In one embodiment, the antibody does not elicit an anti-globulin response in a human.

Also disclosed are antibodies (including full length antibodies or antigen-binding fragments thereof) that bind overlapping epitopes of, or competitively inhibit, the binding of the anti-FcRn antibodies disclosed herein to FcRn e.g., antibodies which bind overlapping epitopes of, or competitively inhibit, the binding of sFabs 532A-M0090-F09, M0084-B03, M0056-G05, M0084-B11, M0092-D02, M0055-G12, M0057-F02, M0062-C09, M0064-H04, M0073-E10, or M0090-F11 to FcRn. It is also possible to use a combination of anti-FcRn antibodies, e.g., two or more antibodies that bind to different regions of FcRn, e.g., antibodies that bind to two different epitopes on the extracellular domain of FcRn. Alternatively, a bispecific antibody can be used. A bispecific antibody is a molecule with two variable heavy and two variable light domains so that the single molecule embodies two specific binding capabilities; one or more of the variable domains or specificities can be of an antibody described herein and bind to FcRn.

In one embodiment, the anti-FcRn antibody (e.g., a full length antibody or antigen-binding fragment thereof) includes at least one light or heavy chain variable domain sequence (e.g., at least one light chain immunoglobulin and at least one heavy chain immunoglobulin). In some embodiments, each immunoglobulin includes a light or a heavy chain variable domain sequence having at least one, two or three complementarity determining regions (CDR's) substantially identical to a CDR from a light or heavy chain variable domain sequence of an antibody that interacts with FcRn, e.g., an sFab described herein, e.g., 532A-M0090-F09, M0084-B03, M0056-G05, M0084-B11, M0092-D02, M0055-G12, M0057-F02, M0062-C09, M0064-H04, M0073-E10, or M0090-F11.

In one embodiment, the antibody binds to FcRn using its antigen binding domain and also through its Fc region. In one embodiment, the antibody binds to FcRn using only its antigen binding domain. For example, the antibody does not include an Fc region or includes a modified Fc region that does not interact with FcRn. In one embodiment, the antibody binds to FcRn at least 1000-fold more tightly through its antigen-binding domains as through its Fc domains.

In one embodiment, the binding of the antibody to FcRn is substantially pH independent in the range of 2-10, of 4-9, of 5-8, of 6-8, or of 6-7.5. The term "pH independent" refers to the ability of the antibody to bind and/or to remain bound to FcRn at a pH in the range of 2-10, 4-9, 5-8, 6-8, or 6-7.5. The affinity may vary at the various pH values. In some embodiments, the $K_D$ is no higher than 200 nM, 50 nM, 10 nM, 1 nM or 100 pM at any value within the range. For example, the antibody can bind FcRn at pH 6 and remain bound at pH 7.5. In one embodiment, the binding of the antibody to FcRn is substantially pH dependent. The term "pH independent" refers to the ability of the antibody to bind/and or remain bound to FcRn at a first pH and the ability to bind or to remain bound to FcRn at a second pH, where the second pH is within a given number of pH units (e.g., 6, 5, 4, 3, 2, 1.5 units) of the first pH. For example, the antibody can bind FcRn at pH 6 and can also bind or remain bound to FcRn at pH 7.5. The term "pH dependent" refers to the ability of the antibody to bind/ and or remain bound to FcRn at a first pH and the lack of ability to bind or to remain bound to FcRn at a second pH, where the second pH is within a given number of pH units (e.g., 6, 5, 4, 3, 2, 1.5 units) of the first pH. For example, the antibody can bind FcRn at pH 6 and cannot bind or remain bound to FcRn at pH 7.5.

In one embodiment, the antibody preferentially binds human FcRn as compared to rat or monkey FcRn in a pH-dependent or pH-independent manner. In one embodiment, the antibody binds both human FcRn and the FcRn of a suitable experimental animal (e.g., rat or monkey) with affinities that differ by no more than two-, five- or ten-fold. In one embodiment, the antibody binds both human FcRn and the FcRn of a suitable experimental animal with $K_D \leq 5$ nM in the pH range of 6.0-7.5. In one embodiment, the antibody binds FcRn in endosomes or under endosomal conditions. For example, the antibody binds FcRn under acidic conditions, e.g., pH 6. In one embodiment, the antibody binds FcRn at pH 6, e.g., at least 1.5, 2, 5, 8, 10, 20, or 50-fold better than at pH 7.5. In one embodiment, the antibody releases FcRn at pH 7.5, e.g., at least 1.5, 2, 5, 8, 10, 20, or 50-fold more rapidly than at pH 6. In one embodiment, the antibody binds FcRn at pH 7.5, e.g., at least 1.5, 2, 5, 8, 10, 20, or 50-fold better than at pH 6. In one embodiment, the antibody releases FcRn at pH 6, e.g., at least 1.5, 2, 5, 8, 10, 20, or 50-fold more rapidly than at pH 7.5. In one embodiment, the antibody does not release FcRn at pH 7.5. In one embodiment, the antibody does not release FcRn at pH 6.

In one embodiment, the interaction with FcRn extends the half-life of the antibody. In one embodiment, the antibody causes the half-life of other IgG molecules to be diminished, e.g., at least 5, 10, 20, 40, 50, 60, 70, 80, or 90%. For example, a reduction of 90% would change the half-life of an antibody from 20 days to 2 days.

In one embodiment, the antibody causes an amelioration of symptoms associated with an autoimmune disorder when administered to a subject. For example, the antibody can alleviate or decrease the severity of symptoms such as joint swelling, pain, or stiffness; levels of circulating antibodies such as auto-antibodies; achy joints (arthralgia); fever; extreme fatigue; skin rashes; anemia; pain in the chest or deep breathing; butterfly-shaped rash across the cheeks and nose; photosensitivity; hair loss; seizures; mouth or nose ulcers; Raynaud's phenomenon; mild erythema; neuropsychiatric manifestations; thrombocytopenia; and pleural effusion.

In one embodiment, the HC and LC variable domain sequences are components of the same polypeptide chain, that is they are part of a single-chain antibody. In one embodiment, HC and LC variable domain sequences are components of different polypeptide chains.

In one embodiment, the antibody is a full-length antibody. For example, the antibody can be a human or humanized antibody and/or can be non-immunogenic in a human. In one embodiment, the antibody comprises a human antibody framework region. In one embodiment, the antibody comprises an Fc domain.

In one embodiment, the HC variable domain sequence comprises a variable domain sequence of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11 and the LC variable domain sequence comprises a variable domain sequence of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11. In one embodiment, the antibody binds to an FcRn epitope bound by 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11. In one embodiment, the antibody competes with 532A-M0090-F09, M0084-B03, M0056-G05, M0084-B11, M0092-D02, M0055-G12, M0057-F02, M0062-C09, M0064-H04, M0073-E10, or M0090-F11 for binding to FcRn.

In one aspect, the invention relates to a method of making a monoclonal antibody comprising: immunizing a rodent with FcRn protein or at least one fragment thereof or with a polynucleotide sequence encoding a FcRn molecule or fragment thereof; obtaining B cells from said rodent; fusing said B cells with a myeloma cell line to obtain a hybridoma cell; culturing said hybridoma cell under conditions such that it secretes a monoclonal antibody, wherein said antibody comprises at least one variable region, which specifically binds to a FcRn molecule, wherein said FcRn molecule comprises a domain capable of binding at least a portion of an IgG constant region, wherein the binding of said antibody to said FcRn molecule inhibits said binding of the portion of an IgG constant region to said FcRn molecule; and isolating the antibody.

In one aspect, the disclosure features a method of identifying a antibody that binds to FcRn, e.g., human FcRn, and includes: providing an FcRn antigen or a fragment thereof; providing a library of antibodies, e.g., a display library; and identifying a member present in the library that binds to the FcRn antigen, where each member of the library displays a heterologous antibody component on its surface and each member includes a nucleic acid encoding the heterologous antibody component, the heterologous antibody component being a member of a set of diverse antibody components. The method can include isolating a nucleic acid molecule from the identified member and the nucleic acid molecule encodes the polypeptide that specifically binds to the FcRn antigen. In one embodiment, the antibody specifically binds human FcRn.

In one embodiment, the library is a phage library, e.g., a phage display library. In one embodiment, the identified phage is eluted using a competitor ligand, e.g., an IgG Fc that binds to FcRn and/or with a competing anti-human FcRn antibody.

In another aspect, the disclosure features a method of detecting an FcRn in a sample, the method includes: contacting the sample with a FcRn binding antibody (e.g., a antibody described herein) and detecting an interaction between the antibody and an FcRn if present. In one embodiment, the antibody includes a detectable label such as a fluorescent tag (e.g. bodipy, fluorescein-5-isothiocyanate, rhodamine, and peroxidase or alkaline phosphatase that are detected in the presence of chromogenic or chemiluminescent substrates.

In one aspect, the disclosure features a method of modulating an FcRn activity, the method includes: contacting an FcRn with a FcRn binding antibody (e.g., a antibody described herein), thereby modulating the activity (e.g., binding to IgG Fc) of the FcRn. In one embodiment, the FcRn is in a human subject; the FcRn can be in an epithelial or endothelial cell or in the blood (e.g., soluble in the blood or in cells circulating in the blood) of a human subject. In one embodiment, the antibody prevents binding of the FcRn to a substrate, e.g., an endogenous substrate such as IgG Fc and/or serum albumin. In one embodiment, the FcRn is in an epithelial or endothelial cell endosome.

In one aspect, the disclosure features a method of treating, preventing, and/or modulating symptoms of a disorder, e.g., an autoimmune disorder or a disorder associated with aberrant FcRn activity. The method includes: administering a FcRn binding antibody (e.g., antibody described herein) to a subject, e.g., a subject having the disorder or at risk of developing the disorder. In one embodiment, the ligand is administered in an amount and/or for a time sufficient to modulate the symptoms of the disorder.

In one embodiment, the autoimmune disorder is a disorder selected from the group consisting of: rheumatoid arthritis (RA), systemic lupus erythematosus (SLE), myasthenia gravis (MG), Graves Disease, idiopathic thrombocytopenia purpura (ITP), Guillain-Barre Syndrome, autoimmune myocarditis, membrane glomerulonephritis, diabetes mellitus, Type I or Type II diabetes, multiple sclerosis, Reynaud's syndrome, autoimmune thyroiditis, gastritis, celiac disease, vitiligo, hepatitis, primary biliary cirrhosis, inflammatory bowel disease, immune neutropenia, spondyloarthropathies, experimental autoimmune encephalomyelitis, juvenile onset diabetes, and immune responses associated with delayed hypersensitivity mediated by cytokines, T-lymphocytes typically found in tuberculosis, sarcoidosis, and polymyositis, polyarteritis, cutaneous vasculitis, pemphigus, pemphigold, Goodpasture's syndrome, Kawasaki's disease, systemic sclerosis, anti-phospholipid syndrome, and Sjogren's syndrome.

In one embodiment, the antibodies of the invention may be used to inhibit the transport of IgG across the blood-brain barrier. In another embodiment, the antibodies of the invention may be used to treat brain tumors or Alzheimer's disease.

In one embodiment, the antibody decreases the half-life of endogenous IgG. In one embodiment, the autoimmune disorder is characterized by unwanted circulating IgG, e.g., unwanted circulating pathogenic IgG.

In one aspect, the disclosure features a method of detecting FcRn in a subject, the method includes: administering a FcRn binding antibody (e.g., antibody described herein) that includes a detectable label, to a subject; and detecting the label in the subject. The method can include imaging the subject, e.g., using tomography, e.g., MRI.

In one aspect, the disclosure features a method of modulating the half life/levels of circulating IgG, the method includes: identifying a subject, e.g., a human, in need of modulated circulating IgG half life/levels; and administering a FcRn binding antibody (e.g., antibody described herein) to the subject in amount effective to modulate the half life/levels of circulating IgG in the subject. In one embodiment, the method reduces circulating IgG half life/levels. In one embodiment, the antibody is administered to decrease the half life/levels of circulating IgG and in combination with another anti-autoimmune disorder agent or therapy. The combination of the administration of the FcRn antibody and the other anti-autoimmune disorder agent or therapy may result in a decrease in the level of other anti-autoimmune disorder agent or therapy needed to modulate or reduce the half life/level of circulating IgG.

In another aspect, the disclosure features an isolated nucleic acid that includes a first sequence that encodes a first polypeptide that includes a sequence at least 80, 85, 90, 92, 94, 95, 96, 97, 98, 99, or 100% identical to the sequence of a first variable domain sequence of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11, or a sequence that hybridizes (e.g., under stringent conditions) to a nucleic acid encoding the sequence of a variable domain of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11. In one embodiment, the nucleic acid further includes a second sequence that encodes a second polypeptide that includes a second variable domain sequence (of a corresponding variable domain), e.g., a sequence at least 80, 85, 90, 92, 94, 95, 96, 97, 98, 99, or 100% identical to the sequence of a second variable domain sequence of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11, or a sequence that hybridizes (e.g., under stringent conditions) to a nucleic acid encoding the sequence of a variable domain of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11. In one embodiment, the nucleic acid further includes regulatory sequences (e.g., a promoter sequence, an untranslated 5' region, and an untranslated 3' region) and/or vector sequences. For example, the nucleic acid constitutes a vector.

In still another aspect, the disclosure features a host cell that can express an antibody. The host cell includes one or more nucleic acids that collectively include: (1) a first sequence that encodes a first variable domain sequence that includes a sequence at least 80, 85, 90, 92, 94, 95, 96, 97, 98, 99, or 100% identical to the sequence of a first variable domain sequence of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11, or a sequence that hybridizes (e.g., under stringent conditions) to a nucleic acid encoding the sequence of a variable domain of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11 and (2) a second sequence that encodes a second variable domain sequence that includes a second variable domain sequence (of a corresponding variable domain), e.g., a sequence at least 80, 85, 90, 92, 94, 95, 96, 97, 98, 99, or 100% identical to the sequence of a second variable domain sequence of 3B3.11, 31.1, 532A-M0090-F09, M0084-B03, M0056-G05, M0084-B11, M0092-D02, M0055-G12, M0057-F02, M0062-C09, M0064-H04, M0073-E10, or M0090-F11, or a sequence that hybridizes (e.g., under stringent conditions) to a nucleic acid encoding the sequence of a variable domain of 532A-M0090-F09, M0084-B03, M0056-G05, M0084-B11, M0092-D02, M0055-G12, M0057-F02, M0062-C09, M0064-H04, M0073-E10, or M0090-F11.

In one aspect, the disclosure features a method of treating or preventing an autoimmune disorder, the method comprising: administering a FcRn binding antibody (e.g., a antibody described herein), e.g., in combination with a second therapy, to a subject having an autoimmune disorder or at risk of developing the disorder. For example, the second therapy can be a therapy suitable for treating or preventing the disorder. In one embodiment, the second therapy can include: intravenous Ig therapy; nonsteroidal anti-inflammatory drugs (NSAID); corticosteroids; cyclosporins, rapamycins, ascomycins, or their immunosuppressive analogs, e.g. cyclosporin A, cyclosporin G, FK-506, rapamycin, 40-O-(2-hydroxy)ethyl-rapamycin; cyclophosphamide; azathioprine; methotrexate;

brequinar; FTY 720; leflunomide; mizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; other immunomodulatory compounds, e.g. CTLA4Ig; or other adhesion molecule inhibitors, e.g. mAbs or low molecular weight inhibitors including selectin antagonists.

In another aspect, the disclosure features a method of treating a fetus, the method includes: conjugating a small molecule or macromolecular drug, e.g., an antibiotic or vaccine (e.g., viral vaccine), to a FcRn binding antibody; and administering the conjugate to a pregnant woman who bears the fetus in utero. In one embodiment, the fetus has a disorder or is at risk for a disorder. Exemplary disorders include an immunological disorder (e.g., an autoimmune disorder, a metabolic disorder, or an infectious disorder, e.g., a bacterial or viral infection, e.g., an enteric infection (e.g., *Helibacter pylori* infection).

In another aspect, the disclosure features a method of treating an infant, the method comprising: conjugating a small molecule or macromolecular drug to an antibody that binds to FcRn, e.g., a antibody described herein; and introducing the conjugated antibody into breast milk. The breast milk can be administered to the infant. In one embodiment, the conjugated antibody is administered to a woman and the woman is providing breast milk to the infant, directly, e.g., nursing, or indirectly.

Although the invention is discussed primarily in terms of a preferred embodiment of antibodies, one of ordinary skill in the art will readily recognize that binding proteins or ligands other than antibodies are within the scope of the disclosure.

The results were expressed as percentage of Synagis remaining when compared to the level of Synagis before mAB injection.

Figure 16:
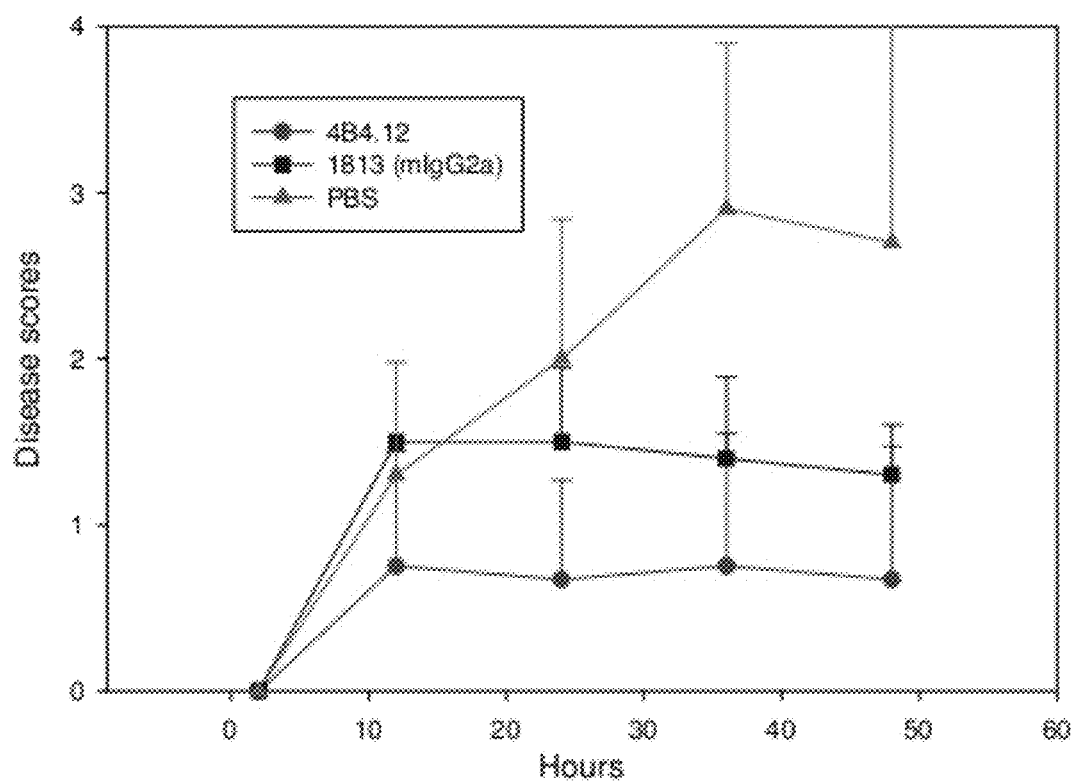

FIG. 16 depicts a time-course of the effect of treatment with either mAb 4B4.12, the isotype control, mIgG2a (1813), or PBS on the severity of the symptoms of experimental autoimmune myasthenia gravis (EAMG). The severity of the disease was assessed by the assignment of a grade from zero to four of increasingly severe symptoms as follows: 0, no symptoms; 1, weak grip, fatigability and sometimes wheezing; 2, general weakness, hunched posture at rest, decreased body weight, tremors; 3, severe weakness, moribund; and 4, death.

Figure 17:
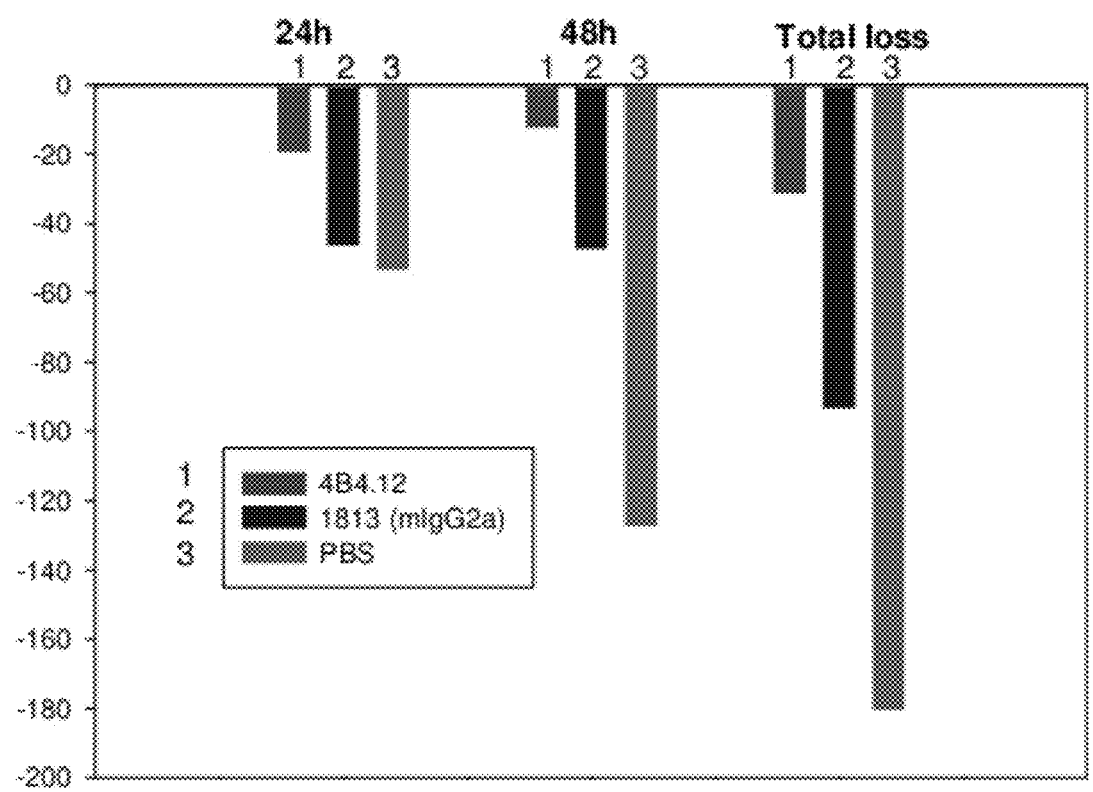

FIG. 17 depicts the effect of treatment with either mAb 4B4.12, the isotype control, mIgG2a (1813), or PBS on weight loss, reported in grams (as depicted on the y-axis) as a result of experimental autoimmune myasthenia gravis (EAMG).

Figure 18:
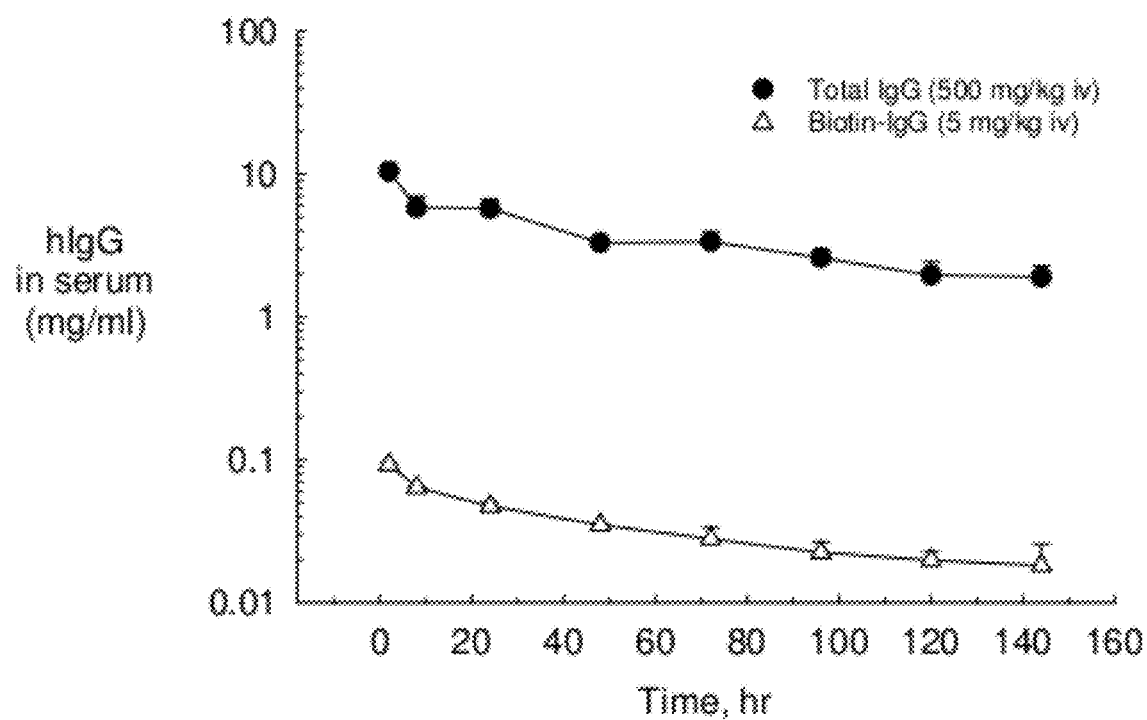

FIG. 18 depicts a comparison of the clearance kinetics of Biotinylated human IgG (Biotin-hIgG) versus unlabeled human IgG (hIgG) for Tg32B mice (hFcRn+/+, hβ2M+/+, mFcRn−/−, mβ2M−/−). The animals were intravenously (IV) injected with 5 mg/kg of biotinylated human IgG (Synagis) and 495 mg/kg of unlabeled hIgG. Sera were collected at the time-points shown in the figure and serum Biotin-hIgG concentrations were determined using Avidin plates (Pierce Chemicals) and unlabeled hIgG was measured by ELISA.

Figure 19:
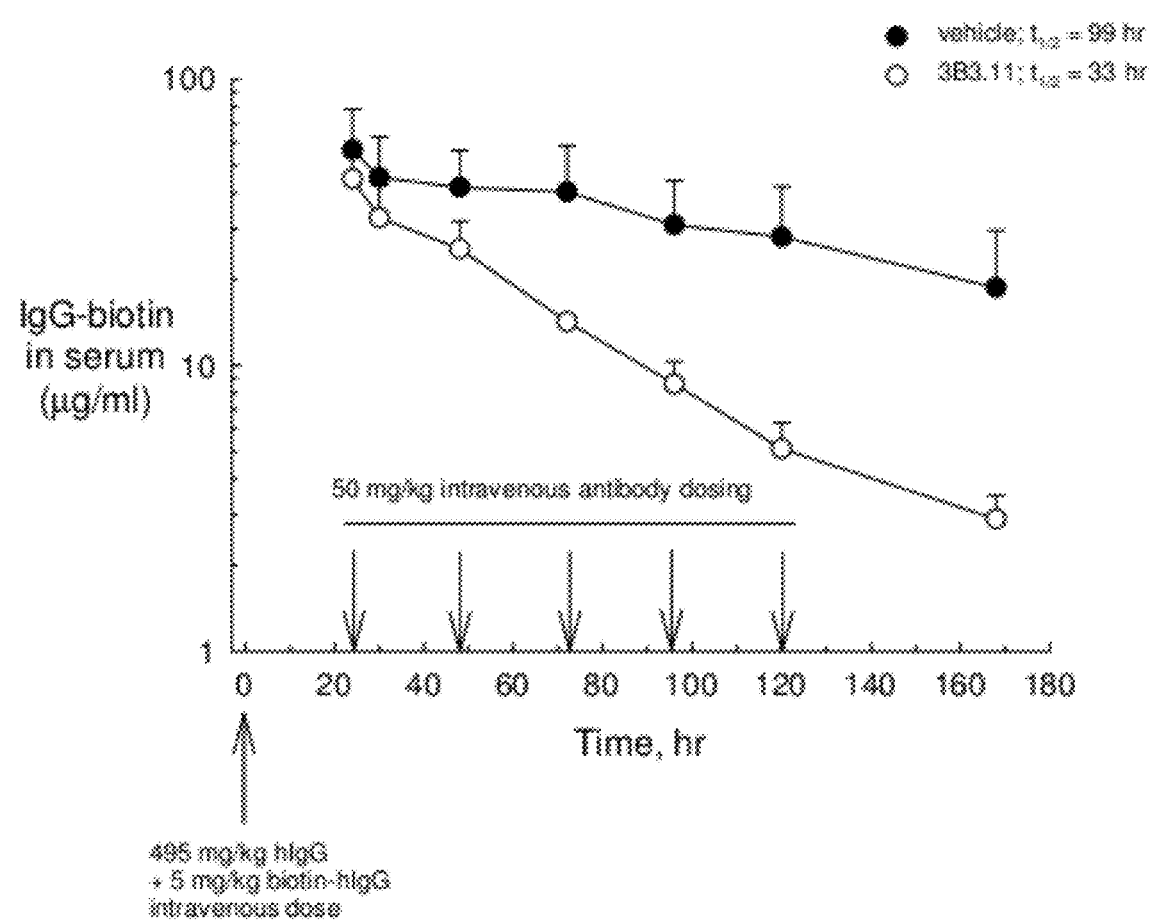

FIG. 19 depicts the clearance kinetics of Biotinylated human IgG (Biotin-hIgG) for Tg32B mice (hFcRn+/+, hβ2M+/+, mFcRn−/−, mβ2M−/−) following treatment of the animals with mAb 3B3.11. The animals were intravenously (IV) injected with 5 mg/kg of biotinylated human IgG (Synagis) and 495 mg/kg of unlabeled hIgG After 24 hours, daily IV injections of 50 mg/kg of mAb 3B3.11 were initiated and then continued for a period of 5 days. Sera were collected at the time-points shown in the figure and serum Biotin-hIgG concentrations were determined using Avidin plates (Pierce Chemicals).

Figure 20:
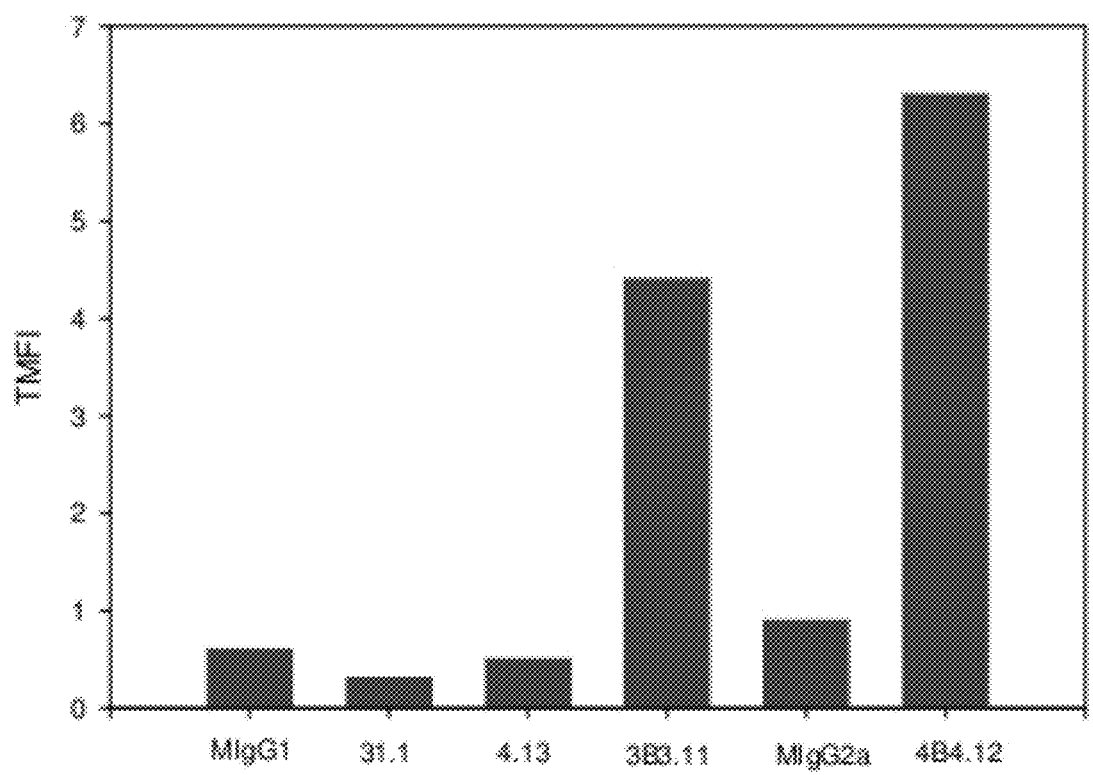

FIG. 20 depicts a bar graph from a FACS analysis that was performed to determine the binding of mAb 3B3.11, mAb 4.13, mAb 31.1, mAb 4B4.12, and mAb 15B6.1 to COS 1 cells transfected with monkey FcRn/β2M. The results are expressed as TMFI.

Figure 21:
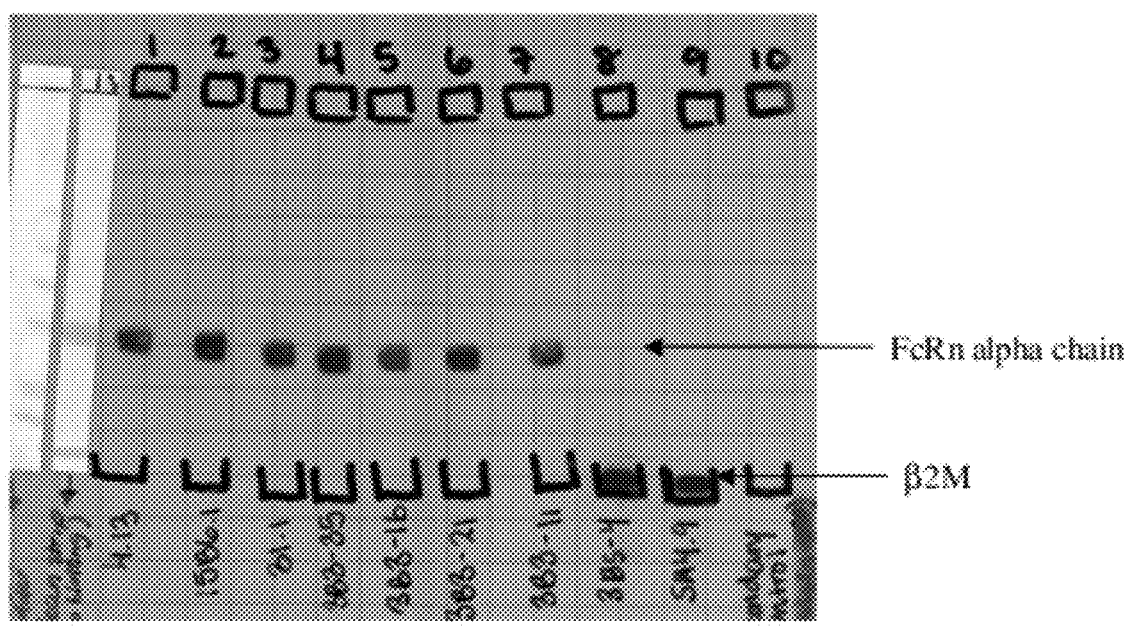
Figure 22A:
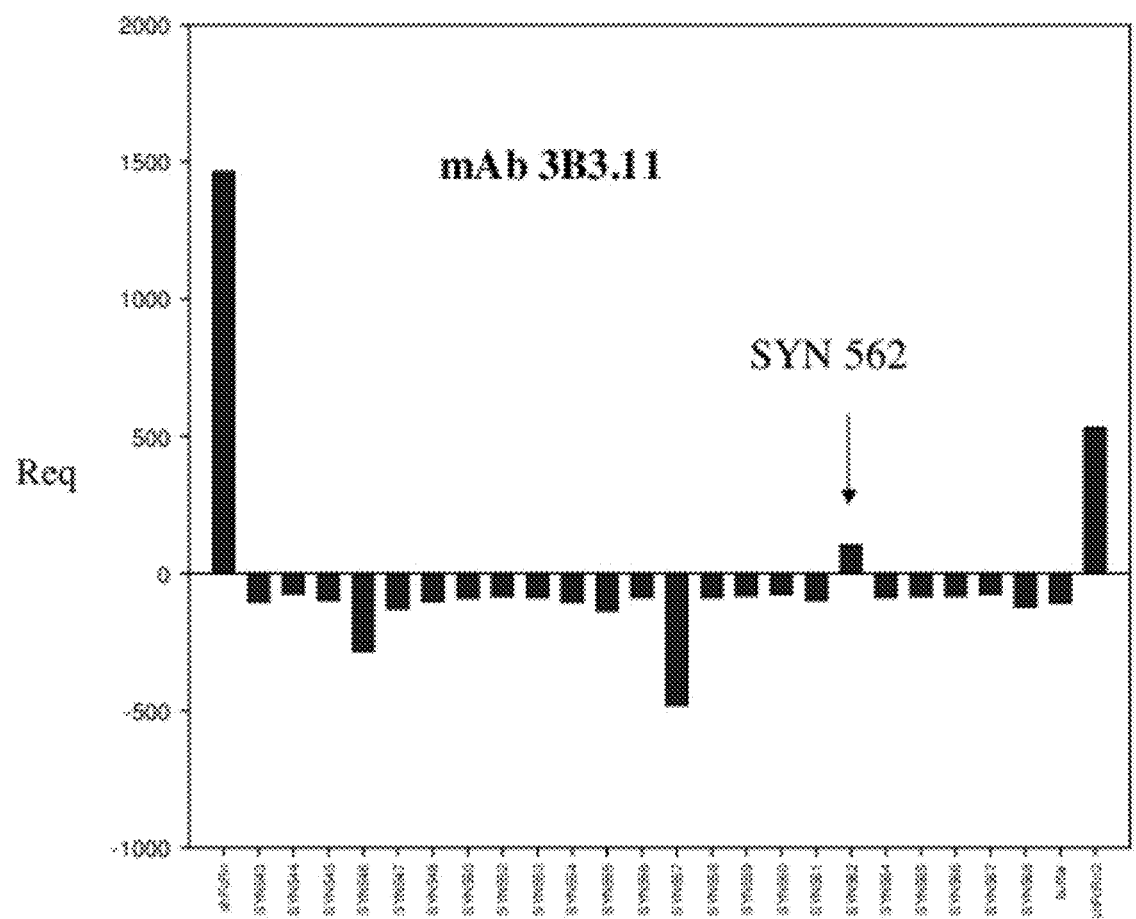
Figure 22B:
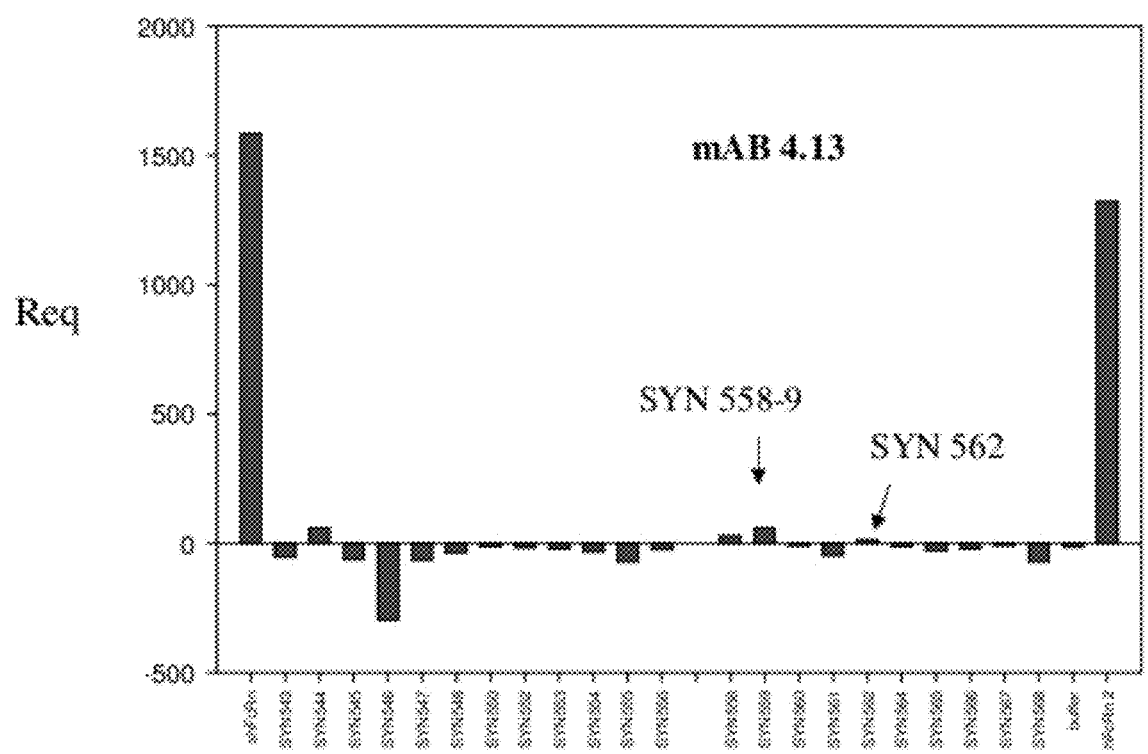
Figure 22C:
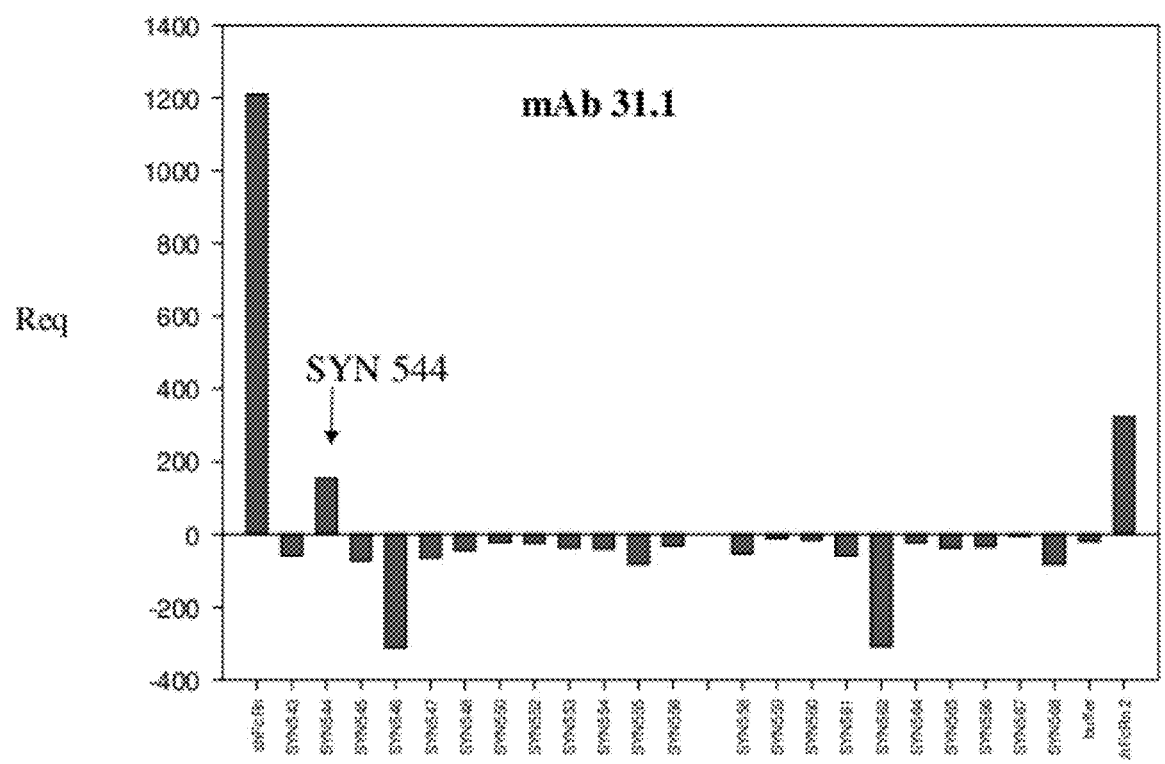
Figure 22D:
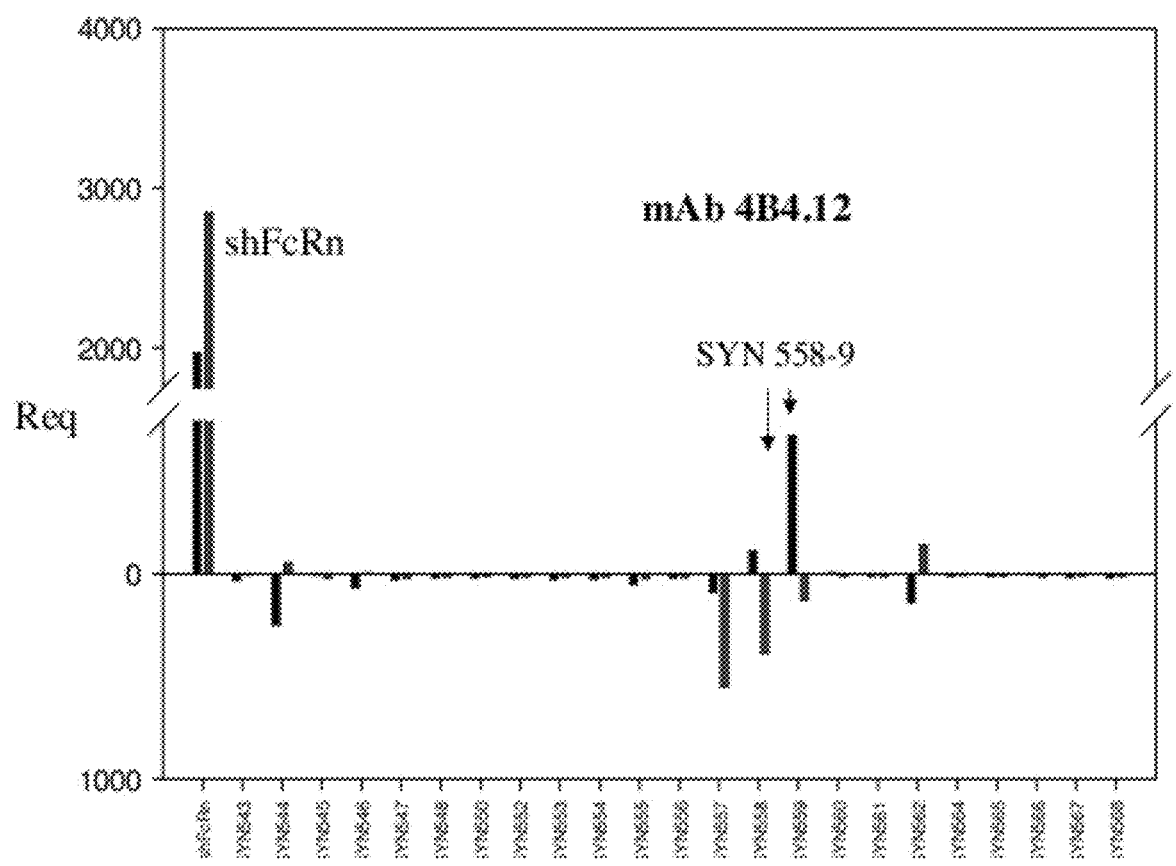

FIG. 21 depicts a Western blot that was performed to determine the specific binding of mAB3B3.11, 15B6.1, 4.13, and 31.1 to hFcRn alpha chain and the specific binding of mAb 3B5.4 and 5A4.9 to β2M.

FIG. 22 depicts Biacore epitope analysis that was performed to determine the epitopes these mABs recognize.

Figure 23:
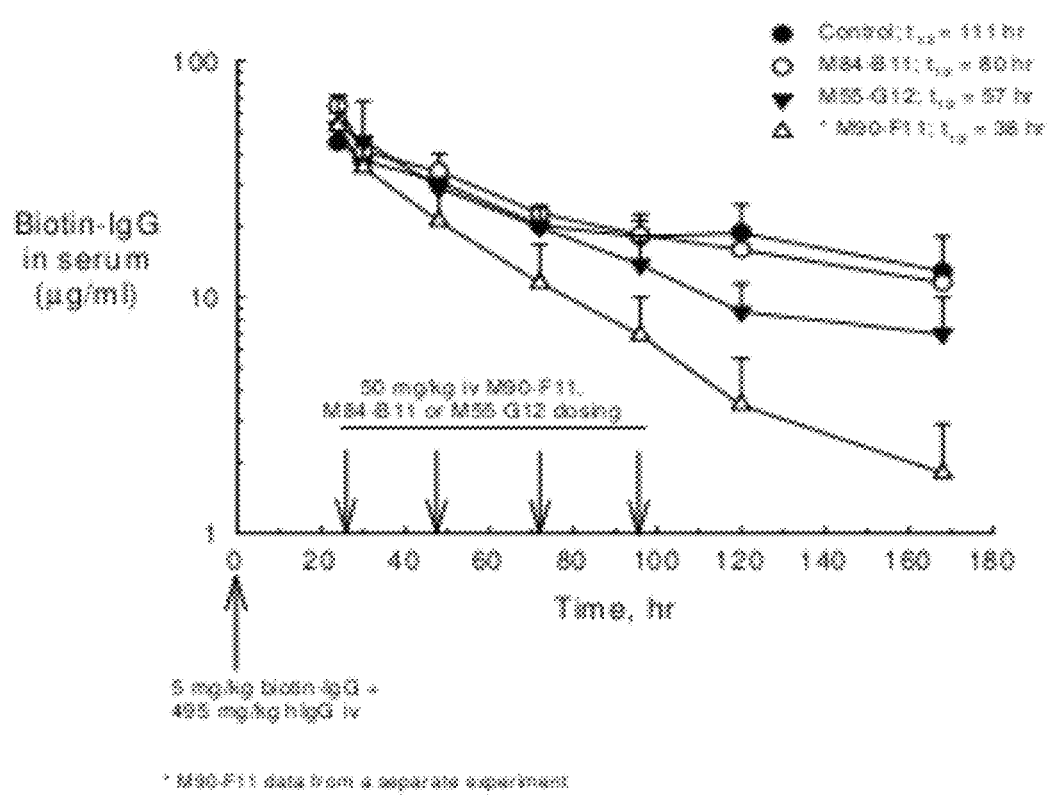

FIG. 23 depicts the effects of four consecutive daily intravenous doses of M90-F11, M84-B11 and M55-G12 on Biotin-IgG Catabolism in TG32B mice.

Figure 24:
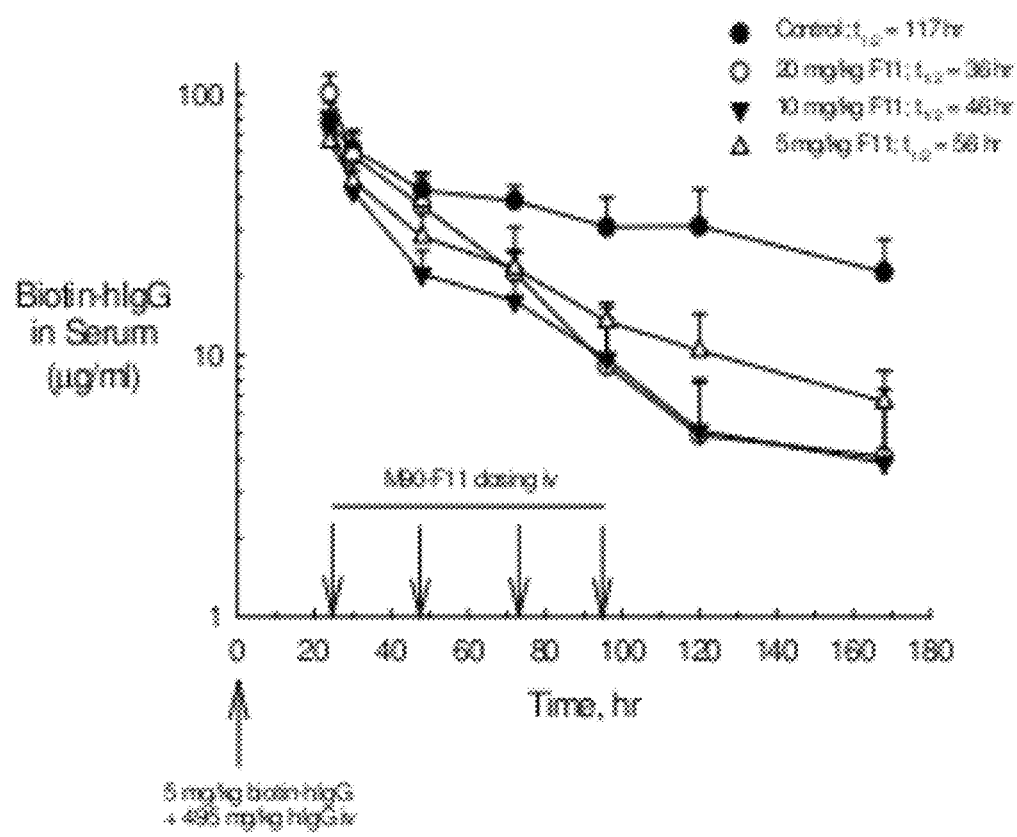

FIG. 24 depicts a dose response of M90-F11 on hIgG catabolism in hFcRn Tg mice (four consecutive daily intravenous doses).

Figure 25:
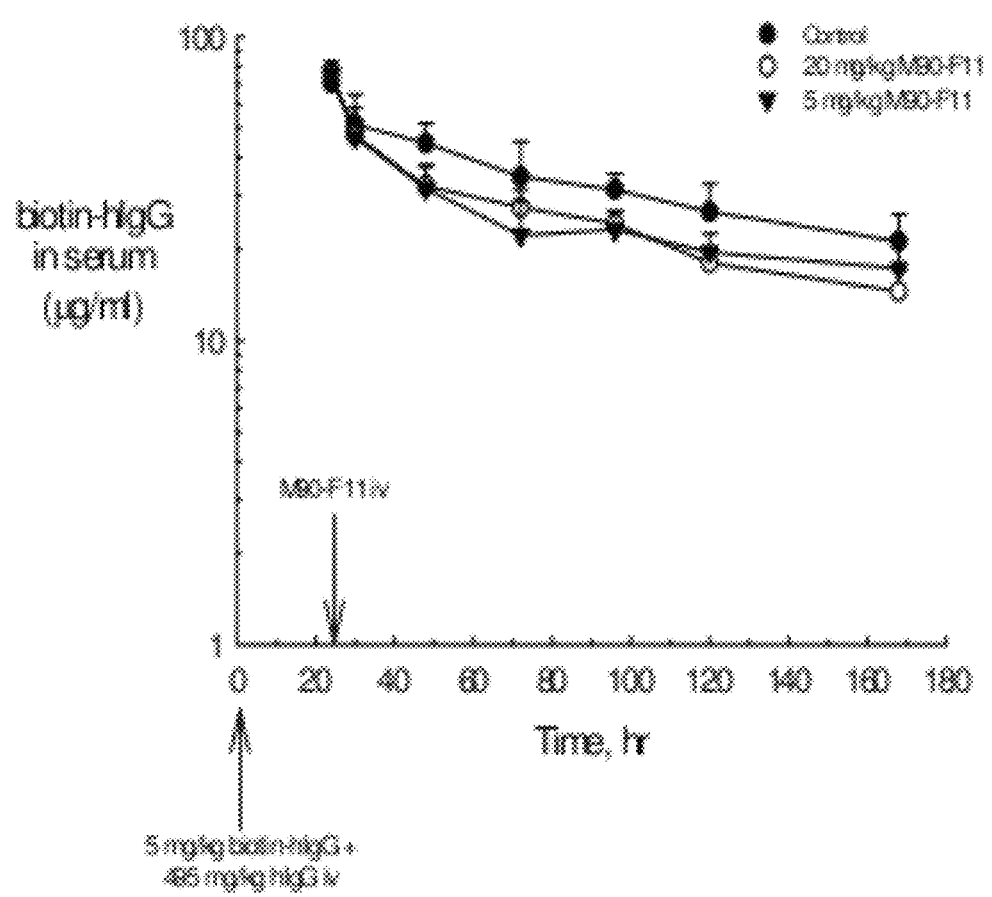

FIG. 25 depicts a single dose response of M90-F11 on hIgG catabolism in hFcRn Tg mice.

Figure 26:
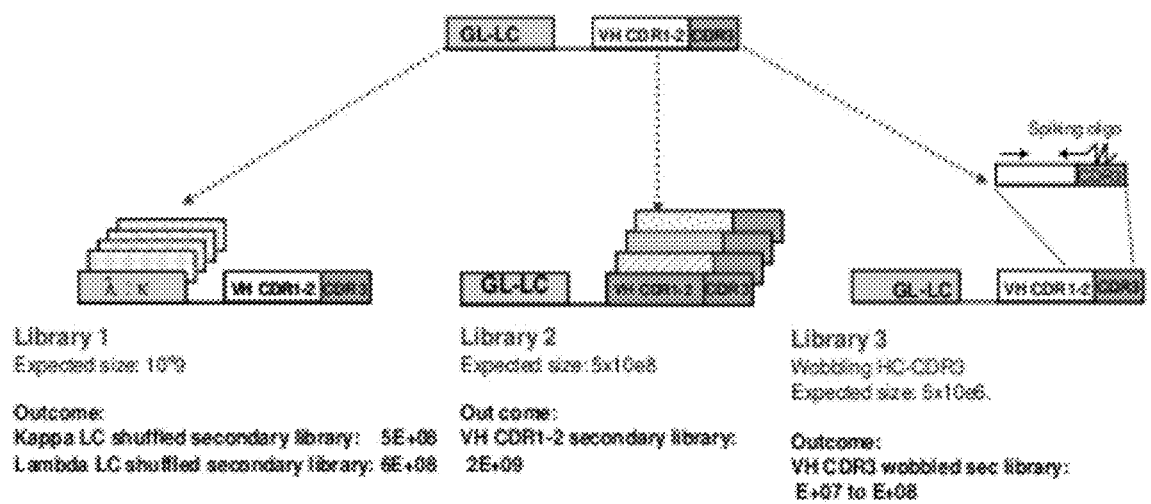

FIG. 26 depicts approaches used to affinity mature the germlined M90-F11.

Figure 27:
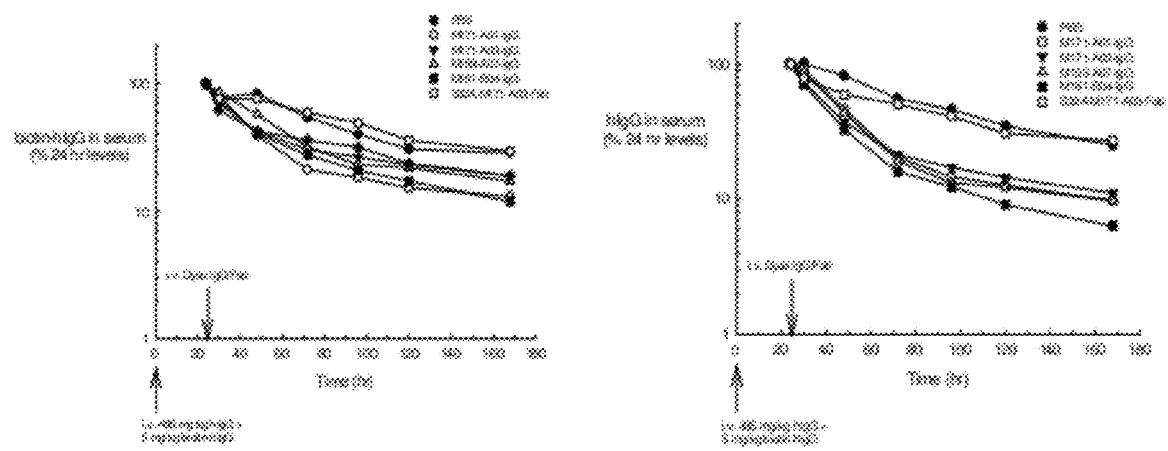

FIG. 27 depicts the effect of affinity matured IgG and soluble FAB in accelerating the hIgG catabolism in Tg32B mice at a 20 mg/kg Intravenous Dose (Biotin IgG & Total IgG).

Figure 28:
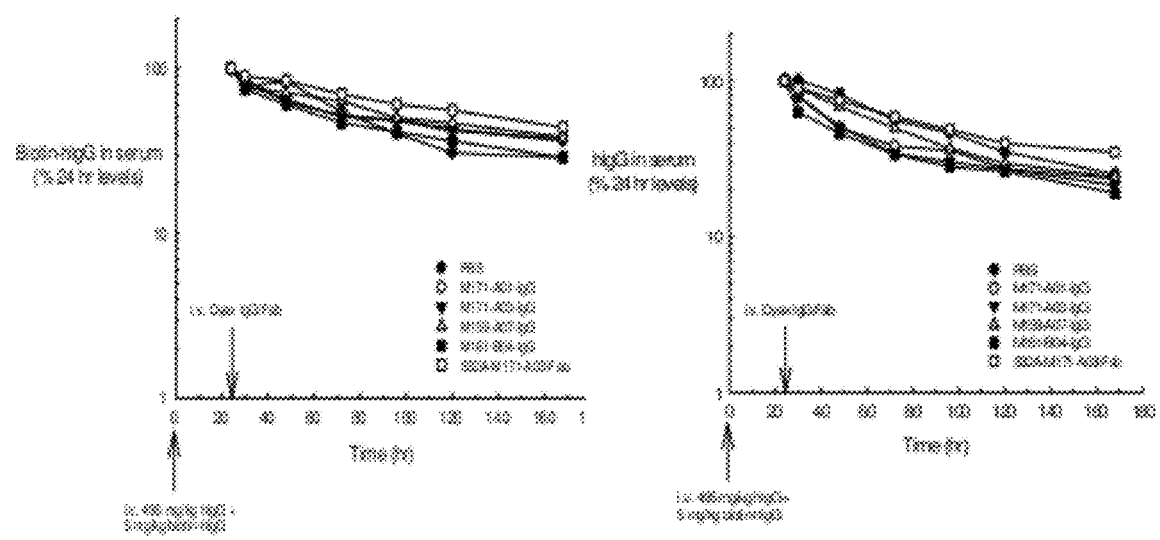

FIG. 28 depicts the effect of affinity matured IgG and soluble FAB in accelerating the hIgG catabolism in Tg32B mice at a 5 mg/kg intravenous dose (Biotin IgG & Total IgG).

FIG. 29 depicts M90-F11 germline changes (highlighted in bold) introduced into the light chain but not in the heavy chain.

FIG. 30 depicts allotype variation of IgG

FIG. 31 depicts the effect of intravenously administered anti-FcRn antibodies on the catabolism of hIgG in Tg32B Mice.

Figure 32:
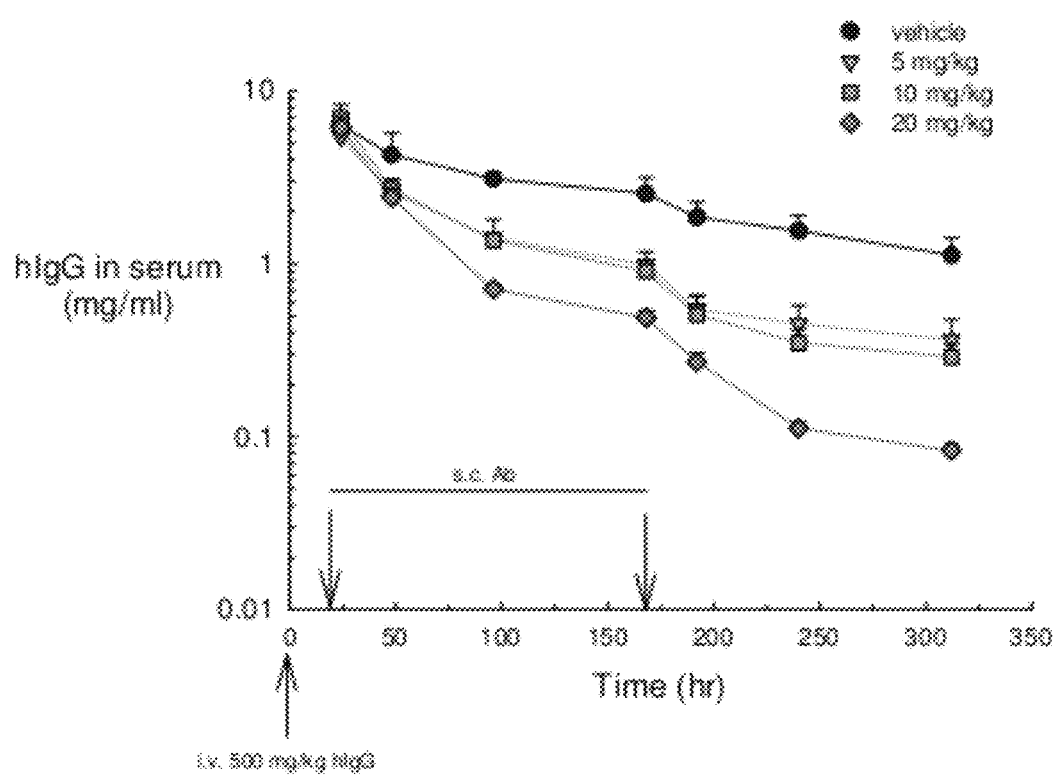

FIG. 32 depicts the effect of subcutaneously administered M161-B04 (DX2504) anti-FcRn antibody on the catabolism of hIgG in Tg32B Mice.

FIG. 33 depicts the effect of anti-FcRn antibodies on the catabolism of hIgG in cynomolgus monkeys. FIG. 33A depicts the times at which a blood sample was taken. FIG. 33B depicts the total serum IgG level when no anti-FcRn antibody M161-B04 was administered.

FIG. 34 depicts the effect of intravenously (FIG. 34A) and subcutaneously (FIG. 34B) administered M161-B04 anti-FcRn antibody at 5 mg/kg in monkeys. The data for individual monkeys are shown.

FIG. 35 depicts the effect of intravenously (FIG. 35A) and subcutaneously (FIG. 35B) administered M161-B04 anti-FcRn antibody at 20 mg/kg in monkeys. The data for individual monkeys are shown.

Figure 36:
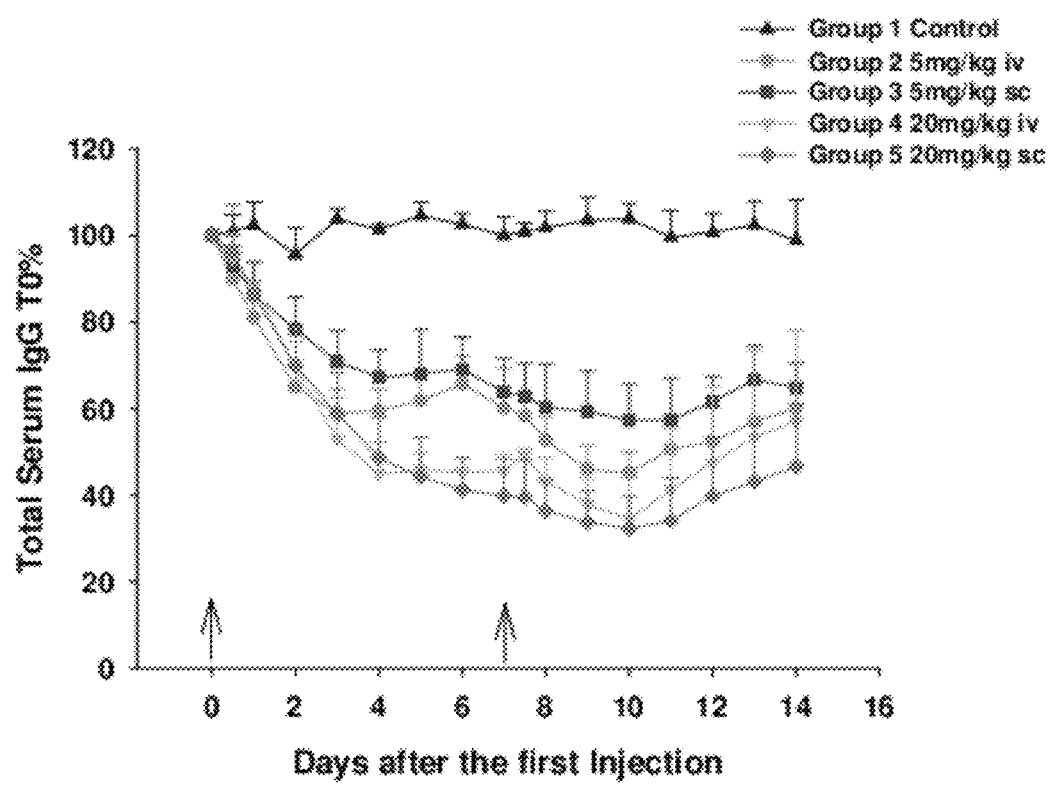

FIG. 36 depicts the effect of intravenously and subcutaneously administered M161-B04 anti-FcRn antibody at various concentrations in monkeys (data normalized on the pre-dose).

Figure 37:
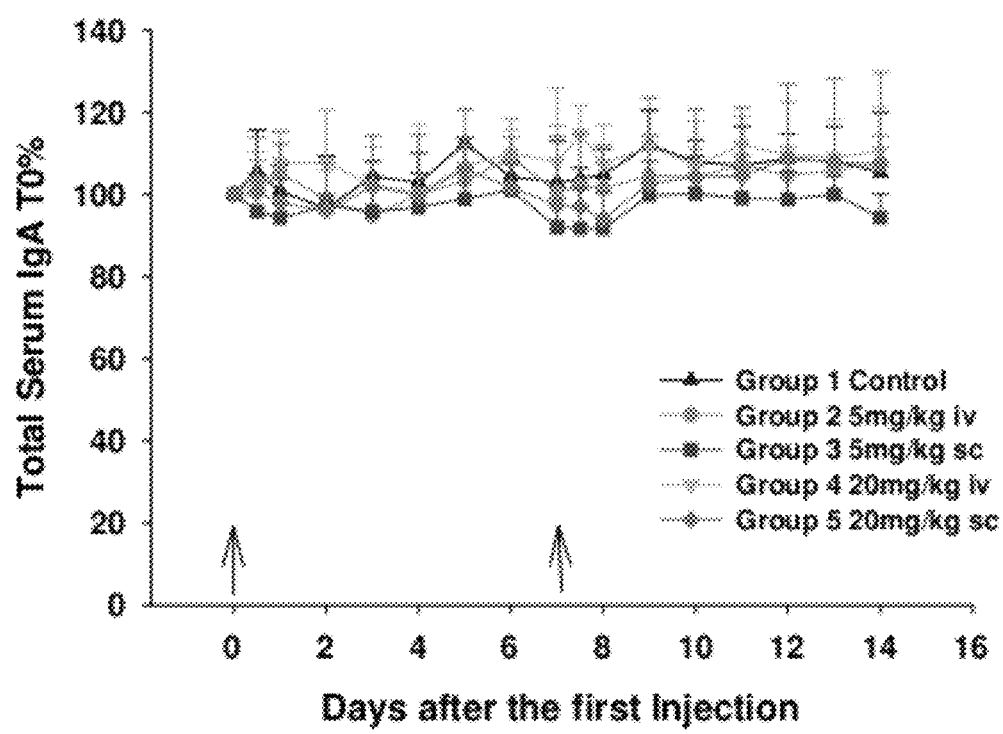
Figure 37:
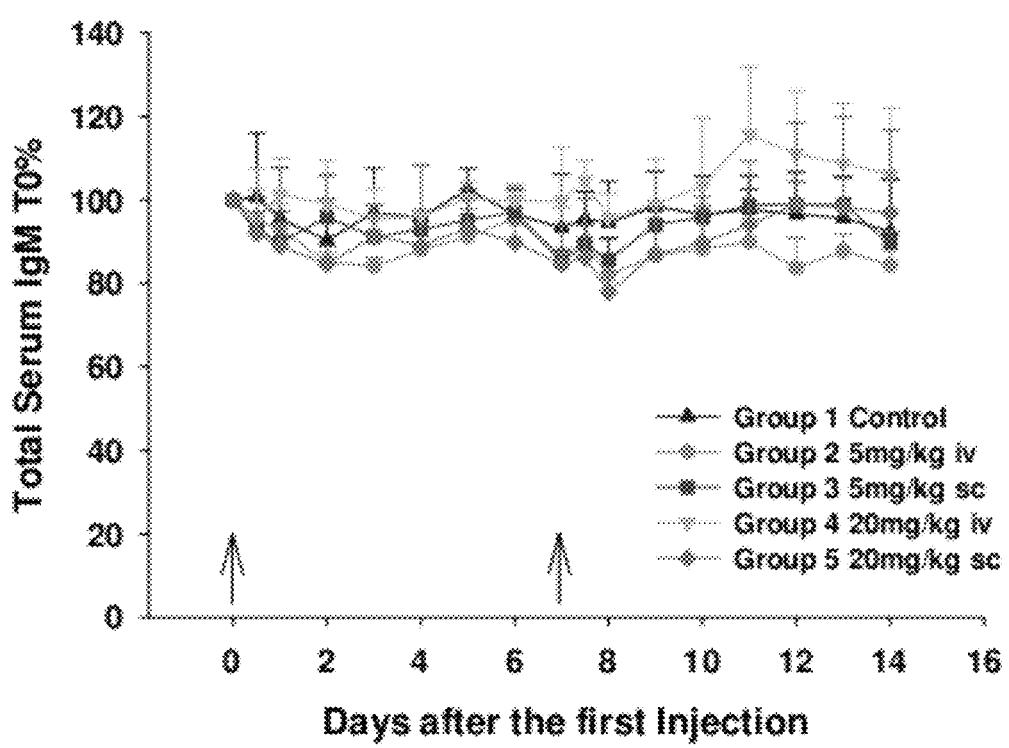
Figure 37:
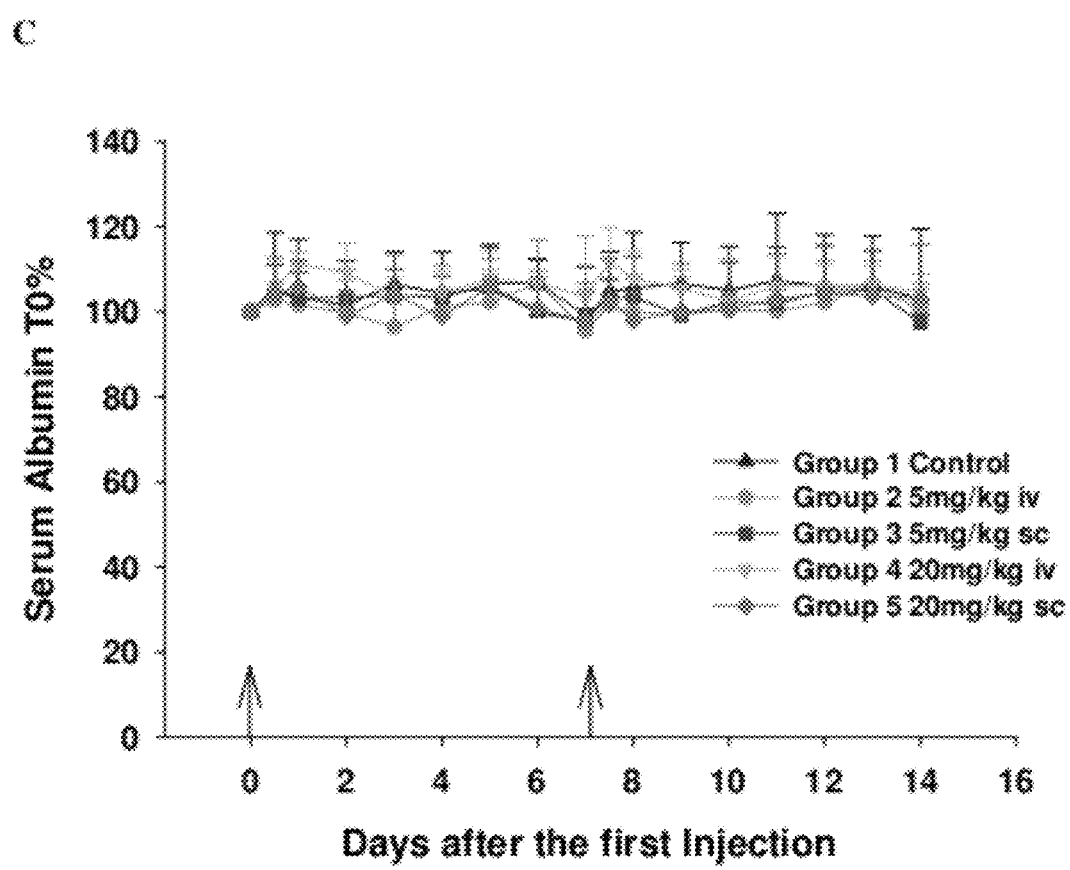

FIG. 37 depicts the effect of intravenously and subcutaneously administered M161-B04 anti-FcRn antibody on the concentration of serum IgA (FIG. 37A), serum IgM (FIG. 37B) and serum albumin (FIG. 37C) in monkeys (data normalized on the pre-dose).

FIG. 38 depicts DX-2504 sequences and alignments thereof.

DETAILED DESCRIPTION

In normal circumstances, FcRn can extend the half-life of circulating IgG. Antibodies that bind to FcRn can be used to modulate FcRn function, for example, by preventing interaction with IgG. In particular, antibodies that block FcRn interaction with IgG can be used to reduce the half-life of IgG molecules.

These antibodies and related strategies can be used to treat and even prevent antibody-mediated autoimmune disorders such as, multiple sclerosis, inflammatory bowel disease, rheumatoid arthritis (RA), and systemic lupus erythematosus (SLE), or another autoimmune disorder described herein. An antagonistic anti-rat FcRn monoclonal antibody (mAb)1G3 successfully prevented Experimental Autoimmune Myasthenia Gravis (EAMG) in a rat passive model at a dose of 30 mg/kg; that is about 100 fold lower than the intravenous IgG (IVIG) used in treatment of MG, SLE, and ITP. Further, FcRn-deficient mice genetically predisposed to develop autoimmune disorder such as lupus or arthritis have significant reduction in severity of the disease. Thus, anti-human FcRn blocking antibodies have therapeutic potential for treatment of autoimmune disorders in humans.

This disclosure further provides, inter alia, human antagonistic anti-human FcRn antibodies that are available for the treatment of autoimmune disorders and reduction of circulating levels of IgGs. Also disclosed is the identification of high affinity soluble Fabs (sFab) with the ability to bind through the antigen binding domain and block the interaction between IgG-Fc and human FcRn or rat FcRn (as assessed in both soluble protein and live cell binding assays using a cell line engineered to overexpress human FcRn or rat FcRn). The sFabs can bind and block in a pH independent fashion or in a pH-dependent fashion, e.g., at an acidic pH such as pH 6. The sFabs can be converted to IgG antibodies.

Definitions

The term "binding protein" refers to a protein that can interact with a target molecule. This term is used interchangeably with "ligand." An "FcRn-binding protein" or "FcRn-binding ligand" refers to a protein that can interact with an FcRn, and includes, in particular, proteins that preferentially interact with an FcRn, e.g., IgG.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and dAb fragments) as well as complete antibodies.

The VH and VL regions can be further subdivided into regions of hypervariability, termed "complementarity determining regions" ("CDR"), interspersed with regions that are more conserved, termed "framework regions" ("FR"). The extent of the framework region and CDR's has been precisely defined (see, Kabat, E. A., et al. (1991) *Sequences of Proteins of Immunological Interest*, Fifth Edition, U.S. Department of Health and Human Services, NIH Publication No. 91-3242, and Chothia, C. et al. (1987) J. Mol. Biol. 196:901-917, see also http://www.hgmp.mrc.ac.uk). Kabat definitions are used herein. Each VH and VL is typically composed of three CDR's and four FR's, arranged from amino-terminus to carboxy-terminus in the following order: FR1, CDR1, FR2, CDR2, FR3, CDR3, FR4.

The term "antigen-binding fragment" of a full length antibody (or simply "antibody portion," or "fragment"), as used herein, refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition. As used herein, "isotype" refers to the antibody class (e.g., IgM or IgG1) that is encoded by heavy chain constant region genes.

As used herein, "binding affinity" refers to the apparent association constant or $K_a$. The $K_a$ is the reciprocal of the dissociation constant ($K_d$). A binding protein may, for example, have a binding affinity of at least $10^{-5}$, $10^{-6}$, $10^{-7}$, $10^{-8}$, $10^{-9}$, $10^{-10}$ and $10^{-11}$ M for a particular target molecule. Higher affinity binding of a binding ligand to a first target relative to a second target can be indicated by a higher $K_a$ (or a smaller numerical value $K_d$) for binding the first target than the $K_a$ (or numerical value $K_d$) for binding the second target. In such cases, the binding protein has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 50, 70, 80, 100, 500, 1000, or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in PBS (phosphate buffered saline) at pH 7.2 at 30° C. These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound]=N\cdot[Free]/((1/Ka)+[Free]).$$

It is not always necessary to make an exact determination of $K_a$, though, since sometimes it is sufficient to obtain a quantitative measurement of affinity, e.g., determined using a method such as ELISA or FACS analysis, is proportional to $K_a$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term "cognate ligand" refers to a naturally occurring ligand of an FcRn, including naturally occurring variants thereof (e.g., splice variants, naturally occurring mutants, and isoforms).

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for many framework and CDR amino acid residues to include one or more conservative substitutions.

Consensus sequences for biopolymers can include positions which can be varied among various amino acids. For example, the symbol "X" in such a context generally refers to any amino acid (e.g., any of the twenty natural amino acids or any of the nineteen non-cysteine amino acids). Other allowed amino acids can also be indicated for example, using parentheses and slashes. For example, "(A/W/F/N/Q)" means that alanine, tryptophan, phenylalanine, asparagine, and glutamine are allowed at that particular position.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blosum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In one embodiment, the length of a reference sequence aligned for comparison purposes is at least 30%, at least 40%, at least 50%, at least 60%, at least 70%, 80%, 90%, 92%, 95%, 97%, 98%, or 100% of the length of the reference sequence. For example, the reference sequence may be the length of the immunoglobulin variable domain sequence.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y (1989), 6.3.1-6.3.6, which is incorporated by reference. Aqueous and non-aqueous methods are described in that reference and either can be used. Specific hybridization conditions referred to herein are as follows: (1) low stringency hybridization conditions in 6× sodium chloride/ sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified. The disclosure includes nucleic acids that hybridize with low, medium, high, or very high stringency to a nucleic acid described herein or to a complement thereof, e.g., nucleic acids encoding a binding protein described herein. The nucleic acids can be the same length or within 30, 20, or 10% of the length of the reference nucleic acid. The nucleic acid can correspond to a region encoding an immunoglobulin variable domain sequence.

An FcRn binding protein may have mutations (e.g., at least one, two, or four, and/or less than 15, 10, 5, or 3) relative to a binding protein described herein (e.g., a conservative or non-essential amino acid substitutions), which do not have a substantial effect on the protein functions. Whether or not a particular substitution will be tolerated, i.e., will not adversely affect biological properties, such as binding activity can be predicted, e.g., using the method of Bowie, et al. (1990) *Science* 247:1306-1310.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405).

As used herein, an "immunoglobulin variable domain sequence" refers to an amino acid sequence which can form the structure of an immunoglobulin variable domain such that one or more CDR regions are positioned in a conformation suitable for an antigen binding site. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that preferentially interacts with an FcRn structure.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system. The term "antibody" includes intact immunoglobulins of types IgA, IgG, IgE, IgD, IgM (as well as subtypes thereof). The light chains of the immunoglobulin may be of types: kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In one embodiment, at least 70, 75, 80, 85, 90, 92, 95, or 98% of, or the entire of, the antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 92, 95, 98, or 99% pure on a weight-weight basis.

The term "mimic," in the context of a mimic of a conformation of an FcRn or portion thereof, refers to a modified FcRn which has a bias for at least one particular conformation relative to a naturally occurring FcRn, or portion thereof.

A "non-essential" amino acid residue is a residue that can be altered from the wild-type sequence of the binding agent, e.g., the antibody, without abolishing or without substantially altering a biological activity, whereas an "essential" amino acid residue results in such a change.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The terms "polypeptide" or "peptide" (which may be used interchangeably) refer to a polymer of three or more amino acids linked by a peptide bond, e.g., between 3 and 30, 12 and 60, or 30 and 300, or over 300 amino acids in length. The polypeptide may include one or more unnatural amino acids. Typically, the polypeptide includes only natural amino acids. A "protein" can include one or more polypeptide chains. Accordingly, the term "protein" encompasses polypeptides. A protein or polypeptide can also include one or more modifications, e.g., a glycosylation, amidation, phosphorylation, nitrosylation, and so forth. The term "small peptide" can be used to describe a polypeptide that is between 3 and 30 amino acids in length, e.g., between 8 and 24 amino acids in length.

A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

As used herein, the term "substantially identical" (or "substantially homologous") is used herein to refer to a first amino acid or nucleic acid sequence that contains a sufficient number of identical or equivalent (e.g., with a similar side chain, e.g., conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50% of the affinity relative to the same antigen.

Sequences similar or homologous (e.g., at least about 85% sequence identity) to the sequences disclosed herein are also part of this application. In some embodiments, the sequence identity can be about 85%, 90%, 91%, 92%, 93%, 94%, 95%, 96%, 97%, 98%, 99% or higher. In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding, that are statistically significant (e.g., P value <0.05 or 0.02). The terms "induce", "inhibit", "potentiate", "elevate", "increase", "decrease" or the like, e.g., which denote distinguishable qualitative or quantitative differences between two states, and may refer to a difference, e.g., a statistically significant difference, between the two states.

A "therapeutically effective dosage" modulates a measurable parameter, e.g., levels of circulating IgG antibodies by a statistically significant degree or at least about 20%, by at least about 40%, by at least about 60%, or by at least about 80% relative to untreated subjects. The ability of a compound to modulate a measurable parameter, e.g., autoimmunity, can be evaluated in an animal model system predictive of efficacy in human autoimmune disorders. Alternatively, this property of a composition can be evaluated by examining the ability of the compound to modulate a parameter in vitro, e.g., by assays known to the skilled practitioner.

Other features and advantages of the instant invention will become more apparent from the following detailed description and claims. Embodiments of the invention can include any combination of features described herein. In no case does the term "embodiment" exclude one or more other features disclosed herein.

FcRn Sequences

The following sequence alignment is of a human FcRn alpha chain amino acid sequence with a rat FcRn alpha chain amino acid sequence An exemplary FcRn protein can include one of these two sequences, or a fragment thereof, e.g., a fragment without the signal sequence:

```
            Signal Sequence                      α₁ domain
α_HUMAN: MGVPPPQPWALGLLLFLLPGSLG AESHLSLLYHLTAVSSPAPGTPAFWVSGWLGPQQYLS   (SEQ ID NO: 1)

α_RAT:   MGMSQPGV-LLSLLLVLLPQTWG AEPRLPLMYHLAAVSDLSTGLPSFWATGWLGAQQYLT   (SEQ ID NO: 2)

α₁ domain                          α₂ domain
α_HUMAN: YNSLRGEAEPCGAWVWENQVSWYWEKETTDLRTKEKLFLEAFKALGGK--GP YTLQGLLG

α_RAT:   YNNLRQEADPCGAWIWENQVSWYWEKETTDLKSKEQLFLEAIRTLENQINGT FTLQGLLG

α₂ domain
α_HUMAN: CELGPDNTSVPTAKFALNGEEFMNFDLKQGTWGGDWPEALAISQRWQQQDKAANKELTFL

☐_RAT:   CELAPDNSSLPTAVFALNGEEFMRFNPRTGNWSGEWPETDIVGNLWMKQPEAARKESEFL

α₂ domain                         α₃ domain
α_HUMAN: LFSCPHRLREHLERGRGNLEWK EPPSMRLKARPSSPGFSVLTCSAFSFYPPELQLRFLRN

α_RAT:   LTSCPERLLGHLERGRQNLEWK EPPSMRLKARPGNSGSSVLTCAAFSFYPPELKFRFLRN

α₃ domain
☐_HUMAN: GLAAGTGQGDFGPNSDGSFHASSSLTVKSGDEHHYCCIVQHAGLAQPLRVELE

☐_RAT:   GLASGSGNCSTGPNGDGSFHAWSLLEVKRGDEHHYQCQVEHEGLAQPLTVDLD

Transmembrane           Cytoplasmic domain
α_HUMAN: SPAKSSVLVVGIVIGVLLLTAAAVGGALLW RRMRSGLPAPWISLRGDDTGVLLPTPGEAQ

α_RAT:   SPARSSVPVVGIILGLLLVVVAIAGGVLLW NRMRSGLPAPWLSLSGDDSGDLLPGGNLPP

α_HUMAN: DADLKDVNVIPATA

α_RAT:   EAEPQGVNAFPATS
```

The following sequence alignment is of a human β2 microglobulin amino acid sequence with a rat β2 microglobulin amino acid sequence. An exemplary FcRn protein can include one of these two sequences, or a fragment thereof, e.g., a fragment without the signal sequence:

```
           Signal Sequence            β2 microglobulin
β2m_human: MSRSVALAVLALLSLSGLEA IQRTPKIQVYSRHPAENGKSNFLNCYVSGFHPSDIEVDLL (SEQ ID NO: 3)

β2m_rat:   MARSVTVIFIVLVSLAVVLA IQKTPQIQVYSRHPPENGKPNFLNCYVSQFHPPQIEIELL (SEQ ID NO: 4)

β2 microglobulin
β2m_human: KNGERIEKVEHSDLSFSKDWSFYLLYYTEFTPTEKDEYACRVNHVTLSQPKIVKWDRDM β2m_rat:   KNGKKIPNIEMSDLSFSKDWSFYILAHTEFTPTETDVYACRVKHVTLKEPKTVTWDRDM
```

An exemplary nucleic acid sequence encoding an FcRn protein alpha chain can include the following sequences:

```
FcRN alpha nucleotide sequence Homo sapiens
GTTCTTCAGGTACGAGGAGGGCATTGTTGTCAGTCTGGACCGAGCCCGCAGAGCCCCTCCTCGGCGTCCT (SEQ ID NO: 5)

GGTCCCGGCCGTGCCCGCGGTGTCCCGGGAGGAAGGGGCGGGCCGGGGGTCGGGAGGAGTCACGTGCCCC

CTCCCGCCCCAGGTCGTCCTCTCAGCATGGGGGTCCCGCGGCCTCAGCCCTGGGCGCTGGGGCTCCTGCT

CTTTCTCCTTCCTGGGAGCCTGGGCGCAGAAAGCCACCTCTCCCTCCTGTACCACCTTACCGCGGTGTCC

TCGCCTGCCCCGGGGACTCCTGCCTTCTGGGTGTCCGGCTGGCTGGGCCCGCAGCAGTACCTGAGCTACA

ATAGCCTGCGGGGCGAGGCGGAGCCCTGTGGAGCTTGGGTCTGGGAAAACCAGGTGTCCTGGTATTGGGA

GAAAGAGACCACAGATCTGAGGATCAAGGAGAAGCTCTTTCTGGAAGCTTTCAAAGCTTTGGGGGGAAAA

GGTCCCTACACTCTGCAGGGCCTGCTGGGCTGTGAACTGGGCCCTGACAACACCTCGGTGCCCACCGCCA

AGTTCGCCCTGAACGGCGAGGAGTTCATGAATTTCGACCTCAAGCAGGGCACCTGGGGTGGGACTGGCC

CGAGGCCCTGGCTATCAGTCAGCGGTGGCAGCAGCAGGACAAGGCGGCCAACAAGGAGCTCACCTTCCTG

CTATTCTCCTGCCCCGCACCGCCTGCGGGAGCACCTGGAGAGGGGCCGCGGAAACCTGGAGTGGAAGGAGC
```

```
CCCCCTCCATGCGCCTGAAGGCCCGACCCAGCAGCCCTGGCTTTTCCGTGCTTACCTGCAGCGCCTTCTC

CTTCTACCCTCCGGAGCTGCAACTTCGGTTCCTGCGGAATGGGCTGGCCGCTGGCACCGGCCAGGGTGAC

TTCGGCCCCAACAGTGACGGATCCTTCCACGCCTCGTCGTCACTAACAGTCAAAAGTGGCGATGAGCACC

ACTACTGCTGCATTGTGCAGCACGCGGGGCTGGCGCAGCCCCTCAGGGTGGAGCTGGAATCTCCAGCCAA

GTCCTCCGTGCTCGTGGTGGGAATCGTCATCGGTGTCTTGCTACTCACGGCAGCGGCTGTAGGAGGAGCT

CTGTTGTGGAGAAGGATGAGGAGTGGGCTGCCAGCCCCTTGGATCTCCCTTCGTGGAGACGACACCGGGG

TCCTCCTGCCCACCCCAGGGGAGGCCCAGGATGCTGATTTGAAGGATGTAAATGTGATTCCAGCCACCGC

CTGACCATCCGCCATTCCGACTGCTAAAAGCGAATGTAGTCAGGCCCCTTTCATGCTGTGAGACCTCCTG

GAACACTGGCATCTCTGAGCCTCCAGAAGGGGTTCTGGGCCTAGTTGTCCTCCCTCTGGAGCCCCGTCCT

GTGGTCTGCCTCAGTTTCCCCTCCTAATACATATGGCTGTTTTCCACCTCGATAATATAACACGAGTTTG

GGCCCGAAAAAAAAAAAAAAAAAAAAAAAAAAAAAAAAAAA
```

The nucleic acid sequence of an exemplary human FcRn (extra-cellular domain) plus GPI DNA sequences (lowercase bold) is set forth below.

```
ATGGGGGTCCCGCGGCCTCAGCCCTGGGCGCTGGGGCTCCTGCTCTTTCTCCTTCCTGGGAGCCTGGGCG    (SEQ ID NO: 6)

CAGAAAGCCACCTCTCCCTCCTGTACCACCTTACCGCGGTGTCCTCGCCTGCCCCGGGGACTCCTGCCTT

CTGGGTGTCCGGCTGGCTGGGCCCGCAGCAGTACCTGAGCTACAATAGCCTGCGGGGCGAGGCGGAGCCC

TGTGGAGCTTGGGTCTGGGAAAACCAGGTGTCCTGGTATTGGGAGAAAGAGACCACAGATCTGAGGATCAA

GGAGAAGCTCTTTCTGGAAGCTTTCAAAGCTTTGGGGGAAAAGGTCCCTACACTCTGCAGGGCCTGCTGG

GCTGTGAACTGGGCCCTGACAACACCTCGGTGCCCACCGCCAAGTTCGCCCTGAACGGCGAGGAGTTCATG

AATTTCGACCTCAAGCAGGGCACCTGGGGTGGGACTGGCCCGAGGCCCTGGCTATCAGTCAGCGGTGGCA

GCAGCAGGACAAGGCGGCCAACAAGGAGCTCACCTTCCTGCTATTCTCCTGCCCGCACCGCCTGCGGGAGC

ACCTGGAGAGGGCCGCGGAAACCTGGAGTGGAAGGAGCCCCCCTCCATGCGCCTGAAGGCCCGACCCAGC

AGCCCTGGCTTTTCCGTGCTTACCTGCAGCGCCTTCTCCTTCTACCCTCCGGAGCTGCAACTTCGGTTCCT

GCGGAATGGGCTGGCCGCTGGCACCGGCCAGGGTGACTTCGGCCCCAACAGTGACGGATCCTTCCACGCCT

CGTCGTCACTAACAGTCAAAAGTGGCGATGAGCACCACTACTGCTGCATTGTGCAGCACGCGGGGCTGGCG

CAGCCCCTCAGGGTGGAGCTGGAATCTCCAGCCAAGTCCTCCcggccgctcgacgggctacgagcatcagt aacactactaggcgcaggcctactactatcactactaccagcactactacgatttgggccataa
```

An exemplary nucleic acid sequence encoding a Beta-2-microglobulin (β2M) can include the following sequences:

```
>Beta-2-microglobulin (B2M) nucleotide Homo sapiens    (SEQ ID NO: 7)
AATATAAGTGGAGGCGTCGCGCTGGCGGGCATTCCTGAAGCTGACAGCATTCGGGCCGAGATGTCTCGCT

CCGTGGCCTTAGCTGTGCTCGCGCTACTCTCTCTTTCTGGCCTGGAGGCTATCCAGCGTACTCCAAAGAT

TCAGGTTTACTCACGTCATCCAGCAGAGAATGGAAAGTCAAATTTCCTGAATTGCTATGTGTCTGGGTTT

CATCCATCCGACATTGAAGTTGACTTACTGAAGAATGGAGAGAGAATTGAAAAAGTGGAGCATTCAGACT

TGTCTTTCAGCAAGGACTGGTCTTTCTATCTCTTGTACTACACTGAATTCACCCCCACTGAAAAAGATGA

GTATGCCTGCCGTGTGAACCATGTGACTTTGTCACAGCCCAAGATAGTTAAGTGGGATCGAGACATGTAA

GCAGCATCATGGAGGTTTGAAGATGCCGCATTTGGATTGGATGAATTCCAAATTCTGCTTGCTTGCTTTT

TAATATTGATATGCTTATACACTTACACTTTATGCACAAAATGTAGGGTTATAATAATGTTAACATGGAC

ATGATCTTCTTTATAATTCTACTTTGAGTGCTGTCTCCATGTTTGATGTATCTGAGCAGGTTGCTCCACA
```

```
GGTAGCTCTAGGAGGGCTGGCAACTTAGAGGTGGGGAGCAGAGAATTCTCTTATCCAACATCAACATCTT

GGTCAGATTTGAACTCTTCAATCTCTTGCACTCAAAGCTTGTTAAGATAGTTAAGCGTGCATAAGTTAAC

TTCCAATTTACATACTCTGCTTAGAATTTGGGGGAAAATTTAGAAATATAATTGACAGGATTATTGGAAA

TTTGTTATAATGAATGAAACATTTTGTCATATAAGATTCATATTTACTTCTTATACATTTGATAAAGTAA

GGCATGGTTGTGGTTAATCTGGTTTATTTTTGTTCCACAAGTTAAATAAATCATAAAACTTGATGTGTTA

TCTCTTA
```

Mouse Anti-Human FcRn Antibodies

Antibody Structure and Sequences

The invention relates to an antibody that specifically binds at least one FcRn epitope, wherein binding of the antibody to the FcRn epitope inhibits the Fc portion of IgG from binding to the FcRn. The invention thus relates to a FcRn blocking antibody. The blocking antibody can be an IgG, an IgM, an IgA, an IgD or an IgE. In one embodiment the blocking antibody is an IgG. In one embodiment the antibody of the invention will have a binding affinity of $10^{10}$ M$^{-1}$. In another embodiment the antibody of the invention will have a binding affinity of $10^{11}$ M$^{-1}$.

In one embodiment the invention relates to a monoclonal antibody produced by a 3B3.11 hybridoma, a 31.1 hybridoma, a 4B4.12 hybridoma, or a 17D3 hybridoma.

In one embodiment the invention relates to an antibody which binds to an FcRn linear epitope. In another embodiment the invention relates to an antibody which binds to an FcRn conformational epitope. In one embodiment the antibody of the invention binds to an amino acid sequence comprising EPPSMRLKAR (SEQ ID NO: 105) or a fragment thereof. In another embodiment the antibody of the invention binds to an amino acid sequence comprising CSAFYPPELQLRFFLRNGL (SEQ ID NO: 106) or a fragment thereof.

In certain embodiments, antibodies of this invention specifically react with an epitope that is the same as the epitope recognized by 3B3.11 and 31.1. Such antibodies can be determined in competitive binding assays.

Amino acid (AA) sequences of illustrative embodiments of the anti-FcRn antibodies of this invention, including their $V_H$ and $V_L$ domains, and CDRs, are enumerated in Table 1. Two specific embodiments of the antibodies are identified as 3B3.11 and 31.1.

TABLE 1

CDR's For Mouse Antibodies Of The Invention.

| Antibody | LV-CDR1 | LV-CDR2 | LV-CDR3 | HV-CDR1 | HV-CDR2 | HV-CDR3 |
|---|---|---|---|---|---|---|
| 3B3.11 | SASSSISSNYLH (SEQ ID NO: 8) | RTSNLAS (SEQ ID NO: 9) | QQGSNIPLT (SEQ ID NO: 10) | RSWMN (SEQ ID NO: 11) | RIHPGDGDTNYNGKFKG (SEQ ID NO: 12) | EGSPYFDY (SEQ ID NO: 13) |
| 31.1 | KASQDINNYIA (SEQ ID NO: 14) | YTSTLQP (SEQ ID NO: 15) | LQYDNLLRT (SEQ ID NO: 16) | DYAMH (SEQ ID NO: 17) | VITNYYGDASYNQKFKG (SEQ ID NO: 18) | GGYDGYYVDFDY (SEQ ID NO: 19) |

The amino acid sequence for the 3B3.11 light chain is set forth below. The CDR regions are underlined and the constant region is in italics.

```
                                        CDR 1                         CDR 2
  1 DIQLTQSPTT VAASPGEKIT ITCSASSSIS SNYLHWYQQK PGFSPKLLIY RTSNLASGVP  (SEQ ID NO: 20)
                                          CDR 3                    CL 1
 61 ARFSGSGSGT SYSLTIGTME AEDVATYYCQ QGSNIPLTFG AGTKLELKRA DAAPTVSIFP
                    CL 1
121 PSSEQLTSGG ASVVCFLNNF YPKDINVKWK IDGSERQNGV LNSWTDQDSK DSTYSMSSTL
            CL 1
181 TLTKDEYERH NSYTCEATHK TSTSPIVKSF NKNE
```

The amino acid sequence for the 3B3.11 heavy chain is set forth below. The CDR regions are underlined and the constant region is in italics.

```
                       CDR 1                    CDR 2
1 VKLQESGPEL VKPGASVKIS CKASGYAFSR SWMNWVKQRP GQGLEWIGRI HPGDGDTNYN   (SEQ ID NO: 21)

CDR 2                              CDR 3              CH 1
61 GKFKGKATLT VAKSSSTAYM QLSSLTSVDS AVYFCANEGS PYFDYWGQGT TLTVSSAKTT

CH 1
121 PPSVYPLAPG SAAQTNSMVT LGCLVKGYFP EPVTVTWNSG SLSSGVHTFP AVLQSDLYTL

CH 1
181 SSSVTVPSST WPSETVTCNV ARPASSTKVD KKLE
```

The amino acid sequence for the 31.1 light chain is set forth below. The CDR regions are underlined and the constant region is in italics.

```
                       CDR 1                    CDR 2
1 DIQLTQSPSS LSASLGDKVT ITCKASQDIN NYIAWYQHKP GKRSRLLIHY TSTLQPGIPS   (SEQ ID NO: 22)

CDR 3                    CL 1
61 RFSGSGSGRD YSFSISNLEP EDIATYYCLQ YDNLLRTFGG GTKLEIKRAD AAPTVSIFPP

CL 1
121 SSEQLTSGGA SVVCFLNNFY PKDINVKWKI DGSERQNGVL NSWTDQDSKD STYSMSSTLT

CL 1
181 LTKDEYERHN SYTCEATHKT STSPIVKSFN KNE
```

The amino acid sequence for the 31.1 heavy chain is set forth below. The CDR regions are underlined and the constant region is in italics.

```
                       CDR 1                    CDR 2
1 VXLQQSGAEL VRPGVSVKIS CKGSGYTFTD YAMHWVKQSH AKSLEWIGVI TNYYGDASYN   (SEQ ID NO: 23)

CDR 2                              CDR 3
61 QKFKGKATMT VDKSSSTAYM ELARLTSEDS AIYYCARGGY DGYYVDFDYW GQGTTLTVSS

CL 1
121 AKTTPPSVYP LAPGSAAQTN SMVTLGCLVK GYFPEPVTVT WNSGSLSSGV HTFPAVLQSD

CL 1
181 LYTLSSSVTV PSSTWPSETV TCNVAHPASS TKVDKKLE
```

Certain embodiments comprise a VH domain, a VL domain, or a combination thereof, of the Fv fragment from 3B3.11 and 31.1. Further embodiments comprise one, two, three, four, five or six complementarity determining regions (CDRs) from the VH and VL domains. Antibodies whose CDR sequences are included within SEQ ID NO: 20, 21, 22, or 23 are encompassed within the scope of this invention.

The disclosure provides a method for obtaining anti-FcRn antibodies that comprise creating antibodies with altered VH and/or VL sequence(s) obtained from SEQ ID NOS: 20, 21, 22, or 23. Such antibodies may be derived by a skilled artisan using techniques known in the art. For example, amino acid substitutions, deletions, or additions can be introduced in FR and/or CDR regions. FR changes are usually designed to improve the stability and immunogenicity of the antibody, while CDR changes are typically designed to increase antibody affinity for its antigen. The changes that increase affinity may be tested by altering CDR sequence and measuring antibody affinity for its target (Antibody Engineering, 2nd ed., Oxford University Press, ed. Borrebaeck (1995).

Antibodies whose CDR sequences differ insubstantially from those included in or included within the sequences in SEQ ID NOS: 20, 21, 22, or 23 are encompassed within the scope of this invention. Typically, this involves substitution of an amino acid with an amino acid having similar charge, hydrophobic, or stereochemical characteristics. More drastic substitutions in FR regions, in contrast to CDR regions, may also be made as long as they do not adversely affect (e.g., reduce affinity by more than 50% as compared to unsubstituted antibody) the binding properties of the antibody. Substitutions may also be made to germline the antibody or stabilize the antigen binding site.

Methods of Making Mouse Monoclonal Antibodies

Methods of making monoclonal antibodies have been described (Harlow et al., Antibodies A Laboratory Manual, Cold Spring Harbor Laboratory, Cold Spring Harbor, N.Y. (1988)). In some instances, as a first step, a rodent, e.g., a mouse is immunized with an antigenic polypeptide to generate an antibody response. Because FcRn is expressed ubiquitously and exhibits high degree of homology between species, polypeptide immunization has not been successful in producing high affinity FcRn specific monoclonal antibodies or FcRn monoclonal blocking antibodies. To solve this problem DNA vaccination can be performed (Castagliola et al., J. Immunology 160:1458 (1998)). DNA vaccination involves immunizing a rodent, e.g., a mouse with a cDNA construct encoding FcRn or a fragment thereof. Immunization can be administered intramuscularly, intraperitoneally, subcutaneously, intravenously, intradermally or directly into the lymph node. In one embodiment the immunizations administered intramuscularly. DNA vaccination can be administered with an adjuvant, e.g. Freunds complete adjuvant or Freund's incomplete adjuvant. The DNA vaccination can be accompanied by administration of a cardiotoxin to increase the antibody titer. Administration of a cardiotoxin causes cell death and cell regeneration which enhances cellular uptake of the administered DNA vaccine. The cardiotoxin can also increase inflammation which results in a more robust immune response.

Antibody secreting cells (B cells) are isolated from the rodent. Typically the B cell can be isolated from the rodents spleen and fused with a myeloma cell line. The myeloma cell lines are immortalized cell lines that do not produce antibodies. The myeloma cell line can be chosen from, but is not limited to P3-X63Ag8, X63Ag8.653, Sp2/0-Ag14, FO, NSI/1-Ag4-1, NSO/1, FOX-NY, Y3-Ag1.2.3, YB2/0 and IR983F.

Splenocytes are fused with the myeloma cell line to form a hybridoma. Fusion can be mediated by mixing the two cell types with polyethylene glycol for an appropriate period of time (e.g. five minutes). The formed hybridomas are grown in cell culture using an appropriate selection media (e.g. HAT) and screened for their ability to produce a monoclonal antibody against FcRn. Screening can be performed using known immunological techniques, e.g. an ELISA.

Another approach to making FcRn specific monoclonal antibodies is to immunize a transgenic FcRn knockout mouse with soluble human FcRn, see, PCT Application WO 02/43658. WO 02/43658 describes a transgenic mouse whose genome comprises a homozygous disruption in its endogenous FcRn gene, wherein said homozygous disruption prevents expression of a functional FcRn protein. The monoclonal antibody of the invention is not made in a transgenic mouse whose genome comprises a homozygous disruption in its endogenous FcRn gene, wherein said homozygous disruption prevents expression of a functional FcRn protein. The monoclonal antibody of the invention is not comprised of a B cell from a transgenic mouse whose genome comprises a homozygous disruption in its endogenous FcRn gene, wherein said homozygous disruption prevents expression of a functional FcRn protein.

Humanized Anti-FcRn Antibodies Display Libraries

A display library can be used to identify antibodies that bind to the FcRn. A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. In a selection, the polypeptide component of each member of the library is probed with the FcRn and if the polypeptide component binds to the FcRn, the display library member is identified, typically by retention on a support. In addition, a display library entity can include more than one polypeptide component, for example, the two polypeptide chains of an sFab.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

A variety of formats can be used for display libraries. Examples include the following.

Phage Display. One format utilizes viruses, particularly bacteriophages. This format is termed "phage display." The protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; WO 90/02809; de Haard et al. (1999) J. Biol. Chem. 274:18218-30; Hoogenboom et al. (1998) Immunotechnology 4:1-20; Hoogenboom et al. (2000) Immunol Today 2:371-8; Fuchs et al. (1991) Bio/Technology 9:1370-1372; Hay et al. (1992) Hum Antibod Hybridomas 3:81-85; Huse et al. (1989) Science 246:1275-1281; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; and Hoogenboom et al. (1991) Nuc Acid Res 19:4133-4137.

Phage display systems have been developed for filamentous phage (phage f1, fd, and M13) as well as other bacteriophage. The filamentous phage display systems typically use fusions to a minor coat protein, such as gene III protein, and gene VIII protein, a major coat protein, but fusions to other coat proteins such as gene VI protein, gene VII protein, gene IX protein, or domains thereof can also been used (see, e.g., WO 00/71694). In one embodiment, the fusion is to a domain of the gene III protein, e.g., the anchor domain or "stump," (see, e.g., U.S. Pat. No. 5,658,727 for a description of the gene III protein anchor domain). It is also possible to physically associate the protein being displayed to the coat using a non-peptide linkage.

Bacteriophage displaying the protein component can be grown and harvested using standard phage preparatory methods, e.g., PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other Display Formats. Other display formats include cell based display (see, e.g., WO 03/029456), protein-nucleic acid fusions (see, e.g., U.S. Pat. No. 6,207,446), and ribosome display (See, e.g., Mattheakis et al. (1994) Proc. Natl. Acad. Sci. USA 91:9022 and Hanes et al. (2000) Nat. Biotechnol. 18:1287-92; Hanes et al. (2000) Methods Enzymol. 328:404-30; and Schaffitzel et al. (1999) J Immunol Methods. 231 (1-2):119-35).

Scaffolds. Scaffolds for display can include: antibodies (e.g., Fab fragments, single chain Fv molecules (scFV), single domain antibodies, camelid antibodies, and camelized antibodies); T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin and heat shock proteins; intracellular signaling domains (such as SH2 and SH3 domains); linear and constrained peptides; and linear peptide substrates. Display libraries can include synthetic and/or natural diversity. See, e.g., US 2004-0005709.

Display technology can also be used to obtain antibodies that bind particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Iterative Selection. In one embodiment, display library technology is used in an iterative mode. A first display library is used to identify one or more antibodies that bind a target. These identified antibodies are then varied using a mutagenesis method to form a second display library. Higher affinity antibodies are then selected from the second library, e.g., by using higher stringency or more competitive binding and washing conditions.

In some implementations, the mutagenesis is targeted to regions known or likely to be at the binding interface. In the case of antibodies, the mutagenesis can be directed to the CDR regions of the heavy or light chains as described herein. Further, mutagenesis can be directed to framework regions near or adjacent to the CDRs. In the case of antibodies, mutagenesis can also be limited to one or a few of the CDRs, e.g., to make precise step-wise improvements. Exemplary mutagenesis techniques include: error-prone PCR, recombination, DNA shuffling, site-directed mutagenesis and cassette mutagenesis.

In one example of iterative selection, the methods described herein are used to first identify an antibody from a display library that binds an FcRn with at least a minimal binding specificity for a target or a minimal activity, e.g., an equilibrium dissociation constant for binding of less than 1 nM, 10 nM, or 100 nM. The nucleic acid sequence encoding the initial identified antibodies are used as a template nucleic acid for the introduction of variations, e.g., to identify a second antibody that has enhanced properties (e.g., binding affinity, kinetics, or stability) relative to the initial antibody.

Off-Rate Selection. Since a slow dissociation rate can be predictive of high affinity, particularly with respect to interactions between antibodies and their targets, the methods described herein can be used to isolate antibodies with a desired kinetic dissociation rate (e.g., reduced) for a binding interaction to a target.

To select for slow dissociating antibodies from a display library, the library is contacted to an immobilized target. The immobilized target is then washed with a first solution that removes non-specifically or weakly bound biomolecules. Then the bound antibodies are eluted with a second solution that includes a saturating amount of free target or a target specific high-affinity competing monoclonal antibody, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting or Screening for Specificity. The display library screening methods described herein can include a selection or screening process that discards display library members that bind to a non-target molecule. Examples of non-target molecules include streptavidin on magnetic beads, blocking agents such as bovine serum albumin, non-fat bovine milk, any capturing or target immobilizing monoclonal antibody, or non-transfected cells which do not express the human FcRn target.

In one implementation, a so-called "negative selection" step is used to discriminate between the target and related non-target molecule and a related, but distinct non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target as well as for cross species reactivity to related targets or subunits of the target (e.g., rat FcRn; β2 microglobulin) and also under different condition such as pH6 or pH 7.5. The non-target and target binding data are compared (e.g., using a computer and software) to identify library members that specifically bind to the target.

Other Expression Libraries

Other types of collections of proteins (e.g., expression libraries) can be used to identify proteins with a particular property (e.g., ability to bind FcRn and/or ability to modulate FcRn), including, e.g., protein arrays of antibodies (see, e.g., De Wildt et al. (2000) Nat. Biotechnol. 18:989-994), lambda gt11 libraries, two-hybrid libraries and so forth.

Antibody Libraries

In one embodiment, the library presents a diverse pool of polypeptides, each of which includes an immunoglobulin domain, e.g., an immunoglobulin variable domain. Display libraries are particularly useful, for example, for identifying human or "humanized" antibodies that recognize human antigens. Such antibodies can be used as therapeutics to treat human disorders such as autoimmune disorders. Because the constant and framework regions of the antibody are human, these therapeutic antibodies may avoid themselves being recognized and targeted as antigens. The constant regions may also be optimized to recruit effector functions of the human immune system. The in vitro display selection process surmounts the inability of a normal human immune system to generate antibodies against self-antigens.

A typical antibody display library displays a polypeptide that includes a VH domain and a VL domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay, 1988, *Ann. Rev. Immunol.* 6:381-405). The display library can display the antibody as a Fab fragment (e.g., using two polypeptide chains) or a single chain Fv (e.g., using a single polypeptide chain). Other formats can also be used.

As in the case of the Fab and other formats, the displayed antibody can include one or more constant regions as part of a light and/or heavy chain. In one embodiment, each chain includes one constant region, e.g., as in the case of a Fab. In other embodiments, additional constant regions are displayed.

Antibody libraries can be constructed by a number of processes (see, e.g., de Haard et al., 1999, *J. Biol. Chem.* 274: 18218-30; Hoogenboom et al., 1998, *Immunotechnology* 4:1-20; and Hoogenboom et al., 2000, *Immunol. Today* 21:371-378. Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either and both of heavy and light chain variable domains. In one embodiment, variation is introduced into all three CDRs of a given variable domain. In another embodiment, the variation is introduced into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al., 2000, *J. Mol. Biol.* 296:57-86 describe a method for constructing CDR encoding oligonucleotides using trinucleotide synthesis and a template with engineered restriction sites for accepting the oligonucleotides.

In another process, an animal, e.g., a rodent, is immunized with the FcRn. The animal is optionally boosted with the antigen to further stimulate the response. Then spleen cells are isolated from the animal, and nucleic acid encoding VH and/or VL domains is amplified and cloned for expression in the display library.

In yet another process, antibody libraries are constructed from nucleic acid amplified from naïve germline immunoglobulin genes. The amplified nucleic acid includes nucleic acid encoding the VH and/or VL domain. Sources of immunoglobulin-encoding nucleic acids are described below. Amplification can include PCR, e.g., with primers that anneal to the conserved constant region, or another amplification method.

Nucleic acid encoding immunoglobulin domains can be obtained from the immune cells of, e.g., a human, a primate, mouse, rabbit, camel, llama or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another embodiment, the B or T cell is cultured in vitro.

The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin, or pokeweed mitogen.

In still one embodiment, the cells are isolated from a subject that has an autoimmune disorder, e.g., systemic lupus erythematosus (SLE), rheumatoid arthritis, vasculitis, Sjogren syndrome, systemic sclerosis, or anti-phospholipid syndrome. The subject can be a human, or an animal, e.g., an animal model for the human disease, or an animal having an analogous disorder. In yet one embodiment, the cells are isolated from a transgenic non-human animal that includes a human immunoglobulin locus.

In one embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al., 2001, *J. Immunol.* 166:2228). In one embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g., by degrading uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al., 1999, *J. Biol. Chem.* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In one embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription. The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Secondary Screening Methods

After selecting candidate library members that bind to a target, each candidate library member can be further analyzed, e.g., to further characterize its binding properties for the target. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. Exemplary assays for binding properties include the following.

ELISA. Antibodies selected from an expression library can also be screened for a binding property using an ELISA. For example, each antibody is contacted to a microtitre plate whose bottom surface has been coated with the target, e.g., a limiting amount of the target. The plate is washed with buffer to remove non-specifically bound polypeptides. Then the amount of the antibody bound to the plate is determined by probing the plate with an antibody that can recognize the test antibody, e.g., a tag or constant portion of the antibody. The detection antibody is linked to an enzyme such as alkaline phosphatase or horse radish peroxidase (HRP) which produces a calorimetric product when appropriate substrates are provided.

In the case of an antibody from a display library, the antibody can be purified from cells or assayed in a display library format, e.g., as a fusion to a filamentous bacteriophage coat. In another version of the ELISA, each antibody selected from an expression library is used to coat a different well of a microtitre plate. The ELISA then proceeds using a constant target molecule to query each well.

Homogeneous Binding Assays. The binding interaction of candidate antibody with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means well known in the art (e.g., using a fluorimeter). By titrating the amount of the first or second binding molecule, a binding curve can be generated to estimate the equilibrium binding constant.

Another example of a homogenous assay is ALPHAS-CREEN™ (Packard Bioscience, Meriden Conn.). ALPHAS-CREEN™ uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

The homogenous assays can be performed while the candidate polypeptide is attached to the display library vehicle, e.g., a bacteriophage.

Surface Plasmon Resonance (SPR). The binding interaction of a molecule isolated from an expression library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, *Anal. Chem.* 63:2338-2345; Szabo et al., 1995, *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a biomolecule to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

Cellular Assays. A library of candidate antibodies (e.g., previously identified by a display library or otherwise) can be screened for target binding on cells which transiently or stably express and display the target of interest on the cell surface. For example, the target can include vector nucleic acid sequences that include segments that encode only the extracellular portion of the polypeptides such that the chimeric target polypeptides are produced within the cell, secreted from the cell, or attached to the cell surface through the anchor e.g., in fusion with a membrane anchoring proteins such as Fc. The cell surface expressed target can be used for screening antibodies that bind to FcRn and block the binding of IgG-Fc. For example, non-specific human IgG-Fc could be fluorescently labeled and its binding to FcRn in the presence of absence of antagonistic antibody can be detected by a change in fluorescence intensity using flow cytometry e.g., a FACS machine.

Other Methods for Obtaining FcRn-Binding Antibodies

In addition to the use of display libraries, other methods can be used to obtain a FcRn-binding antibody. For example, the FcRn protein or a region thereof can be used as an antigen in a non-human animal, e.g., a rodent.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies (Mabs) derived from the genes with the desired specificity may be produced and selected. See, e.g., XENOMOUSE™, Green et al., 1994, *Nat. Gen.* 7:13-21; U.S. 2003-0070185, WO 96/34096, published Oct. 31, 1996, and PCT Application No. PCT/US96/05928, filed Apr. 29, 1996.

In one embodiment, a monoclonal antibody is obtained from the non-human animal, and then modified, e.g., humanized or deimmunized. Winter describes a CDR-grafting method that may be used to prepare the humanized antibodies (UK Patent Application GB 2188638A, filed on Mar. 26, 1987; U.S. Pat. No. 5,225,539. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

An FcRn-binding antibody may also be modified by specific deletion of human T cell epitopes or "deimmunization" by the methods disclosed in WO 98/52976 and WO 00/34317, the contents of which are specifically incorporated by reference herein. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions or by single amino acid substitutions. As far as possible conservative substitutions are made, often but not exclusively, an amino acid common at this position in human germline antibody sequences may be used. Human germline sequences are disclosed in Tomlinson, I. A. et al., 1992, *J. Mol. Biol.* 227:776-798; Cook, G. P. et al., 1995, *Immunol. Today* Vol. 16 (5): 237-242; Chothia, D. et al., 1992, *J. Mol. Bio.* 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding $V_H$ and $V_L$ can be constructed by mutagenesis or other synthetic methods (e.g., de novo synthesis, cassette replacement, and so forth). Mutagenized variable sequence can, optionally, be fused to a human constant region, e.g., human IgG1 or κ constant regions.

In some cases, a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be used to modify any antibody, e.g., an antibody that includes a non-human sequence, e.g., a synthetic antibody, a murine antibody other non-human monoclonal antibody, or an antibody isolated from a display library.

Germlining Antibodies.

An Antibody used to treat an IgG-mediated autoimmune disease can be used for multiple administrations. Precautions that would lower the immunogenicity of the therapeutic antibody include reverting one or more non-germline amino acids in framework regions to corresponding germline amino acids (e.g., so long as binding properties are substantially retained) of the antibody (especially of Fabs).

It is possible to modify an antibody that binds FcRn, e.g., an antibody described herein, in order to make the variable regions of the antibody more similar to one or more germline sequences. For example, an antibody can include one, two, three, or more amino acid substitutions, e.g., in a framework, CDR, or constant region, to make it more similar to a reference germline sequence. One exemplary germlining method can include identifying one or more germline sequences that are similar (e.g., most similar in a particular database) to the sequence of the isolated antibody. Mutations (at the amino acid level) can then be made in the isolated antibody, either incrementally or in combination with other mutations. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a framework and/or constant region. For example, a germline framework and/or constant region residue can be from a germline sequence that is similar (e.g., most similar) to the non-variable region being modified. After mutagenesis, activity (e.g., binding or other functional activity) of the antibody can be evaluated to determine if the germline residue or residues are tolerated (i.e., do not abrogate activity). Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at least 30, 50, 60, 70, 80, 90 or 100% of the FR regions are identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, or 99.5% identical to a germline sequence in a region outside the CDRs (e.g., framework regions). Further, an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity) can be within a factor or 100, 10, 5, 2, 0.5, 0.1, and 0.001 of the original antibody.

Exemplary germline reference sequences for $V_{kappa}$ include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al., 1995, *EMBO J.* 14 (18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al., 1992, *J. Mol. Biol.* 227:799-817; Tomlinson et al., 1992, *J. Mol. Biol.* 227:776-798); and Tomlinson et al., 1995, *EMBO J.* 14 (18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

Ligand Production

Standard recombinant nucleic acid methods can be used to express an antibody that binds to FcRn. Generally, a nucleic acid sequence encoding the antibody is cloned into a nucleic acid expression vector. Of course, if the antibody includes multiple polypeptide chains, each chain can be cloned into an expression vector, e.g., the same or different vectors, that are expressed in the same or different cells.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, *J. Immunol. Methods.* 251:123-35), *Hanseula*, or *Saccharomyces*.

In one embodiment, antibodies are produced in mammalian cells. Mammalian host cells for expressing the clone antibodies or antigen-binding fragments thereof include Chinese Hamster Ovary (CHO cells) (including dhfr- CHO cells, described in Urlaub and Chasin, 1980, *Proc. Natl. Acad. Sci. USA* 77:4216-4220, used with a DHFR selectable marker, e.g., as described in Kaufman and Sharp, 1982, *Mol. Biol.* 159:601 621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, *Adv. Immunol.* 51:1-84; Jefferis et al., 1998, *Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

One method for producing a transgenic mouse is as follows. Briefly, a targeting construct that encodes the antibody is microinjected into the male pronucleus of fertilized oocytes. The oocytes are injected into the uterus of a pseudopregnant foster mother for the development into viable pups. Some offspring incorporate the transgene.

Assay Systems for FcRn Candidate Antibodies

FcRn candidate antibodies can be further characterized in assays that measure their modulatory activity toward FcRn or fragments thereof in vitro or in vivo. For example, FcRn can be combined with a substrate such as non-specific IgG or Fc portion of the IgG or albumin under assay conditions permitting reaction of the FcRn with the substrate. The assay is performed in the absence of the FcRn candidate antibody, and in the presence of increasing concentrations of the FcRn candidate antibody. The concentration of candidate antibody at which 50% of the FcRn activity (e.g., binding to the substrate) is inhibited by the candidate antibody is the $IC_{50}$ value (Inhibitory Concentration 50%) or $EC_{50}$ (Effective Concentration 50%) value for that antibody. Within a series or group of candidate antibodies, those having lower $IC_{50}$ or $EC_{50}$ values are considered more potent inhibitors of FcRn than those antibodies having higher $IC_{50}$ or $EC_{50}$ values. In some embodiments, antibodies have an $IC_{50}$ value of 800 nM, 400 nM, 100 nM, 25 nM, 5 nM, 1 nM, or less as measured in an in vitro assay for inhibition of FcRn activity.

The candidate antibodies can also be evaluated for selectivity toward FcRn. For example, a FcRn candidate antibody can be assayed for its potency toward FcRn and a panel of cell surface receptors, such as receptors that also utilize the β2M domain, and an $IC_{50}$ value or $EC_{50}$ value can be determined for each receptor protein. In one embodiment, a compound that demonstrates a low $IC_{50}$ value or $EC_{50}$ value for the FcRn, and a higher $IC_{50}$ value or $EC_{50}$ value for other receptors within the test panel (e.g., MHC class I molecules) is considered to be selective toward FcRn.

Ex vivo endothelial cells or epithelial cells expressing the endogenous FcRn could be used to follow the endocytosis or transcytosis of the candidate antibodies under different pH and temperature conditions. IgG transcytosis or recycling by FcRn can be measured by following a labeled antibody in the presence or absence of various chemicals and under different conditions that are known to influence or affect the intracellular trafficking pathway.

A pharmacokinetics study in rat, mice, or monkey could be performed with pH dependent and independent FcRn binding antibodies for determining their half-life in the serum. Likewise, the protective effect of the antibody can be assessed in vivo for potential use in immunomodulating therapy or as an salvage immunotherapy by injecting the antibody in the presence or absence of a labeled IgG or the labeled Fc portion of the IgG. A decrease in the half-life of the labeled IgG/Fc in the presence of the candidate antibody is an indication of the therapeutic efficacy of the antibody.

Pharmaceutical Compositions

In another aspect, the disclosure provides compositions, e.g., pharmaceutically acceptable compositions or pharmaceutical compositions, which include an FcRn-binding antibody. The FcRn-binding antibody can be formulated together with a pharmaceutically acceptable carrier. Pharmaceutical compositions include therapeutic compositions and diagnostic compositions, e.g., compositions that include labeled FcRn-binding antibodies for in vivo imaging.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal, or epidermal administration (e.g., by injection or infusion). Depending on the route of administration, the FcRn-binding antibody may be coated in a material to protect the compound from the action of acids and other natural conditions that may inactivate the compound.

A pharmaceutically acceptable salt is a salt that retains the desired biological activity of the parent compound and does not impart any undesired toxicological effects (see e.g., Berge, S. M., et al., 1977, *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the FcRn-binding antibody is administered by intravenous infusion or injection. In another embodiment, the FcRn-binding antibody is administered by intramuscular or subcutaneous injection.

The composition can be formulated as a solution, microemulsion, dispersion, liposome, or other ordered structure suitable to high drug concentration. Sterile injectable solutions can be prepared by incorporating the active compound (i.e., the ligand) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An FcRn-binding antibody can be administered by a variety of methods known in the art, although for many applications, the route/mode of administration is intravenous injection or infusion. For example, for therapeutic applications, the FcRn-binding antibody can be administered by intravenous infusion at a rate of less than 30, 20, 10, 5, or 1 mg/min to reach a dose of about 1 to 100 mg/m² or 7 to 25 mg/m². The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., 1978, Marcel Dekker, Inc., New York.

In certain embodiments, the antibody may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound disclosed herein by other than parenteral administration, it may be necessary to coat the compound with, or co-administer the compound with, a material to prevent its inactivation.

Pharmaceutical compositions can be administered with medical devices known in the art. For example, in one embodiment, a pharmaceutical composition disclosed herein can be administered with a device, e.g., a needleless hypodermic injection device, a pump, or implant.

In certain embodiments, an FcRn-binding antibody can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody disclosed herein is 0.1-20 mg/kg, or 1-10 mg/kg. An anti-FcRn antibody can be administered, e.g., by intravenous infusion, e.g., at a rate of less than 30, 20, 10, 5, or 1 mg/min to reach a dose of about 1 to 100 mg/m$^2$ or about 5 to 30 mg/m$^2$. Dosage values may vary with the type and severity of the condition to be alleviated. For a particular subject, specific dosage regimens can be adjusted over time according to the individual need and the professional judgment of the person administering or supervising the administration of the compositions.

The pharmaceutical compositions disclosed herein may include a therapeutically effective amount or a prophylactically effective amount of an FcRn-binding antibody disclosed herein. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the antibody to elicit a desired response in the individual. A therapeutically effective amount is also one in which any toxic or detrimental effects of the composition is outweighed by the therapeutically beneficial effects.

Stabilization and Retention

In one embodiment, an FcRn-binding antibody is physically associated with a moiety that improves its stabilization and/or retention in circulation, e.g., in blood, serum, lymph, or other tissues, e.g., by at least 1.5, 2, 5, 10, or 50 fold. For example, an FcRn-binding antibody can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. For example, an FcRn-binding antibody can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

Kits

An FcRn-binding antibody described herein can be provided in a kit, e.g., as a component of a kit. For example, the kit includes (a) an FcRn-binding antibody, e.g., a composition that includes an FcRn-binding antibody, and, optionally (b) informational material. The informational material can be descriptive, instructional, marketing or other material that relates to the methods described herein and/or the use of an FcRn-binding antibody for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to using the antibody to treat, prevent, or diagnosis a disorder described herein, e.g., an autoimmune disorder.

In one embodiment, the informational material can include instructions to administer an FcRn-binding antibody in a suitable manner to perform the methods described herein, e.g., in a suitable dose, dosage form, or mode of administration (e.g., a dose, dosage form, or mode of administration described herein). In one embodiment, the informational material can include instructions to administer an FcRn-binding antibody to a suitable subject, e.g., a human, e.g., a human having, or at risk for, an autoimmune disorder (e.g., rheumatoid arthritis or systemic lupus erythematosis). For example, the material can include instructions to administer an FcRn-binding antibody to a patient with lupus or a patient with another autoimmune disorder.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In one embodiment, the informational material of the kit is contact information, e.g., a physical address, email address, website, or telephone number, where a user of the kit can obtain substantive information about an FcRn-binding antibody and/or its use in the methods described herein. Of course, the informational material can also be provided in any combination of formats.

In addition to an FcRn-binding antibody, the composition of the kit can include other ingredients, such as a solvent or buffer, a stabilizer, a preservative, a flavoring agent (e.g., a bitter antagonist or a sweetener), a fragrance or other cosmetic ingredient, and/or a second agent for treating an autoimmune disorder described herein, e.g., rheumatoid arthritis or systemic lupus erythematosis. Alternatively, the other ingredients can be included in the kit, but in different compositions or containers than an FcRn-binding antibody. In such embodiments, the kit can include instructions for admixing an FcRn-binding antibody and the other ingredients, or for using an FcRn-binding antibody together with the other ingredients.

An FcRn-binding antibody can be provided in any form, e.g., liquid, dried or lyophilized form. It is preferred that an FcRn-binding antibody be substantially pure and/or sterile. When an FcRn-binding antibody is provided in a liquid solution, the liquid solution preferably is an aqueous solution, with a sterile aqueous solution being preferred. When an FcRn-binding antibody is provided as a dried form, reconstitution generally is by the addition of a suitable solvent. The solvent, e.g., sterile water or buffer, can optionally be provided in the kit.

The kit can include one or more containers for the composition containing an FcRn-binding antibody. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an FcRn-binding antibody. For example, the kit includes a plurality of syringes, ampules, foil packets, or blister packs, each containing a single unit dose of an FcRn-binding antibody. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In one embodiment, the device is an implantable device that dispenses metered doses of the antibody. The disclosure also features a method of providing a kit, e.g., by combining components described herein.

Treatments

Antibodies that bind to FcRn and identified by the method described herein and/or detailed herein have therapeutic and prophylactic utilities. These antibodies can be administered to a subject to treat, prevent, and/or diagnose a variety of disorders, including autoimmune disorders, or even to cells in culture, e.g., in vitro or ex vivo.

The term "treating" refers to administering a therapy in an amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject. The subject can be a human or a non-human animal, e.g., a non-human mammal.

The FcRn-binding antibody can be administered in a therapeutically effective amount, e.g., such that upon single or multiple dose administration to a subject, the subject exhibits an amelioration of symptoms of a disorder, e.g., an autoimmune disorder (e.g., rheumatoid arthritis or systemic lupus erythematosis) or of a parameter indicative of presence or risk for the disorder.

Exemplary disorders which affect many organs or localized organs in the body include: Multiple Sclerosis, rheumatoid arthritis, inflammatory bowel diseases (IBD), lupus, and ankylosing spondylitis. Some of these disorders are discussed below. In one aspect, the invention provides methods for the treatment of cancer. Still other disorders that can be treated using an FcRn-binding antibody include: scleroderma, Sjogren's syndrome, Goodpasture's syndrome, Wegener's granulomatosis, polymyalgia rheumatica, temporal arteritis/gian cell arteritis, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, CREST Syndrome, Crohn's disease, Dego's disease, dermatomyositis, juvenile dermatomyositis, discoid lupus, essential mixed cryoglobulinemia, fibromyalgia, fibromyositis, Grave's disease, Guillain-Barre syndrome, Hashimoto's thyroiditis, idiopathic pulmonary fibrosis, idiopathic thrombocytopenia purpura (ITP), IgA nephropathy, insulin dependent diabetes (Type I), juvenile arthritis, Meniere's disease, mixed connective tissue disease, myasthenia gravis, pemphigus vulgaris, pemphigus foliaceus, paraneoplastic pemphigus, pernicious anemia, polyarteritis nodosa, polychondritis, polyglancular syndromes, polymyalgia rheumatica, polymyositis, dermatomyositis, primary agammaglobulinemia, primary biliary cirrhosis, psoriasis, Raynaud's phenomenon, Reiter's syndrome, rheumatic fever, sarcoidosis, stiff-man syndrome, Takayasu arteritis, ulcerative colitis, uveitis, vasculitis, vitiligo.

In some embodiments, the anti-FcRn binding antibody is administered to remove an unwanted therapeutic antibody from the bloodstream.

In some embodiments, the anti-FcRn binding antibody is administered to suppress the level of anti-HLA antibodies. In some embodiments the level of anti-HLA antibodies is suppressed in connection with organ transplant.

Methods of administering FcRn-binding antibodies are described in "Pharmaceutical Compositions." Suitable dosages of the molecules used will depend on the age and weight of the subject and the particular drug used. The antibodies can be used as competitive agents to inhibit or reduce an undesirable interaction, e.g., between a natural or pathological agent and the FcRn.

The FcRn binding antibody can be used to deliver macro and micromolecules, e.g., a gene into the cell for gene therapy purposes into the endothelium or epithelium and target only those tissues expressing the FcRn. The antibodies may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short range radiation emitters, including, for example, short range, high energy α-emitters, as described herein.

In the case of polypeptide toxins, recombinant nucleic acid techniques can be used to construct a nucleic acid that encodes the antibody and the cytotoxin (or a polypeptide component thereof) as translational fusions. The recombinant nucleic acid is then expressed, e.g., in cells and the encoded fusion polypeptide isolated.

Alternatively, the FcRn-binding antibody can be coupled to high energy radiation emitters, for example, a radioisotope, such as $^{131}$I, a γ-emitter, which, when localized at a site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303 316 (Academic Press 1985). Other suitable radioisotopes include a emitters, such as $^{212}$Bi, $^{213}$Bi, and $^{211}$At, and b emitters, such as $^{186}$Re and $^{90}$Y. Moreover, $^{177}$Lu may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide is very critical in order to deliver maximum radiation dose to a tissue of interest. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al., 1995, *Clin. Canc. Res.* 1: 1447-1454; Meredith R F, et al., 1996, *J. Nucl. Med.* 37:1491-1496; Alvarez R D, et al., 1997, *Gynecol. Oncol.* 65: 94-101).

Use of the therapeutic methods to treat autoimmunity has a number of benefits. Since the antibodies specifically recognize FcRn, other tissue is spared and high levels of the agent are delivered directly to the site where therapy is required. Treatment can be effectively monitored with clinical parameters. Alternatively, these parameters can be used to indicate when such treatment should be employed.

An FcRn-binding antibody can be administered in combination with one or more of the existing modalities for treating autoimmune disorders including, but not limited to: intravenous Ig therapy, nonsteroidal anti-inflammatory drugs (NSAID), and corticosteroids; and anti-inflammatory treatments such as cyclosporins, rapamycins or ascomycins, or their immunosuppressive analogs, e.g., cyclosporin A, cyclosporin G, FK-506, rapamycin, 40-O-(2-hydroxy)ethyl-rapamycin etc.; cyclophosphamide; azathioprene; methotrexate; brequinar; FTY 720; leflunomide; mnizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; or other immunomodulatory compounds, e.g., CTLA4Ig, or other adhesion molecule inhibitors, e.g. mAbs or low molecular weight inhibitors including selectin antagonists and VLA-4 antagonists. These combination therapies can be part of an immunomodulating regimens or a regimen for the treatment or prevention of allo- or xenograft acute or chronic rejection, an inflammatory disorder, or an autoimmune disorders.

Multiple Sclerosis

Multiple sclerosis (MS) is a central nervous system disease that is characterized by inflammation and loss of myelin sheaths.

Patients having MS may be identified by criteria establishing a diagnosis of clinically definite MS as defined by the workshop on the diagnosis of MS (Poser et al., Ann. Neurol. 13:227, 1983). MS may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose MS. McDonald et al. (2001) *Recommended diagnostic criteria for multiple sclerosis: guidelines from the International Panel on the Diagnosis of Multiple Sclerosis*, Ann Neurol 50:121-127. The McDonald criteria include the use of MRI evidence of CNS impairment over time to be used in diagnosis of MS, in the absence of multiple clinical attacks.

Effective treatment of multiple sclerosis may be evaluated in several different ways. The following parameters can be used to gauge effectiveness of treatment. Two exemplary criteria include: EDSS (extended disability status scale), and appearance of exacerbations on MRI (magnetic resonance imaging). The EDSS is a means to grade clinical impairment due to MS (Kurtzke, Neurology 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step can indicate an effective treatment (Kurtzke, Ann. Neurol. 36:573-79, 1994).

Exemplary symptoms associated with multiple sclerosis, which can be treated with the methods described herein, include: optic neuritis, diplopia, nystagmus, ocular dysmetria, internuclear opthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, frigidity, constipation, fecal urgency, fecal incontinence, depression, cognitive dysfunction, dementia, mood swings, emotional lability, euphoria, bipolar syndrome, anxiety, aphasia, dysphasia, fatigue, uhthoff's symptom, gastroesophageal reflux, and sleeping disorders.

In addition to or prior to human studies, an animal model can be used to evaluate the efficacy of using the two agents. An exemplary animal model for multiple sclerosis is the experimental autoimmune encephalitis (EAE) mouse model, e.g., as described in (Tuohy et al. (J. Immunol. (1988) 141:

1126-1130), Sobel et al. (J. Immunol. (1984) 132: 2393-2401), and Traugott (Cell Immunol. (1989) 119: 114-129). Mice can be administered a first and second agent described herein prior to EAE induction. Then the mice are evaluated for characteristic criteria to determine the efficacy of using the two agents in the model.

IBD

Inflammatory bowel diseases (IBD) include generally chronic, relapsing intestinal inflammation. IBD refers to two distinct disorders, Crohn's disease and ulcerative colitis (UC). The clinical symptoms of IBD include intermittent rectal bleeding, crampy abdominal pain, weight loss and diarrhea. A clinical index can also be used to monitor IBD such as the Clinical Activity Index for Ulcerative Colitis. See also, Walmsley et al. Gut. 1998 July; 43 (1):29-32 and Jowett et al. (2003) *Scand J Gastroenterol*. 38 (2):164-71. An FcRn-binding antibody can be used to ameliorate at least one symptom of IBD or to ameliorate a clinical index of IBD.

Rheumatoid Arthritis

Rheumatoid arthritis is an autoimmune inflammatory disease that causes pain, swelling, stiffness, and loss of function in the joints. Rheumatoid arthritis often presents in a symmetrical pattern. The disease can affect the wrist joints and the finger joints closest to the hand. It can also affect other parts of the body besides the joints. In addition, people with rheumatoid arthritis may have fatigue, occasional fevers, and a general malaise. Positive factors for diagnosis of rheumatoid arthritis include the "rheumatoid factor" blood antibody and citrulline antibody. An FcRn-binding antibody can be useful in treating, preventing, or alleviating rheumatoid arthritis or one or more symptoms of rheumatoid arthritis.

Lupus

Systemic lupus erythematosus (SLE) is an autoimmune disorder that leads to inflammation and damage to various body tissues. SLE can be mediated by self-antibodies directed against its own DNA. Lupus can affect many parts of the body, including the joints, skin, kidneys, heart, lungs, blood vessels, and brain. Although various symptoms may present, some of the most common include extreme fatigue, painful or swollen joints (arthritis), unexplained fever, skin rashes, and kidney problems. Exemplary symptoms of lupus include painful or swollen joints, unexplained fever, and extreme fatigue. A characteristic red skin rash may appear across the nose and cheeks. Rashes may also occur on the face and ears, upper arms, shoulders, chest, and hands. Other symptoms of lupus include chest pain, hair loss, anemia, mouth ulcers, and pale or purple fingers and toes from cold and stress. Some people also experience headaches, dizziness, depression, confusion, or seizures. Positive factors for SLE diagnosis include circulating anti-nuclear antibodies, anti-DNA antibodies, and anti-Sm antibodies. An FcRn-binding antibody can be useful in treating, preventing, or alleviating SLE or one or more symptoms of SLE. Lupus, as used herein includes cutaneous lupus and lupus nephritis.

Immune Thromocytopenia (ITP)

ITP is a disease of increased peripheral platelet destruction, where patients develop antibodies that bind to specific platelet membrane proteins. The anti-platelet antibodies opsonize the platelets, leading to destruction by macrophages. Attempts to treat ITP have generally involved suppressing the immune system, which causes an increase in platelet levels. An FcRn-binding antibody can be useful in treating, preventing, or alleviating ITP, or one or more symptoms thereof.

Ankylosing Spondylitis

Ankylosing spondylitis is an autoimmune disorder that not only affects the spine, but may also affect the hips, shoulders, and knees as the tendons and ligaments around the bones and joints become inflamed, resulting in pain and stiffness. Ankylosing spondylitis tends to affect people in late adolescence or early adulthood. An FcRn-binding antibody can be useful in treating, preventing, or alleviating ankylosing spondylitis, or one or more symptoms thereof.

Pemphigus

Pemphigus is an autoimmune disorder that affects mucous membranes and the skin. The disorder is characterized by the generation of auto-antibodies against desmoglein. Desmoglein is a protein in the family of cadherins and is involved with the formation of desmosomes, which join cells to one another. Pemphigus can be classified as one of three types: pemphigus vulgaris, the most common form of the disorder, wherein auto-antibodies target desmoglein 3. In pemphigus folicaeus auto-antibodies against desmoglein 1 are generated. The third type, and least common disorder is paraneoplastic pemphigus, wherein autoantibodies target desmoplakins and which is associated with cancers such as lymphoma. The disorders are commonly diagnosed by a dermatologist by the appearance of the skin and is conformed by the detection of auto-antibodies against desmoglein. Methods of treatment include the administration of steroids and/or the administration of a CD20 antibody such as Rituximab (Rituxan)

Cancer

"Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Carcinomas are malignant cancers that arise from epithelial cells and include adenocarcinoma and squamous cell carcinoma. Sarcomas are cancer of the connective or supportive tissue and include osteosarcoma, chondrosarcoma and gastrointestinal stromal tumor. Hematopoietic cancers, such as leukemia, are able to outcompete the normal hematopoietic compartments in a subject, thereby leading to hematopoietic failure (in the form of anemia, thrombocytopenia and neutropenia) ultimately causing death. A person of ordinary skill in the art can classify a cancer as a sarcoma, carcinoma or hematopoietic cancer.

Cancer, as used herein, includes the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

Treatment of Fetuses

FcRn mediates the transport of maternal IgG across epithelial cell barriers to fetus. The antibodies described herein can be used to deliver macromolecular drugs, e.g., antibiotics, and/or small molecules to fetuses in utero. The fetus may be suffering from a condition or disorder (e.g., an enteric infection or metabolic disorder) that requires treatment. The drug or molecule for treating the condition or disorder can be conjugated to a FcRn binding antibody and administered to a pregnant woman who has an in utero fetus that is in need of treatment. The conjugated FcRn-binding antibody binds to FcRn and is thereby transported to the fetus via the placenta. The fetus receives the drug or molecule treatment.

Immunoadsorption

In some embodiments, the invention provides methods for the removal of an unwanted therapeutic antibody from an individual. In some embodiments, the unwanted therapeutic antibody is an IgG antibody. In some embodiments the unwanted therapeutic antibody is an anti-VLA4 antibody such as Natalizumab (Tysabri, Biogen Idec/Elan), efalizumab (Raptiva, Genetech), bevacizumab (Avastin, Genentech) and Fc fusion proteins such as etanercept (Enbrel, Amgen/Wyeth). Natalizumab monoclonal antibody therapy has been associated with Progressive Multifocal Leukoencephalopathy (PML). Depletion of the therapeutic antibody from the bloodstream and/or the rest of the body may alter the progression of PML.

In some embodiments, the treatment methods presented herein may be combined with methods to remove or partially remove therapeutic antibodies from the bloodstream of a subject. In some embodiments, the anti-FcRn antibodies presented herein may be combined with a capture protein that can bind a therapeutic antibody, the combinations resulting in an increased clearance of the therapeutic antibody from the bloodstream. In some embodiments, the method of removal or partial removal of the therapeutic antibody from the bloodstream of a subject is plasma exchange (PLEX). In some embodiments, the anti-FcRn antibodies can be administered to a subject undergoing plasma exchange. In some embodiments, the anti-FcRn antibodies can be used as an immunoadsorbant for FcRn in the plasma exchange process.

In plasma exchange (also called apheresis or plasmapheresis) blood is taken from the body and plasma containing an unwanted agent, such as cholesterol or a therapeutic antibody, is removed from the blood by a cell separator. Blood can be removed from the body in batches or it can be removed in a continuous flow mode, with the latter allowing for the reintroduction of the processed blood into the body. The removed plasma comprising the unwanted agent can be discarded and the patient can receive donor plasma or saline with added proteins in return. In some embodiments, multiple rounds of plasma exchange may be needed to remove the unwanted agent from the blood or to lower the level of the unwanted agent in the blood to an acceptable level. In some embodiments the blood is "filtered" and the unwanted agent removed, before returning the blood to the patient. Methods of plasma exchange are known in the art and are described, for example, in U.S. Pat. No. 6,960,178.

Plasma exchange has been shown to reduce therapeutic antibody levels in the blood of a subject and the restoration of homeostasis (See e.g., Khatri et al; 2009; Neurology 72:402-409).

An IgG based therapeutic antibody (such as natalizumab) can be removed from blood, plasma or serum by contacting the blood with the capture protein Staphylococcal protein A, which will bind the Fc region of IgG and remove the IgG antibody from the bloodstream. Other capture proteins can be used for different isotype antibodies. In some embodiments, the anti-FcRn antibodies can be used as a capture protein in the plasma exchange process, resulting in the removal of FcRn from the bloodstream, thereby increasing the amount of "free" therapeutic antibody. The resulting "free" therapeutic antibody will have a shorter half-life than antibody present prior to treatment and/or can be removed from the blood more readily with a different capture protein (such as protein A). In some embodiments, the anti-FcRn antibodies are administered to a patient during or before plasma exchange. In some embodiments, the anti-FcRn antibodies can be immobilized and used in a column, resulting in the binding of FcRn. In some embodiments, the blood of a patient that contains a therapeutic antibody is contacted both with immobilized anti-FcRn antibody and immobilized protein A.

In some embodiments the anti-FcRn antibodies presented herein can be used in "rescue" therapy for therapeutic antibodies that have been administered and have shown an adverse effect. In some embodiments, an anti-FcRn antibody can be used as an alternative for plasma exchange. The administration of an anti-FcRn can accomplish therapeutic antibody depletion without the risks associated with plasmapheresis and plasma exchange such as vascular access, citrate therapy and donor plasma sourcing.

Human Leukocyte Antigens

Human leukocyte antigens (HLA) present peptides and antigens on the outside of the cell, which are subsequently recognized by T-cells, which in their turn can activate B-cells. The panel of HLA genes available is unique for each person. Any cell displaying an HLA that is "non-self" will result in the induction of an immune response. In general, the more different the "non-self" HLA from the self HLA, the stronger the immune response. For instance, in the case of organ transplants, subjects with similar HLA genes are preferred to minimize the immune response. Donor-specific HLA antibodies have been found to be associated with graft failure in kidney, heart, lung and liver transplantation.

In some embodiments, the invention provides methods for the decreasing the level of "non-self" HLA antibodies in an individual. Decreasing the level of "non-self" HLA antibodies can result in the suppression of an immune response, e.g., during organ transplantation. In some embodiments a person that will be undergoing organ transplantation is administered an anti-FcRn antibody. In some embodiments a person that is undergoing organ transplantation is administered an anti-FcRn antibody. In some embodiments a person that has received an organ transplantation is administered an anti-FcRn antibody. Assays for measuring the levels of HLA antibodies are well-known in the art.

Diagnostic Uses

Antibodies that bind to FcRn and identified by the method described herein and/or detailed herein have in vitro and in vivo diagnostic utilities.

In one aspect, the disclosure provides a diagnostic method for detecting the presence of an FcRn, in vitro or in vivo (e.g., in vivo imaging in a subject). The method can include localizing FcRn to a subcellular location, e.g., the endosome. The method can include: (i) contacting a sample with FcRn-binding antibody; and (ii) detecting formation of a complex between the FcRn-binding antibody and the sample. The method can also include contacting a reference sample (e.g., a control sample) with the antibody, and determining the extent of formation of the complex between the antibody and the sample relative to the same for the reference sample. A change, e.g., a statistically significant change, in the formation of the complex in the sample or subject relative to the control sample or subject can be indicative of the presence of FcRn in the sample.

Another exemplary method includes: (i) administering the FcRn-binding antibody to a subject; and (iii) detecting formation of a complex between the FcRn-binding antibody and the subject. The detecting can include determining location or time of formation of the complex.

The FcRn-binding antibody can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the FcRn-binding antibody and FcRn can be detected by measuring or visualizing either the antibody bound to the FcRn or unbound antibody. Conventional detection assays can be used, e.g., an enzyme-linked immunosorbent assays (ELISA), a radioimmunoassay (RIA) or tissue immunohistochemistry. Further to labeling the FcRn-binding antibody, the presence of FcRn can be assayed in a sample by a competition immunoassay utilizing standards labeled with a detectable substance and an unlabeled FcRn-binding antibody. In one example of this assay, the biological sample, the labeled standards, and the FcRn-binding antibody are combined and the amount of labeled standard bound to the unlabeled antibody is determined. The amount of FcRn in the sample is inversely proportional to the amount of labeled standard bound to the FcRn-binding antibody.

Fluorophore and chromophore labeled antibodies can be prepared. Because antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, 1968, *Science* 162:526 and Brand, L. et al., 1972, *Annu. Rev. Biochem.* 41:843 868. The antibodies can be labeled with fluorescent chromophore groups by conventional procedures such as those disclosed in U.S. Pat. Nos. 3,940,475, 4,289,747, and 4,376,110. One group of fluorescers having a number of the desirable properties described above is the xanthene dyes, which include the fluoresceins and rhodamines. Another group of fluorescent compounds are the naphthylamines. Once labeled with a fluorophore or chromophore, the antibody can be used to detect the presence or localization of the FcRn in a sample, e.g., using fluorescent microscopy (such as confocal or deconvolution microscopy).

Histological Analysis. Immunohistochemistry can be performed using the antibodies described herein. For example, the antibody can be synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation.

Of course, the antibody can be unlabeled at the time of binding. After binding and washing, the antibody is labeled in order to render it detectable.

Protein Arrays. The FcRn-binding antibody can also be immobilized on a protein array. The protein array can be used as a diagnostic tool, e.g., to screen medical samples (such as isolated cells, blood, sera, biopsies, and the like). Of course, the protein array can also include other ligands, e.g., that bind to FcRn or to other target molecules.

Methods of producing polypeptide arrays are described, e.g., in De Wildt et al., 2000, *Nat. Biotechnol.* 18:989-994; Lueking et al., 1999, *Anal. Biochem.* 270:103-111; Ge, 2000, *Nucleic Acids Res.* 28, e3, I-VII; MacBeath and Schreiber, 2000, *Science* 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the antibodies can be grown on a filter in an arrayed format. Antibody production is induced, and the expressed polypeptides are immobilized to the filter at the location of the cell. An antibody array can be contacted with a labeled target to determine the extent of binding of the target to each immobilized antibody. Information about the extent of binding at each address of the array can be stored as a profile, e.g., in a computer database. The antibody array can be produced in replicates and used to compare binding profiles, e.g., of a target and a non-target.

FACS (Fluorescence Activated Cell Sorting). The FcRn-binding antibody can be used to label cells, e.g., cells in a sample (e.g., a patient sample). The antibody is also attached (or attachable) to a fluorescent compound. The cells can then be sorted using fluorescence activated cell sorter (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the antibody from those cells not bound by the antibody. The separated cells can be cultured and/or characterized.

In vivo Imaging. Also featured is a method for detecting the presence of a FcRn-expressing tissues in vivo. The method includes (i) administering to a subject (e.g., a patient having an autoimmune disorder) an anti-FcRn antibody, conjugated to a detectable marker; (ii) exposing the subject to a means for detecting said detectable marker to the FcRn-expressing tissues or cells. For example, the subject is imaged, e.g., by NMR or other tomographic means.

Examples of labels useful for diagnostic imaging include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short range radiation emitters, such as isotopes detectable by short range detector probes can also be employed. The antibody can be labeled with such reagents using known techniques. For example, see Wensel and Meares, 1983, *Radioimmunoimaging and Radioimmunotherapy*, Elsevier, New York for techniques relating to the radiolabeling of antibodies and D. Colcher et al., 1986, *Meth. Enzymol.* 121: 802 816.

A radiolabeled antibody can also be used for in vitro diagnostic tests. The specific activity of a isotopically-labeled antibody depends upon the half life, the isotopic purity of the radioactive label, and how the label is incorporated into the antibody.

Procedures for labeling polypeptides with the radioactive isotopes (such as $^{14}C$, $^{3}H$, $^{35}S$, $^{125}I$, $^{32}P$, $^{131}I$) are generally known. For example, tritium labeling procedures are described in U.S. Pat. No. 4,302,438. Iodinating, tritium labeling, and $^{35}S$ labeling procedures, e.g., as adapted for murine monoclonal antibodies, are described, e.g., by Goding, J. W. (*Monoclonal antibodies: principles and practice: production and application of monoclonal antibodies in cell biology, biochemistry, and immunology* 2nd ed. London; Orlando: Academic Press, 1986. pp 124 126) and the references cited therein. Other procedures for iodinating polypeptides, such as antibodies, are described by Hunter and Greenwood, 1962, Nature 144:945, David et al., 1974, *Biochemistry* 13:1014 1021, and U.S. Pat. Nos. 3,867,517 and 4,376,110. Radiolabeling elements which are useful in imaging include $^{123}I$, $^{131}I$, $^{111}In$, and $^{99m}Tc$, for example. Procedures for iodinating antibodies are described by Greenwood, F. et al., 1963, *Biochem. J.* 89:114 123; Marchalonis, J., 1969, *Biochem. J.* 113:299 305; and Morrison, M. et al., 1971, *Immunochemistry* 289 297. Procedures for $^{99m}Tc$ labeling are described by Rhodes, B. et al. in Burchiel, S. et al. (eds.), *Tumor Imaging The Radioimmunochemical Detection of Cancer*, New York: Masson 111 123 (1982) and the references cited therein. Procedures suitable for $^{111}In$ labeling antibodies are described by Hnatowich, D. J. et al., 1983, *J. Immunol. Methods*, 65:147 157, Hnatowich, D. et al., 1984, *J. Applied Radiation*, 35:554 557, and Buckley, R. G. et al., 1984, *F.E.B.S.* 166:202 204.

In the case of a radiolabeled antibody, the antibody is administered to the patient, is localized to cells bearing the antigen with which the antibody reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65 85 (Academic Press 1985). Alternatively, a positron emission transaxial tomography scanner, such as designated Pet VI located at Brookhaven National Laboratory, can be used where the radiolabel emits positrons (e.g., $^{11}C$, $^{18}F$, $^{15}O$, and $^{13}N$).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments is used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 mm to about 10 nM in diameter). Particles can have ferromagnetic, antiferromagnetic, or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like.

The FcRn-binding antibody can also be labeled with an indicating group containing of the NMR active $^{19}F$ atom, or a plurality of such atoms inasmuch as (i) substantially all of naturally abundant fluorine atoms are the $^{19}F$ isotope and, thus, substantially all fluorine containing compounds are NMR active; (ii) many chemically active polyfluorinated compounds such as trifluoracetic anhydride are commercially available at relatively low cost; and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett, 1982, *Sci. Am.* 246:78 88 to locate and image tissues expressing FcRn.

The disclosure also features kits comprising an antibody that binds to FcRn and instructions for diagnostic use, e.g., the use of the FcRn-binding antibody or antigen-binding fragment thereof, to detect FcRn, in vitro, e.g., in a sample, e.g., a biopsy or cells from a patient having an autoimmune disorder, or in vivo, e.g., by imaging a subject. The kit can further contain a least one additional reagent, such as a label or additional diagnostic agent. For in vivo use the antibody can be formulated as a pharmaceutical composition.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1

Cloning FcRn, FcRn-GPI and $\beta_2M$

The full length FcRn cDNA construct used for these Examples was originally constructed in the Simister lab (Brandeis University, Waltham Mass.) using pcDNA6 (Invitrogen, Carlsbad, Calif.) as the plasmid vector (FcRn: pcDNA6). The Human $\beta 2m$ cDNA construct used for these Examples was originally constructed in the Blumberg lab (Harvard Medical School, Boston, Mass.) using pcDNA3 (Invitrogen) as the plasmid vector ($\beta 2M$:pcDNA3).

Plasmids were transfected into One Shot TOP10 chemically competent *E. coli* (Invitrogen, Carlsbad, Calif.) according to the manufacturer's instruction. A single colony was picked from each of the transformed plates, inoculated into 500-1000 ml of LB medium and cultured overnight in a shaker. Plasmid DNA was purified from these cultures with Maxi Prep kit (Qiagen, Valencia, Calif.). The pcDNA6-Full length hFcRn plasmid construct was digested with Nhe1 and Xba1. The pcDNA3.1-$\beta$2-M plasmid construct was digested with Hind III and Xba 1. The pcDNA6-hFcRn-GPI plasmid construct was digested with Nhe1 and Xba 1. The digested products were resolved on a 1% agarose gel to verify the size of the insert was correct. The correct size for full-length FcRn and GPI-FcRn were about 1 kb in length. Human $\beta 2M$ was about 0.4 kb in length. The plasmid DNA (4 mg/ml in ethanol) was diluted to 2 mg/ml in sterile DPBS (Invitrogen, Carlsbad, Calif.) before intra-muscular injection.

Example 2

Immunization of Mice with FcRn-Encoding Plasmid DNA

Balb/c mice were treated with 100 μl of 10 mM cardiotoxin (Calbiochem, San Diego) 5 days before plasmid DNA injection. Cardiotoxin treatment was used to provoke an inflammatory response and to recruit antigen presenting cells (e.g., dendritic cells) to the injected area, thereby improving antigen presentation when the protein encoded by the plasmid was expressed.

100 μg of full-length or GPI-hFcRn plasmid construct resuspended in 50 μl of PBS were injected into the anterior tibialis muscle of the mice. Mice immunized with the combination of hFcRn and $\beta_2$M received a dose of 50 μg of hFcRn plasmid in 25 μl PBS and 50 μg Of $\beta_2$M plasmid in 25 μl PBS. All intra-muscular injections were performed under systemic anesthesia with pentobarbital (50 mg/kg, intraperitoneally) or ketamine (100 mg/kg)/Xylazine (10 mg/kg). Animals were boosted with additional injections of hFcRn plasmid DNA at 21 and 42 days after the first immunization using the same dose and volume as used for the first injection.

Mice were also boosted with the soluble form of recombinant hFcRn (shFcRn, 100 μg/mouse, intraperitoneally) on day 76 after the initial immunization. Next, 30 to 50 μl of sera was obtained by tail vein bleeding at 56 and 94 days after the initial immunization. The sera as then tested for antibody titers as described below in Example 3. In addition, mouse number 182 was given an intra-venous (IV) boost with recombinant shFcRn (50 μg/mouse) on days 129, 130 and 131 before fusion. On day 132, spleen cells from mouse number 182 were fused with NS-1 or Sβ2/0 myeloma cells (ATCC, Manassas, Va.) as described below in Example 4. About 35 anti-human FcRn specific mAB hybridoma lines were generated from this fusion.

Mouse number 187 was further boosted IV with 50 μg of recombinant shFcRn on days 276, 277, and 278 after the initial immunization. On day 279, spleen cells from 187 were fused with SP2/0 myeloma cells as described below in Example 4. 10% of the resulting fusions were plated in eleven 96 well plates. The remaining 90% of the fusions were stored in liquid nitrogen. From the fusions plated, 35 lines that secrete mAB recognizing hFcRn were generated. The immunization protocol is summarized in Table 2.

TABLE 2

| | | | | | | | | | | Day 129-131 | Day 132 | Day 276-278 | Day 279 |
|---|---|---|---|---|---|---|---|---|---|---|---|---|---|
| Vaccination | No. of mice | Day 5 | Day 0 | Day 21 | Day 42 | Day 56 | Day 76 | | Day 94 | #182 | #182 | #187 | #187 |
| Human FL-FcRn – DNA | 5 | Cardiotoxin treatment | Immunization | Boost | Boost | $1^{st}$ Serum test | Boost IP with sHFcRn | | $2^{nd}$ Serum test | Daily boost with shFcRn IV | Fusion | | |
| Human FL-FcRn DNA + Human beta 2M DNA | 5 | Cardiotoxin treatment | Immunization | Boost | Boost | Serum test | Boost IP with sHFcRn | | Serum test | | | Daily boost with shFcRn IV | Fusion |
| Human GPI-FcRn DNA | 5 | Cardiotoxin treatment | Immunization | Boost | Boost | Serum test | Boost IP with sHFcRn | | Serum test | | | | |
| Human GPI-FcRn + Human beta 2M DNA | 5 | Cardiotoxin treatment | Immunization | Boost | Boost | Serum test | Boost IP with sHFcRn | | Serum test | | | | |
| No DNA | 5 | Cardiotoxin treatment | | | | Serum test | | | Serum test | | | | |

Example 3

Antibody Titer in Mouse Serum

Figure 1:
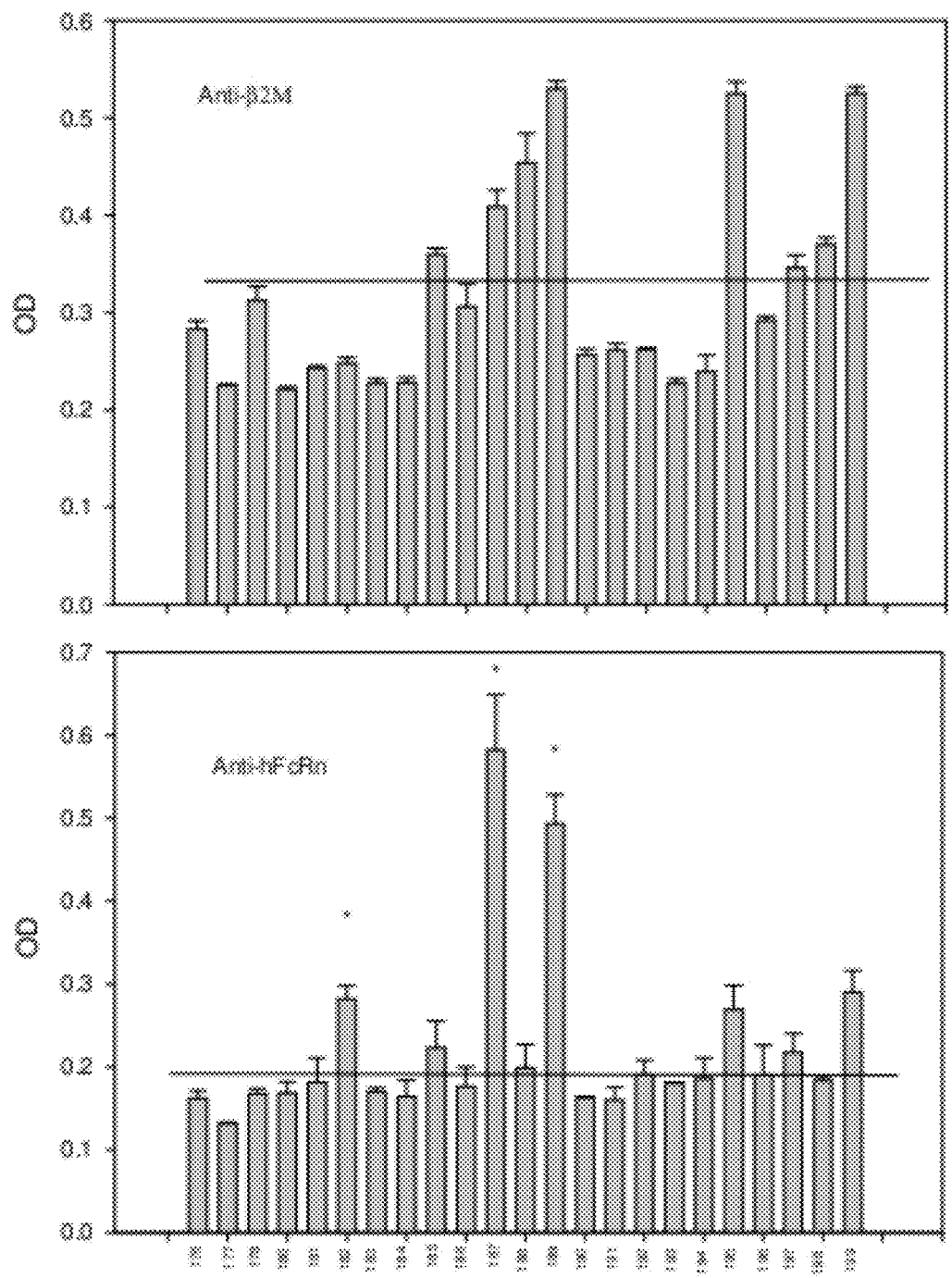
FIG. 1 depicts the result of an ELISA analysis of antibodies in mouse sera obtained 56 days after immunization from animals immunized with DNA encoding hFcRn or GPI linked hFcRn; as well as with DNA encoding human β2M for reactivity with either hFcRn or human β2M. Mice #180-184 were immunized with plasmid encoded hFcRn; Mice #185-189 with plasmid encoded hFcRn and plasmid encoded hβ2M; Mice #190-194 were immunized with plasmid encoded GPI-linked hFcRN; Mice #195-199 were immunized with plasmid encoded GPI-linked hFcRn and plasmid encoded hβ2M.
Figure 2:
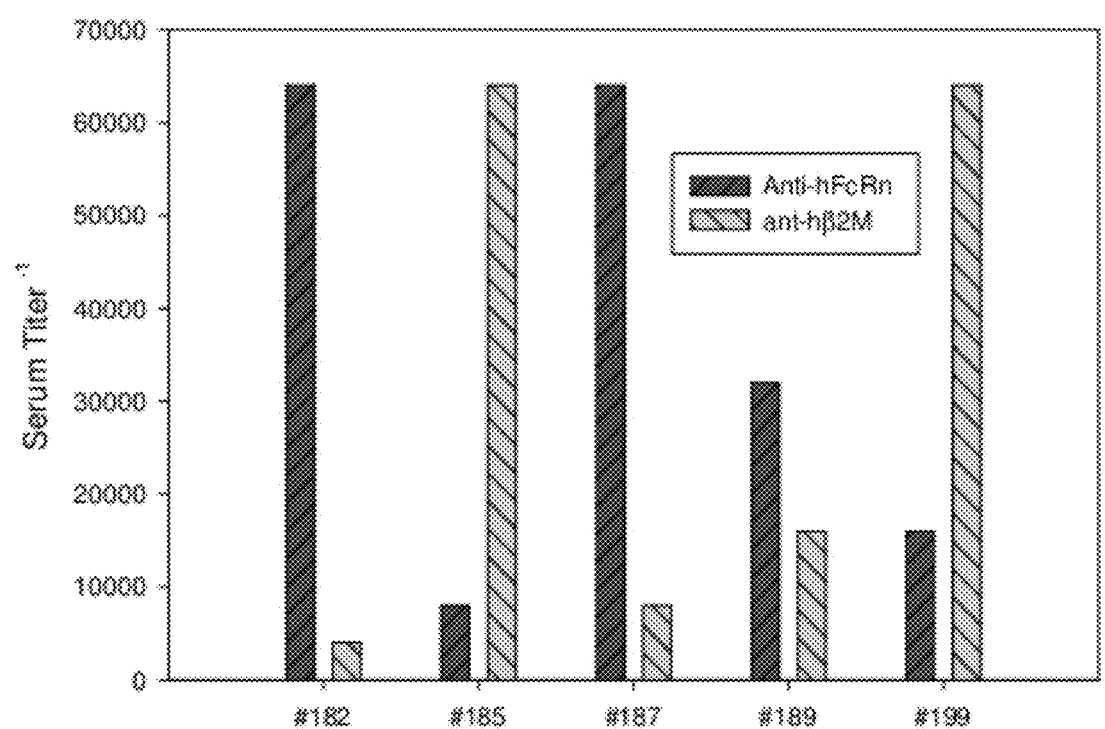
FIG. 2 depicts the result of an ELISA analysis of antibodies in mouse sera obtained 94 days after immunization from animals immunized with DNA encoding hFcRn or GPI linked hFcRn; as well as with DNA encoding human β2M for reactivity with either hFcRn or human β2M.

Anti-hFcRn and anti-$\beta_2$M titer in mouse serum was measured by ELISA. ELISA plates were coated with 2 μg/ml of soluble hFcRn or h$\beta_2$M (Sigma, St. Louis, Mo.) in ELISA coating buffer (Sigma, St. Louis, Mo.). Plates were incubated at 37° C. for 1 hour. The plates were washed twice with PBS+0.05% Tween (PBST). The plates were blocked with 1% fish gelatin in PBS for 1 hour at 37° C. The plates were washed twice with PBST. Serially diluted mouse serum (in PBS) was added (100 μl/well) and incubated for 2 hours at 37° C. The plates were washed 5 times with PBST. Goat anti-mouse IgG-HRP (Pierce, Rockford, Ill.) at 1 to 10,000 dilution was added to the plates and incubated for 1 hour at room temperature. The plates were washed 5 times with PBST. Tetramethylbenzidine (TMB) solution (KPL, Gaithersburg, Md.) was added to the plates for color development. The substrate reaction was stopped after approximately 5 minutes when appropriate color developed. The plates were read at 450 nM in a microplate reader (Bio-rad, Hercules, Calif.). Serum was tested in all mice at day 56 (FIG. 1). Those mice with serum reactive with hFcRn were tested again on day 94 and the serum titers are shown in FIG. 2.

Example 4

Hybridoma Fusions

Mouse 182 and mouse 187 were selected for making hybridoma fusions. The spleens of both mice were removed and single cell suspensions of spleen cells were prepared by teasing the spleens apart followed by repeated pipetting with 10 ml of DMEM media (Invitrogen, Carlsbad, Calif.). The spleen cells were centrifuged at 500 g for 5 minutes. Red blood cells were lysed by resuspending the spleen cells in 2 ml ACK lysis buffer (8.29 g $NH_4Cl$, 1 g $KHCO_3$, 37.2 mg $Na_2EDTA$, $H_2O$ to a final volume of 1 liter, pH 7.2-7.4). The cells were incubated on ice for 5 minutes. ACK buffer treated cells were washed three times with DMEM. The total number of spleen cells obtained from mouse 182 was $216 \times 10^6$. One half of the cells was fused with $70 \times 10^6$ SP2/0 myeloma cells and the other half was fused with $27 \times 10^6$ NS-1 cells.

The #182 fusion was carried out according to the method described in *Current Protocol of Immunology* Unit 2.5, Wayne M. Yokoyama, Publisher: John Wiley and Son Inc. Electronic version. SP2/0 fused cells were diluted in 314 ml HAT medium and seeded onto 16.5 plates (96 well plate, 0.2 ml/well). NS-1 fused cells were diluted in 216 ml HAT medium and seeded onto 11 plates (96 well plate, 0.2 ml/well).

In the #187 fusion, $2 \times 108$ spleen cells were fused with $8 \times 107$ SP2/0 myeloma cells using a protocol from "Monoclonal Antibodies" edited by J. H. Peters and H. Baumgarten, published by Springer-Verlag, 1992, Page 149-156. New York.

On days 2, 3, 4, 5, 7, 9 after the fusion, half of the HAT medium was replaced with fresh HAT medium. One to two weeks after the fusion, hybridoma cells from positive wells (determined by clear growth under the microscope and by naked eye inspection) were transferred to 24 well culture plates. Within 2 weeks after the fusion, hybridoma cells were cultured in HAT media containing complete medium. On day 16, cells were transferred to CDMEM without HAT.

When the medium turned slightly yellow, an aliquot of supernatant was harvested and screened for anti-hFcRn activity by ELISA as described in Example 3. A total of 384 hybridoma lines from SP2/0-#182 spleen cell fusion were screened. A total of 60 hybridoma lines from NS-1-#182 spleen cell fusion were screened. Supernatants from 31 lines of SP2/0 fusion tested positive by ELISA for anti-hFcRn reactivity. Supernatants from 8 hybridoma lines of NS-1 fusion tested positive by ELISA for anti-hFcRn reactivity. A total of 16 hybridoma lines from #182 fusion were cloned by limiting dilution and 3 subclones from each line were selected for further characterization.

Example 5

Hybridoma Cloning

Hybridoma cloning media was prepared as follows: 12.5 ml hepes buffer solution (100×/1M) (Invitrogen, Carlsbad, Calif.), 5 ml sodium pyruvate (100×/100 mM) (Invitrogen, Carlsbad, Calif.), 5 ml penicillin/streptomycin (100×/10,000 units) (Invitrogen, Carlsbad, Calif.), 5 ml non-essential amino acids (100×/100 mM) (Invitrogen, Carlsbad, Calif.), 5 ml L-glutamine (100×/200 mM) (Invitrogen, Carlsbad, Calif.), 0.5 ml 2-mercaptoethanol ($1000 \times / 5.5 \times 10^{-2}$ M) (Invitrogen, Carlsbad, Calif.), 100 ml FBS (prescreened for hybridoma growth) (Cambrex, East Rutherford, N.J.), and 50 ml of hybridoma cloning factor (ICN, Irvine, Calif.) were added to 317 ml high glucose DMEM (Invitrogen, Carlsbad, Calif.). The media was filtered through a 0.22 μm filter and stored at 4° C.

Two days before cloning, the cDMEM culture media was replaced with hybridoma cloning media. On the day of cloning, the cells were washed once in DMEM and the cells were counted. The cells were resuspended in cloning medium at a concentration varied from $1 \times 10^5$-$1 \times 10^6$/ml. 3000, 300 or 100 cells were transferred to 20 ml cloning medium to make concentration of 150 cells/ml, 15 cells/ml or 3 cells/ml. The cells were then transferred to 3 individual plates (one for each cell concentration) of a 96 well plate. Each well has final volume of 0.2 ml. The plates were incubated at 37° C., 10% $CO_2$ for 1-2 weeks at which point positive wells were counted. 20 30 clones were selected from plates with the least positive wells and expanded into 24 well plates. The supernatants were tested by anti-FcRn ELISA as described in Example 3 for reactivity to soluble FcRn.

Example 6

Cell Competition Assay Using FcRn Specific mAb Supernatants

A. Labeling of Synagis® with Alexa-Fluor-488

Synagis (humanized IgG1, MedImmune, Gaithersburg, Md.) was labeled with the Alexa Fluor 488 Protein Labeling Kit (Molecular Probes/Invitrogen, Carlsbad, Calif.) according to the manufacturer's suggested protocol. Briefly, 50 μl of 1 M sodium bicarbonate, pH 9.0 was added to 500 μl of a 2 mg/ml solution of IgG in PBS. This protein solution was then added to the Alexa Fluor 488 succinimidyl ester (dry powder) and incubated at room temperature for 1 hour. The protein was purified by size-exclusion chromatography using the kit component column (Bio-Rad BioGel P-30 Fine size exclusion purification resin). The sample was loaded onto the column and eluted with PBS. The first colored band contained the labeled protein. The degree of labeling was determined by measuring the absorbance of the eluted IgG at A280 and A494. The protein molar concentration was determined using the formula:

$$(M) = \frac{[A_{280} - (A_{494} \times 0.11) \times \text{dilution factor}]}{203,000}$$

In addition, the formula used to derive the moles of dye per mole of protein was:

$$(M) = \frac{A_{494} \times \text{dilution factor}}{71,000 \times \text{protein concentration}}$$

Typically, 4 to 7 moles of Alexa-Fluor 488 were incorporated per mole of IgG.

B. Cell Competition Assay with FcRn Specific Supernatants

293 C11 cells expressing hFcRn and human $\beta_2M$ were used to test FcRn mAB supernatants in a competition assay with a fluorescently labeled IgG1. 300,000 293 C11 cells were washed in PBS and pelleted in a table top micro-centrifuge at 2500 RPM for 5 minutes. The pelleted cells were resuspended in 100-200 μl of supernatant from clones producing FcRn specific mABs and incubated on ice for 60-90 minutes. The cells were washed twice with binding buffer (PBS pH 6.0 10 mM EDTA). The cells were resuspended in 100 μl of binding buffer. Alexa fluor 488 (Molecular Probes, Eugene, Oreg.) labeled hIgG1 was prepared using a kit (Molecular Probes, Eugene, Oreg.) according to the manufacturer's instructions and added to each tube (100 nM in 0.6-1.5 µl). The cells were incubated for 40 minutes on ice. The cells were washed once in binding buffer and analyzed by fluorescent activated cell sorter (FACS) using EXPO032 software (Beckman Coulter, Inc., Miami, Fla.). The results are presented as total mean fluorescence intensity (TMFI).

Figure 3A:
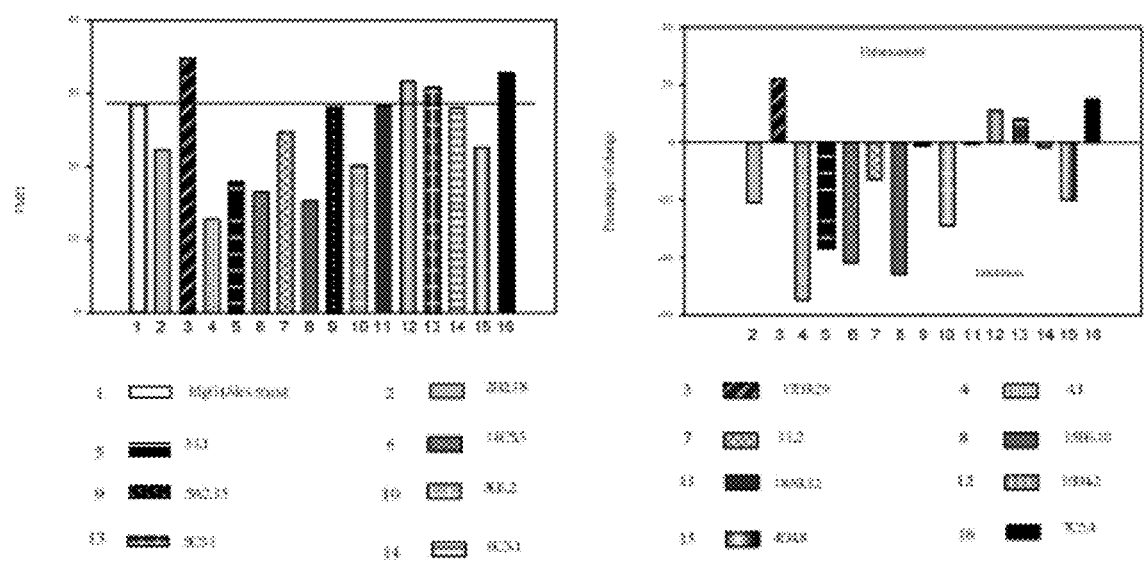
FIG. 3 depicts the results of a FACS analysis that was performed to determine whether the supernatants of #182 mouse derived clones were capable of blocking hIgG binding to hFcRn on 293C11 cells (HEK 293 cells engineered to overexpress FcRn). 293C11 cells were incubated with hybridoma supernatants for 60-90 minutes then washed with PBS followed by incubation with Alexa fluor-488 labeled hIgG Results are expressed in terms of either (A) total mean fluorescence intensity (TMFI) or (B) the percent changed (inhibition or enhancement) in the binding of human IgG to FcRn.
Figure 3B:
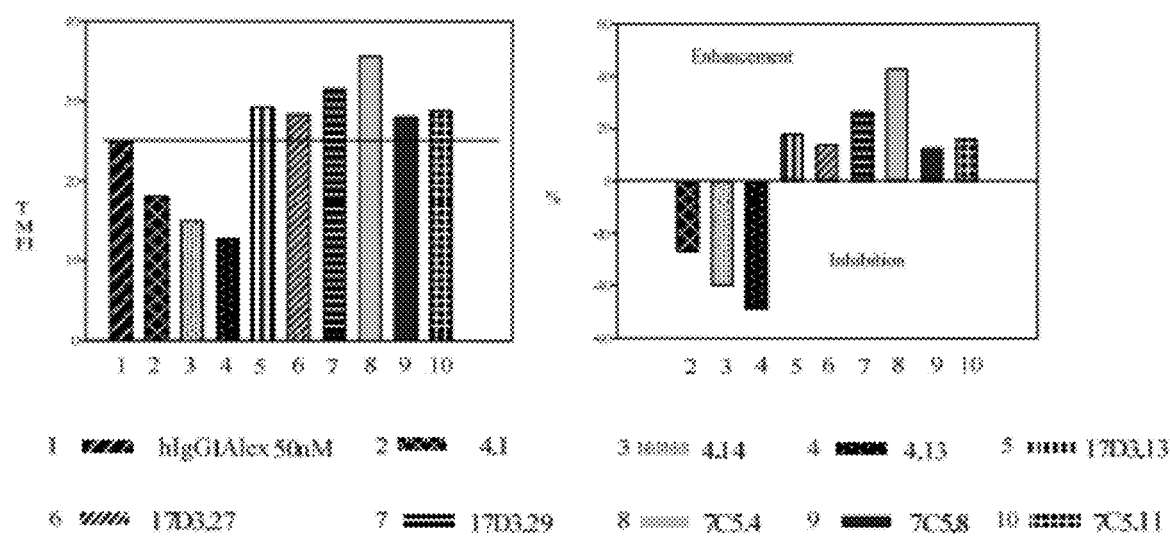

FIG. 3 depicts results from the 182 fusions. If the TMFI of the control tube (Alexa Fluor 488 alone and without competitor) is higher than the TMFI of the tube containing competitor (mAB sup), the inhibition rate was calculated as follows:

TMFI of control tube−TMFI of competitor containing tube/TMFI of control tube.

If TMFI of the control tube is lower than the TMFI of competitor containing tube, there is enhancement of hIgG1 binding to FcRn expressing cells. The enhancement was calculated as follows:

TMFI of competitor containing tube−TMFI of control tube/TMFI of control tube.

Figure 4A:
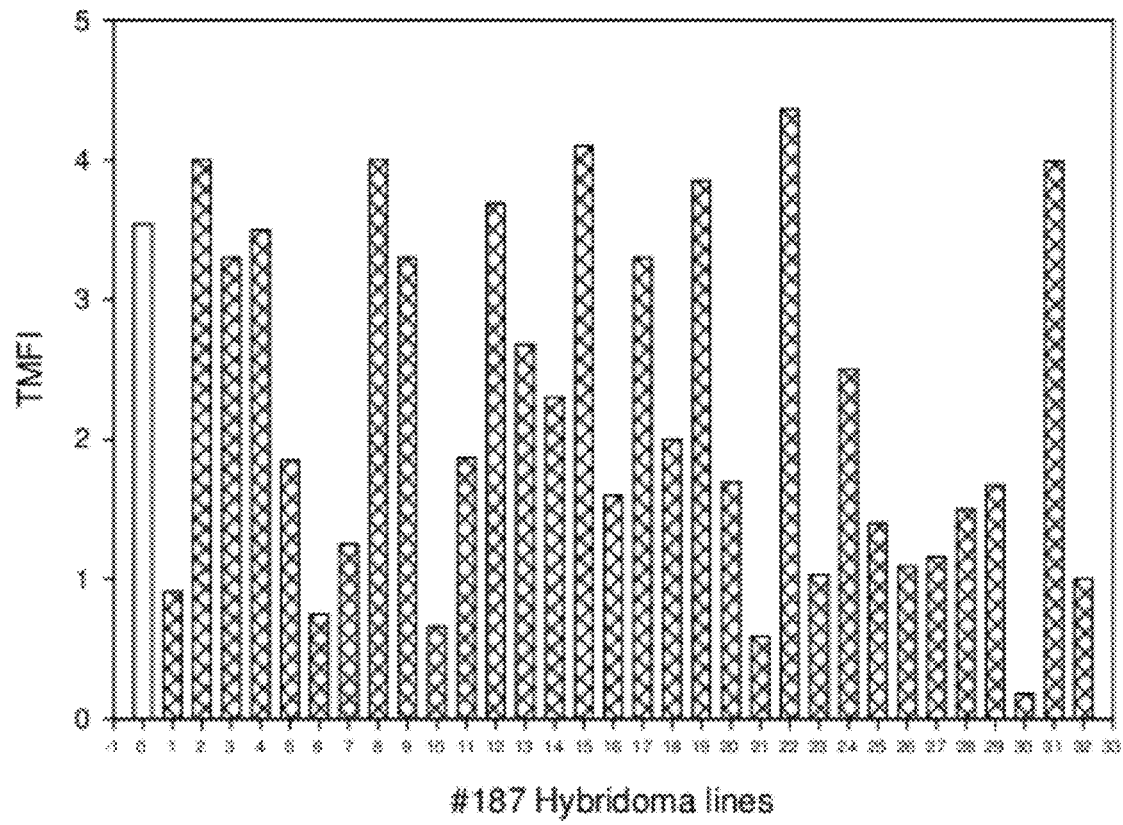
FIG. 4 depicts the results of a FACS analysis that was performed to determine the blocking activity of #187 mouse derived hybridoma supernatants with the method described in Example 6. Results are expressed in terms of either (A) Total mean fluorescence intensity (TMFI) or (B) the percent changed (inhibition or enhancement) in the binding of human IgG to FcRn.
Figure 4B:
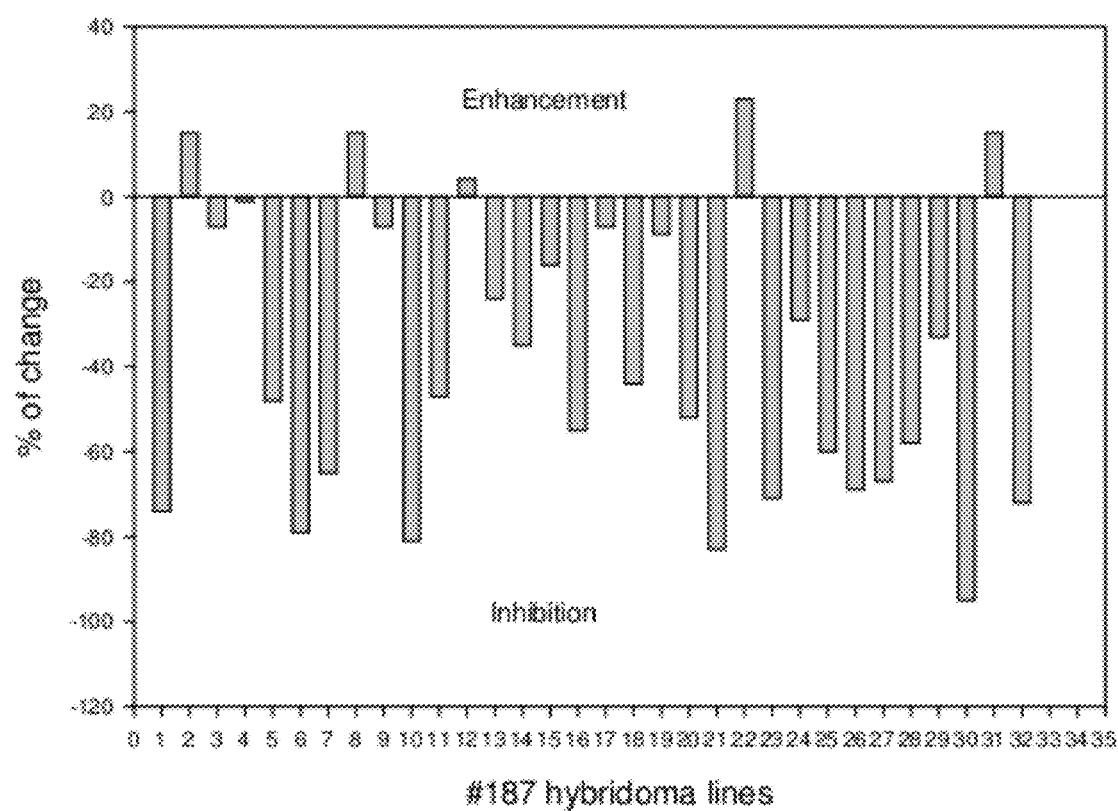

FIG. 4 depict results from the 187 fusion. TMFI was calculated as fraction of cells in the gated region multiplied by mean fluorescence in the region. The results of one experiment indicated 11 of the supernatants tested inhibited IgG1 labeled with Alexa fluor 188 binding to 293C11 cells, while 4 of the supernatants enhanced binding of IgG1 labeled with Alexa fluor 188 binding to 293C11 (FIG. 4A). The results of a second experiment indicated that 3 supernatants inhibited IgG1 binding to 293 C11 cells, while 5 supernatants enhanced binding (FIG. 4B).

Example 7

Cell Competition Assay Using Purified FcRn Specific mABs

Figure 5A:
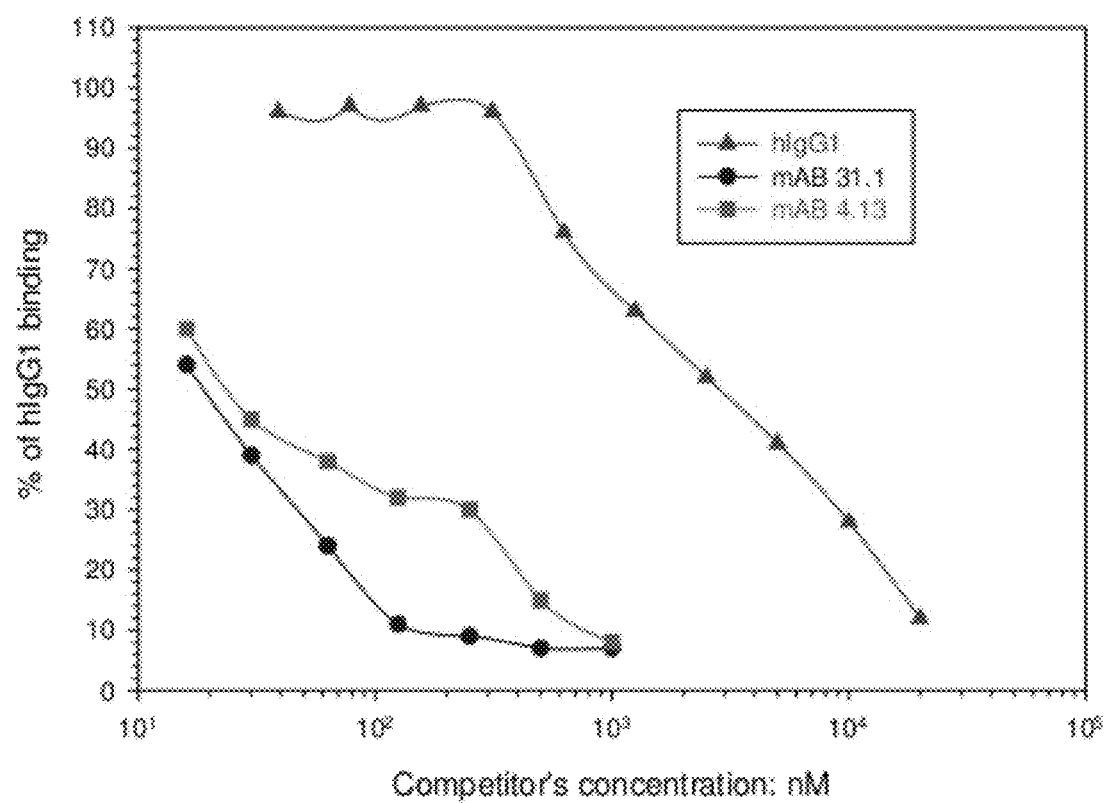
FIG. 5 depicts the results of a FACS analysis that was performed to determine the potency of FcRn blocking activity at various concentrations of (A) mAb 31.1, mAb 4.13, and hIgG1; or (B) mAb 3B3.11, mAb 4B4.12, and hIgG1, by examining the cell surface staining of 293 C11 cells (HEK 293 cells engineered to overexpress FcRn) that were incubated in the presence of Alexa-488-labeled hIgG and anti-FcRn blocking monoclonal antibodies or hIgG1. Results are expressed as percentages of hIgG binding to 293C11 cells defined as TMFI at various concentration divided by TMFI of samples without competitor times 100%).
Figure 5B:
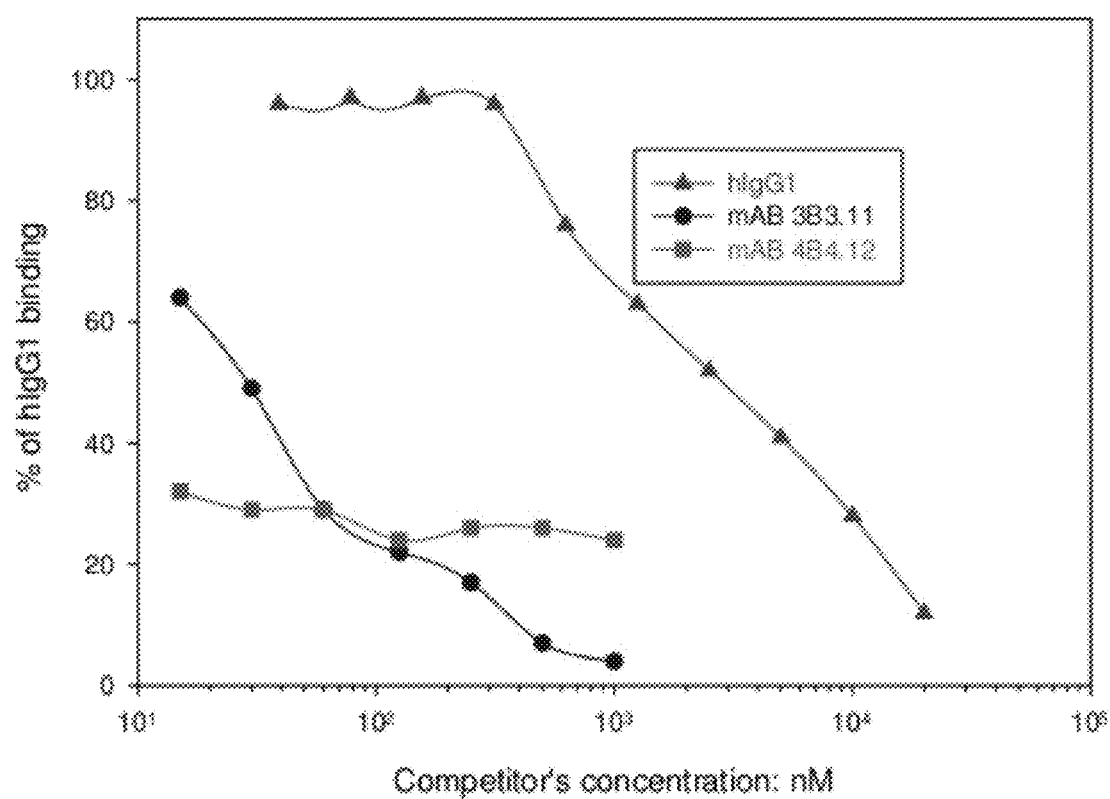

293 C11 cells expressing hFcRn and human $\beta_2M$ were used to test FcRn mAB supernatants in a competition assay with a fluorescently labeled IgG1. The cells were washed once with binding buffer (PBS pH 6.0, 10 mM EDTA) and pelleted at 1800 RPM, 4° C. in a table top centrifuge. The cells were aliquoted into micro-centrifuge tubes ($1-3 \times 10^5$/vial/ml binding buffer). The cells were pelleted in a micro-centrifuge at 2500 RPM for five minutes. The supernatant was aspirated and the cell pellet was resuspended in 100 µl of binding buffer. Purified FcRn specific mABs were added at various concentrations. Alexa fluor 488 (Molecular Probes, Eugene, Oreg.) labeled IgG was added at a concentration of 100 nM (final concentration) to each tube. The samples were incubated at 4° C. for 40 minutes. The samples were washed once with binding buffer and resuspended in binding buffer for FACS analysis (Beckman Coulter, Inc., Miami, Fla.). Before sample analysis the FACS was equilibrated with binding buffer. The results are presented as total mean fluorescence intensity (TMFI). TMFI was calculated as percentage of cells in the gated region×mean fluorescence in the region. The results indicated the mAB 3B3.11, mAB 4B4.12, mAB 31.1 and mAB 4.13 inhibited IgG1 binding to 293 C11 cells significantly (FIG. 5).

Example 8

Cell Surface Staining for FcRn Using Monoclonal Antibodies

Figure 6:
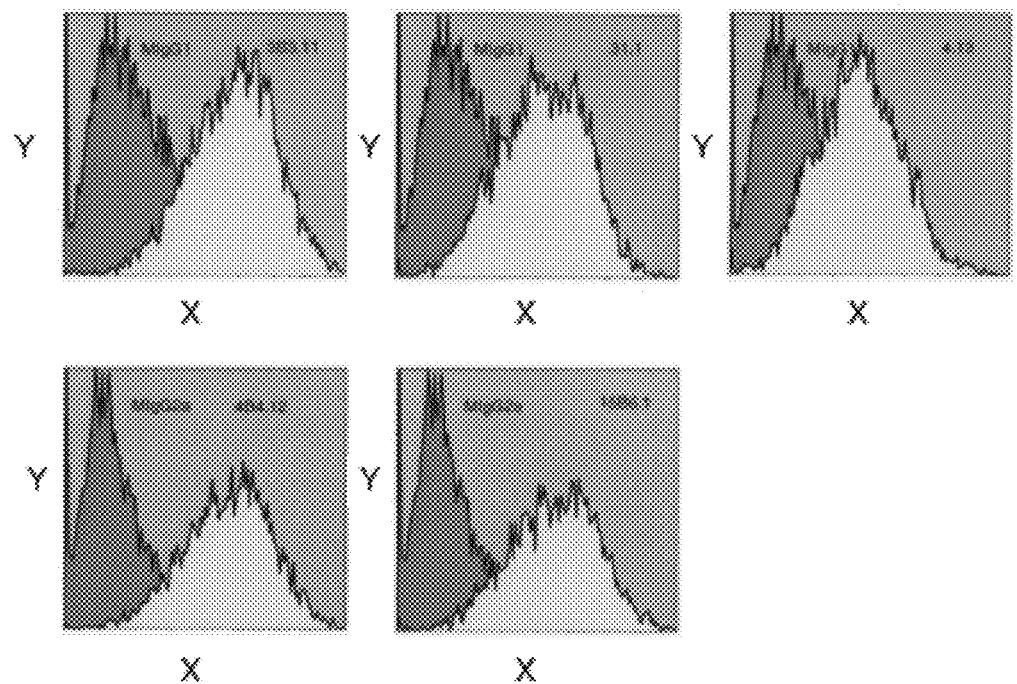
FIG. 6 depicts the histograms from a FACS analysis that was performed to determine the binding of mAb 3B3.11, mAb 31.1, mAb 4.13, mAb 4B4.12, and mAb 15B6.1 to the cell surface of hFcRn expressing 293 C11 cells (HEK 293 cells engineered to overexpress hFcRn).
Figure 7:
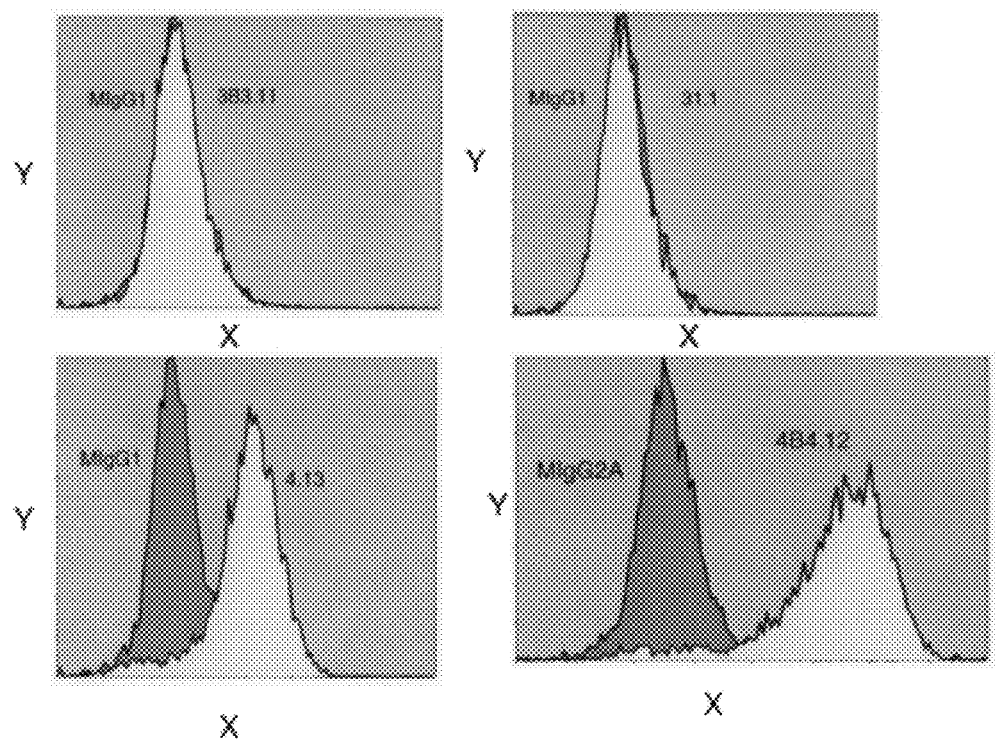
FIG. 7 depicts the histograms from a FACS analysis that was performed to determine the binding of mAb 3B3.11, mAb 31.1, mAb 4.13, and mAb 4B4.12 to the cell surface of rat FcRn-expressing cells (rat fibroblasts engineered to overexpress rat FcRn).
Figure 8:
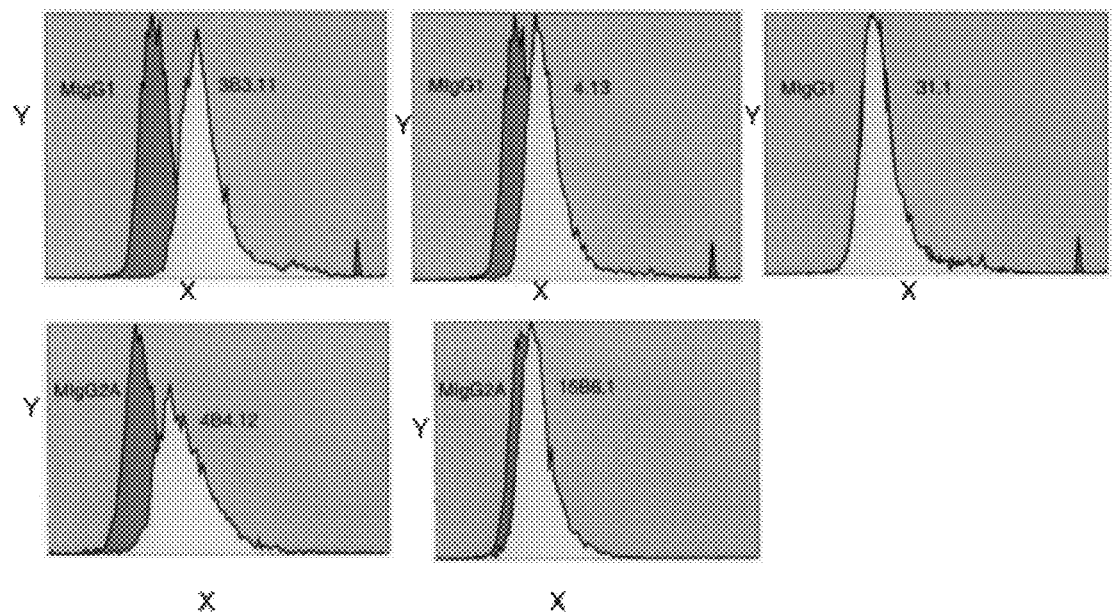
FIG. 8 depicts the histograms from a FACS analysis that was performed to determine the binding of mAb 3B3.11, mAb 4.13, mAb 31.1, mAb 4B4.12, and mAb 15B6.1 to the cell surface of FcRn-expressing mouse 3T3 cells (NIH 3T3 cells engineered to overexpress mouse FcRn).

Surface expression of FcRn using mABs was detected by FACS. Rat fibroblasts (expressing rat FcRn/rat $\beta_2M$) 293 C11 cells (expressing hFcRn/human $\beta_2M$), 3T3 FcRn cells (expressing murine FcRn/murine $\beta_2M$) and COS cells transfected with plasmid pcDNA6 encoding monkey FcRN/$\beta_2M$ were studied. A micro-centrifuge was used to pellet $1-3 \times 10^5$ of each cell type. The supernatant was removed and the cells were resuspended in 1 µg of mAB labeled with Alexa 488 (Molecular Probes, Eugene, Oreg.) in a final volume of 100 µl of PBS/1% bovine serum albumin (pH 7.4). Purified mABs specific to FcRn were previously labeled with Alexa Fluor 488 (Molecular Probes, Eugene, Oreg.) using the Alexa Fluor Protein Labeling Kit (Molecular Probes, Eugene, Oreg.) according to the manufacturers instructions. The cells were incubated on ice for 45 minutes and then washed once with PBS/1% bovine serum albumin (pH 7.2). FACS analysis was performed using a Beckman Coulter, Inc. FACS (Beckman Coulter, Inc., Miami Fla.). The results are presented in FIGS. 6, 7, and 8. FIG. 6 shows that mABs 3B3.11, 31.1, 4.13, 4B.12 and 15B6.1 all recognized hFcRn expressed on the cell surface of 293 C11 cells. FIG. 7 shows that mABs 4.13 and 4B4.12 also recognized rat FcRn expressed on the surface of cells expressing rat FcRn while mABS 3B3.11 and 31.1 did not cross react with rat FcRn. FIG. 8 shows that mABs 3B3.11, 4B4.12 and 4.13 recognized murine FcRn expressed on the cell surface of mouse 3T3 cells, while 15B6.1 and 31.1 did not cross react.

Example 9

Sub-Cloning of Various Hybridoma Cell Lines

Hybridomas from mouse 187 were selected for sub-cloning. Hybridomas 6A4, 6A1, 5A4, 7D2, 4B4, 3C5, 3B3, 10B4, 1C1, and 11A5 were selected for sub-cloning. Sub-cloning was performed by limiting dilution. 3B5 clones secrets anti-h$\beta_2M$ antibody. Between 20 and 30 sub-clones were grown and the supernatants from the cultures were tested by ELISA as described in Example 3. Cultures from 2-10 positive clones were expanded into T150 flasks (4 flasks per clone). A total of 350-400 ml of supernatant was harvested for mAB purification. The mAB yield from each clone ranged from 3-20 mg. The purified mABs were tested for FcRn blocking using the 293 C11 competition assay as described in Example 7. The mABs were titrated 2-fold from 1000 nM to 16 nM for the competition assay. A summary of the results obtained for the 187 sub-clones and the 182 clones is presented in Table 3.

TABLE 3

Characterization of mABs from #182 fusion and #187 fusion

| Clones | ELISA (shFcRn) | Blocking test (sup) % of inhibition | IgG isotyping | Blocking (purified) % Inhibition |
|---|---|---|---|---|
| #182 fusions | | | | |
| 4.13 | + | >50 | IgG1 | 90 |
| 15B6.1 | ++ | >50 | IgG2a | |
| 14C5.3 | + | >40 | IgG2a | |
| 31.1 | + | >40 | IgG1 | 93 |
| 3C6.2 | + | >35 | IgG2a | 74 |
| #187 fusion | | | | |
| 3B3.11 | ++ | >60 | IgG1 | 92 |
| 3B3.16 | ++ | >60 | IgG1 | 73 |
| 3B3.21 | ++++ | >60 | IgG1 | 84 |
| 3B3.35 | ++ | >60 | IgG1 | 86 |
| 6A4.1 | + | >40 | IgG1 | 42 |
| 6A4.4 | + | >40 | IgG1 | 52 |
| 6A4.16 | + | >40 | IgG1 | 65 |

TABLE 3-continued

Characterization of mABs from #182 fusion and #187 fusion

| Clones | ELISA (shFcRn) | Blocking test (sup) % of inhibition | IgG isotyping | Blocking (purified) % Inhibition |
|---|---|---|---|---|
| 6A4.17 | + | >40 | IgG1 | 42 |
| 6A1.12 | + | 21 | IgG1 IgG2a | 35 |
| 6A1.13 | + | 25 | IgG2a | 39 |
| 6A1.29 | + | 33 | IgG2a | 81 |
| 3B5.2 (@β2m) | +++ | 71 | IgG2a | 90 |
| 3B5.4 (@β2m) | +++ | 79 | IgG2a | 52 |
| 3B5.5 (@β2m) | +++ | 63 | IgG2a | |
| 3B5.9 (@β2m) | +++ | 71 | IgG2a | 80 |
| 7D2.13 | + | 49 | IgG1 IgG2a | 11 |
| 7D2.21 | ++ | 43 | | |
| 7D2.22 | + | 49 | IgG1 IgG2a | 43 |
| 7D2.27 | + | 46 | IgG1 | 52 |
| 5A4.9 | + | 57 | | |
| 5A4.10 | + | 49 | IgG1 | 63 |
| 5A4.25 | + | 54 | IgG1 | 31 |
| 5A4.27 | + | 51 | | 39 |
| 5A4.38 | + | 43 | | 15 |
| 5A4.39 | + | 49 | | 20 |
| 5A4.40 | + | 53 | | 30 |
| 5A4.41 | + | 66 | | 35 |
| 5A4.42 | + | 72 | | |
| 4B4.1 | ++ | 70 | IgG2a | |
| 4B4.2 | ++ | 66 | IgG2a | 69 |
| 4B4.12 | ++ | 70 | IgG2a | 71 |
| 4B4.13 | ++ | 66 | IgG2a | 60 |
| 3C5.10 | + | 30 | | |
| 3C5.11 | + | 40 | | |
| 3C5.14 | + | 40 | | |
| 3C5.16 | + | 33 | | |
| 10B4.5 | +++ | 23 | | 54 |
| 10B4.9 | ++ | 23 | | 31 |
| 1C1.7 | +++ | 32 | IgG1 | 23 |
| 1C1.22 | +++ | 27 | IgG1 | 61 |
| 1C1.23 | +++ | 32 | IgG1 | 27 |
| 1C1.25 | ++ | 32 | IgG1 | 38 |
| 11A5.5 | +++ | 49 | IgG1 | 13 |
| 11A5.9 | + | 43 | | |
| 11A5.11 | + | 45 | | |
| 11A5.12 | + | 51 | IgG1/IgG2a | 76 |

Example 10

Intracellular Staining of FcRN

Figure 9:
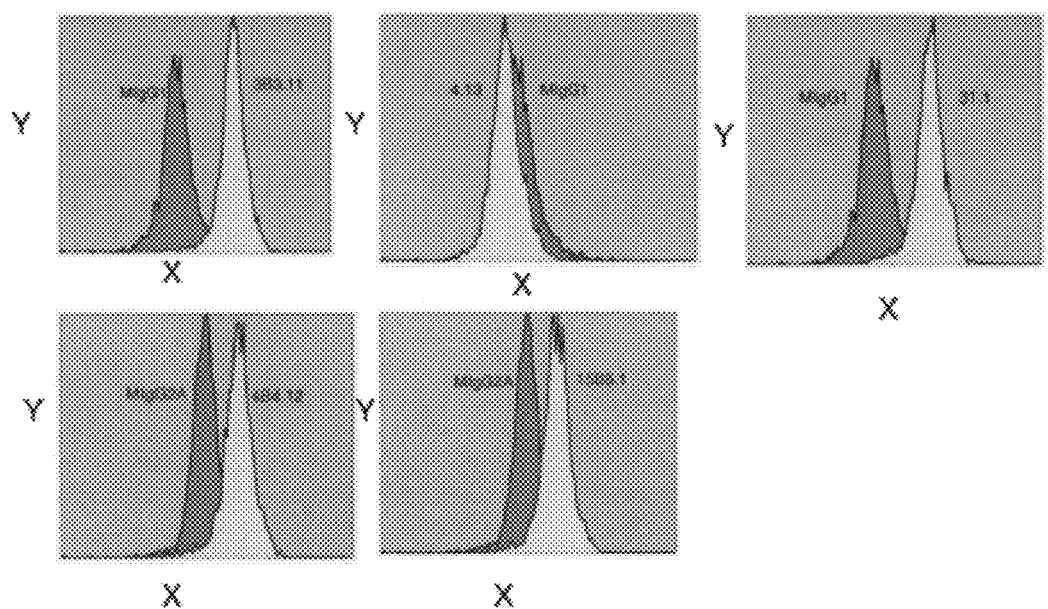
FIG. 9 depicts the histograms from a FACS analysis that was performed to determine the binding of mAb 3B3.11, mAb 4.13, mAb 31.1, mAb 4B4.12, and mAb 15B6.1 to hFcRn expressed intracellularly in THP cells (a human monocytic cell line).
Figure 10:
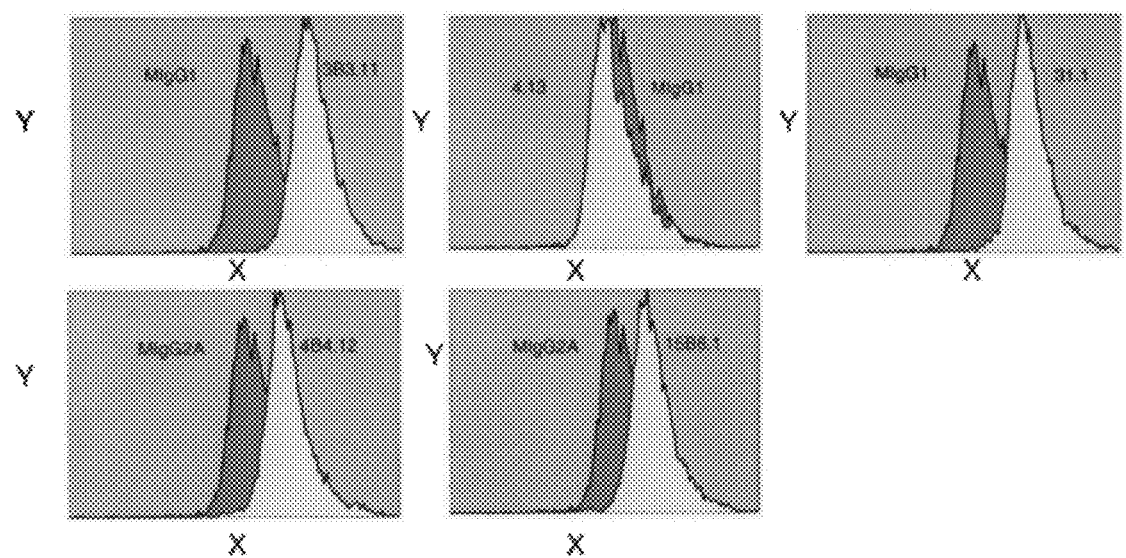
FIG. 10 depicts the histograms from a FACS analysis that was performed to determine the binding of mAb 3B3.11, mAb 4.13, mAb 31.1, mAb 4B4.12, and mAb 15B6.1 to hFcRn expressed intracellularly in Caco-2 cells (a human intestinal epithelial cell line).

THP-1 cells (a human monocytic cell line) and Caco-2 cells (a human intestinal epithelial cell line) were studied for intracellular staining of FcRn using purified monoclonal antibodies (mABs) specific to FcRn. Aliquots of 300,000 cells/tube of THP-1 or Caco-2 cells were pelleted and resuspended in 250 µl of BD Cytofix/Cytoperm (BD Biosciences Pharmingen, San Diego, Calif.). The cells were washed twice with 1 ml of BD Perm/wash solution (BD Biosciences Pharmingen, San Diego, Calif.) and resuspended in the same solution. Alexa fluor 488 (Molecular Probes, Eugene, Oreg.) labeled mABs (1 □g/tube) were added to the cells and the cells were incubated for 45 minutes on ice. The cells were washed twice with BD Perm/wash solution (BD Biosciences Pharmingen, San Diego, Calif.) and resuspended in PBS/1% bovine serum albumin. The cells were analyzed by FACS (Beckman Coulter, Inc., Miami Fla.). The results are presented in FIGS. 9 and 10 and indicated that mABs 3B3.11, 31.1, 4B4.12 and 15B6.1 all effectively bound to intra-cellular FcRn in THP-1 cells (FIG. 9), while the 4.13 mAB did not. Similar results were obtained for the Caco-2 cells (FIG. 10).

Example 11

Intracellular and Surface Staining of Mouse Spleen Cells with Anti-FcRN mABs

Figure 11A:
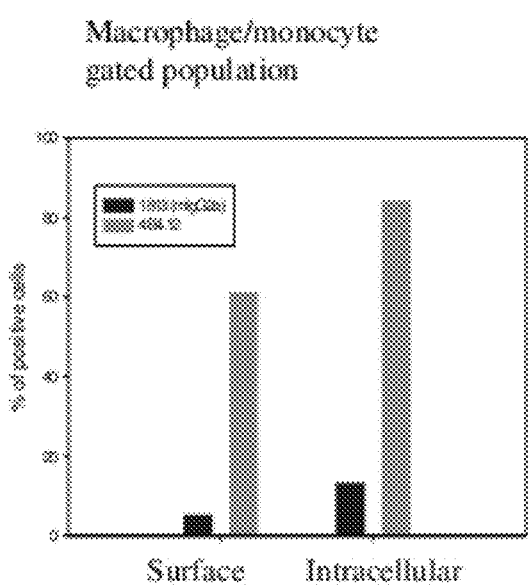
FIG. 11 depicts the percentage of (A) macrophage population from mouse spleen and the (B) total mouse spleen cell population, that are reactive on surface or intracellularly with either mAb 4B4.12 or the isotype control, mIgG2a (1813).
Figure 11B:
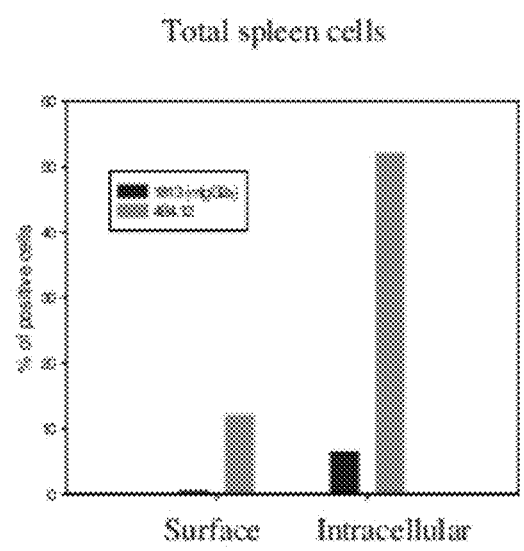

Forceps were used to tease apart cells from the mouse spleen. The cells were pelleted and resuspended in ACK lysis buffer (8.29 g NH$_4$Cl, 1 g KHCO$_3$, 37.2 mg Na$_2$EDTA, H$_2$0 to a final volume of 1 liter, pH 7.2-7.4) and incubated at room temperature for 5 minutes. The cells were washed three times with DMEM/5% FBS (Invitrogen, Carlsbad, Calif.). 1×10$^6$ cells were transferred to a microfuge tube and pelleted in a table top micro-centrifuge. For intracellular staining a fixation and permeabilization step was performed as described in Example 10. The cells were resuspended in washing buffer (PBS/1% BSA) containing 20 µg/ml mouse isotype control antibody and incubated on ice 20 minutes. The cells were pelleted and Alexa 488 (Molecular Probes, Eugene, Oreg.) labeled mABs (1 µg/tube) in 100 µl washing buffer containing 1 µg/ml isotype control antibody was added to the cells. The cells were incubated on ice for 40 minutes and then washed twice with washing buffer. Scatter was gated as macrophages/monocytes enriched population using EXPO.32 software. By adjusting forward scatter and size scatter, macrophage/monocytes (unique population with large size and high granuality) enriched population was analyzed. The cells were analyzed by FACS (Beckman Coulter, Inc., Miami Fla.). The results are presented in FIG. 11 and indicate that mAB 4B4.12 detected mouse FcRn on the surface and intracellularly in both spleen cells and macrophage/monocytes obtained from the spleen cell population.

Example 12

Effect of Anti-FcRN mAb 4B4.12 on Immune Response

Female Balb/c mice, 6-8 weeks old, were immunized with 50 µl of an emulsion of complete Freund's adjuvant mixed 1:1 with ovalbumin. Mice were immunized subcutaneously once on each side of the flank on day 0 and boosted on day 10 with 100 µg of ovalbumin/mouse. Mice were treated by injecting intra-peritoneally either the 4B4.12 mAB specific to FcRn or the isotype control (1813; ATCC1813) antibody (1 mg/ml in PBS/mouse) or PBS. Treatments were administered on day −1, day 0, day 1, and every other day there after. The mice were bled on day 9 for serum samples and euthanized on day 16. A maximum serum draw was made after euthanization. The protocol is summarized below in Table 4.

TABLE 4

Treatment Protocol

| Group# | Day −1 | Day 0 IP | Day 0 SC | Day +1 | Every other day | Day +9 | Day +10 | Day +16 |
|---|---|---|---|---|---|---|---|---|
| 1 | 4B4.12 | 4B4.12 | OVA + CFA | 4B4.12 | 4B4.12 | Bleed | OVA | Assays |
| 2 | 1813 | 1813 | OVA + CFA | 1813 | 1813 | Bleed | OVA | Assays |
| 3 | PBS | PBS | OVA + CFA | PBS | PBS | Bleed | OVA | Assays |

Figure 12A:
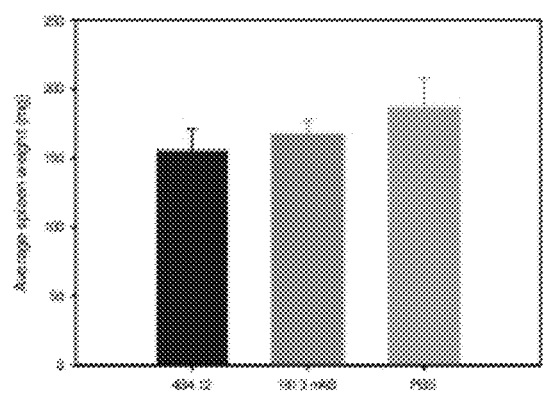
FIG. 12 depicts the average weight of the (A) spleen and (B) inguinal lymph nodes from mice immunized with OVA plus CFA and treated with mAb 4B4.12, the isotype control, mIgG2a (1813) or PBS. Mice were immunized with OVA plus CFA and treated IP with 10 injections of 1 mg of 4B4.12 or isotype control 1813.
Figure 12B:
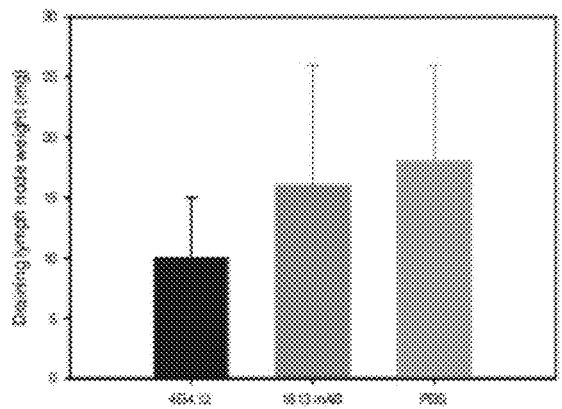

Spleens and draining lymph nodes were obtained and weighed in an analytical balance. The results presented in FIG. 12 indicate that the weight of both the spleen and the draining (inguinal) lymph node was reduced in the mice treated with the 4B4. 12 mAB compared to the 2 controls.

Figure 13:
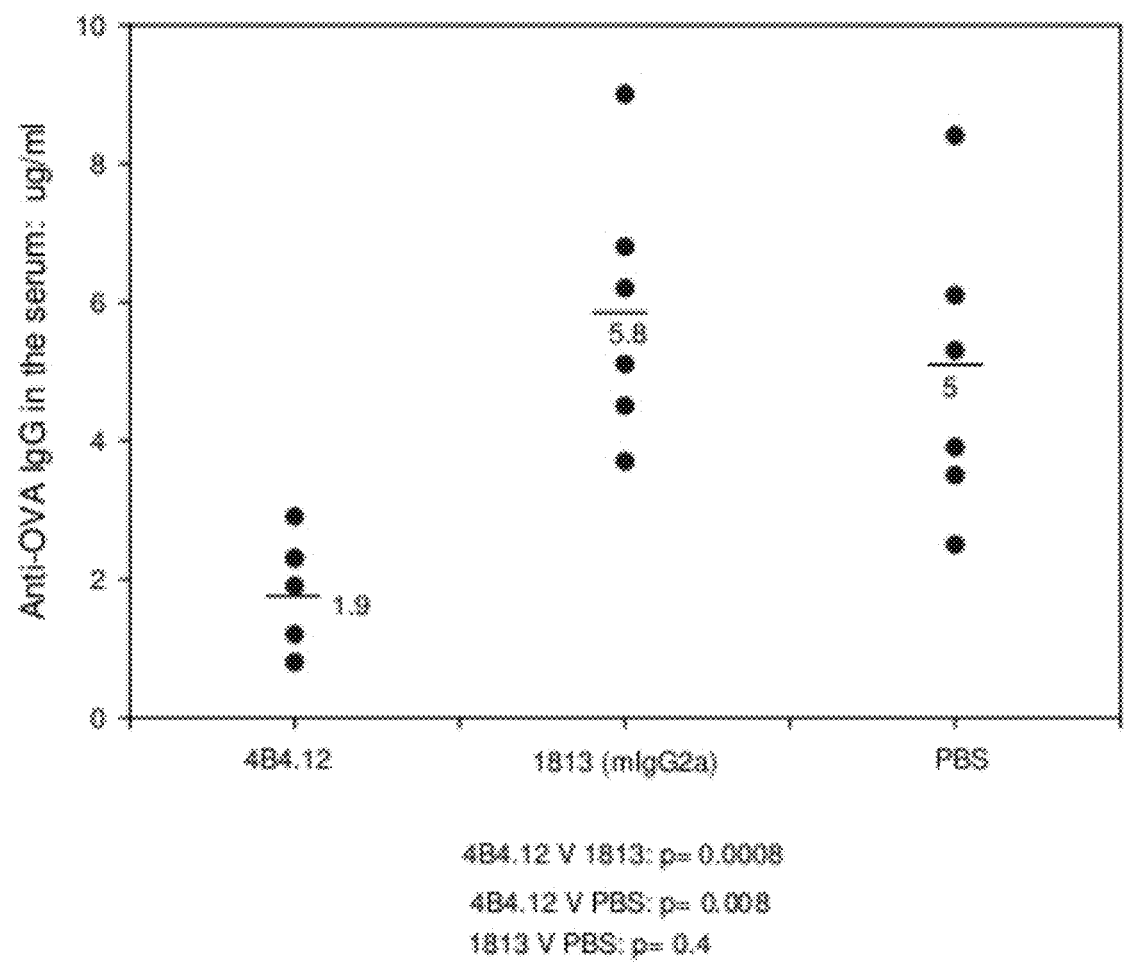
FIG. 13 depicts the effect on serum levels of anti-ovalbumin (OVA) IgG of Balb/c mice, that have been immunized with OVA, and then treated with either mAb 4B4.12, the positive control, mIgG2a (1813), or PBS. Antibody treatment consisted of three daily intraperitoneal (IP) injections of antibodies, followed by 10 antibody injections IP every other day. The results shown were obtained after 9 days of antibody treatment (5 injections).

Ovalbumin antibody titer was measured by ELISA. Ovalbumin at a concentration of 10 µg/ml was coated on ELISA plates and blocked with PBS/1% BSA. Titrated serum (starting with 1 to 50 then 2 fold dilution of 2 µg/ml in PBS/1% BSA) and standard mouse IgG1 (mouse mAB anti-OVA) was added to the plates and incubated at 37° C. for 2 hours. Goat anti-mouse IgG HRP (Pierce, Rockford, Ill.) was added and the plates were incubated for 30 minutes. TMB solution (KPL, Gaithersburg, Md.) was added and the color developed. Optical density was measured at 450 nM using a microplate reader (Bio-rad, Hercules, Calif.). The results are presented in FIG. 13 and demonstrate that the 4b4.12 mAB significantly reduced anti-ovalbumin serum concentration.

Example 13

Effect of 4B4.12 on Catabolism of Synagis in CD1 Mice

CD1 Mice (n=4) (Charles River Laboratories) were injected intra-peritoneally with Synagis 1 mg/kg. 72 hours later, 4B4.12, MIgG1 or PBS were injected intra-peritoneally (20 mg/kg). After 4, 6 and 10 days, mouse serum was obtained and Synagis concentration was determined by ELISA. Anti-human IgG (FAB')2 antibody at the concentration of 10 □g/ml in ELISA coating buffer (Sigma) was coated on ELISA plates at 37° C. for 1 hour. After two washes with PBST, the plates were blocked with PBS/2% BSA for 1 hour at 37° C. Following two washes, serum samples were diluted two fold starting at a 1 to 50 dilution and added to the plates in duplicates (100 µl/well). The plates were incubated for 2 hours at 37° C. After three washes with PBST, HRP conjugate of Goat anti-human IgG Fc was added to the plates and incubated at room temperature for 40 minutes. After 4 washes with PB ST, TMB substrates (KPL) were added to the plates and incubate for 5 minutes at room temperature. The color reaction was stopped with stop solution (KPL) and the plates were read at a microplate reader (Molecular Devices).

Figure 14:
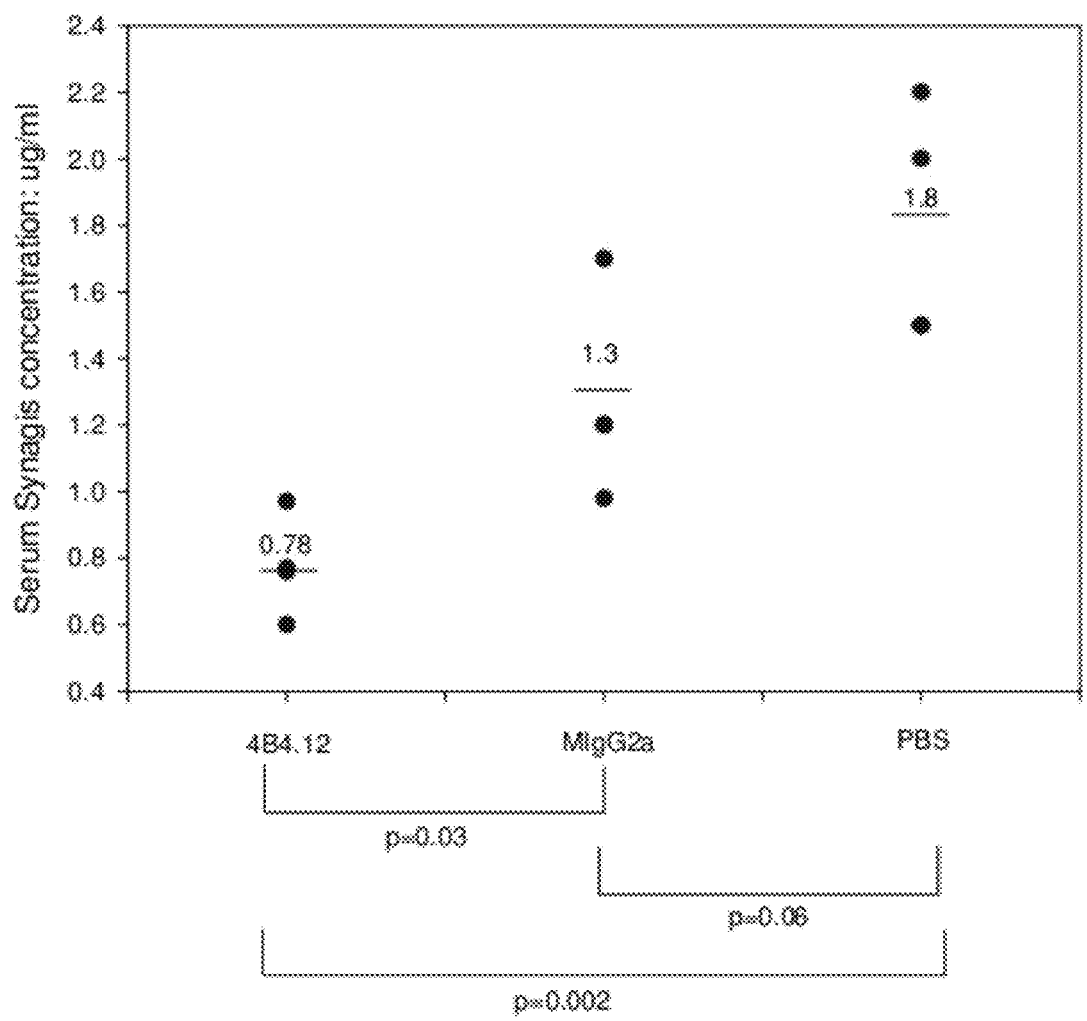
FIG. 14 depicts the effect on serum levels of human IgG of CD-1 mice, that have been intraperitoneally (IP) injected with 1 mg/kg of human IgG (Synagis), and then treated 72 hours later by single IP injection of either 20 mg/kg of mAb 4B4.12, 20 mg/kg of the isotype control, mIgG2a (1813), or PBS. Serum samples were obtained immediately before mAB injection (72 hr after Synagis injection), 72, and 168 hours after mAB injection. The results shown were obtained from serum taken 24 hours after antibody treatment.
Figure 15:
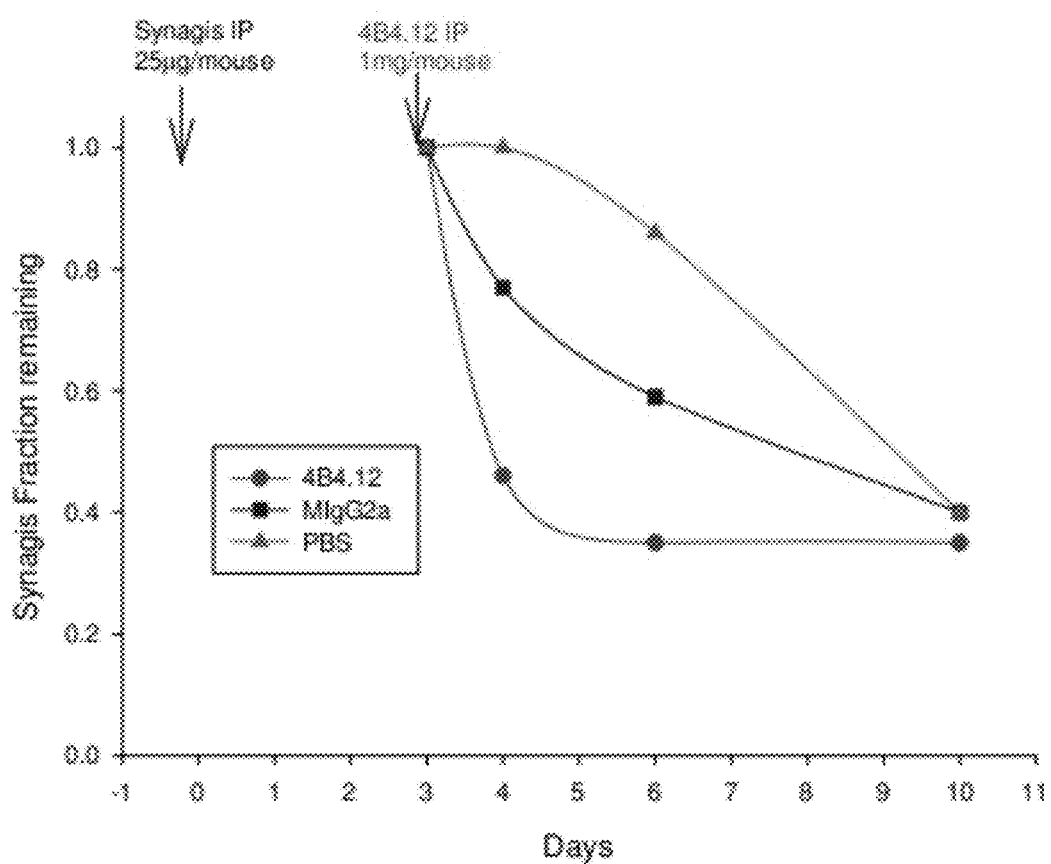
FIG. 15 depicts the same experiment as described in FIG. 14 with two extra serum sampling points (72 and 168 hours).

The results at day 4 are presented in FIG. 14 and demonstrate the 4B4.12 mAB increases catabolism of Synagis compared to control antibody MIgG2a or PBS. The concentration of Synagis over 10 days in the three treatment groups is depicted in FIG. 15 and demonstrates that mAb 4B4.12 increased Synagis catabolism consistently from day 4 through day 10 when compared to MIgG2a or PBS.

Example 14

Therapeutic Effect of mAB 4B4.12 in a Rat Model for Autoimmune Disease

The experimental autoimmune disease, myasthenia gravis (EAMG), can be induced in the rat by passive transfer of anti-AchR mAB35 (Socrates et al. Journal of Neuroimmunology. 15:185-194 (1987)). Monoclonal antibody 4B4.12 which cross-reacts with rat FcRn was evaluated for its ability to effect disease status in the EAMG rat model.

4-5 week-old female Lewis rats (75-100 g) were used. Rats were clearly ear-marked. Monoclonal antibodies were administered intra-peritoneally 24 hours before the disease induction, on the day of disease induction and 24 hours after the disease induction. On the day of disease induction, FcRn blocking or control mABs were given first intra-peritoneally followed by intra-peritoneally injection of mAB35 two hours later. Injection volume was 1 ml. Three groups (6 rats/group) of rats were used for the experiment: group 1 was treated with mAB 4B4.12, group 2 was treated with 1813 (control mAB), group 3 was treated with PBS. 48 hours after the disease induction, 100 µl of serum was obtained from each rat for the measurement of mAB35 and mouse mABs. The protocol is summarized in Table 5.

TABLE 5

Treatment Protocol

| Group# | Day −1 | Day 0 | Day +1 | Samples Day +2 |
|---|---|---|---|---|
| 1 | 4B4.12 40 mg/kg IP lot 2 - 4.98 mg/ml | 4B4.12 IP followed (2 h later) by mAB35 IP | 4B4.12 40 mg/kg IP | Bleed for serum |
| 2 | 1813 40 mg/kg IP lot 2 - 4.67 mg/ml | 1813 IP followed (2 h later) by mAB35 IP | 1813 40 mg/kg IP | Bleed for serum |
| 5 | PBS | PBS followed (2 h later) by mAB35 IP | PBS | Bleed for serum |

Rats were observed for the signs of disease twice daily 12 hours after the disease induction. The following scoring system was used: Grade 0, no symptoms; (1) weak grip, fatigability and sometimes wheezing; (2) general weakness, hunched posture at rest, decreased body weight, tremors; (3) severe weakness, moribund; and (4) death. The protocol is summarized in Table 5. The results are presented in Table 6 and FIG. 16 and demonstrate that mAB 4B4. 12 decreased disease severity in the EAMG model.

TABLE 6

| | Disease Status | |
|---|---|---|
| Group | Disease free | Disease |
| 4B4.12 | 2 | 4 |
| 1813 (mIgG2a) | 0 | 6 |
| PBS | 0 | 6 |

Weight loss or weight gain was determined for rats in each of the experimental groups. The results are presented in Table 7 and FIG. 17 and demonstrate that rats treated with the 4B4.12 mAB lost less weight than the corresponding control groups.

TABLE 7

| | Weight Change | |
|---|---|---|
| Group | Gained weight | Lost weight |
| 4B4.12 | 3 | 3 |
| 1813 (mIgG2a) | 0 | 6 |
| PBS | 1 | 5 |

Example 15

Effect of Antibodies of the Invention on Human IgG Catabolism in Tg32b Mice

Adult TG32B mice were injected intravenously with 5 mg/kg of biotin-hIgG and 495 mg/kg of human IgG (MP Biomedicals, Irvine, Calif.) at t=0 hours ($T_0$). Then at 24, 48, 72, 96 and 120 hours, the mice were injected intravenously with 50 mg/kg of an antibody of the invention. Control injections were performed at each timepoint using PBS. Blood samples were taken prior to injections at all timepoints, as well as at 168 hours. Serum was prepared and stored at −20° C. until an ELISA measuring Biotin-hIgG was performed.

Streptavidin coated plates (Pierce) were rehydrated with three washes (200 μl/well) of PBST (PBS containing 0.05% Tween 20). Serum samples and standards were diluted in PBS containing 2% BSA (dilution buffer). Sample dilutions were 1:10,000, 1:20,000, 1:30,000 and 1:40,000. Standard was diluted from 200 ng/ml to 1.56 ng/ml in 2 fold dilutions. The plates were incubated at 37° C. for 2 hours followed by washing three times with PBST. Then the plates were incubated with 100 μl/well goat anti-human Fc-HRP conjugate (Pierce) diluted 1:25,000 in dilution buffer at room temperature for 30 minutes. After three washes of PBST, 100 μl TMB solution (BioFx) was added to the plates and the plates were incubated in dark at room temperature until appropriate color developed (when the wells of highest standard turn dark blue). Then 100 μl/well of 0.25M $H_2SO_4$ was added to stop the color reaction and OD was measured at 450 nM.

The results showed that 3B3.11 significantly reduced the serum concentration of Biotin-hIgG, indicating the increased catabolism of hIgG after FcRn blockade (FIGS. 18 & 19).

Example 16

Summary of mAbs in Reactivity Across Species

MAB 4B4.12, 3B3.11, 31.1, 4.13 and 3B5.4 were studied in FACS binding assays and FACS blocking assays for reactivity to FcRn across species. Human FcRn expressing cells (293C11) and monkey FcRn expressing cells were produced. Rat and mouse FcRn expressing cells were from Neil Simister of Brandeis University. For blocking experiments, FcRn expressing cells were incubated with Alexa-A488 labeled hIgG1 (100 nM) and various concentrations of mABs (4B4.12, 3B3.11, 31.1, 4.13 and 3B5.4 or isotype controls such as IgG1, IgG2a) in pH6 PBS buffer. 45 minutes later, the cells were analyzed by fluorescence staining and TMFI was calculated (see Example 6 for detailed method). If the mAB inhibits hIgG1 binding to respective FcRn expressing cells above 30%, this mAb is considered a blocking mAB in this species. For binding experiments, FcRn expressing cells were incubated with Alexa-A488 labeled mABs (4B4.12, 3B3.11, 31.1, 4.13 and 3B5.4 or isotype controls such as IgG1, IgG2a) in pH7.4 PBS buffer for 60 minutes. After one wash with PBS buffer, the cells were examined in a Coulter flow cytometer for fluorescence staining. If the binding of particular mAB to the cells is significant above isotype control binding (TMFI is 50% higher), this mAb is considered capable of binding to such species FcRn. Table 8 and FIG. 20 show a summary of the results.

TABLE 8

| Summary of mAB for cross reactivity | | | | | | | | | |
|---|---|---|---|---|---|---|---|---|---|
| | | Binding | | | | Blocking | | | |
| mAB | Isotype | Human | Monkey | Rat | Mouse | Human | Monkey | Rat | Mouse |
| 4B4.12 | IgG2a | Yes | Yes | Yes | Yes | Yes | Yes | Yes | Yes |
| 3B3.11 | IgG1 | Yes | Yes | No | Yes | Yes | Yes | No | No |
| 31.1 | IgG1 | Yes | No | No | No | Yes | No | No | No |
| 4.13 | IgG1 | Yes | No | Yes | Yes | Yes | No | No | No |
| 3B5.4 (anti-β2m) | IgG2a | Yes | Yes | Yes | Yes | Yes | Yes | Yes | No |

Example 17

Monkey FcRN Transient Transfectants Stained with Anti-hFcRN mABs

Cos1 cells were transfected with monkey FcRn heavy chain (in pcDNA6) and β2M (pED.dc) with Gene Jammer transfection reagent (Strategene). 48 hours later, the cells were harvested and washed once with PBS containing 0.5% BSA. $5\times10^5$ cells were incubated with mABs for 45 minutes on ice. Then the cells were washed once with PBS containing 0.5% BSA. The cells were then incubated with Alexa 488 labeled goat anti-mouse IgG (1:2500 dilution) for 45 minutes on ice. After one wash, the cells were analyzed for fluorescence staining in a Coulter flow cytometer. The results are expressed as TMFI.

Example 18

Western Blots with Anti-hFcRN mABs

3 µg of soluble human FcRn (Extra-cellular domain of heavy chain and β2M) was loaded to each lane of a 4-20% Tris-glycine gel (Invitrogen) and was run at 200V for 60 minutes. Then the gel was loaded to a gel blotting apparatus (Xcell II, Invitrogen) with a PVDF membrane (Amersham) and run at 55V for 1 hr at room temperature. Then the membrane was blocked with 5% milk in PBST (PBS plus 0.05% Tween 20) for 1 hour. After that, the membrane was incubated with 10 µg/ml of various mABs overnight at 4° C. After washing twice with PBST, the membrane was incubated with goat anti-human IgG HRP (Southern Biotech Associates) at 1:10,000 dilution for 90 min. After another two washes, the membrane was developed with a ECL kit (Amersham). The results show that mAB 3B3.11, 3B3.16, 3B3.21, 3B3.35, 4.13, 15B6.1 and 31.1 recognized the human FcRn heavy chain while 3B5.4 and 5A4.9 recognized β2M (FIG. 21).

Example 19

Biacore Analysis of 3B3.11

A CM5 chip (Biacore) was coated with approximately 500 RU of soluble human FcRn or soluble monkey FcRn (diluted 100× into acetate at pH 4.5) using standard amine coupling. Five five-fold serial dilutions of antibody were made, starting from an initial concentration of 10 µg/mL. Each dilution was passed over the chip in duplicate at 50 □l/min for 1 minute. The data were solved for a 1:1 binding interaction. Both bindings at pH 6 and pH 7.4 were examined (FIG. 22 and Table 9).

TABLE 9

Biacore analysis of anti-hFcRn mAb 3B3.11

| | Human FcRn | | | |
|---|---|---|---|---|
| | pH 6.0 | | pH 7.4 | |
| mAb | KD (nM) | Off-Rate $(\text{sec}^{-1}) \times 10^{-4}$ | KD (nM) | Off-Rate $(\text{sec}^{-1} \times 10^{-4})$ |
| 3B3.11 | 1.17 ± 0.39 | 1.76 ± 0.79 | 0.16 (n = 2) | 0.0145 (n = 2) |
| 3B3_11 (cyno) | 3.23 ± 0.14 | 5.52 ± 5.4 | 3.24 ± 0.30 | 2.47 ± 2.3 |

Example 20

Epitope Mapping of Anti-hFcRN mABs

Soluble human FcRn and mouse monoclonal antibodies are prepared routinely in house. All reagents, buffers and chemicals were purchased form Biacore AB (Uppsala, Sweden) unless otherwise noted.

Instrumentation and surface preparation: Analysis of macromolecular interactions using surface plasmon resonance has been described in detail (1). A BIACORE 3000 instrument (Biacore AB) was used and all binding interactions were performed at 25° C. A carboxymethyl-modified dextran (CM5) sensor chip (Biacore AB) was used for the analysis. Anti-FcRn monoclonal antibodies was diluted to 1-10 µg/mL in 10 mM sodium acetate (pH 5.0) and immobilized to one flow-cell of the sensor chip, using amine coupling as described in (1). Final immobilization level was approximately 10000 Resonance Units (RU). A control antibody surface using a separate flow-cell was created using the same procedure in the presence of a non-FcRn specific antibody (mAB1745) and served as a reference for the binding studies.

Assay Design: The amino acid sequence of soluble human FcRn (shFcRn) was synthesized as a continuous series of 27 peptides, with each peptide extending 20 residues in length. These peptides had an overlapping sequence of 10 amino acids. The peptides were dissolved in 100% DMSO to a final concentration of 1-5 mg/mL. For analysis, the peptide solutions were diluted 100-fold in HBS-N buffer (10 mM HEPES, pH 7.4; 150 mM NaCl) and injected over the FcRn-specific antibody and reference surfaces for 3 minutes at a rate of 20 uL/min. After a 35 s. dissociation phase, the surface was regenerated by a 30 s pulse of 10 mM glycine (pH 2.0) and a 15 s pulse of 1% SDS at a flow rate of 60 uL/min. As a positive control, shFcRn was injected over the specific and control flow-cells before the first peptide tested and after the last peptide tested to ensure chip stability. A buffer control (1% DMSO in HBS-N) was also passed over both flow-cells as a negative control.

Data Evaluation: The sensorgrams (RU versus time) generated for the control-coated (non-specific mAB) flow-cell were automatically subtracted from the FcRn-coated sensograms. Response at equilibrium (Req) was measured 30 s before the end of the injection phase (1). Positive response indicates specific binding of the peptide to the specific antibody (Frostell-Karlsson, et al. J. Med. Chem., 43: 1986-1992 (2000)).

Summary of mAb Epitopes

```
Syn 558: Ac-SCPHRLREHLERGRGNLEWK-CONH2 -----mAB 4B4.12, 4.13    (SEQ ID NO: 24)

Syn 559: Ac-ERGRGNLEWKEPPSMRLKAR-CONH2 ------mAB 4B4.12, 4.13   (SEQ ID NO: 25)

Syn 562: Ac-CSAFSFYPPELQLRFLRNGL-CONH2 ---------mAB 3B3.11, 4.13 (SEQ ID NO: 26)

Syn 544: Ac-APGTPAFWVSGWLGPQQYLS-CONH2 ------mAB 31.1           (SEQ ID NO: 27)
```

Example 21

Selection and Primary Screening of Fabs

A. Selection Protocols

Soluble Fabs (sFabs) were identified from a phage display library that displays Fab fragments. Four different selections using soluble human (shFcRn) or rat FcRn proteins and 293 C11 cells expressing the human FcRn protein were carried out. Additional selections were also carried out using a combination of cells and protein targets using the same elution strategy as outlined below:

1) Selections against biotinylated shFcRn: Three rounds of selection against biotinylated shFcRn were carried out with depletion on streptavidin beads. Phagemid were allowed to bind to target in acidic binding buffer (pH 6), and were then eluted with non-specific commercial human IgG (Calbiochem, 401114 http://www.emdbiosciences.com/product/401114) and monoclonal mouse anti-human FcRn mAb (3B3) in an acidic buffer. After competitive elution, all remaining bound phage were eluted by direct bead infection of cells. The eluted phage output was used as input for next round of selection.

2) Selections against non-biotinylated shFcRn: Three rounds of selection against non-biotinylated hFcRn which were passively immobilized on a 96 well ELISA plate were carried out with depletion on BSA coated wells. Phagemid were allowed to bind to target in acidic binding buffer (pH 6), and then were eluted with non-specific commercial human IgG and anti-human FcRn mAb (3B3) in the same acidic buffer. After competitive elution, all remaining bound phage were eluted by using pH 7.4 buffer as well by direct infection of cells. The eluted phage output was used as input for next round of selection.

3) Selections against anti-human FcRn antibody (17D3)-immobilized non-biotinylated shFcRn: Three rounds of selection against hFcRn captured using biotinylated 17D3 on streptavidin beads was carried out. Also included was a step of depletion using biotinylated 17D3 on streptavidin beads in the absence of FcRn. Phagemid were allowed to bind to target in acidic binding buffer (pH 6), and then were eluted with non-specific commercial human IgG and anti-human FcRn mAb (3B3) in the same acidic buffer. After competitive elution, all remaining bound phage were eluted by direct bead infection of cells. The eluted phage output was used as input for next round of selection.

4) Selections against hFcRn expressing cells: Three rounds of selection against hFcRn-transfected cells were carried out with depletion on untransfected parental cells. Phagemid were allowed to bind to cells in acidic binding buffer (pH 6), and then were eluted with non-specific human IgG and anti-Fc-Rn mAb in the same acidic buffer. After competitive elution, all remaining bound phage were eluted by cell lysis with magnetic streptavidin beads and subsequent infection of bacteria. The eluted phage output is used as input for next round of selection. Selection against both soluble human FcRn protein (shFcRn) and hFcRn-expressing cells:

Outputs from (1) and (2) and (4) above were used in alternate protein:cell:protein and cell:protein:cell (Round 1:Round2:Round3:Round4) selections using the same elution strategy as above. ELISA Screening for Fab inhibitors of FcRn.

To identify hFcRn binders, primary screening of round 2 and/or 3 outputs from each selection arm described above against biotinylated shFcRn in phage ELISA was carried out. Approximately 768 primary ELISA-positive Fabs on phagemid were re-arrayed, the DNA sequenced, and further secondary screened for pH-dependent binding (pH 6 vs. pH 7.5), species specificity (rat vs. human), beta 2 microglobulin binding, and IgG competition.

One hundred sixty-one unique phagemids that passed the secondary ELISA screening had distinct heavy chains. All 161 unique phagemids were subcloned and expressed as sFabs and screened in a FACS blocking assay.

Blocking of IgG-Fc binding to human FcRn-expressing 293 C11 cells performed at 4° C. in an acidic environment resulted in the discovery of eleven sFabs with antagonistic anti-FcRn properties. All eleven sFab Fc-FcRn blockers were reformatted into IgG1 and reformatted as AZ allotypes and further characterized in vitro for affinity to soluble human and rat FcRn ($K_D$ determination by SPR method), Fc-FcRn blocking using FACS analysis ($IC_{50}$), beta 2 microglobulin binding (by SPR), pH dependent binding and blocking at pH 6 and pH 7.5 to soluble proteins and cells (human FcRn and rat FcRn in FACS and by SPR).

Example 22

Anti-FcRN Fabs

The CDR sequences of exemplary ant-FcRn Fabs identified in the phage display library selections are shown in Table 10.

TABLE 10

Summary of anti-FcRn phagemid Fab Amino Acid CDR Sequences

| Fab | LV-CDR1 | LV-CDR2 | LV-CDR3 | HV-CDR1 | HV-CDR2 | HV-CDR3 |
|---|---|---|---|---|---|---|
| 532A-M0090-F09 | SGSSSNIGSNTVS (SEQ ID NO: 28) | SDNQRPS (SEQ ID NO: 29) | AAWDDSLKGWV (SEQ ID NO: 30) | DYTMS (SEQ ID NO: 31) | SIWSSGGATVYADSVKG (SEQ ID NO: 32) | DIRGSRNWFDP (SEQ ID NO: 33) |

TABLE 10-continued

Summary of anti-FcRn phagemid Fab Amino Acid CDR Sequences

| Fab | LV-CDR1 | LV-CDR2 | LV-CDR3 | HV-CDR1 | HV-CDR2 | HV-CDR3 |
|---|---|---|---|---|---|---|
| 532A-M0090-F11 | TGTGSDVGSYNLVS (SEQ ID NO: 34) | GDSQRPS (SEQ ID NO: 35) | CSYAGSGIYV (SEQ ID NO: 36) | EYAMG (SEQ ID NO: 37) | SIGSSGGQTKYADSVKG (SEQ ID NO: 38) | LSTGELY (SEQ ID NO: 39) |
| 532A-M0062-C09 | RSSQSLLHSNGYNYLD (SEQ ID NO: 40) | LVSNRAS (SEQ ID NO: 41) | MQAQQTPIT (SEQ ID NO: 42) | IYSMT (SEQ ID NO: 43) | SIVPSGGETSYADSVKG (SEQ ID NO: 44) | GHSGVGMDV (SEQ ID NO: 45) |
| M532A-M0064-H04 | RSSQSLLHGNGHTYLD (SEQ ID NO: 46) | LVSNRAS (SEQ ID NO: 47) | MQGLQTPRT (SEQ ID NO: 48) | FYSMT (SEQ ID NO: 49) | GIRSSGGSTRYADSVKG (SEQ ID NO: 50) | GWGLDAFDV (SEQ ID NO: 51) |
| 532A-M0057-F02 | RSSLSLLHSNGYIYLD (SEQ ID NO: 52) | LGSHRAS (SEQ ID NO: 53) | MQPLQTPYT (SEQ ID NO: 54) | YYHMN (SEQ ID NO: 55) | VISPSGGVTMYADSVKG (SEQ ID NO: 56) | GKAFDI (SEQ ID NO: 57) |
| 532A-M0084-B11 | SGDKLGDKYVS (SEQ ID NO: 58) | QDNRRPS (SEQ ID NO: 59) | QAWLSNTASVA (SEQ ID NO: 60) | FYGMH (SEQ ID NO: 61) | GIYSSGGITGYADSVKG (SEQ ID NO: 62) | GLRTFDY (SEQ ID NO: 63) |
| 532A-M0084-B03 | RASQPVGSYLA (SEQ ID NO: 64) | GASNRAT (SEQ ID NO: 65) | QHYGHSPPYT (SEQ ID NO: 66) | SYAMY (SEQ ID NO: 67) | RIVPSGGGTMYADSVQG (SEQ ID NO: 68) | GMDV (SEQ ID NO: 69) |
| 532A-M0073-E10 | RASQSVSSYLA (SEQ ID NO: 70) | DASNRAT (SEQ ID NO: 71) | QQRSNWPLT (SEQ ID NO: 72) | NYNMS (SEQ ID NO: 73) | YISPSGGSTWYADSVKG (SEQ ID NO: 74) | YHYGMDV (SEQ ID NO: 75) |
| 532A-M0056-G05 | RASQSISNHLV (SEQ ID NO: 76) | DASNRAT (SEQ ID NO: 77) | QQRSNWPPT (SEQ ID NO: 78) | YYGMT (SEQ ID NO: 79) | SISPSGGHTSYADSVKG (SEQ ID NO: 80) | GPEYFFGVY (SEQ ID NO: 81) |
| 532A-M0055-G12 | RASQSVGSYLN (SEQ ID NO: 82) | AAYILQS (SEQ ID NO: 83) | QQSYSNRIT (SEQ ID NO: 84) | AYNMI (SEQ ID NO: 85) | SIGPSGGKTVYADSVKG (SEQ ID NO: 86) | VRSGFWSGHDY (SEQ ID NO: 87) |
| 532A-M0092-D02 | RASQSVSSSYLA (SEQ ID NO: 88) | GASSRAT (SEQ ID NO: 89) | QQYGSSPRT (SEQ ID NO: 90) | HYGMS (SEQ ID NO: 91) | YIRPSGGKTIYADSVKG (SEQ ID NO: 92) | DSWGSFPNDAFDI (SEQ ID NO: 93) |

The DNA sequences of these Fab light chain variable regions (LV) are shown below:

```
>M0062-C09 LV kappa                (SEQ ID NO: 94)
CAAGACATCCAGATGACCCAGTCTCCAGACTCCCTGCCCGTCACCCCTGG

AGAGCCGGCCTCCATCTCCTGCAGGTCTAGTCAGAGCCTCCTGCATAGTA

ATGGATACAACTATTTGGATTGGTACCTGCAGAGGCCAGGGCAGTCTCCG

CAGCTCCTGATCTATTTGGTTTCTAATCGGGCCTCCGGGGTCCCTGACAG

GTTCAGTGGCAGTGGGTCAGGCACAGATTTTACACTGAAAATCAGCAGAG

TGGAGGCTGAAGATGCTGGATTTTATTACTGCATGCAAGCTCAACAAACT

CCGATCACCTTCGGCCAAGGGACACGACTGGAGATTAAA

>M0057-F02 LV kappa                (SEQ ID NO: 95)
CAAGACATCCAGATGACCCAGTCTCCACTCTCCCTGCCCGTCACCCCTGG

AGAGCCGGCCTCCATGTCCTGCAGGTCTAGTCTGAGCCTCCTGCATAGTA

ATGGATACATCTATTTGGATTGGTACCTGCAGAGGCCAGGACAGTCTCCA

CAGCTCCTGATGTATTTGGGTTCTCATCGGGCCTCCGGGGTCCCTGACAG

GTTCAGTGGCAGTGGGTCAGGCACAGATTTTACACTGAACATCAGCAGAG

TGGAGGCGGAGGATGTTGGGGTTTATTACTGCATGCAACCTCTACAAACT

CCGTACACTTTTGGCCAGGGGACCAAGCTGGAGATCAAA

>M0055-G12 LV kappa                (SEQ ID NO: 96)
CAAGACATCCAGATGACCCAGTCTCCATCCTCCCTGTCTGCATCTGTAGG

AGACAGAGTCACCATCACTTGCCGGGCAAGTCAGAGCGTTGGCAGTTATT

TAAATTGGTATCAGCAGAAACCAGGCGAAGCCCCTAAGGCCCTGATCTAT

GCTGCATACATTTTGCAAAGTGGGGTCCCATCGAGGTTCAGTGGCAGCGG

CTCTGGGACAGATTTCACTCTCACCATCAACAGTCTACAACCTGAAGATT

TTGCAACTTATTACTGTCAACAGAGTTACAGTAATAGAATCACTTTCGGC

CCTGGGACCAGAGTGGATGTCAAA

>M0064-H04 LV kappa                (SEQ ID NO: 97)
CAAGACATCCAGATGACCCAGTCTCCACTCTCCCTGCCCGTCACCCCTGG

AGAGCCGGCCTCCATCTCCTGCAGGTCTAGTCAGAGCCTCCTGCACGGAA

ATGGACACACCTATTTGGATTGGTATCTGCAGAAGCCAGGGCAGTCTCCA

CAGCTCCTGATCTATTTGGTTTCTAATCGGGCCTCCGGGGTCCCTGACAG

GTTCAGTGGCAGTGGATCAGGCACAGATTTTACACTGAAAATCAGCAGAG

TGGAGGCTGAAGATGTTGGGGTTTATTACTGCATGCAAGGTCTACAAACT

CCGAGGACGTTCGGCCAGGGGACCAAGGTGGAAATCAAA
```

```
>M0056-G05 LV kappa                (SEQ ID NO: 98)
CAAGACATCCAGATGACCCAGTCTCCAGCCACCCTGTCTTTGTCTCCAGG

GGAAAGAGCCACCCTCTCCTGCAGGGCCAGTCAGAGTATTAGCAACCACT

TAGTCTGGTTCCAACAGAAACCTGGCCAGGCTCCCAGGCTCCTCATCTAT

GATGCATCCAACAGGGCCACTGGCATCCCAGCCAGGTTCAGTGGCAGTGG

GTCTGGGACAGACTTCACTCTCACCATCAGCAGCCTAGAGCCTGAAGATT

TTGCAGTTTATTACTGTCAGCAGCGTAGCAACTGGCCTCCCACCTTCGGC

CAAGGGACACGACTGGAGATTAAA

>M0084-B03 LV kappa                (SEQ ID NO: 99)
CAAGACATCCAGATGACCCAGTCTCCAGCCACCCTGTCTTTGTCTCCAGG

GGAAACAGCCACCCTCTCCTGCCGGGCCAGTCAGCCTGTTGGCAGCTACT

TAGCCTGGTACCAACAGAAACCTGGCCAGGCTCCCAGGCTCCTCATCTAT

GGTGCATCCAATAGGGCCACTGGCATCCCAGCCAGGTTCAGTGGCAGTGG

GTCTGGGACAGACTTCACTCTCGCCATCAGCAGCCTGGAGCCTGAAGATT

TTGGAGTGTATTACTGTCAGCACTATGGTCACTCACCTCCGTACACTTTT

GGCCAGGGGACCAAGCTGGAGATCAAA

>M0092-D02 LV kappa                (SEQ ID NO: 100)
CAAGACATCCAGATGACCCAGTCTCCAGGCACCCTGTCTTTGTCTCCAGG

GGAAAGAGCCACCCTCTCCTGCAGGGCCAGTCAGAGTGTTAGCAGCAGCT

ACTTAGCCTGGTACCAGCAGAAACCTGGCCAGGCTCCCAGGCTCCTCATC

TATGGTGCATCCAGCAGGGCCACTGGCATCCCAGACAGGTTCAGTGGCAG

TGGGTCTGGGACAGACTTCACTCTCACCATCAGCAGACTGGAGCCTGAAG

ATTTTGCAGTGTATTACTGTCAGCAGTATGGTAGCTCACCTCGGACGTTC

GGCCAAGGGACCAAGGTGGAAATCAAA

>M0090-F09 LV lambda               (SEQ ID NO: 101)
CAGAGCGCTTTGACTCAGCCACCCTCAGCGTCTGAGACCCCCGGGCAGAG

AGTCACCATCTCTTGTTCTGGAAGCAGCTCCAACATCGGAAGTAATACTG

TAAGCTGGTACCAGCAGCTCCCAGGAACGGCCCCCAAACTCCTCATCTAT

AGTGATAATCAGCGGCCCTCAGGGGTCCCTGACCGATTCGCTGGCTCCAA

GTCTGGCACCTCTGCCTCCCTGGCCATCAGTGGGCTCCAGTCTGAGGATG

AGGCTGAATATCACTGTGCAGCATGGGATGACAGCCTGAAGGGTTGGGTG

TTCGGCGGAGGGACAAAGCTGACCGTCCTA

>M0084-B11 LV lambda               (SEQ ID NO: 102)
CAGAGCGCTTTGACTCAGACACCCTCAGTGTCCGTGTCCCCGGACAGAC

AGCCACCATCACCTGCTCTGGAGATAAATTGGGGGATAAGTATGTTTCTT

GGTTTCAACAGAAGCCAGGCCAGTCCCCTATCCTACTCCTTTATCAAGAC

AACAGGCGGCCCTCTGGGATCCCTGAACGATTCTCTGGCTCCAATTCTGG

GAACACAGCCTCTCTGACCATCAGCGGGACCCAGGCTATGGATGAGGCTG

ACTACCACTGTCAGGCGTGGCTCAGCAATACTGCTTCCGTGGCATTCGGC

GGAGGGACCAGGCTGACCGTCCTC

>M0073-E10 LV kappa                (SEQ ID NO: 103)
CAAGACATCCAGATGACCCAGTCTCCAGCCACCCTGTCTTTGTCTCCAGG

GGAAAGAGCCACCCTCTCCTGCAGGGCCAGTCAGAGTGTTAGCAGCTACT

TAGCCTGGTACCAACAGAAACCTGGCCAGGCTCCCAGGCTCCTCATCTAT

GATGCATCCAACAGGGCCACTGGCATCCCAGCCAGGTTCAGTGGCAGTGG

GTCTGGGACAGACTTCACTCTCACCATCAGCAGCCTAGAGCCTGAAGATT

TTGCAGTTTATTACTGTCAGCAGCGTAGCAACTGGCCCCTCACTTTCGGC

GGAGGGACCAAGGTGGAGATCAAA

>M0090-F11 LV lambda               (SEQ ID NO: 104)
CAGAGCGTCTTGACTCAGCCTGCCTCCGTGTCGGGGTCTCCTGGACAGTC

GATCACCATCTCCTGCACTGGGACCGGGAGTGATGTTGGAAGTTATAACC

TTGTCTCCTGGTACCAAAAGTACCCCGGCAAAGCCCCCAAACTCATCATT

TATGGGGACAGTCAGCGGCCCTCGGGACTTTCTAGTCGCTTCTCTGGCTC

CAAGTCTGGCAACTCGGCCTCCCTGACAATCTCTGGGCTCCAGGCTGAGG

ACGAGGCTGATTATTACTGTTGCTCATATGCAGGTAGTGGCATTTACGTC

TTTGGCAGTGGGACCAAGGTCACCGTCCTA
```

Example 23

Binding of sFabs and Antibodies to FcRN

To further characterize the Fabs and their respective IgG1, SPR 8500/BIACORE™ analysis was performed on eleven exemplary antagonsitic anti FcRn antibody clones that were positive for FcRn binding to determine the $K_D$. Exemplary SPR 8500/BIACORE™ data is provided in Tables 2 and 3. SFabs and antibodies (IgG) were tested for their ability to bind to human FcRn (hFcRn) or rat FcRn (rat FcRn) and pH 6 and 7.5. Binding was measured by SPR 8500 and by BIACORE™ and is expressed by $K_D$ values (nM). The binding of 8 clones was observed to be pH independent and 3 pH dependent.

Tables 11A Through E: Summary of In Vitro SPR 8500 Binding Data ($K_D$ (nM)) of FcRN Binding sFabs; On and Off Rate Analyses A. Binding Data

| | Antagonistic anti-FcRn IgG data | | | |
|---|---|---|---|---|
| | SPR 8500 | SPR 8500 soluble Fabs | SPR 8500 | SPR 8500 |
| Clone # | sol FAB sol hFcRn $K_D$ nM @ pH 6 | sol FAB sol hFcRn $K_D$ nM @ pH 7.5 | sol FAB sol rat FcRn $K_D$ nM @ pH 6 | sol FAB sol rat FcRn $K_D$ nM @ pH 7.5 |
| 532A-M0090-F11 | 9.2 | 19.1 | 31.2 | 9.9 |
| 532A-M0064-H04 | 28 | 25.9 | no binding | no binding |
| 532A-M0090-F09 (pH dependent) | 5.7 | no binding | no binding | no binding |
| 532A-M0084-B03 (pH dependent) | No fit | no binding | no binding | no binding |
| 532A-M0062-C09 (pH dependent) | 25 | no binding | no binding | no binding |
| 532A-M0055-G12 | 12 | 39.7 | no binding | no binding |
| 532A-M0056-G05 | 13.6 | 18.1 | no binding | no binding |
| 532A-M0084-B11 | 17.4 | 19.6 | no binding | no binding |
| 532A-M0092-D02 | 3.9 | 18.7 | no binding | no binding |
| 532A-M0073-E10 | 82 | 9.7 | no binding | no binding |
| 532A-M0057-F02 | 29 | 11.3 | no binding | no binding |

B. hFcRn pH 6

|  | kon | koff | KD |
|---|---|---|---|
| 17D3 | 2.77E+05 | 4.30E−04 | 1.5E−09 |
| 3B3 | 3.82E+06 | 1.31E−03 | 3.4E−10 |
| FcI | — | — | — |
| hIgG Myeloma | — | — | — |
| hIgG plasma | 4.32E+03 | 2.31E−03 | 5.3E−07 |
| X0002 - G07 | 2.06E+04 | 1.24E−04 | 6.0E−09 |
| M0055 - G12 | 1.27E+06 | 1.53E−02 | 1.2E−08 |
| M0057 - F02 | 1.48E+05 | 4.26E−03 | 2.9E−08 |
| M0062 - C09 | 9.44E+04 | 2.38E−03 | 2.5E−08 |
| M0064 - H04 | 1.29E+05 | 3.68E−03 | 2.8E−08 |
| M0073 - E10 | 3.36E+05 | 2.75E−02 | 8.2E−08 |
| M0090 - F11 | 9.68E+04 | 8.97E−04 | 9.2E−09 |
| X0002 - A07 | — | — | — |

C. hFcRn pH 7.4

|  | kon | koff | KD ( |
|---|---|---|---|
| 17D3 | 3.24E+05 | 5.23E−04 | 1.61E−09 |
| 3B3 | 2.97E+06 | 1.76E−03 | 5.93E−10 |
| FcI | — | — | — |
| hIgG Myeloma | — | — | — |
| hIgG plasma | — | — | — |
| X0002 - G07 | — | — | — |
| M0055 - G12 | 2.01E+05 | 7.96E−03 | 3.97E−08 |
| M0057 - F02 | 3.25E+05 | 3.67E−03 | 1.13E−08 |
| M0062 - C09 | — | — | — |
| M0064 - H04 | 1.55E+05 | 4.02E−03 | 2.59E−08 |
| M0073 - E10 | 3.59E+05 | 3.49E−03 | 9.71E−09 |
| M0090 - F11 | 5.94E+04 | 1.13E−03 | 1.91E−08 |
| X0002 - A07 | — | — | — |

D. rat FcRn pH 6

|  | kon | koff | KD |
|---|---|---|---|
| 17D3 | 1.74E+04 | 6.03E−03 | 3.40E−07 |
| 3B3 | 6.83E+05 | 1.04E−03 | 1.50E−09 |
| FcI | 2.08E+05 | 3.29E−03 | 1.58E−08 |
| hIgG Myeloma | 1.30E+05 | 1.27E−03 | 9.80E−09 |
| hIgG plasma | 9.13E+04 | 2.42E−03 | 2.65E−08 |
| X0002 - G07 | 9.70E+04 | 8.62E−04 | 8.90E−09 |
| M0055 - G12 | — | — | — |
| M0057 - F02 | — | — | — |
| M0062 - C09 | — | — | — |
| M0064 - H04 | — | — | — |
| M0073 - E10 | — | — | — |
| M0090 - F11 | 1.84E+04 | 5.73E−04 | 3.12E−08 |
| X0002 - A07 | — | — | — |

E. rat FcRn pH 7.4

|  | kon | koff | KD |
|---|---|---|---|
| 17D3 | — | — | — |
| 3B3 | — | — | — |
| FcI | — | — | — |
| hIgG Myeloma | — | — | — |
| hIgG plasma | — | — | — |
| X0002 - G07 | — | — | — |
| M0055 - G12 | — | — | — |
| M0057 - F02 | — | — | — |
| M0062 - C09 | — | — | — |
| M0064 - H04 | — | — | — |
| M0073 - E10 | — | — | — |
| M0090 - F11 | 2.75E+04 | 7.40E−04 | 9.96E−09 |
| X0002 - A07 | — | — | — |

Table 12A Through E: Summary of In Vitro SPR 8500 Binding Data ($K_D$ (nM)) of FcRn Binding Antibodies; On and Off Rate Analyses A. Binding Data

| | Antagonistic anti-FcRn IgG data | | | |
|---|---|---|---|---|
| | SPR 8500 | SPR 8500 | SPR 8500 | SPR 8500 |
| | Format | | | |
| Clone # | IgG hFcRn $K_D$ @pH 6 | IgG hFcRn $K_D$ @pH 7.5 | IgG ratFcRn $K_D$ @pH 6 | IgG ratFcRn $K_D$ @pH 7.5 |
| 532A-M0090-F11 | 2.44 | 10.8 | 9.8 | 9.14 |
| 532A-M0064-H04 | 6.82 | 12.5 | 31 | no binding |
| 532A-M0090-F09 (pH dependent) | 3.64 | No fit | 13.9 | no binding |
| 532A-M0084-B03 (pH dependent) | 2.99 | No fit | 29.6 | no binding |
| 532A-M0062-C09 (pH dependent) | 29.5 | No fit | no fit | no binding |
| 532A-M0055-G12 | 3.1 | 10.2 | 16 | no binding |
| 532A-M0056-G05 | 2.48 | 2.1 | 22.9 | no binding |
| 532A-M0084-B11 | 3.3 | 2.59 | 6.43 | no binding |
| 532A-M0092-D02 | 17.9 | 24.2 | 30.2 | no binding |
| 532A-M0073-E10 | No fit | No fit | No fit | no binding |
| 532A-M0057-F02 | NA | NA | NA | no binding |

B. hFcRn pH 6

|  | Kon | Koff | KD |
|---|---|---|---|
| M62-C9 (Fab) | 8.12E+04 | 1.60E−03 | 1.97E−08 |
| M90-F11(Fab) | 9.21E+04 | 5.63E−04 | 6.11E−09 |
| M62-C09 (IgG) | 2.36E+05 | 6.95E−03 | 2.95E−08 |
| M90-F11 (IgG) | 1.02E+06 | 2.48E−03 | 2.44E−09 |
| 3B3 | 2.30E+06 | 9.40E−04 | 4.09E−10 |
| 17D3 | 8.17E+04 | 1.81E−04 | 2.22E−09 |
| M92-D2 | 3.87E+04 | 6.92E−04 | 1.79E−08 |
| M56-G05 | 1.13E+05 | 2.80E−04 | 2.48E−09 |
| M84-B03 | 1.14E+05 | 3.40E−04 | 2.99E−09 |
| SA-A08 | — | — | — |
| FCI | — | — | — |
| human IgG Myeloma | — | — | — |
| human IgG plasma | 3.89E+04 | 6.85E−04 | 1.76E−08 |
| X11-5 | | | |
| M55-G12 | 7.49E+04 | 2.32E−04 | 3.10E−09 |
| M73-E10 | — | — | — |
| M84-B11 | 7.53E+04 | 2.48E−04 | 3.30E−09 |
| M64-H04 | 1.04E+05 | 7.06E−04 | 6.82E−09 |
| M90-F09 | 3.14E+05 | 1.14E−03 | 3.64E−09 |

C. hFcRn pH 7.4

|  | Kon | Koff | KD |
|---|---|---|---|
| M90-F11(Fab) | 9.12E+04 | 6.45E−04 | 7.08E−09 |
| M90-F11 (IgG) | 1.59E+05 | 1.73E−03 | 1.08E−08 |
| SA-A08 | — | — | — |
| FCI | — | — | — |
| M84-B11 | 1.31E+05 | 3.41E−04 | 2.59E−09 |
| M64-H04 | 2.17E+05 | 2.71E−03 | 1.25E−08 |

-continued

| | Kon | Koff | KD |
|---|---|---|---|
| M73-E10 | — | — | — |
| M55-G12 | 7.78E+04 | 7.97E−04 | 1.02E−08 |
| X11-5 | — | — | — |
| M62-C09 | — | — | — |
| M62-C09 IgG | — | — | — |
| M84-B03 | — | — | — |
| M56-G05 | 4.14E+05 | 8.68E−04 | 2.10E−09 |
| M90-F09 | — | — | — |
| 3B3 | 3.41E+06 | 2.30E−03 | 6.75E−10 |
| M92-D2 | 8.16E+04 | 1.98E−03 | 2.42E−08 |
| 17D3 | 1.21E+05 | 2.42E−04 | 2.01E−09 |
| human IgG Myeloma | — | — | — |
| human IgG Plasma | — | — | — |

D. rat FcRn pH 6

| | Kon | Koff | KD |
|---|---|---|---|
| M90-F11 (IgG) | 1.19E+05 | 1.17E−03 | 9.80E−09 |
| M90-F11(Fab) | 4.30E+04 | 8.72E−04 | 2.03E−08 |
| M90-F09 | 3.21E+05 | 4.46E−03 | 1.39E−08 |
| M62-C09 (Fab) | — | — | |
| M62-C09 | — | — | |
| M64-H04 | 7.80E+04 | 2.42E−03 | 3.10E−08 |
| M84-B11 | 3.14E+05 | 2.02E−03 | 6.43E−09 |
| M73-E10 | — | — | — |
| M55-G12 | 1.99E+05 | 3.20E−03 | 1.60E−08 |
| X11-5 | — | — | — |
| M84-B03 | 1.56E+05 | 4.63E−03 | 2.96E−08 |
| M56-G05 | 4.78E+04 | 1.09E−03 | 2.29E−08 |
| M92-D2 | 4.93E+04 | 1.49E−03 | 3.02E−08 |
| M55-G12 | 1.99E+05 | 3.20E−03 | 1.60E−08 |
| 3B3 | — | — | — |
| human IgG Plasma | 2.33E+05 | 1.42E−03 | 6.12E−09 |
| human IgG Myeloma | — | — | — |
| FCI | — | — | — |
| SA-A08 | — | — | — |

E. rat FcRn pH 7.4

| | Kon | Koff | KD |
|---|---|---|---|
| M90-F11 | 1.17E+06 | 3.84E−03 | 3.29E−09 |
| M90-F11 (IgG) | 1.25E+05 | 1.14E−03 | 9.14E−09 |
| SA-A08 | — | — | — |
| FCI | — | — | — |
| M84-B11 | — | — | — |
| M64-H04 | — | — | — |
| M73-E10 | — | — | — |
| M55-G12 | — | — | — |
| X11-5 | — | — | — |
| M62-C09 | — | — | — |
| M62-C09 (IgG) | — | — | — |
| M84-B03 | — | — | — |
| M56-G05 | — | — | — |
| M90-F09 | — | — | — |
| 3B3 | — | — | — |
| M92-D2 | — | — | — |
| 17D3 | — | — | — |
| human IgG Myeloma | — | — | — |
| human IgG Plasma | — | — | — |

Example 24

$IC_{50}$ Values of sFabs and Antibodies

The sFabs and IgG antibodies of eleven exemplary antagonistic anti-FcRn clones that were positive for FcRn binding were tested in an in vitro model for their ability to block non-specific human IgG-Fc binding to FcRn. Cultures of 293 C11 cells expressing human FcRn (hFcRn) or rat FcRn (rat FcRn) were treated with an sFab or IgG1 of a binding-positive clone, a positive control anti-rat FcRn antibody (1G3), a positive control anti-human FcRn antibody (3B3), or a SA-A2 negative control. The cell cultures were treated with ALEXAFLUOR® labeled non-specific IgG-Fc and incubated at 4° C. in pH 6 buffer conditions. The amount of IgG-Fc-FcRn binding was determined. Results of exemplary sFabs and/or the respective IgGs are presented in Table 13. The $IC_{50}$ values were determined by flow cytometry (i.e., FACS) and are expressed in nM.

TABLE 13

Summary of in vitro FACS inhibition data ($IC_{50}$ (nM)) of FcRn binding antibodies

| | Antagonistic anti-FcRn IgG data | | | |
|---|---|---|---|---|
| | FACS (blocking) | FACS (blocking) | FACS (blocking) | FACS (blocking) |
| | | | IC50 | |
| Clone # | sol FAB hFcRn (cells) IC50 nM @ pH 6 | sol FAB rat FcRn (cells) IC50 nM @ pH 6 | IgG hFcRn (cells) IC50 nM @ pH 6 | IgG rat FcRn (cells) IC50 nM @ pH 6 |
| 532A-M0090-F11 | 13 | 6481 | 2.6 | 4.9 |
| 532A-M0064-H04 | 63 | no blocking | 1.8 | 20 |
| 532A-M0090-F09 (pH dependent) | 645 | no blocking | 4.6 | 5.5 |
| 532A-M0084-B03 (pH dependent) | 754 | no blocking | 1.8 | 91 |
| 532A-M0062-C09 (pH dependent) | 35 | no blocking | 3.9 | 148 |
| 532A-M0055-G12 | 228 | no blocking | 1.7 | 30 |
| 532A-M0056-G05 | 337 | no blocking | 1.4 | 18 |
| 532A-M0084-B11 | 355 | no blocking | 1.9 | 25 |
| 532A-M0092-D02 | 271 | no blocking | 1.2 | 15 |
| 532A-M0073-E10 | 110 | no blocking | 377 | 161 |
| 532A-M0057-F02 (amber stop) | 70 | no blocking | NA | NA |
| Streptavidin binder SA-A2 IgG (negative control) | NA | NA | 562 | 101 |
| lead 3B3 mouse anti-human FcRn IgG | | | 9.7 | |
| lead 1G3 mouse anti-rat FcRn IgG | NA | NA | | 1.5 |

Example 25

Efficacy Testing of FcRN Binding Antibodies in Animals

Experiments with human FcRn Knock-in Tg32B transgenic mice showed that four consecutive daily intravenous doses of M090-F11 (also referred to as M090-F11 and M0090-F11) IgG significantly reduced the serum half-life of human IgG tracer (biotinylated hIgG) at all doses tested (50, 20, 10 and 5 mg/kg) (FIGS. 23 & 24). At 50 mg/kg, four iv injections of M55-G12 only moderately reduced the serum half-life of tracer hIgG while M84-B11 was not efficacious (FIG. 23). An experiment with single doses of M90-F11 (20 mg/kg and 5 mg/kg) showed moderate reduction of Biotin-hIgG1 tracer in the serum of TG32B mice (FIG. 25).

The protocol used for testing anti-FcRn IgGs in transgenic mice was:
1) Administer 500 mg/kg tracer hIgG intravenously at time 0 (approximately 1% is biotinylated for quantitation purposes)
2) Anti-FcRn antibodies given intravenously at 24, 48, 72, 96 and 120 hr at 50, 20, 10 and 5 mg/kg
3) Blood samples collected at 24, 48, 72, 96, 120 and 168 hours 4) Quantitate hIgG in serum by ELISA Based on the Tg mouse model in vivo data, M90-F11 was chosen as lead candidate for further lead optimization. The 10 germline changes that were introduced into the M90-F11 light chain is given below and in FIG. 29. The one germline changes that was required in the heavy chain was not introduced, however the allotype of the heavy chain was changed from AZ to F allotype.

```
LIGHT CONSTANT
          S   Q   P   K   A   N   P   T   V   T   L   F   P   P   S   S   E   E   L   Q   A
CONST: AGTCAGCCCAAGGCCAACCCCACTGTCACTCTGTTCCCGCCCTCCTCTGAGGAGCTCCAAGCC

GRMLN: GGTCAGCCCAAGGCCAACCCCACGGTCACTCTGTTCCCGCCCTCCTCTGAGGAGCTCCAAGCC
          G   Q   P   K   A   N   P   T   V   T   L   F   P   P   S   S   E   E   L   Q   A

N   K   A   T   L   V   C   L   I   S   D   F   Y   P   G   A   V   T   V   A   W
CONST: AACAAGGCCACACTAGTGTGTCTGATCAGTGACTTCTACCCGGGAGCTGTGACAGTGGCCTGG

GRMLN: AACAAGGCCACACTAGTGTGTCTGATCAGTGACTTCTACCCGGGAGCTGTGACAGTGGCTTGG
          N   K   A   T   L   V   C   L   I   S   D   F   Y   P   G   A   V   T   V   A   W

K   A   D   G   S   P   V   K   A   G   V   E   T   T   K   P   S   K   Q   S   N
CONST: AAGGCAGATGGCAGCCCCGTCAAGGCGGGAGTGGAGACCACCAAACCCTCCAAACAGAGCAAC

GRMLN: AAGGCAGATGGCAGCCCCGTCAAGGCGGGAGTGGAGACGACCAAACCCTCCAAACAGAGCAAC
          K   A   D   G   S   P   V   K   A   G   V   E   T   T   K   P   S   K   Q   S   N

N   K   Y   A   A   S   S   Y   L   S   L   T   P   E   Q   W   K   S   H   R   S
CONST: AACAAGTACGCGGCCAGCAGCTACCTGAGCCTGACGCCCGAGCAGTGGAAGTCCCACAGAAGC

GRMLN: AACAAGTACGCGGCCAGCAGCTACCTGAGCCTGACGCCCGAGCAGTGGAAGTCCCACAGAAGC
          N   K   Y   A   A   S   S   Y   L   S   L   T   P   E   Q   W   K   S   H   R   S

Y   S   C   Q   V   T   H   E   G   S   T   V   E   K   T   V   A   P   A   E   C   S
CONST: TACAGCTGCCAGGTCACGCATGAAGGGAGCACCGTGGAGAAGACAGTGGCCCCTGCAGAATGCTCT

GRMLN: TACAGCTGCCAGGTCACGCATGAAGGGAGCACCGTGGAGAAGACAGTGGCCCCTACAGAATGTTCA
          Y   S   C   Q   V   T   H   E   G   S   T   V   E   K   T   V   A   P   T   E   C   S

CONST Amino acid    (SEQ ID NO: 107)

CONST Nucleic acid  (SEQ ID NO: 108)

GRMLN Nucleic acid  (SEQ ID NO: 110)

GRMLN Amino acid    (SEQ ID NO: 109)

HEAVY Amino Acid    (SEQ ID NO: 111)

HEAVY Nucleic Acid  (SEQ ID NO: 112)

GRMLN Nucleic Acid  (SEQ ID NO: 114)

GRMLN Amino Acid    (SEQ ID NO: 113)

HEAVY:V:V323; J:JH1
                              FR1-H
          E   V   Q   L   L   E   S   G   G   G   L   V   Q   P   G   G   S   L   R   L   S   C
HEAVY: GAAGTTCAATTGTTAGAGTCTGGTGGCGGTCTTGTTCAGCCTGGTGGTTCTTTACGTCTTTCTTGC

GRMLN: GAGGTGCAGCTGTTGGAGTCTGGGGGAGGCTTGGTACAGCCTGGGGGGTCCCTGAGACTCTCCTGT
          E   V   Q   L   L   E   S   G   G   G   L   V   Q   P   G   G   S   L   R   L   S   C

CDR1-H
          A   A   S   G   F   T   F   S       E   Y   A   M   G       W   V   R   Q   A   P   G   K   G
HEAVY: GCTGCTTCCGGATTCACTTTCTCT    GAGTACGCTATGGGT    TGGGTTCGCCAAGCTCCTGGTAAAGGT

GRMLN: GCAGCCTCTGGATTCACCTTTAGC    AGCTATGCCATGAGC    TGGGTCCGCCAGGCTCCAGGGAAGGGG
          A   A   S   G   F   T   F   S       S   A   Y   M   S       W   V   R   Q   A   P   G   K   G

FR2-H                              CDR2-H
          L   E   W   V   S       S   I   G   S   S   G   G   Q   T   K   Y   A   D   S   V   K   G
HEAVY: TTGGAGTGGGTTTCT    TCTATCGGTTCTTCTGGTGGCCAGACTAAGTATGCTGACTCCGTTAAAGGT

GRMLN: CTGGAGTGGGTCTCA    GCTATTAGTGGTAGTGGTGGTAGCACATACTACGCAGACTCCGTGAAGGGC
          L   E   W   V   S       A   I   S   G   S   G   G   S   T   Y   Y   A   D   S   V   K   G
```

```
                          FR3-H
       R  F  T  I  S  R  D  N  S  K  N  T  L  Y  L  Q  M  N  S  L  R  A
HEAVY: CGCTTCACTATCTCTAGAGACAACTCTAAGAATACTCTCTACTTGCAGATGAACAGCTTAAGGGCT

GRMLN: CGGTTCACCATCTCCAGAGACAATTCCAAGAACACGCTGTATCTGCAAATGAACAGCCTGAGAGCC
       R  F  T  I  S  R  D  N  S  K  N  T  L  Y  L  Q  M  N  S  L  R  A

CDR3-H                FR4-H
       E  D  T  A  V  Y  Y  C  A  R     L  S  T  G  E  L  Y     W  G  Q  G  T
HEAVY: GAGGACACGGCCGTGTATTACTGTGCGAGA CTCTCAACAGGGGAGCTCTAC TGGGGCCAGGGCACC

GRMLN: GAGGACACGGCCGTATATTACTGTGCGAAA GA................TAC TGGGGCCAGGGCACC
       E  D  T  A  V  Y  Y  C  A  K                       Y  W  G  Q  G  T

FR4-H
       L  V  T  V  S  S
HEAVY: CTGGTCACCGTCTCAAGC

GRMLN: CTGGTCACCGTCTCATCA (a, z) ASTKGPSVFPLAPSSKSTSGGTAALGCLVKDYFPEPVTVSWNSGALTS
(f)    ------------------------------------------------

(a, z) GVHTFPAVLQSSGLYSLSSVVTVPSSSLGTQTYICNVNHKPSNTKVDKK
(f)    -----------------------------------------------R (a, z) VEPKECDKTKTCPPCAPELLGGPSVFLFPPKPKDTLMISRTPEVTCVVV
(f)    ------------------------------------------------

(a, z) DVSHEDPEVKFNWYVDGVEVHNAKTKPREEQYNSTYRVVSVLTVLHQDW
(f)    ------------------------------------------------

(a, z) LNGKEYKCKVSNKALPAPIEKTISKAKGQPREPQVYTLPPSPREPQVYT
(f)    ------------------------------------------------

(a, z) LPPSRDELTKNQVSLTCLVKGFYPSDIAVEWESNGQPENNYKTTPPVLD
(f)    -----E-M----------------------------------------

(a, z) SDGSFFLYSKLTVDKSRWQQGNVFSCSVMHEALHNHYTQKSLSLSPGK*
(f)    ------------------------------------------------

(a, z) (SEQ ID NO: 115)
(f)    (SEQ ID NO: 116)
```

Example 26

Germlining, Reformatting and Affinity Maturation of Parental Clone M90-F11

Allotype variation of IgG is shown in FIG. 30, the three amino acid changes (highlighted in bold) from AZ to F allotype were introduced to germlined M90-F11 IgG which already had 10 amino acid changes as part of germlining in the light chain.

The parental clone M90-F11 as germ lined had 10 amino acid changes in the light chain and as part of lead optimization the germlined clone was reformatted to IgG which had sequences for F allotype in the heavy chain Fc region. In total there were 13 amino acid changes as compared to parent M90-F11, the reformatted clone was nucleotide sequence optimized for expression in CHO cell lines. Nucleotide sequence/Geneart optimized clone was given a DX-2500 name, which was used for making stable pool. Parental M90-F11, Germlined M90-F11 (GL) and DX-2500 were characterized in vitro by Biacore and FACS to assess binding and blocking ability.

Tables 14 and 15 contain the results of Biacore and FACS analysis comparing the highly purified, parental, germlined and reformatted IgG's:

TABLE 14

Biacore analysis: hFcRn immobilized on the chip and IgG were flowed over the chip and FACS analysis (IC50).

| | Antagonistic anti-FcRn antibody data | | | | | | |
|---|---|---|---|---|---|---|---|
| Clone # | biacore IgG hFcRn $K_{on}$ @pH 6 | biacore IgG hFcRn $K_{off}$ @pH 6 | biacore IgG hFcRn $K_D$ @pH 6 | biacore IgG hFcRn $K_{on}$ @pH 7.4 | biacore IgG hFcRn $K_{off}$ @pH 7.4 | biacore IgG hFcRn $K_D$ @pH 7.4 | FACS (blocking) IgG hFcRn (cells) IC50 nM @pH 6 |
| 532A-M0090-F11 | 2.13E+06 | 2.52E−04 | 1.18E−10 | 9.09E+05 | 7.02E−04 | 7.72E−10 | 0.43 |
| 532A-M0090-F11 (germlined LC changes) | 4.45E+06 | 7.64E−04 | 1.72E−10 | 9.96E+05 | 7.76E−04 | 7.79E−10 | 0.38 |
| DX-2500 (germlined LC & allotype HC changes) | 2.11E+06 | 3.36E−04 | 1.60E−10 | 1.26E+06 | 3.38E−04 | 2.68E−10 | 0.65 |

TABLE 15

Biacore analysis: IgG immobilized on the chip and hFcRn were flowed over the chip.

| | Antagonistic anti-FcRn antibody data | | | | | |
|---|---|---|---|---|---|---|
| Clone # | biacore IgG hFcRn $K_{on}$ @pH 6 | biacore IgG hFcRn $K_{off}$ @pH 6 | biacore IgG hFcRn $K_D$ @pH 6 | biacore IgG hFcRn $K_{on}$ @pH 7.4 | biacore IgG hFcRn $K_{off}$ @pH 7.4 | biacore IgG hFcRn $K_D$ @pH 7.4 |
| 532A-M0090-F11 | 3.03E+05 | 3.12E−03 | 1.03E−08 | 1.81E+05 | 3.73E−03 | 2.05E−08 |
| 532A-M0090-F11 (germlined LC changes) | 5.74E+05 | 1.72E−02 | 2.99E−08 | 4.33E+05 | 1.52E−02 | 3.52E−08 |
| DX-2500 (germlined LC & allotype HC changes) | 6.42E+05 | 1.77E−02 | 2.76E−08 | 3.72E+05 | 7.52E−02 | 2.02E−08 |

Previous experience with anti-FcRn monoclonal antibody suggested that the Koff at pH 7.4 is very critical for in vivo efficacy of the antibody, it became apparent during biacore analysis that when the antibody was immobilized on the chip and target hFcRn was flowed over the chip, the Koff was much faster for germlined and DX-2500 antibody at both pH 6 & 7.4. A decision was made to affinity mature the germlined M90-F11 to select for clones with improved Koff value over DX2500.

A parallel approach was used to affinity mature the germlined M90-F11. Three different libraries (LC shuffled, CDR 1 & 2 and CDR 3 library) were built and are depicted in FIG. 26. A germlined light chain was used to build library 2 and 3 in order to avoid further sequence optimization after selecting the affinity matured lead.

Selection Protocols

Soluble Fabs (sFabs) were identified from the affinity matured M90-F11 phagemid display library that displays Fab fragments. Two different selections using soluble human (shFcRn) and 293 C11 cells expressing the human FcRn protein were carried out using three different affinity matured libraries. Additional selections were also carried out using a combination of cells and protein targets using the same elution strategy as outlined below:

i) Selections against biotinylated shFcRn: Two rounds of selection against biotinylated shFcRn were carried out with depletion on streptavidin beads. Phagemid were allowed to bind to target in acidic binding buffer (pH 6), and were then eluted with parental M90-F11 IgG in an pH 7.4 buffer. After competitive elution/wash, all remaining bound phage were eluted by direct bead infection of cells. The eluted phage output was used as input for next round of selection. Round 2 output was used in alternate round 3 selection against hFcRn-transfected cells followed by a fourth round selection using biotinylated shFcRn selections using the same elution strategy.

ii) Selections against hFcRn expressing cells: Two rounds of selection against hFcRn-transfected cells were carried out. Phagemid were allowed to bind to cells in acidic binding buffer (pH 6) at 4 degree, and were then eluted with parental M90-F11 IgG in an pH 7.4 buffer. After competitive elution/wash, all remaining bound phage were eluted by cell lysis with magnetic streptavidin beads and subsequent infection of bacteria. The eluted phage output is used as input for next round of selection. Two additional rounds of selection against biotinylated shFcRn were carried out as described in (i).

ELISA Screening for Fab Inhibitors of FcRN

To identify hFcRn binders, primary screening of round 3 and 4 outputs from each selection arm (4 per library) against biotinylated shFcRn in phage ELISA was carried out at pH 6 & 7.4. Approximately 1152 primary ELISA-positive Fabs on phagemid were screened and DNA sequenced.

One hundred seventy eight unique phagemids from three affinity matured libraries (16 from light chain shuffled library, 46 from CDR 1 & 2 library and from 116 CDR3 library) that were pH independent binders to hFcRn were selected and subcloned for expression as sFabs.

15 out of 16 phagemid clones screened from LC library had same CDR as the parent M90-F11 suggesting selection and screening strategy was biased in enriching for the parental clones. Affinity matured Sol FAB clones (~165) were subjected to high throughput SPR analysis and ranked by pH 7.4 off-rate and by pH 6 $K_D$ values and there were 21 affinity matured clones from CDR3 library and one clone from CDR1 & 2 library that were better than germlined M90-F11. Based on the high throughput SPR screening data, affinity matured M0159-C09 clone from CDR 1 & 2 library was swapped into HV CDR 1 & 2 position of the affinity matured M0157-H04 and M0157-E05 from CDR3 library. The constructed two hybrid clones M0171-A01 (also referred to as M171-A01) and M0171-A03 (also referred to as M171-A03) had complete affinity matured HV CDR 1, 2 & 3 with germlined M90-F11 LC sequences.

In total there were 24 sFAB clones (parental and Germlined M90-F11, 19 from CDR3 library, 1 from CDR 1& 2 library and 2 hybrid clones) that were sequenced, purified in medium scale and ranked by repeated SPR analysis (Table 16) and confirmed their antagonistic anti-FcRn properties in an Fc-FcRn blocking assay using FACS analysis.

TABLE 16

Top 22 affinity matured sol FAB binding kinetics, ranking and HV-CDR sequences

| 1st Mdm scale-2nd SPR Master Clone # | pH 7.4 | | | pH 6.0 | | | Fold Kd Improvement Over Germlined M90-F11 | | pH | CDR Sequence Differences | | |
|---|---|---|---|---|---|---|---|---|---|---|---|---|
| | ka (1/Ms) | kd (1/s) | KD (M) | ka (1/Ms) | kd (1/s) | KD (M) | pH 7.4 | pH 6.0 | 7.4 Rank | HV-CDR1 | HV-CDR2 | HV-CDR3 |
| 532A-M0171-A03 | 1.3E+05 | 1.7E−05 | 1.3E−10 | 1.3E+05 | 1.8E−04 | 1.4E−09 | 261.0 | 41.5 | 1 | VYAMG | SIGSSGGPTKYADSVKG | LSIRELV |

TABLE 16-continued

Top 22 affinity matured sol FAB binding kinetics, ranking and HV-CDR sequences

| 1st Mdm scale- 2nd SPR Master Clone # | pH 7.4 ka (1/Ms) | pH 7.4 kd (1/s) | pH 7.4 KD (M) | pH 6.0 ka (1/Ms) | pH 6.0 kd (1/s) | pH 6.0 KD (M) | Fold Kd Improvement Over Germlined M90-F11 pH 7.4 | Fold Kd Improvement Over Germlined M90-F11 pH 6.0 | pH 7.4 Rank | HV-CDR1 | HV-CDR2 | HV-CDR3 |
|---|---|---|---|---|---|---|---|---|---|---|---|---|
| 532A-M0171-A01 | 1.6E+05 | 2.3E-04 | 1.5E-09 | 1.6E+05 | 2.9E-04 | 1.9E-09 | 19.2 | 25.7 | 3 | VYAMG | SIGSSGGPTKYADSVKG | LSIVDSY |
| 532A-M0161-B04 | 1.7E+05 | 2.2E-04 | 1.3E-09 | 1.6E+05 | 1.9E-04 | 1.2E-09 | 20.5 | 39.6 | 2 | EYAMG | SIGSSGGQTKYADSVKG | LAIGDSY |
| 532A-M0157-F09 | 1.7E+05 | 2.8E-04 | 1.6E-09 | 1.8E+05 | 2.9E-04 | 1.6E-09 | 16.2 | 26.0 | 5 | EYAMG | SIGSSGGQTKYADSVKG | LSIRELI |
| 532A-M0157-B08 | 1.6E+05 | 3.5E-04 | 2.2E-09 | 1.6E+05 | 2.9E-04 | 1.8E-09 | 12.7 | 25.4 | 8 | EYAMG | SIGSSGGQTKYADSVKG | LSIRELS |
| 532A-M0157-H04 | 1.7E+05 | 3.6E-04 | 2.2E-09 | 1.7E+05 | 3.0E-04 | 1.8E-09 | 12.4 | 25.0 | 10 | EYAMG | SIGSSGGQTKYADSVKG | LSIRELV |
| 532A-M0159-A07 | 1.9E+05 | 2.5E-04 | 1.4E-09 | 1.8E+05 | 2.6E-04 | 1.4E-09 | 17.7 | 29.1 | 4 | EYAMG | SIGSSGGQTKYADSVKG | LSLGDSY |
| 532A-M0158-H06 | 2.1E+05 | 3.5E-04 | 1.7E-09 | 2.1E+05 | 3.1E-04 | 1.5E-09 | 12.9 | 24.1 | 7 | EYAMG | SIGSSGGQTKYADSVKG | LSIVDSF |
| 532A-M0157-A12 | 1.8E+05 | 4.9E-04 | 2.8E-09 | 1.5E+05 | 5.1E-04 | 3.3E-09 | 9.1 | 14.7 | 16 | EYAMG | SIGSSGGQTKYADSVKG | LSIRELD |
| 532A-M0158-C04 | 1.5E+05 | 4.2E-04 | 2.7E-09 | 1.5E+05 | 4.5E-04 | 3.0E-09 | 10.7 | 16.7 | 12 | EYAMG | SIGSSGGQTKYADSVKG | LSIRELH |
| 532A-M0157-C05 | 1.8E+05 | 4.7E-04 | 2.6E-09 | 2.0E+05 | 4.2E-04 | 2.1E-09 | 9.5 | 17.9 | 15 | EYAMG | SIGSSGGQTKYADSVKG | LSIRELS |
| 532A-M0155-F05 | 1.8E+05 | 5.4E-04 | 3.1E-09 | 1.9E+05 | 4.6E-04 | 2.5E-09 | 8.3 | 16.3 | 19 | EYAMG | SIGSSGGQTKYADSVKG | LSIDDSY |
| 532A-M0158-A03 | 1.4E+05 | 3.5E-04 | 2.5E-09 | 1.4E+05 | 4.8E-04 | 3.4E-09 | 12.9 | 15.6 | 6 | EYAMG | SIGSSGGQTKYADSVKG | LSIVELD |
| 532A-M0159-A10 | 1.6E+05 | 4.2E-04 | 2.6E-09 | 1.6E+05 | 4.0E-04 | 2.5E-09 | 10.6 | 18.6 | 13 | EYAMG | SIGSSGGQTKYADSVKG | LSIRELF |
| 532A-M0157-D11 | 1.7E+05 | 4.6E-04 | 2.6E-09 | 1.7E+05 | 3.9E-04 | 2.3E-09 | 9.8 | 19.1 | 14 | EYAMG | SIGSSGGQTKYADSVKG | LSIRDSY |
| 532A-M0155-D12 | 1.4E+05 | 5.1E-04 | 3.6E-09 | 1.5E+05 | 4.5E-04 | 3.0E-09 | 8.8 | 16.6 | 18 | EYAMG | SIGSSGGQTKYADSVKG | LSIDDFY |
| 532A-M0157-D04 | 1.9E+05 | 5.1E-04 | 2.7E-09 | 1.8E+05 | 4.4E-04 | 2.5E-09 | 8.9 | 17.0 | 17 | EYAMG | SIGSSGGQTKYADSVKG | LSIRELF |
| 532A-M0155-G01 | 1.6E+05 | 5.7E-04 | 3.5E-09 | 1.7E+05 | 5.1E-04 | 2.9E-09 | 7.9 | 14.6 | 20 | EYAMG | SIGSSGGQTKYADSVKG | LSTRELY |
| 532A-M0157-E05 | 1.8E+05 | 3.6E-04 | 2.0E-09 | 1.8E+05 | 3.1E-04 | 1.7E-09 | 12.6 | 24.1 | 9 | EYAMG | SIGSSGGQTKYADSVKG | LSIVDSY |
| 532A-M0159-C09 | 1.4E+05 | 9.1E-04 | 6.6E-09 | 1.3E+05 | 7.9E-04 | 6.0E-09 | 4.9 | 9.5 | 22 | VYAMG | SIGSSGGPTKYADSVKG | LSTGELY |
| 532A-M0161-G06 | 1.2E+05 | 8.1E-04 | 6.9E-09 | 1.7E+05 | 4.2E-04 | 2.6E-09 | 5.6 | 17.7 | 21 | EYAMG | SIGSSGGQTKYADSVKG | LSIRELH |
| Parent M90-F11 | 1.4E+05 | 1.9E-03 | 1.3E-08 | 1.4E+05 | 1.6E-03 | 1.2E-08 | 2.3 | 4.7 | 23 | EYAMG | SIGSSGGQTKYADSVKG | LSTGELY |
| 532A-M0155-H05 | 2.9E+05 | 6.1E-03 | 2.1E-08 | 2.0E+06 | 3.4E-04 | 1.7E-08 | 0.7 | 0.2 | 26 | EYAMG | SIGSSGGQTKYADSVKG | LSTGALS |
| Germlined M90-F11 | 1.9E+05 | 4.5E-03 | 2.4E-08 | 6.5E+05 | 7.5E-03 | 1.2E-08 | 1.0 | 1.0 | 25 | EYAMG | SIGSSGGQTKYADSVKG | LSTGELY |

TABLE 16A

Sequences corresponding to Table 16

| 1st Mdm scale-2nd SPR Master Clone # | HV-CDR1 | HV-CDR2 | HV-CDR3 | SEQ ID NO: |
|---|---|---|---|---|
| 532A-M0171-A03 | VYAMG | SIGSSGGPTKYADSVKG | LSIRELV | 117 |
| 532A-M0171-A01 | VYAMG | SIGSSGGPTKYADSVKG | LSIVDSY | 118 |
| 532A-M0161-B04 | EYAMG | SIGSSGGQTKYADSVKG | LAIGDSY | 119 |
| 532A-M0157-F09 | EYAMG | SIGSSGGQTKYADSVKG | LSIRELI | 120 |
| 532A-M0157-B08 | EYAMG | SIGSSGGQTKYADSVKG | LSIRELS | 121 |
| 532A-M0157-H04 | EYAMG | SIGSSGGQTKYADSVKG | LSIRELV | 122 |
| 532A-M0159-A07 | EYAMG | SIGSSGGQTKYADSVKG | LSLGDSY | 123 |
| 532A-M0158-H06 | EYAMG | SIGSSGGQTKYADSVKG | LSIVDSF | 124 |
| 532A-M0157-A12 | EYAMG | SIGSSGGQTKYADSVKG | LSIRELD | 125 |
| 532A-M0158-C04 | EYAMG | SIGSSGGQTKYADSVKG | LSIRELH | 126 |
| 532A-M0157-C05 | EYAMG | SIGSSGGQTKYADSVKG | LSIRELS | 127 |
| 532A-M0155-F05 | EYAMG | SIGSSGGQTKYADSVKG | LSIDDSY | 128 |
| 532A-M0158-A03 | EYAMG | SIGSSGGQTKYADSVKG | LSIVELD | 129 |
| 532A-M0159-A10 | EYAMG | SIGSSGGQTKYADSVKG | LSIRELF | 130 |
| 532A-M0157-D11 | EYAMG | SIGSSGGQTKYADSVKG | LSIRDSY | 131 |
| 532A-M0155-D12 | EYAMG | SIGSSGGQTKYADSVKG | LSIDDFY | 132 |
| 532A-M0157-D04 | EYAMG | SIGSSGGQTKYADSVKG | LSIRELF | 133 |
| 532A-M0155-G01 | EYAMG | SIGSSGGQTKYADSVKG | LSIRELY | 134 |
| 532A-M0157-E05 | EYAMG | SIGSSGGQTKYADSVKG | LSIVDSY | 135 |
| 532A-M0159-C09 | VYAMG | SIGSSGGPTKYADSVKG | LSTGELY | 136 |
| 532A-M0161-G06 | EYAMG | SIGSSGGQTKYADSVKG | LSIRELH | 137 |
| Parent M90-F11 | EYAMG | SIGSSGGQTKYADSVKG | LSTGELY | 138 |
| 532A-M0155-H05 | EYAMG | SIGSSGGQTKYADSVKG | LSTGALS | 139 |
| Germlined M90-F11 | EYAMG | SIGSSGGQTKYADSVKG | LSTGELY | 140 |

All 22 sFAB clones were reformatted to IgG but only 8 IgG were expressed, purified and subjected to Flexchip analysis at pH 6 & 7.4. Based on the Flexchip SPR 8500 data the following 4 affinity matured IgG clones were selected for further in vitro (Biacore analysis) and in vivo study in hFcRn transgenic mouse model.

Table 17A shows the total number of amino acid changes in the HV-CDR1 &2 or 3 of the 4 affinity matured IgG in comparison to the parental or DX2500 clone.

TABLE 17A

Top 4 affinity matured IgG LV & HV-CDR sequences and # of mutation compared to parent M90-F11

| Initial Name | LV-CDR1 | LV-CDR2 | LV-CDR3 | HV-CDR1 | HV-CDR2 | HV-CDR3 |
|---|---|---|---|---|---|---|
| Parent M90-F11 | TGTGSDVGSYNLVS | GDSQRPS | CSYAGSGIYV | EYAMG | SIGSSGGQTKYADSVKG | LSTGELY |
| DX-2500 | TGTGSDVGSYNLVS | GDSQRPS | CSYAGSGIYV | EYAMG | SIGSSGGQTKYADSVKG | LSTGELY |
| 532A-M0171-A03 | TGTGSDVGSYNLVS | GDSQRPS | CSYAGSGIYV | VYAMG | SIGSSGGPTKYADSVKG | LSIRELV |
| 532A-M0171-A01 | TGTGSDVGSYNLVS | GDSQRPS | CSYAGSGIYV | VYAMG | SIGSSGGPTKYADSVKG | LSIVDSY |
| 532A-M0159-A07 | TGTGSDVGSYNLVS | GDSQRPS | CSYAGSGIYV | EYAMG | SIGSSGGQTKYADSVKG | LSLGDSY |
| 532A-M0161-B04 | TGTGSDVGSYNLVS | GDSQRPS | CSYAGSGIYV | EYAMG | SIGSSGGQTKYADSVKG | LAIGISY |

* 10 Germline changes, 3 changes due to AZ to F allotype switch + HV-CDR mutation

TABLE 17A1

SEQ ID NOs corresponding to Table 17A

| SEQ ID NOs | LV-CDR1 | LV-CDR2 | LV-CDR3 | HV-CDR1 | HV-CDR2 | HV-CDR3 |
|---|---|---|---|---|---|---|
| Parent M90-F11 | 141 | 142 | 143 | 144 | 145 | 146 |
| Dx-2500 | 147 | 148 | 149 | 150 | 151 | 152 |
| 532A-M0171-A03 | 153 | 154 | 155 | 156 | 157 | 158 |
| 532A-M0171-A01 | 159 | 160 | 161 | 162 | 163 | 164 |
| 532A-M0171-A07 | 165 | 166 | 167 | 168 | 169 | 170 |
| 532A-M0171-B04 | 171 | 172 | 173 | 174 | 175 | 176 |

Biacore analysis of the 4 affinity matured clone done at pH 7.4 by immobilizing the IgG on the chip and hFcRn flowed over and their raw data and fold improvement ($K_{off}$ and $K_D$) over DX-2500 and parental M90-F11 clone is presented in Table 17B.

TABLE 17B

Top 4 affinity matured IgG binding kinetics, fold improvement over DX-2500 & Parent M90-F11

| Comparison of Biacore Data done at pH 7.4 | | | | K off Fold improvement over | | $K_D$ Fold improvement over | |
|---|---|---|---|---|---|---|---|
| Clone # + SPR Method | Ka s−1 M−1 | Kd s−1 | KD (M) | DX2500 | M90-F11 | DX2500 | M90-F11 |
| M171-A01 IgG Biacore | 1.26E+05 | 1.92E−04 | 1.52E−09 | 103 | 16 | 58 | 12 |
| M171-A03 IgG Biacore | 1.42E+05 | 2.84E−04 | 2.00E−09 | 69 | 11 | 44 | 9 |
| M159-A07 IgG Biacore | 1.27E+05 | 6.88E−04 | 5.40E−09 | 29 | 4 | 16 | 3 |
| M161-B04 IgG Biacore | 1.21E+05 | 8.57E−04 | 7.06E−09 | 23 | 3 | 12 | 3 |
| M90-F11 parental Biacore | 1.61E+05 | 2.99E−03 | 1.86E−08 | 7 | 1 | 5 | 1 |
| DX-2500 Biacore | 2.24E+05 | 1.97E−02 | 8.79E−08 | 1 | 0.15 | 1 | 0.21 |

The protocol used for testing affinity matured anti-FcRn IgG and sol FAB in hFcRn transgenic mice was:

6 groups (1 placebo, 4 IgG, 1 Fab. 4 mice/group)
Intravenous dose of 495 mg/kg hIgG+5 mg/kg biotin-hIgG at time=0 hr
Intravenous dose of 5 or 20 mg/kg of Ab (1.67 or 6.67 mg/kg of Fab) at time=24 hr:
  M171-A01-IgG,
  M171-A03-IgG,
  M159-A07-IgG,
  M161-B04-IgG or
  S32A-M171-A01-Fab
Blood samples collected at 24 (pre-dose), 30, 48, 72, 96, 120 and 168 hr.
Biotin-hIgG serum levels quantified using a streptavidin capture/Fc detection ELISA and total IgG quantified using an Fab capture/Fc detection ELISA.

Based on the in vivo data shown in FIGS. 27 and 28, and Table 18 below, M0161-B04 and M0171-A01 have been selected to be tested head to head with M90-F11 and DX-2500 in Tg32B mice.

TABLE 18

Effect of affinity matured IgG and sol FAB in accelerating the hIgG Catabolism in Tg32B Mice: 5 & 20 mg/kg Intravenous Dose (Biotin IgG & Total IgG).

| | % PBS control of Biotin-IgG remaining in the serum at 168 hrs | | % PBS control of total gG remaining in the serum at 168 hrs | |
|---|---|---|---|---|
| IgGName | 5 mg/kg (1.7 mg/ kg sFAb) | 20 mg/kg (6.7 mg/ kg sFAb) | 5 mg/kg (1.7 mg/ kg sFAb) | 20 mg/kg (6.7 mg/ kg sFAb) |
| Parent M90-F11 | 77 | 63 | NA | NA |
| 532A-M0171-A01 | 124 | 45 | 96 | 40 |
| 532A-M0171-A03 | 128 | 66 | 84 | 44 |
| 532A-M0159-A07 | 131 | 59 | 96 | 40 |
| 532A-M0161-B04 | 100 | 41 | 76 | 24 |
| S32A-M171-A03-sFAb | 152 | 103 | 140 | 108 |

Example 27

Effect of Anti-FcRn Antibodies on the Catabolism of hIgG

In vivo studies with anti-FcRn antibodies demonstrated efficacy in depleting circulating IgG. Dose dependent depletion was exhibited in two species, mice and monkeys, and by two routes of administration, intravenous and subcutaneous. In monkeys, reduction of IgG was not accompanied by any change in circulating IgA, IgM or serum albumin.

A) Effect of Anti-FcRN Antibodies on the Catabolism of hIgG in Mice

Tg32B mice (mouse FcRn and mouse β2-macroglobulin knock-out)/knock-in (human FcRn and human β2-macroglobulin knock-in) were administered human IgG at day 0. At day 1 and day 7 the mice were intravenously administered different doses of the anti-FcRn antibodies M161-B04 (DX-2504) and M171-A01. The level of human IgG in the serum of the mice was measured over 14 days. As shown in FIG. 31, the level of human IgG was reduced significantly over the 14 day period for each of the antibodies administered. The decrease in IgG was dependent on the concentration of anti-FcRn antibody administered.

B) Effect of Anti-FcRN Antibodies on the Catabolism of hIgG in Mice by Subcutaneous Administration.

Tg32B mice (mouse FcRn and mouse β2-macroglobulin knock-out)/knock-in (human FcRn and human β2-macroglobulin knock-in) were administered human IgG at day 0. At day 1 and day 7 the mice were subcutaneously administered different doses of the anti-FcRn antibody M161-B04 (DX-2504). The level of human IgG in the serum of the mice was measured over 14 days. As shown in FIG. 32, the level of human IgG was reduced significantly over the 14 day period for each of the antibodies administered. The decrease in IgG was dependent on the concentration of anti-FcRn antibody administered. The efficacy of subcutaneous administration is similar to intravenous administration.

C) Effect of Anti-FcRn Antibodies on the Catabolism of hIgG in Cynomolgus Monkeys Cynomolgus monkeys were administered different doses of the anti-FcRn antibody M161-B04 (DX-2504) and a vehicle control. FIG. 33 shows the timeline of administration (FIG. 33A) and the results for the control (FIG. 33B). The level of IgG in the serum of the monkeys was measured over 14 days. As shown in FIGS. 34-35 (individual monkeys) and FIG. 36 (group mean data), the level of IgG was reduced significantly over the 14 day period for each of the antibodies administered. The decrease in IgG was dependent on the concentration of anti-FcRn antibody administered. The efficacy of subcutaneous administration is similar to intravenous administration. FIGS. 37A-37C show that the serum levels of IgA, IgM and serum albumin are unaffected by the administration of the anti-FcRn antibody.

The contents of all cited references including literature references, issued patents, published or non-published patent applications cited throughout this application as well as those listed below are hereby expressly incorporated by reference in their entireties. In case of conflict, the present application, including any definitions herein, will control.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated antibody comprising a heavy chain (HC) immunoglobulin variable domain sequence and a light chain (LC) immunoglobulin variable domain sequence, wherein the antibody binds to human FcRn; and wherein the HC comprises:
- a HC CDR1 comprising the amino acid sequence EYAMG (SEQ ID NO:144) or VYAMG (SEQ ID NO:156),
- a HC CDR2 comprising the amino acid sequence SIGSSGGQTKYADSVKG (SEQ ID NO:145) or SIGSSGGPTKYADSVKG (SEQ ID NO:157), and
- a HC CDR3 comprising the amino acid sequence LSTGELY (SEQ ID NO:146), LSIRELV (SEQ ID NO:158), LSIVDSY (SEQ ID NO:164), LSLGDSY (SEQ ID NO:170), or, LAIGDSY (SEQ ID NO:176); and the LC comprises:
- a LC CDR1 comprising the amino acid sequence TGTGSDVGSYNLVS (SEQ ID NO:141),
- a LC CDR2 comprising the amino acid sequence GDSQRPS (SEQ ID NO:142), and
- a LC CDR3 comprising the amino acid sequence CSYAGSGIYV (SEQ ID NO:143).

2. The isolated antibody of claim 1, wherein the HC comprises,
- a HC CDR1 comprising the amino acid sequence EYAMG (SEQ ID NO:144),
- a HC CDR2 comprising the amino acid sequence SIGSSGGQTKYADSVKG (SEQ ID NO:145), and
- a HC CDR3 comprising the amino acid sequence LAIGDSY (SEQ ID NO:176).

3. The isolated antibody of claim 1, wherein the HC comprises,
- a HC CDR1 comprising the amino acid sequence VYAMG (SEQ ID NO:156),
- a HC CDR2 comprising the amino acid sequence SIGSSGGPTKYADSVKG (SEQ ID NO:157), and
- a HC CDR3 comprising the amino acid sequence LSIVDSY (SEQ ID NO:164).

4. The isolated antibody of claim 1, wherein the HC comprises,
- a HC CDR1 comprising the amino acid sequence EYAMG (SEQ ID NO:144),
- a HC CDR2 comprising the amino acid sequence SIGSSGGQTKYADSVKG (SEQ ID NO:145), and
- a HC CDR3 comprising the amino acid sequence LSTGELY (SEQ ID NO:146).

5. A pharmaceutical composition comprising the antibody of claim 1 and a pharmaceutically acceptable carrier.

6. The isolated antibody of claim 1, wherein the HC comprises:
(i) a HC CDR1 of EYAMG (SEQ ID NO:144), a HC CDR2 of SIGSSGGQTKYADSVKG (SEQ ID NO:145), and a HC CDR3 of LSTGELY (SEQ ID NO:146);
(ii) a HC CDR1 of VYAMG (SEQ ID NO:156), a HC CDR2 of SIGSSGGPTKYADSVKG (SEQ ID NO:157), and a HC CDR3 of LSIRELV (SEQ ID NO:158);
(iii) a HC CDR1 of VYAMG (SEQ ID NO:156), a HC CDR2 of SIGSSGGPTKYADSVKG (SEQ ID NO:157), and a HC CDR3 of LSIVDSY (SEQ ID NO:164);
(iv) a HC CDR1 of EYAMG (SEQ ID NO:144), a HC CDR2 of SIGSSGGQTKYADSVKG (SEQ ID NO:145), and a HC CDR3 of LSLGDSY (SEQ ID NO:170); or
(v) a HC CDR1 of EYAMG (SEQ ID NO:144), a HC CDR2 of SIGSSGGQTKYADSVKG (SEQ ID NO:145), and a HC CDR3 of LAIGDSY (SEQ ID NO:176).

* * * * *

UNITED STATES PATENT AND TRADEMARK OFFICE
CERTIFICATE OF CORRECTION

PATENT NO. : 8,273,351 B2  
APPLICATION NO. : 12/429529  
DATED : September 25, 2012  
INVENTOR(S) : Christopher TenHoor et al.

Page 1 of 1

It is certified that error appears in the above-identified patent and that said Letters Patent is hereby corrected as shown below:

On the Title Page:

Item (75) Inventors should read: Christopher TenHoor, Hopkinton, MA (US);
Arumugam Muruganandam, Bangalore (IN);
Robert Charles Ladner, Ijamsville, MD (US);
Clive Wood, Boston, MA (US);
Alan J. Bitonti, Acton, MA (US);
James Stattel, Hagerstown, MD (US);
Kevin McDonnell, Waltham, MA (US);
Liming Liu, Upper Dublin, PA (US);
Jennifer Dumont, Groton, MA (US);
Aaron Sato, Richmond, CA (US);
Malini Viswanathan, Burlington, MA (US)

Signed and Sealed this  
Twentieth Day of November, 2012

David J. Kappos  
*Director of the United States Patent and Trademark Office*